United States Patent
Congreve et al.

(10) Patent No.: US 12,391,641 B2
(45) Date of Patent: Aug. 19, 2025

(54) PROSTAGLANDIN EP$_4$ RECEPTOR ANTAGONIST COMPOUNDS

(71) Applicant: NXERA PHARMA UK LIMITED, Cambridge (GB)

(72) Inventors: Miles Stuart Congreve, Cambridge (GB); Nigel Alan Swain, Cambridge (GB); Benjamin Whitehurst, Cambridge (GB)

(73) Assignee: Nxera Pharma UK Limitied (GB)

( * ) Notice: Subject to any disclaimer, the term of this patent is extended or adjusted under 35 U.S.C. 154(b) by 637 days.

(21) Appl. No.: 17/767,188

(22) PCT Filed: Oct. 9, 2020

(86) PCT No.: PCT/GB2020/052530
§ 371 (c)(1),
(2) Date: Apr. 7, 2022

(87) PCT Pub. No.: WO2021/069927
PCT Pub. Date: Apr. 15, 2021

(65) Prior Publication Data
US 2022/0411364 A1 Dec. 29, 2022

(30) Foreign Application Priority Data
Oct. 9, 2019 (GB) ..................... 1914585

(51) Int. Cl.
| | | |
|---|---|---|
| *C07C 233/55* | (2006.01) | |
| *A61K 31/165* | (2006.01) | |
| *A61K 31/36* | (2006.01) | |
| *A61K 31/437* | (2006.01) | |
| *A61K 31/4412* | (2006.01) | |
| *A61P 13/12* | (2006.01) | |
| *A61P 15/00* | (2006.01) | |
| *A61P 19/02* | (2006.01) | |
| *A61P 25/06* | (2006.01) | |
| *A61P 25/28* | (2006.01) | |
| *C07C 235/12* | (2006.01) | |
| *C07C 235/14* | (2006.01) | |
| *C07C 311/51* | (2006.01) | |
| *C07C 317/22* | (2006.01) | |
| *C07D 235/26* | (2006.01) | |
| *C07D 257/04* | (2006.01) | |
| *C07D 305/06* | (2006.01) | |

(52) U.S. Cl.
CPC .......... *C07C 233/55* (2013.01); *C07C 311/51* (2013.01); *C07C 317/22* (2013.01); *C07D 257/04* (2013.01); *C07D 305/06* (2013.01)

(58) Field of Classification Search
CPC ... C07C 233/55; C07C 235/12; C07C 235/14; C07C 2601/02; C07C 2601/04; C07D 235/26; A61K 31/165; A61K 31/36; A61K 31/437; A61K 31/4412; A61P 13/12; A61P 15/00; A61P 19/02; A61P 25/06; A61P 25/28
See application file for complete search history.

(56) References Cited

U.S. PATENT DOCUMENTS

2015/0141471 A1* 5/2015 Nazare ................ A61P 19/00
546/342

FOREIGN PATENT DOCUMENTS

| CN | 101952244 A | 1/2011 | |
|---|---|---|---|
| EP | 2422779 A1 | 2/2012 | |
| WO | 2003/008377 A1 | 1/2003 | |
| WO | 2009/056582 A1 | 5/2009 | |
| WO | 2009/108720 A2 | 9/2009 | |
| WO | 2013/171316 A1 | 11/2013 | |
| WO | WO-2014126746 A1 * | 8/2014 | .......... C07C 235/06 |

OTHER PUBLICATIONS

Blouin et al., The discovery of 4-{1-[({2,5-dimethyl-4-[4-(trifluoromethyl)benzyl]-3-thienyl}carbonyl)amino]cyclopropyl}benzoic acid (MK-2894), a potent and selective prostaglandin E2 subtype 4 receptor antagonist. J Med Chem. Mar. 11, 2010;53(5):2227-38.
International Search Report and Written Opinion for Application No. PCT/GB2020/052530, dated Jan. 29, 2021, 8 pages.

* cited by examiner

*Primary Examiner* — Joseph K McKane
*Assistant Examiner* — Sagar Patel
(74) *Attorney, Agent, or Firm* — Barnes & Thornburg; Amy H. Fix

(57) ABSTRACT

The disclosures herein relate to novel compounds of formula (1): (1) and salts thereof, wherein A, X, $R^1$, $R^2$, $R^3$, $R^4$, $R^{10}$ and $R^{11}$ are defined herein, and their use in treating, preventing, ameliorating, controlling or reducing the risk of disorders associated with EP$_4$ receptors.

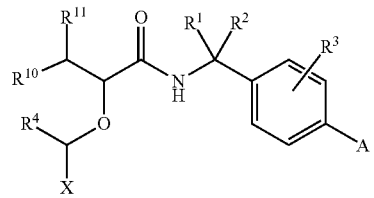

27 Claims, No Drawings

PROSTAGLANDIN EP$_4$ RECEPTOR ANTAGONIST COMPOUNDS

CROSS-REFERENCE TO RELATED APPLICATIONS

This application is a U.S. national stage filing, under 35 U.S.C. § 371 (c), of International Application No. PCT/GB2020/052530, filed on Oct. 9, 2020, which claims priority to United Kingdom Patent Application No. 1914585.3, filed on Oct. 9, 2019.

This application relates to novel compounds and their use as prostaglandin E$_2$ receptor 4 (EP$_4$) antagonists. Compounds described herein may be useful in the treatment or prevention of diseases in which EP$_4$ receptors are involved. The application is also directed to pharmaceutical compositions comprising these compounds and the manufacture and use of these compounds and compositions in the prevention or treatment of such diseases in which EP$_4$ receptors are involved.

BACKGROUND OF THE INVENTION

Prostaglandins (PG) are small-molecule (~400 Da) products produced by cyclooxygenases (COX; constitutively active COX1 and inducible COX2) and PG synthases, with a minor contribution from the isoprostane pathway, acting on arachidonic acid (AA). Prostaglandin E$_2$ (PGE$_2$) is the main COX product in myeloid and stromal cells whose levels are determined by the balance between synthesis and 15-hydroxyprostaglandin dehydrogenase (15-PGDH)-mediated degradation. PGE$_2$ has 4 receptors (EP$_1$-EP$_4$) which are present on multiple cell types including macrophages, monocytes, platelets, sensory neurons, gastrointestinal tract, kidney, thymus, heart, lung, and uterus and drives a broad pharmacology mediating nociception, aspects of neuronal signalling, haematopoiesis, regulation of blood flow, renal filtration and blood pressure, regulation of mucosal integrity, vascular permeability, smooth muscle function and both pro-inflammatory (vasodilation, recruitment and activation of mast cells, macrophages and neutrophils) and immunosuppressive immune function (detailed below). Functional PGE$_2$ antagonism has therapeutic potential in a wide variety of disease settings, discussed below.

Abdominal aortic aneurysm (AAA). AAA is a life-threatening inflammatory vascular disease associated with connective tissue degeneration, loss of smooth muscle leading to a dilated aorta which is prone to rupture. Diseased aortic tissue is associated with EP$_4$, PGE$_2$ expression and macrophage and smooth muscle COX2 expression (Walton, L. J. et al. *Circulation* 100, 48-54 (1999)). EP$_4$ antagonism or gene deletion is associated with beneficial outcomes in human and mouse preclinical systems (Yokoyama, U. et al. *PLoS One* 7, e36724 (2012)).

Ankylosing spondyltis (AS). AS is a heritable autoimmune disease associated with HLA-B27 and EP$_4$. Inflammatory pain in rodent models can be PGE$_2$ and EP$_4$ driven. AS patients' pain is NSAID responsive suggesting that EP$_4$ antagonists may also be analgesic in AS with the long-term safety benefits associated with specific EP$_4$ antagonism versus general AA metabolism inhibition as discussed below in the cancer section (Murase, A. et al. *Eur. J. Pharmacol.* 580, 116-121 (2008)).

Alzheimer's disease (AD). Amyloid-β peptide (Aβ), generated by β- and γ-secretase-mediated proteolysis of β-amyloid precursor protein (APP), plays a key role AD pathogenesis. PGE$_2$ stimulates Aβ production through endocytosis and activation of γ-secretase. Transgenic mice expressing mutant APP (APP23) crossed with EP$_4$-deficient mice have been shown to exhibit lower levels of Aβ plaque deposition and less neuronal and synaptic loss than control mice. Oral treatment with a specific EP$_4$ has been shown to improve cognitive performance and decrease Aβ levels in the brain (Hoshino, T. et al. *J. Neurochem.* 120, 795-805 (2012)).

Atherosclerosis. EP$_4$ has been associated with destabilisation of human atherosclerotic plaques via PGE$_2$-induction of MMP-2 and MMP-9 (Cipollone, F. et al. *Arteiosder. Thromb. Vasc. Biol.* 25, 1925-31 (2005)). EP$_4$ has also been validated as a target for prevention of atherosclerosis development by analysis of EP$_4$-deficient macrophages, which had compromised survival, in a mouse model (Babaev, V. R. et al. *Cell Metab.* 8, 492-501 (2008)).

Cancer. Cancers or neoplasms are a leading cause of global mortality and morbidity. Literature strongly supports a role for PGE$_2$ in epithelial cancers (GBD neoplasm categories of colon and rectum, lip and oral cavity, nasopharynx, other pharynx, gallbladder and biliary tract, pancreatic, non-melanoma skin, ovarian, testicular, kidney, bladder, thyroid, mesothelioma, esophageal, stomach, liver, larynx, tracheal, bronchus and lung, breast, cervical, uterine, prostate).

PGE$_2$ and associated receptors are upregulated in a wide variety of epithelial neoplasms (colon, lip and oral cavity, gallbladder, pancreas, non-melanoma skin, ovarian, kidney, bladder, thyroid, mesothelioma, oesphageal squamous cell carcinoma, stomach, liver, squamous cell lung carcinoma, breast, triple negative breast cancer, cervical, uterine, prostate cancer, head and neck squamous cell carcinoma) and expression level correlates with disease progression (lip and oral cavity, oesphageal squamous cell carcinoma, cervical, prostate cancer, head and neck squamous cell carcinoma).

Celecoxib (COX-2-selective inhibitor) use was shown to decrease incidence of adenoma development and rate of advanced adenoma development but increase serious cardiovascular events in participants who had an adenoma removed (Arber, N. et al. *N. Engl. J. Med.* 355, 885-895 (2006)). Celecoxib has also been trialed as a co-treatment for various cancers. A meta-analysis of 5 randomised trials utilising aspirin (COX-1 and COX-2 inhibitor) has demonstrated that doses of at least 75 mg daily reduced the 20-year risk of colon cancer (Rothwell, P. M. et al. *Lancet* 376, 1741-1750 (2010)). PI3K mutations are present in 15-20% of colorectal cancers (CRC) with many activating; PI3K upregulation enhances PTGS2 (COX-2) activity and hence PGE$_2$ synthesis. Post-CRC diagnosis regular aspirin use was associated with a survival benefit in patients with mutated-, but not wild type-, PIK3CA (Liao, X. et al. *N. Engl. J. Med.* 367, 1596-1606 (2012)).

The therapeutic utility of COX inhibitors are limited by their potential to cause either GI (NSAIDs e.g. aspirin) or CV (NSAIDs and Coxibs e.g. celecoxib) toxicity. Hence although the utility of aspirin and NSAIDs in general in cancer chemoprevention has been recognised by international consensus, the risk/benefit ratio remains challenging and so, definitive use recommendations have not been made. Taken together these data suggest that broad spectrum suppression of prostaglandin synthesis is too blunt a pharmacological tool to deliver appropriate benefit:risk balance and there is a need for more specific medicines to be evaluated. We hence hypothesise that specific neutralisation of PGE$_2$ biology through EP$_4$ antagonism will deliver clinical benefit whilst minimising the side effect profile.

PGE$_2$ represents an attractive therapeutic target that drives immunosuppressive, immunological and oncological processes to facilitate cancer development and progression. The COX-2 and epidermal growth factor receptor (EGFR) pathways are activated in most human cancers. When human colorectal cancer (CRC) cells are transfected with COX2 they proliferate in association with EGFR induction suggesting crosstalk between the pathways. Mice bearing CRC tumours have shown reduced tumour growth when administered PGE$_2$-neutralising antibody (Stolina, M. et al. *J. Immunol.* 164, 361-70 (2000)). PGE$_2$ is generally anti-apoptotic in hypoxic and treatment (such as radiotherapy) conditions, and activates the Ras-MAPK/ERK and PI3K/AKT survival pathways (Wang, D. & Dubois, R. N. *Gut* 55, 115-22 (2006)). Preclinical rodent and human studies support the view that PGE$_2$ plays a key role in cancer development and progression and have started to elucidate the mechanism. COX expression in tumours generates PGE2 which subverts myeloid function; COX ablation with knockouts or aspirin/coxib enables immune control of the tumour and COX inhibition synergises with immune checkpoint blockade in the form of PD1-blocking antibody (Zelaney et al., *Cell*, 2015). These data suggest that other known immune checkpoint blocking agents may synergise with PGE2 suppression. Finally the COX inflammatory signature is conserved across mouse and human cancer biopsies (Zelaney et al., *Cell*, 2015). It is highly likely that doses of coxibs required to fully suppress PGE2 in the tumour microenvironment exceed those licensed for clinical use in people further supporting the need for a drug to block the cancer-supporting biology of PGE2 without generating dose-limiting toxicities.

Multiple immune cells bear adenosine receptors (primarily A2$_A$ and A2$_b$) which, in common with EP$_2$ and EP$_4$, act to increase intracellular cAMP and mediate immunosuppression. PGE2 and adenosine are co-expressed in neoplasms supporting the concept that clinical benefit will accrue by combining PGE2 and adenosine pathway modulators.

These findings suggest that functional antagonism of PGE$_2$ has strong potential to both deliver strong clinical benefit to patients with various epithelial cancers but also to synergise with current standard of care and new IO agents in development.

Diabetic nephropathy. Diabetes mellitus is associated with multiple macrovascular complications including nephropathy, retinopathy and neuropathy. Diabetic nephropathy is the leading cause of end-stage renal disease, associated with high cardiovascular risk and is a common sequelae for approximately $\frac{1}{3}^{rd}$ of diabetes mellitus patients. Current therapy centres on control of blood glucose and blood pressure, to minimise the key risk factors of hyperglycaemia, hypertension, dyslipidemia, obesity, but is insufficiently efficacious. PGE$_2$ is the most abundant renal prostaglandin and plays a variety of roles in renal physiology; inflammation, volume homeostasis, regulation of salt and water balance, renal blood flow, renin release, glomerular haemodynamics (Breyer, M. D., Jacobson, H. R. & Breyer, R. M. *J. Am. Soc. Nephrol.* 7, 8-17 (1996)); EP$_1$ and EP$_3$ are generally vasoconstrictive whereas EP$_2$ and EP$_4$ mediate vasodilation. EP$_4$ has been implicated in mediating renal damage in preclinical models mimicking aspects of diabetic nephropathy. Four weeks repeated oral administration of the EP$_4$ antagonist ASP7657 has been shown to dose-dependently attenuate albuminuria in type 2 diabetic db/db mice (Mizukami, K. et al. *Naunyn. Schmiedebergs. Arch. Pharmacol.* 391, 1319-1326 (2018)).

Endometriosis. Endometriosis is characterised by persistent colonisation of endometrial tissue outside the uterine cavity, likely via retrograde menstruation, leading to typical foci and the formation of "endometriotic lesions" which have upregulated COX2 and elevated PGE$_2$.

PGE$_2$ stimulates integrin-mediated adhesion of endometriotic epithelial and stromal cells and drives proliferation of endometriotic epithelial cells and stromal cells via EP$_2$ and EP$_4$; when PGE$_2$ is blocked this drives cells into apoptosis. Data suggest that EP$_4$ antagonism may be of therapeutic utility in endometriosis (Lee, J., Banu, S. K., Burghardt, R. C., Starzinski-Powitz, A. & Arosh, J. A. *Biol. Reprod.* 88, 77 (2013)).

Inflammatory bowel disease. PGE2 directly promotes differentiation and proinflammatory functions of IL-17-producing T helper (Th17) cells (Boniface et al, *JEM*, 2009) via upregulation of IL-23 receptors (Lee et al., *JACI*, 2019) which have been implicated in driving IBD; the IL-12/23 neutralising ustekinumab is efficacious in ulcerative colitis and crohn's disease.

Migraine. PGE$_2$ has strong target validation in migraine. PGE$_2$ is upregulated in jugular blood, plasma and saliva of people experiencing migraine. IV infusion of prostaglandins can trigger migraine-symptoms in migraine patients; PGE$_2$ relaxes human cerebral arteries in an EP$_4$-dependent fashion (Maubach, K. A. K. A. et al. *Br. J. Pharmacol.* 156, 316-327 (2009)). In vitro and in vivo chemical stimulation of dura, trigeminal neurons, afferent nerves and sensory afferents causes PGE$_2$ release. PGE$_2$ induces augmentation of peptide release and sensitization of sensory neurons via EP$_4$ (Southall, M. D. & Vasko, M. R. *J. Biol. Chem.* 276, 16083-91 (2001)). These data suggest that EP$_4$ antagonists may have therapeutic utility in the treatment of migraine.

Multiple sclerosis (MS). PGE$_2$ levels are dearly detectable in MS cerebrospinal fluid (CSF) but not CSF from people without neurological disease. Functional PGE$_2$ antagonists are predicted to provide clinical benefit in MS via inhibition of IL-23 production and suppression of Th1 and Th17 cell development (Cua, D. J. et al. *Nature* 421, 744-8 (2003)).

Osteoarthritis (OA). PGE$_2$ is upregulated in synovial fluid and cartilage from OA patients and PGE$_2$ stimulates matrix degradation on OA chondrocytes via EP$_4$ (Attur, M. et al. *J. Immunol.* 181, 5082-8 (2008)).

Osteoporosis. PGE$_2$ plays a key role in driving bone resorption, primarily through EP$_4$. Bone loss is often seen when tumours metastasise to bone; preclinical data from a breast metastasis model shows that EP$_4$ antagonism reduces loss of bone mineral density (Takita, M., Inada, M., Maruyama, T. & Miyaura, C. *FEBS Lett.* 581, 565-571 (2007)).

Overactive bladder. Cyclophosphamide injection induces an overactive bladder in rats. EP$_4$ antagonist given concurrently, systemically or directly into bladder tissue, has been shown to reduce bladder inflammation and frequency of bladder contraction (overactivity) (Chuang, Y.-C., Tyagi, P., Huang, C.-C., Chancellor, M. B. & Yoshimura, N. *BJU Int.* 110, 1558-1564 (2012)).

Rheumatoid arthritis. PGE$_2$ can act as both an immunosuppressant and an immunostimulant and perhaps should be considered a context-dependent immunomodulator. EP$_4$-deficient, versus WT or EP$_{1-3}$-deficient, mice have been shown to develop reduced arthritis symptom in a CAIA model clearly implicating EP$_4$ (McCoy, J. M., Wicks, J. R. & Audoly, L. P. *J. Clin. Invest.* 110, 651-658 (2002)).

Data suggest that functional antagonism of $PGE_2$ has the potential to ameliorate the clinically-relevant Th17 axis in rheumatoid arthritis and hence provide strong clinical benefit.

The invention described herein relates to novel compounds and their use as $EP_4$ antagonists. Compounds described herein may be useful in the treatment or prevention of diseases in which $EP_4$ receptors are involved. The invention is also directed to pharmaceutical compositions comprising these compounds and the manufacture and use of these compounds and compositions in the prevention or treatment of such diseases in which $EP_4$ receptors are involved. Thus the compounds of the invention may be useful in the treatment of Abdominal aortic aneurysm (AAA), Ankylosing spondylitis (AS), Alzheimer's disease (AD), Atherosclerosis, Cancer including epithelial cancers (GBD neoplasm categories of colon and rectum, lip and oral cavity, nasopharynx, other pharynx, gallbladder and biliary tract, pancreatic, non-melanoma skin, ovarian, testicular, kidney, bladder, thyroid, mesothelioma, esophageal, stomach, liver, larynx, tracheal, bronchus and lung, breast, cervical, uterine, prostate), Diabetic nephropathy, Endometriosis, Inflammatory bowel disease, Migraine, Multiple sclerosis (MS), Osteoarthritis (OA) and Rheumatoid arthritis.

Compounds of the invention may be used as single therapeutics or in combinations with one or more other therapeutics of any type. For the treatment or prevention of cancer this may include radiotherapy and/or chemotherapy and/or immunotherapy and/or other oncology modulators.

THE INVENTION

The present invention provides compounds having activity as prostaglandin $E_2$ receptor 4 ($EP_4$) antagonists.

The invention provides a compound of Formula (1):

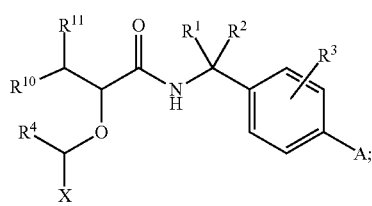
(1)

or a salt thereof, wherein;
A is selected from the group consisting of:

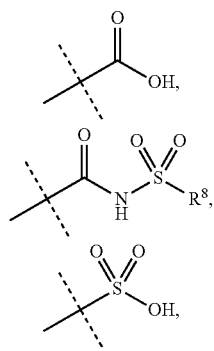

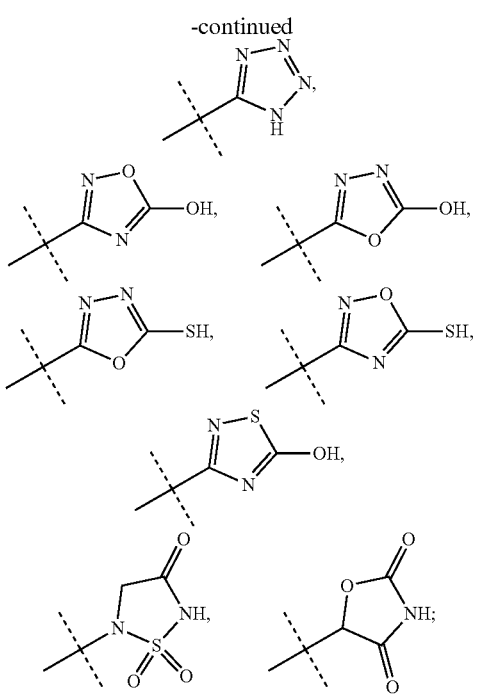

X is an optionally substituted phenyl ring, an optionally substituted pyridyl ring or an optionally substituted imidazopyridine ring system;

$R^1$ and $R^2$ are independently H or a $C_{1-3}$ alkyl group which is optionally substituted with one or more fluorine atoms; or $R^1$ and $R^2$ are joined to form a 3-6 membered carbocyclic ring which is optionally substituted with one or more fluorine atoms;

$R^3$ is H, $C_{1-3}$ alkyl or F;

$R^4$ is H or $C_{1-3}$ alkyl;

$R^8$ is $C_{1-3}$ alkyl or a $C_{3-6}$ cycloalkyl ring;

and either $R^{10}$ and $R^{11}$ are both methyl or $R^{10}$ and $R^{11}$ are joined to form a cyclobutyl ring.

The compounds may be used as $EP_4$ receptor antagonists. The compounds may be used in the manufacture of medicaments. The compounds or medicaments may be for use in treating, preventing, ameliorating, controlling or reducing the risk of diseases or disorders in which $EP_4$ receptors are involved. Thus the compounds of the invention may be useful in the treatment of Abdominal aortic aneurysm (AAA), Ankylosing spondylitis (AS), Alzheimer's disease (AD), Atherosclerosis, Cancer including epithelial cancers (GBD neoplasm categories of colon and rectum, lip and oral cavity, nasopharynx, other pharynx, gallbladder and biliary tract, pancreatic, non-melanoma skin, ovarian, testicular, kidney, bladder, thyroid, mesothelioma, esophageal, stomach, liver, larynx, tracheal, bronchus and lung, breast, cervical, uterine, prostate), Diabetic nephropathy, Endometriosis, Inflammatory bowel disease, Migraine, Multiple sclerosis (MS), Osteoarthritis (OA) and Rheumatoid arthritis.

DETAILED DESCRIPTION OF THE INVENTION

The invention relates to novel compounds. The invention also relates to the use of novel compounds as antagonists of the $EP_4$ receptor. The invention further relates to the use of novel compounds in the manufacture of medicaments for use as EP$_4$ receptor antagonists.

The invention further relates to compounds, compositions and medicaments for the treatment of Abdominal aortic aneurysm (AAA), Ankylosing spondylitis (AS), Alzheimer's disease (AD), Atherosclerosis, Cancer including epithelial cancers (GBD neoplasm categories of colon and rectum, lip and oral cavity, nasopharynx, other pharynx, gallbladder and biliary tract, pancreatic, non-melanoma skin, ovarian, testicular, kidney, bladder, thyroid, mesothelioma, esophageal, stomach, liver, larynx, tracheal, bronchus and lung, breast, cervical, uterine, prostate), Diabetic nephropathy, Endometriosis, Inflammatory bowel disease, Migraine, Multiple sclerosis (MS), Osteoarthritis (OA) and Rheumatoid arthritis.

The invention provides a compound of Formula (1):

or a salt thereof, wherein;
A is selected from the group consisting of:

X is an optionally substituted phenyl ring, an optionally substituted pyridyl ring or an optionally substituted imidazopyridine ring system;

R$^1$ and R$^2$ are independently H or a C$_{1-3}$ alkyl group which is optionally substituted with one or more fluorine atoms; or R$^1$ and R$^2$ are joined to form a 3-6 membered carbocyclic ring which is optionally substituted with one or more fluorine atoms;

R$^3$ is H, C$_{1-3}$ alkyl or F;

R$^4$ is H or C$_{1-3}$ alkyl;

R$^8$ is C$_{1-3}$ alkyl or a C$_{3-6}$ cycloalkyl ring;

and either R$^{10}$ and R$^{11}$ are both methyl or R$^{10}$ and R$^{11}$ are joined to form a cyclobutyl ring.

Also provided is a compound of Formula (1a):

or a salt thereof, wherein;
A is selected from the group consisting of:

-continued

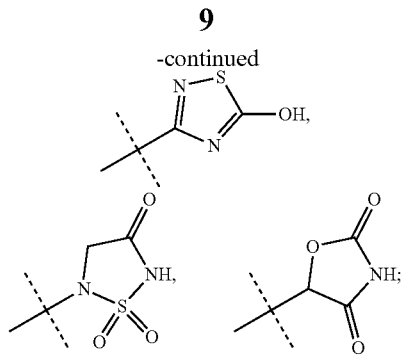

X is an optionally substituted phenyl ring, an optionally substituted pyridyl ring or an optionally substituted imidazopyridine ring system;

$R^1$ and $R^2$ are independently H or a $C_{1-3}$ alkyl group which is optionally substituted with one or more fluorine atoms; or $R^1$ and $R^2$ are joined to form a 3-6 membered carbocyclic ring which is optionally substituted with one or more fluorine atoms;

$R^3$ is H, $C_{1-3}$ alkyl or F;

$R^4$ is H or $C_{1-3}$ alkyl;

and $R^8$ is $C_{1-3}$ alkyl or a $C_{3-6}$ cycloalkyl ring.

Also provided is a compound of Formula (1b):

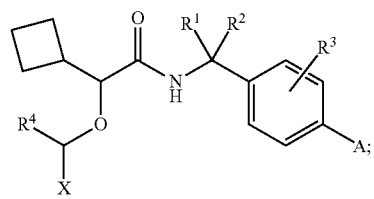

(1b)

or a salt thereof, wherein;

A is selected from the group consisting of:

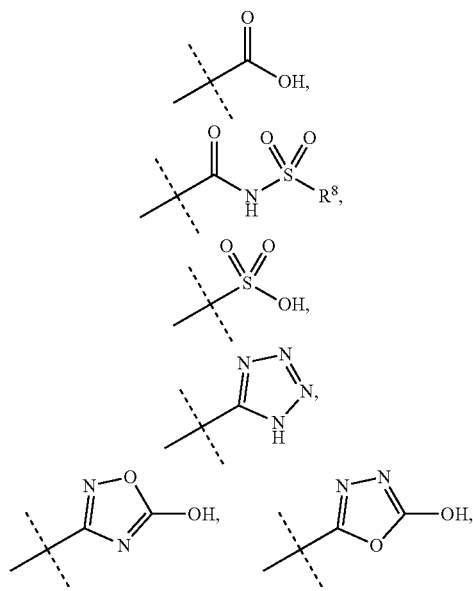

-continued

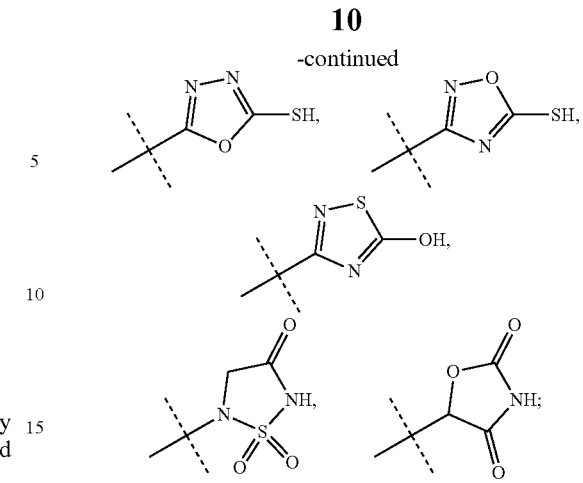

X is an optionally substituted phenyl ring, an optionally substituted pyridyl ring or an optionally substituted imidazopyridine ring system;

$R^1$ and $R^2$ are independently H or a $C_{1-3}$ alkyl group which is optionally substituted with one or more fluorine atoms; or $R^1$ and $R^2$ are joined to form a 3-6 membered carbocyclic ring which is optionally substituted with one or more fluorine atoms;

$R^3$ is H, $C_{1-3}$ alkyl or F;

$R^4$ is H or $C_{1-3}$ alkyl;

and $R^8$ is $C_{1-3}$ alkyl or a $C_{3-6}$ cycloalkyl ring.

The invention provides a compound of Formula (1c):

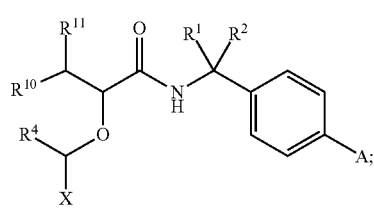

(1c)

or a salt thereof, wherein:

A is selected from the group consisting of:

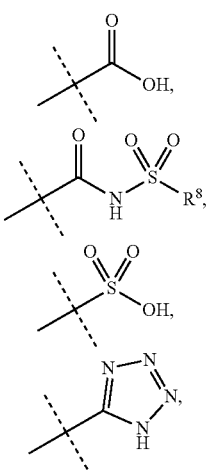

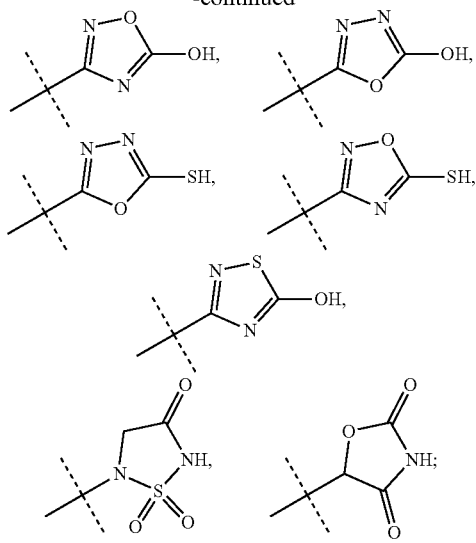

X is an optionally substituted phenyl ring, an optionally substituted pyridyl ring or an optionally substituted imidazopyridine ring system;

$R^1$ and $R^2$ are independently H or a $C_{1-3}$ alkyl group which is optionally substituted with one or more fluorine atoms; or $R^1$ and $R^2$ are joined to form a 3-6 membered carbocyclic ring which is optionally substituted with one or more fluorine atoms;

$R^4$ is H or $C_{1-3}$ alkyl;

$R^8$ is $C_{1-3}$ alkyl or a $C_{3-6}$ cycloalkyl ring;

and either $R^{10}$ and $R^{11}$ are both methyl or $R^{10}$ and $R^{11}$ are joined to form a cyclobutyl ring.

Particular compounds include compounds of Formula (2) and (2i):

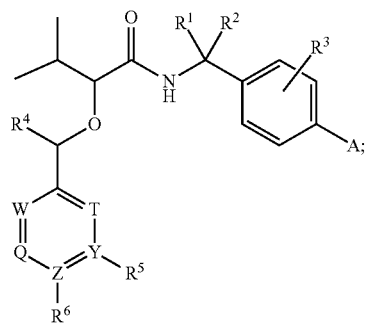

(2)

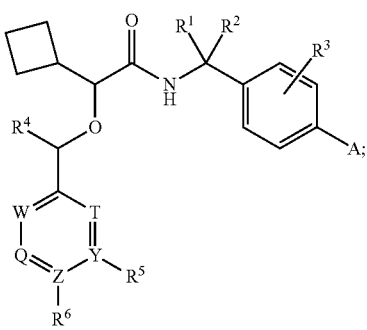

(2i)

or a salt thereof, wherein;

A, $R^1$, $R^2$, $R^3$ and $R^4$ are as defined above;

Q, W and T are CH or N;

Z and Y are C or N;

where either one or none of Q, W, T, Y and Z is N, $R^5$ is absent if Y is N and $R^6$ is absent if Z is N;

$R^5$ and $R^6$ are independently selected from H, halo, CN, OH, $SF_5$, $C_{1-6}$ alkyl, $C_{3-6}$ cycloalkyl, $C_{1-5}$ alkoxy, $OR^7$ and $SO_2R^7$, wherein the alkyl, cycloalkyl and alkoxy groups are optionally substituted with one or more fluorine atoms and any one atom of the alkyl or cycloalkyl group may be optionally replaced by a heteroatom selected from O, S and N; or $R^5$ and $R^6$ are joined to form a 5 or 6-membered carbocyclic or heterocyclic ring which is optionally substituted with one or more fluorine atoms; and $R^7$ is a $C_{1-6}$ alkyl group which is optionally substituted with one or more fluorine atoms or a $C_{3-6}$ cycloalkyl group which is optionally substituted with one or more fluorine atoms.

Particular compounds include compounds of Formula (2a) and (2b):

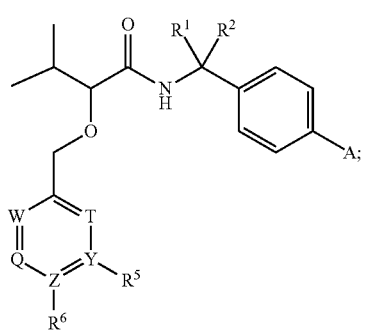

(2a)

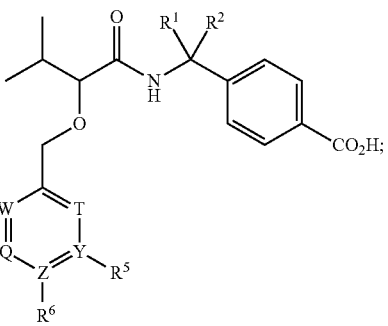

(2b)

and salts thereof, wherein A, T, Y, Z, Q, W, $R^1$, $R^2$, $R^5$ and $R^6$ are as defined above.

Particular compounds include compounds of Formula (2ia) and (2ib):
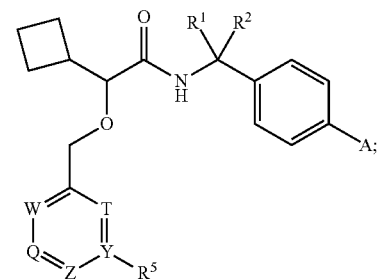
(2ia)
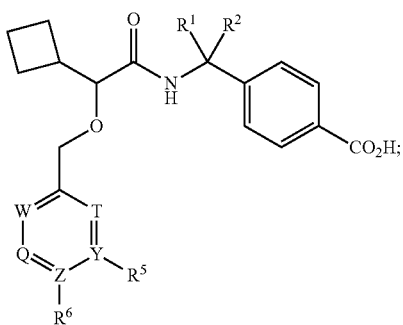
(2ib)
and salts thereof, wherein A, T, Y, Z, Q, W, R$^1$, R$^2$, R$^5$ and R$^6$ are as defined above.
Particular compounds include compounds of Formula (3), (3a), (3b), (3i), (3ia), (3ib):
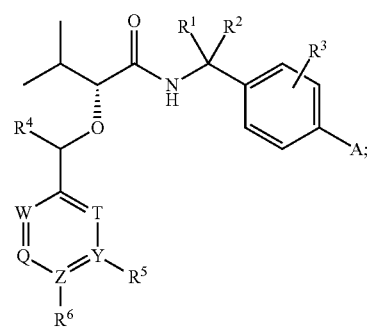
(3)
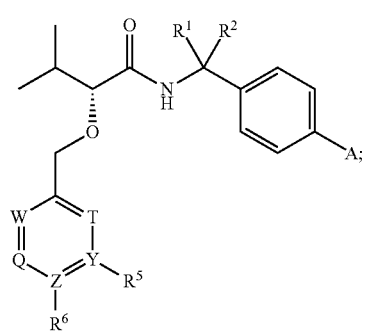
(3a)
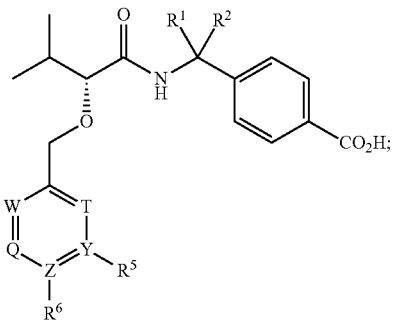
(3b)
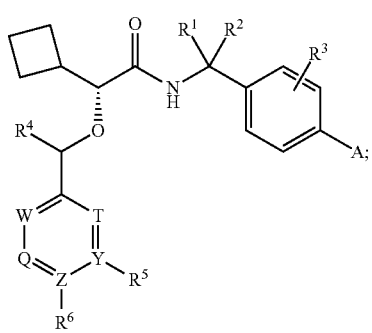
(3i)
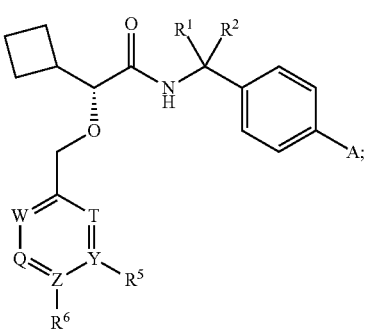
(3ia)
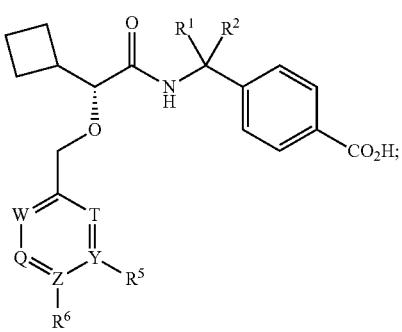
(3ib)
and salts thereof, wherein A, T, Y, Z, Q, W, R$^1$, R$^2$, R$^3$, R$^4$, R$^5$ and R$^6$ are as defined above.

Particular compounds include compounds of Formula (4), (4a), (4b), (4i), (4ia) and (4ib):
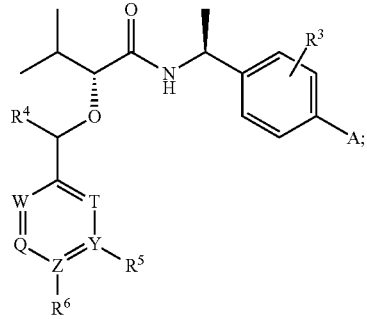
(4)
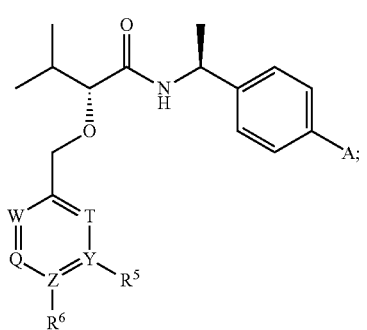
(4a)
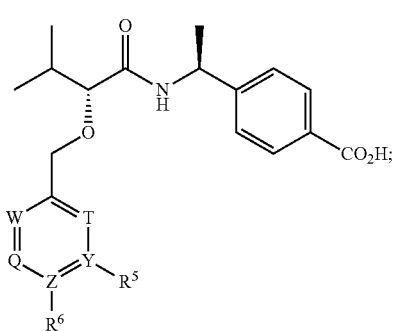
(4b)
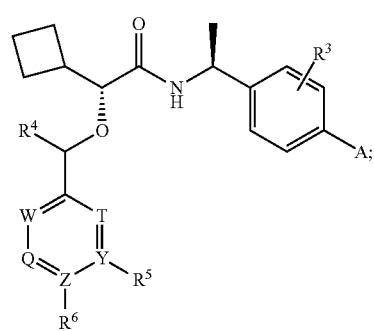
(4i)
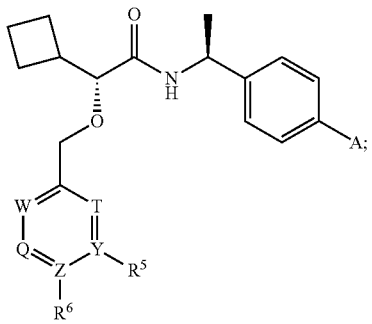
(4ia)
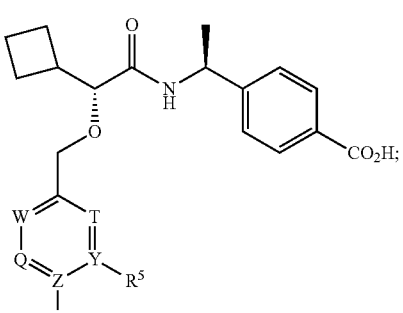
(4ib)
and salts thereof, wherein A, T, Y, Z, Q, W, $R^3$, $R^4$, $R^5$ and $R^6$ are as defined above.
Particular compounds include compounds of Formula (5), (5a), (5b), (5i), (5ia) and (5ib):
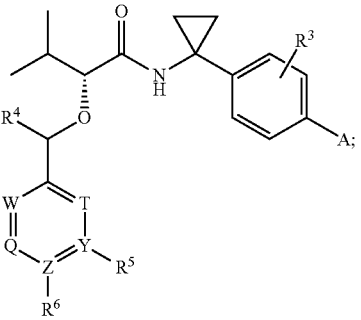
(5)
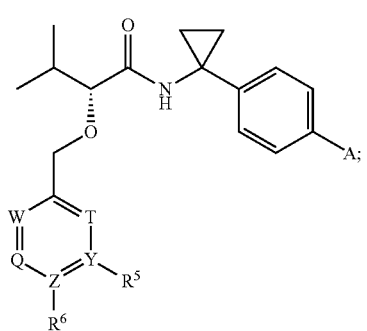
(5a)

-continued
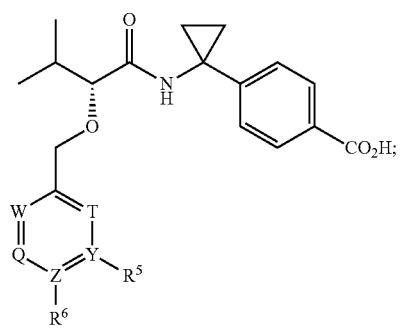
(5b)
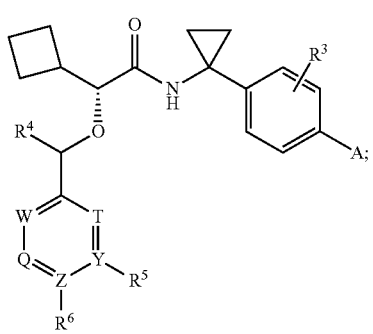
(5i)
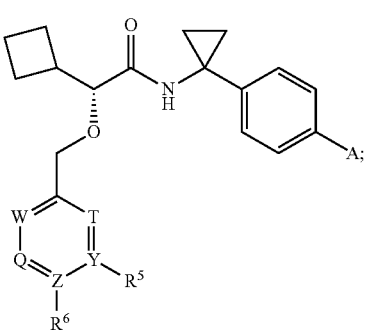
(5ia)
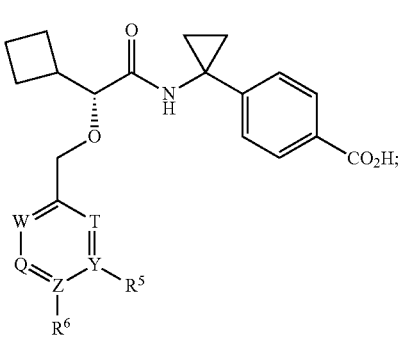
(5ib)
and salts thereof, wherein A, T, Y, Z, Q, W, $R^3$, $R^4$, $R^5$ and $R^6$ are as defined above.
Particular compounds include compounds of Formula (6), (6a), (6b), (6c), (6d), (6e), (6f), (6g), (6h), (6j), (6k) and (6l):
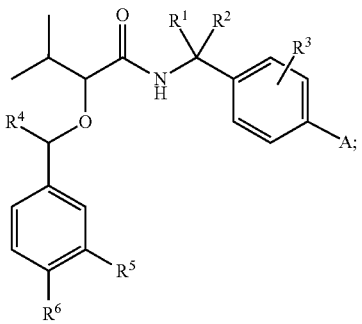
(6)
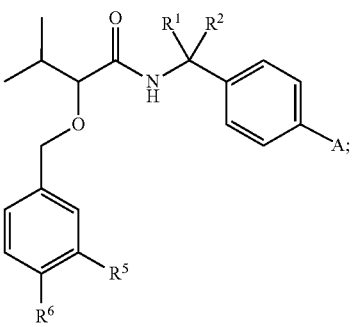
(6a)
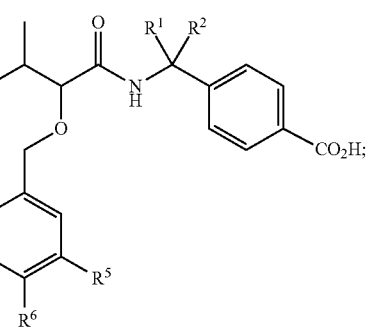
(6b)
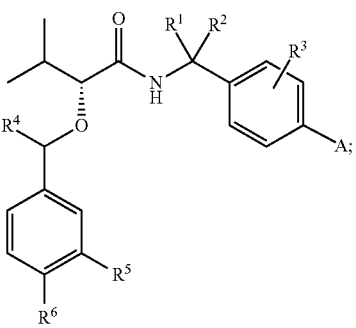
(6c)
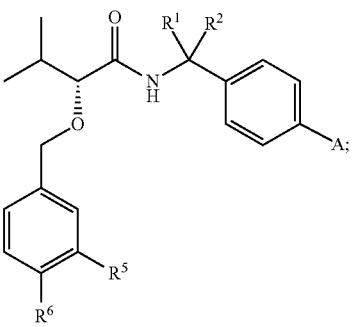
(6d)

(6e)
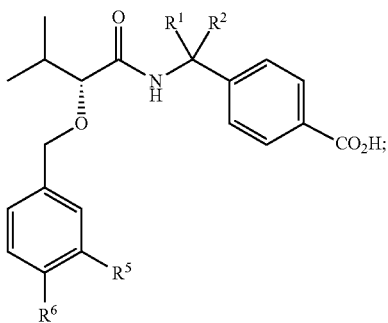
(6f)
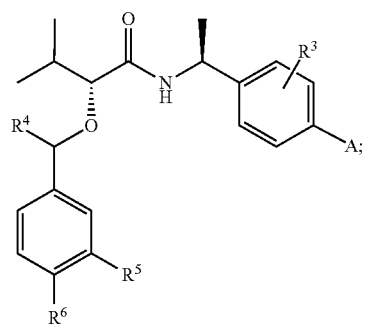
(6g)
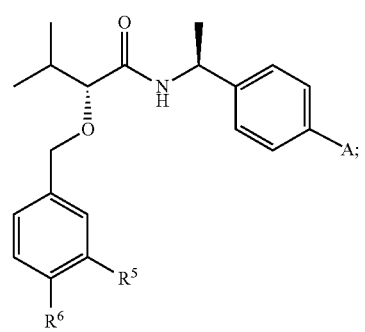
(6h)
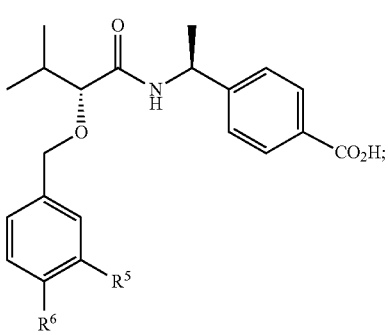
(6j)
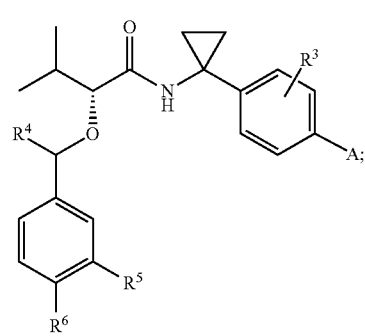
(6k)
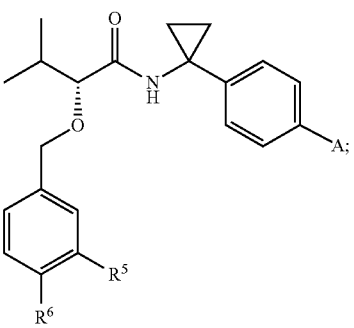
(6l)
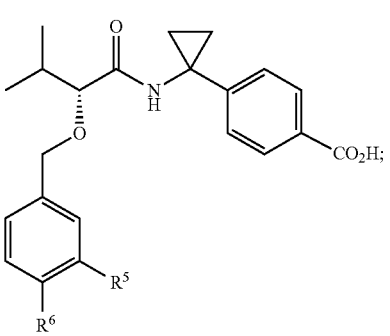
and salts thereof, wherein A, $R^1$, $R^2$, $R^3$, $R^4$, $R^5$ and $R^6$ are as defined above.
Particular compounds include compounds of Formula (6i), (6ia), (6ib), (6ic), (6id), (6ie), (6if), (6ig), (6ih), (6ij), (6ik) and (6il):
(6i)
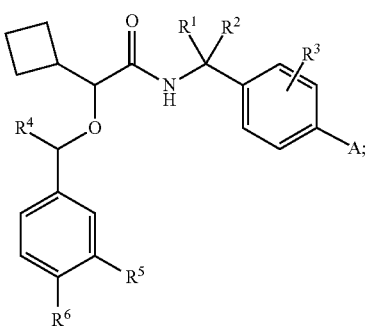
(6ia)
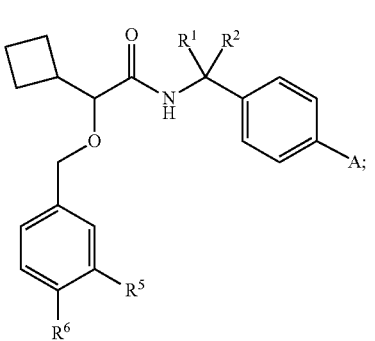

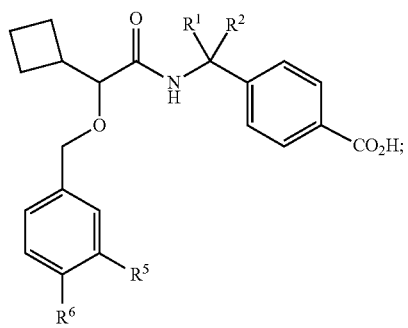 (6ib)
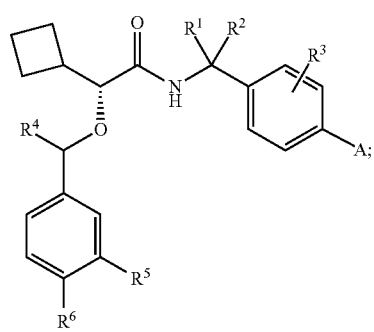 (6ic)
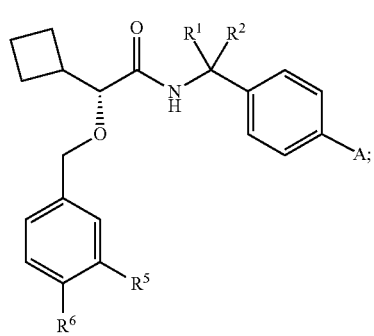 (6id)
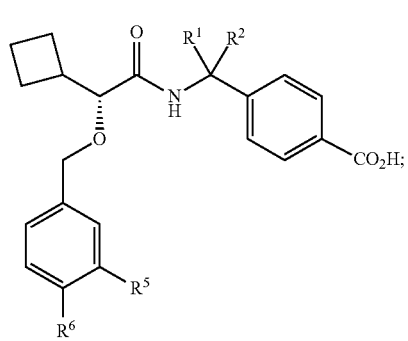 (6ie)
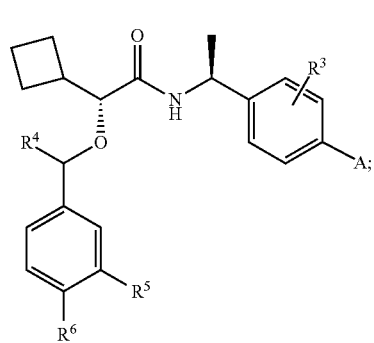 (6if)
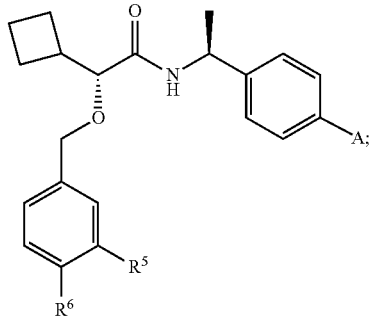 (6ig)
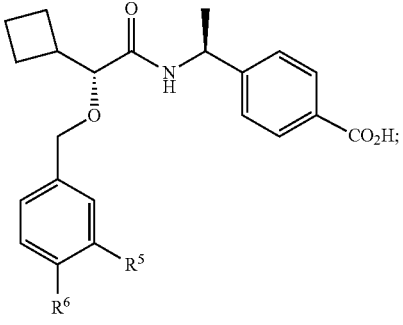 (6ih)
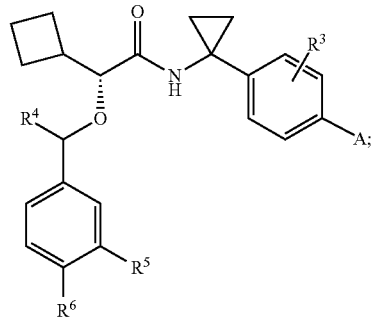 (6ij)
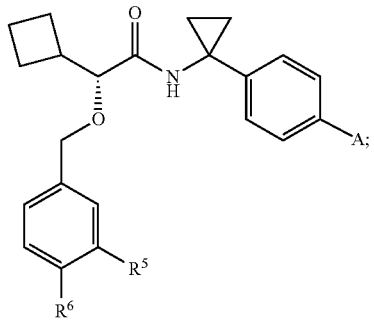 (6ik)
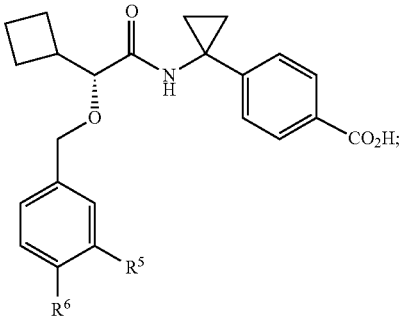 (6il)

and salts thereof, wherein A, $R^1$, $R^2$, $R^3$, $R^4$, $R^5$ and $R^6$ are as defined above.

The compound can be a compound of Formula (7):

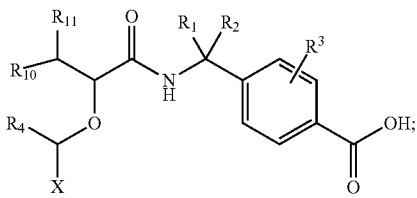

(7)

and salts thereof, wherein X, $R^1$, $R^2$, $R^3$, $R^4$, $R^{10}$ and $R^{11}$ are as defined above.

In the compounds herein, A can be selected from:

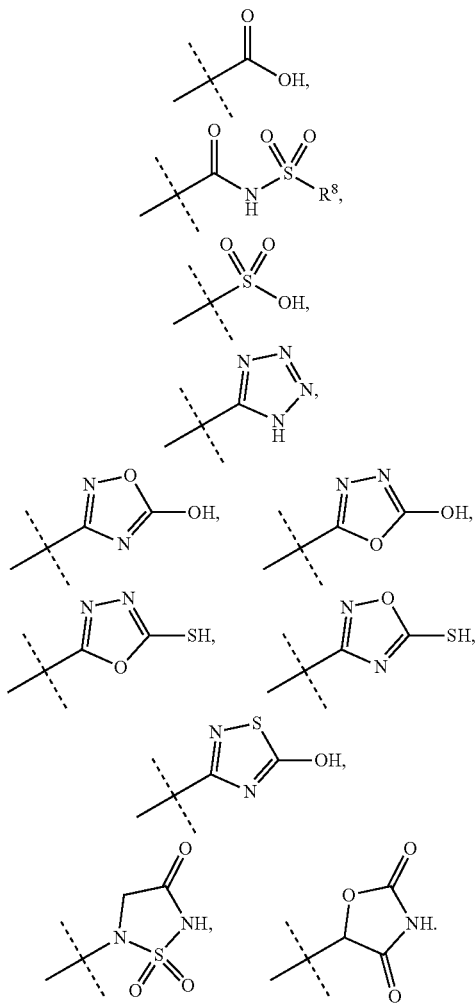

In the compounds herein, A can be selected from the group consisting of: $CO_2H$, tetrazole, 1,2,4-oxadiazol-5(2H)-one, 1,3,4-oxadiazol-2(3H)-one, $CONHSO_2R^8$, $CONHSO_2Me$, $SO_3H$, 1,3,4-oxadiazole-2(3H)-thione, 1,2,4-oxadiazole-5(2H)-thione, 1,2,4-thiadiazol-5(2H)-one, 1,2,5-thiadiazolidin-3-one 1,1-dioxide and 2,4-oxazolidinedione.

In the compounds herein, A can be selected from $CO_2H$, $CONHSO_2Me$ and a tetrazole ring. A can be $CO_2H$. A can be $CONHSO_2Me$. A can be a tetrazole ring.

In the compounds herein, $R^1$ and $R^2$ can independently be H or a $C_{1-3}$ alkyl group which is optionally substituted with one or more fluorine atoms. $R^1$ and $R^2$ can be joined to form a 3-6 membered carbocyclic ring which is optionally substituted with one or more fluorine atoms.

In the compounds herein, $R^1$ can be H. $R^1$ can be a $C_{1-3}$ alkyl group which is optionally substituted with one or more fluorine atoms. $R^1$ can be joined to $R^2$ to form a 3-6 membered carbocyclic ring which is optionally substituted with one or more fluorine atoms. $R^1$ can be joined to $R^2$ to form a 3-6 membered carbocyclic ring. $R^1$ can be a $C_{1-3}$ alkyl group optionally substituted with 1-3 fluorine atoms. $R^1$ can be a $C_{1-3}$ alkyl group. $R^1$ can be methyl. $R^1$ can be joined to $R^2$ to form a cyclopropyl ring.

In the compounds herein, $R^2$ can be H. $R^2$ can be a $C_{1-3}$ alkyl group which is optionally substituted with one or more fluorine atoms. $R^2$ can be joined to $R^1$ to form a 3-6 membered carbocyclic ring which is optionally substituted with one or more fluorine atoms. $R^2$ can be joined to $R^1$ to form a 3-6 membered carbocyclic ring. $R^2$ can be a $C_{1-3}$ alkyl group optionally substituted with 1-3 fluorine atoms. $R^2$ can be a $C_{1-3}$ alkyl group. $R^2$ can be methyl. $R^2$ can be joined to $R^1$ to form a cyclopropyl ring.

In the compounds herein, $R^1$ can be methyl and $R^2$ can be H. $R^1$ and $R^2$ can both be methyl. $R^1$ and $R^2$ can both be H. $R^1$ and $R^2$ can be joined to form a cyclopropyl ring.

In the compounds herein $R^3$ can be H, $C_{1-3}$ alkyl or F. $R^3$ can be H, methyl or F. $R^3$ can be $C_{1-3}$ alkyl. $R^3$ can be methyl. $R^3$ can be H. $R^3$ can be F.

In the compounds herein $R^4$ can be H or $C_{1-3}$ alkyl. $R^4$ can be H or methyl. $R^4$ can be $C_{1-3}$ alkyl. $R^4$ can be methyl. $R^4$ can be H.

In the compounds herein X can be an optionally substituted phenyl ring. X can be an optionally substituted pyridyl ring. X can be an optionally substituted imidazopyridine ring system.

In the compounds herein, X can be any of the following ring systems, which may be optionally substituted:

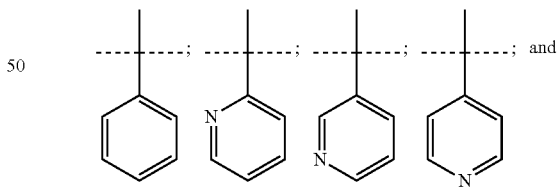

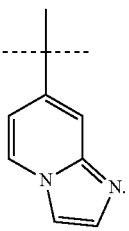

In the compounds herein, X can be:

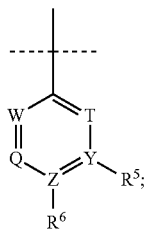

wherein T, Y, Z, Q, W, $R^5$ and $R^6$ are as defined above.

In the compounds herein, X can be selected from the group consisting of:

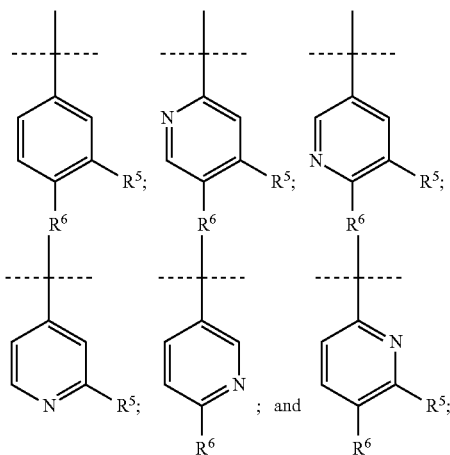

wherein $R^5$ and $R^6$ are as defined herein.

In the compounds herein, $R^5$ and $R^6$ can be independently selected from H, halo, CN, OH, $SF_5$, $C_{1-6}$ alkyl, $C_{3-6}$ cycloalkyl, $C_{1-6}$ alkoxy, $OR^7$ and $SO_2R^7$, wherein the alkyl, cycloalkyl and alkoxy groups are optionally substituted with one or more fluorine atoms and any one atom of the alkyl or cycloalkyl group may be optionally replaced by a heteroatom selected from O, S and N. $R^5$ and $R^6$ can be joined to form a 5 or 6-membered carbocyclic or heterocyclic ring which is optionally substituted with one or more fluorine atoms. $R^5$ and $R^6$ can be independently selected from H, Cl, F, CN, OH, $SO_2Me$, $SO_2Et$, $SO_2$-cyclopropyl, $SF_5$, $CF_3$, $CF_2H$, OMe $OCF_3$, $OCF_2H$, $CH_2OH$, $CH_2OMe$, cyclopropyl and oxetanyl.

In the compounds herein, $R^5$ can be selected from H, halo, CN, OH, $SF_5$, $OR^7$ and $SO_2R^7$. $R^5$ can be $C_{1-6}$ alkyl, $C_{1-6}$ alkoxy or $C_{3-6}$ cycloalkyl, wherein the alkyl, cycloalkyl and alkoxy groups are optionally substituted with one or more fluorine atoms and any one atom of the alkyl or cycloalkyl group may be optionally replaced by a heteroatom selected from O, S and N. $R^5$ can be $C_{1-6}$ alkyl, $C_{1-6}$ alkoxy or $C_{3-6}$ cycloalkyl, wherein the alkyl, cycloalkyl and alkoxy groups are optionally substituted with one or more fluorine atoms. $R^5$ can be $C_{1-6}$ alkyl, $C_{1-6}$ alkoxy or $C_{3-6}$ cycloalkyl. $R^5$ can be selected from H, C, F, CN, OH, $SO_2Me$, $SO_2Et$, $SO_2$-cyclopropyl, $SF_5$, $CF_3$, $CF_2H$, OMe $OCF_3$, $OCF_2H$, $CH_2OH$, $CH_2OMe$, cyclopropyl and oxetanyl. $R^5$ can be H. $R^5$ can be $CF_3$ or F. $R^5$ can be $CF_3$. $R^5$ can be F. $R^5$ can be joined to $R^6$ to form a 5 or 6-membered carbocyclic or heterocyclic ring which is optionally substituted with one or more fluorine atoms. $R^5$ can be joined to $R^6$ to form a fused dioxolane ring which is optionally substituted with one or two fluorine atoms. $R^5$ can be joined to $R^6$ to form a fused dioxolane ring. $R^5$ can be joined to $R^6$ to form a fused dioxolane ring substituted with one or two fluorine atoms. $R^5$ can be joined to $R^6$ to form a fused dioxolane ring substituted with two fluorine atoms. $R^5$ and $R^6$ can be joined to form a fused imidazole ring. $R^5$ and $R^6$ can be joined to form an imidazo[1,2-a]pyridine ring system together with the ring to which they are attached.

In the compounds herein, $R^6$ can be selected from H, halo, CN, OH, $SF_5$, $OR^7$ and $SO_2R^7$. $R^6$ can be $C_{1-6}$ alkyl, $C_{1-6}$ alkoxy or $C_{3-6}$ cycloalkyl, wherein the alkyl, cycloalkyl and alkoxy groups are optionally substituted with one or more fluorine atoms and any one atom of the alkyl or cycloalkyl group may be optionally replaced by a heteroatom selected from O, S and N. $R^6$ can be $C_{1-6}$ alkyl, $C_{1-6}$ alkoxy or $C_{3-6}$ cycloalkyl, wherein the alkyl, cycloalkyl and alkoxy groups are optionally substituted with one or more fluorine atoms. $R^6$ can be $C_{1-6}$ alkyl, $C_{1-6}$ alkoxy or $C_{3-6}$ cycloalkyl. $R^6$ can be selected from H, Cl, F, CN, OH, $SO_2Me$, $SO_2Et$, $SO_2$-cyclopropyl, $SF_5$, $CF_3$, $CF_2H$, OMe $OCF_3$, $OCF_2H$, $CH_2OH$, $CH_2OMe$, cyclopropyl and oxetanyl. $R^6$ can be H. $R^6$ can be $CF_3$ or F. $R^6$ can be $CF_3$. $R^6$ can be F. $R^6$ can be joined to $R^5$ to form a 5 or 6-membered carbocyclic or heterocyclic ring which is optionally substituted with one or more fluorine atoms. $R^6$ can be joined to $R^5$ to form a fused dioxolane ring which is optionally substituted with one or two fluorine atoms. $R^6$ can be joined to $R^5$ to form a fused dioxolane ring. $R^6$ can be joined to $R^5$ to form a fused dioxolane ring substituted with one or two fluorine atoms. $R^6$ can be joined to $R^5$ to form a fused dioxolane ring substituted with two fluorine atoms. $R^6$ and $R^5$ can be joined to form a fused imidazole ring. $R^6$ and $R^5$ can be joined to form an imidazo[1,2-a]pyridine ring system together with the ring to which they are attached.

In the compounds herein, Q, W and T can be CH or N. Z and Y can be C or N.

In the compounds herein, either one or none of Q, W, T, Y and Z is N. $R^5$ is absent if Y is N. $R^6$ is absent if Z is N.

In the compounds herein, Q, W and T can be CH and Z and Y can be C. Q, W and T can be CH, Z can be C and Y can be N. Q, W and T can be CH, Z can be N and Y can be C. Q and W can be CH, T can be N and Z and Y can be C. Q and T can be CH, W can be N and Z and Y can be C. T and W can be CH, Q can be N and Z and Y can be C.

In the compounds herein, $R^7$ can be a $C_{1-6}$ alkyl group which is optionally substituted with one or more fluorine atoms. $R^7$ can be a $C_{3-6}$ cycloalkyl group which is optionally substituted with one or more fluorine atoms. $R^7$ can be a $C_{1-6}$ alkyl group. $R^7$ can be a $C_{3-6}$ cycloalkyl group. $R^7$ can be methyl. $R^7$ can be ethyl. $R^7$ can be $CF_3$. $R^7$ can be $CF_2H$.

In the compounds herein $R^8$ can be $C_{1-3}$ alkyl. $R^8$ can be $C_{3-6}$ cycloalkyl. $R^8$ can be methyl.

In the compounds herein, $R^{10}$ and $R^{11}$ can both be methyl or $R^{10}$ and $R^{11}$ can be joined to form a cyclobutyl ring. $R^{10}$ can be methyl or joined to $R^{11}$ form a cyclobutyl ring. $R^{11}$ can be methyl or joined to $R^{10}$ form a cyclobutyl ring.

The compound can be selected from any one of Examples 1 to 101, shown in Table 1, or a salt thereof.

The compound can be selected from the group consisting of:

4-((S)-1-((R)-3-methyl-2-((4-(trifluoromethyl)benzyl)oxy) butanamido)ethyl)benzoic acid;

(R)-4-(1-(3-methyl-2-((4-(trifluoromethyl)benzyl)oxy)bu- tanamido)cyclopropyl)benzoic acid;

4-((1S)-1-(2-((3-methoxybenzyl)oxy)-3-methylbutana- mido)ethyl)benzoic acid;

4-((S)-1-((S)-2-((4-fluorobenzyl)oxy)-3-methylbutanamido)ethyl)benzoic acid;
4-((S)-1-((R)-2-((4-fluorobenzyl)oxy)-3-methylbutanamido)ethyl)benzoic acid;
4-(1S)-1-(2-((4-methoxybenzyl)oxy)-3-methylbutanamido)ethyl)benzoic acid;
4-((S)-1-((S)-3-methyl-2-((3-(methylsulfonyl)benzyl)oxy)butanamido)ethyl)benzoic acid;
4-((S)-1-((R)-3-methyl-2-((3-(methylsulfonyl)benzyl)oxy)butanamido)ethyl)benzoic acid;
4-((S)-1-((S)-3-methyl-2-((4-(methylsulfonyl)benzyl)oxy)butanamido)ethyl)benzoic acid;
4-((S)-1-((R)-3-methyl-2-((4-(methylsulfonyl)benzyl)oxy)butanamido)ethyl)benzoic acid;
4-((S)-1-((R)-2-((4-chlorobenzyl)oxy)-3-methylbutanamido)ethyl)benzoic acid;
4-((S)-1-((R)-2-((3-chlorobenzyl)oxy)-3-methylbutanamido)ethyl)benzoic acid;
4-((S)-1-((R)-2-((4-(difluoromethyl)benzyl)oxy)-3-methylbutanamido)ethyl)benzoic acid;
4-((S)-1-((R)-2-((3-(difluoromethyl)benzyl)oxy)-3-methylbutanamido)ethyl)benzoic acid;
4-((S)-1-((R)-3-methyl-2-((3-(trifluoromethyl)benzyl)oxy)butanamido)ethyl)benzoic acid;
4-((S)-1-((S)-3-methyl-2-((4-(trifluoromethyl)benzyl)oxy)butanamido)ethyl)benzoic acid;
4-((1S)-1-(2-((3-fluorobenzyl)oxy)-3-methylbutanamido)ethyl)benzoic acid;
4-((S)-1-((R)-2-(benzyloxy)-3-methylbutanamido)ethyl)benzoic acid;
4-((S)-1-((R)-3-methyl-2-((3-(trifluoromethoxy)benzyl)oxy)butanamido)ethyl)benzoic acid;
4-((S)-1-((R)-2-((4-cyanobenzyl)oxy)-3-methylbutanamido)ethyl)benzoic acid;
4-((S)-1-((R)-2-((3-cyanobenzyl)oxy)-3-methylbutanamido)ethyl)benzoic acid;
4-((S)-1-((R)-2-((4-(difluoromethoxy)benzyl)oxy)-3-methylbutanamido)ethyl)benzoic acid;
4-((S)-1-((R)-2-((3-(difluoromethoxy)benzyl)oxy)-3-methylbutanamido)ethyl)benzoic acid;
4-((S)-1-((R)-3-methyl-2-((5-(trifluoromethyl)pyridin-2-yl)methoxy)butanamido)ethyl)benzoic acid;
4-((S)-1-((R)-3-methyl-2-((4-(pentafluoro-$\lambda^6$-sulfaneyl)benzyl)oxy)butanamido)ethyl)benzoic acid;
4-((S)-1-((R)-2-((3,4-difluorobenzyl)oxy)-3-methylbutanamido)ethyl)benzoic acid;
4-((S)-1-((R)-2-((2,2-difluorobenzo[d][1,3]dioxol-5-yl)methoxy)-3-methylbutanamido)ethyl)benzoic acid;
4-((S)-1-((R)-2-((4-(difluoromethyl)-3-fluorobenzyl)oxy)-3-methylbutanamido)ethyl)benzoic acid;
4-((S)-1-((R)-2-((4-cyclopropylbenzyl)oxy)-3-methylbutanamido)ethyl)benzoic acid;
(R)-4-(1-(2-((4-fluorobenzyl)oxy)-3-methylbutanamido)cyclopropyl)benzoic acid;
4-((S)-1-((R)-2-((3-(difluoromethoxy)-4-fluorobenzyl)oxy)-3-methylbutanamido)ethyl)benzoic acid;
(R)-4-(1-(3-methyl-2-((3-(methylsulfonyl)benzyl)oxy)butanamido)cyclopropyl)benzoic acid;
4-((S)-1-((R)-2-((5-(difluoromethyl)pyridin-2-yl)methoxy)-3-methylbutanamido)ethyl)benzoic acid;
4-((S)-1-((R)-2-((4-fluoro-3-(methylsulfonyl)benzyl)oxy)-3-methylbutanamido)ethyl)benzoic acid;
2-methyl-4-((S)-1-((R)-3-methyl-2-((4-(trifluoromethyl)benzyl)oxy)butanamido)ethyl)benzoic acid;
(R)-4-(1-(2-((3,4-difluorobenzyl)oxy)-3-methylbutanamido)cyclopropyl)benzoic acid;
4-((S)-1-((R)-2-((3-hydroxybenzyl)oxy)-3-methylbutanamido)ethyl)benzoic acid;
4-((S)-1-((R)-2-((3-cyclopropylbenzyl)oxy)-3-methylbutanamido)ethyl)benzoic acid;
4-((S)-1-((R)-2-((3-(methoxymethyl)benzyl)oxy)-3-methylbutanamido)ethyl)benzoic acid;
4-((S)-1-((R)-2-((4-hydroxybenzyl)oxy)-3-methylbutanamido)ethyl)benzoic acid;
(R)—N—((S)-1-(4-(1H-tetrazol-5-yl)phenyl)ethyl)-2-((4-fluorobenzyl)oxy)-3-methylbutanamide;
(R)—N—((S)-1-(4-(1H-tetrazol-5-yl)phenyl)ethyl)-3-methyl-2-((4-(trifluoromethyl)benzyl)oxy)butanamide;
4-((S)-1-((R)-2-((3-(ethylsulfonyl)benzyl)oxy)-3-methylbutanamido)ethyl)benzoic acid;
4-((S)-1-((R)-2-((3-(hydroxymethyl)benzyl)oxy)-3-methylbutanamido)ethyl)benzoic acid;
4-((1S)-1-((2R)-2-(1-(4-fluorophenyl)ethoxy)-3-methylbutanamido)ethyl)benzoic acid;
4-((1S)-1-(3-methyl-2-((4-(oxetan-3-yl)benzyl)oxy)butanamido)ethyl)benzoic acid;
4-((1S)-1-(3-methyl-2-((3-(oxetan-3-yl)benzyl)oxy)butanamido)ethyl)benzoic acid;
(R)-4-(1-(2-((3-chlorobenzyl)oxy)-3-methylbutanamido)cyclopropyl)benzoic acid;
4-((1S)-1-((2R)-3-methyl-2-(1-(4-(trifluoromethyl)phenyl)ethoxy)butanamido)ethyl)benzoic acid;
(R)-4-(1-(2-((3-(difluoromethoxy)benzyl)oxy)-3-methylbutanamido)cyclopropyl)benzoic acid;
4-((S)-1-((R)-3-methyl-2-((4-(trifluoromethyl)benzyl)oxy)butanamido)ethyl)-N-(methylsulfonyl)benzamide;
(R)-4-(1-(2-((3-cyanobenzyl)oxy)-3-methylbutanamido)cyclopropyl)benzoic acid;
(R)-4-(1-(2-((2,2-difluorobenzo[d][1,3]dioxol-5-yl)methoxy)-3-methylbutanamido)cyclopropyl)benzoic acid;
(R)-4-(1-(2-((3-(ethylsulfonyl)benzyl)oxy)-3-methylbutanamido)cyclopropyl)benzoic acid;
(R)-4-(1-(2-((3-(difluoromethoxy)-4-fluorobenzyl)oxy)-3-methylbutanamido)cyclopropyl)benzoic acid;
(R)-4-(1-(3-methyl-2-((3-(trifluoromethoxy)benzyl)oxy)butanamido)cyclopropyl)benzoic acid;
(R)-4-((3-methyl-2-((4-(trifluoromethyl)benzyl)oxy)butanamido)methyl)benzoic acid;
(R)-4-(1-(2-((3-(methoxymethyl)benzyl)oxy)-3-methylbutanamido)cyclopropyl)benzoic acid;
(R)-4-(1-(2-((4-(difluoromethyl)-3-fluorobenzyl)oxy)-3-methylbutanamido)cyclopropyl)benzoic acid;
(R)-4-(1-(2-((4-(difluoromethyl)benzyl)oxy)-3-methylbutanamido)cyclopropyl)benzoic acid;
(R)-4-(1-(3-methyl-2-((4-(trifluoromethyl)benzyl)oxy)butanamido)cyclopropyl)-N-(methylsulfonyl)benzamide;
(R)-4-(2-(3-methyl-2-((4-(trifluoromethyl)benzyl)oxy)butanamido)propan-2-yl)benzoic acid;
(R)-4-(1-(2-((3-cyclopropylbenzyl)oxy)-3-methylbutanamido)cyclopropyl)benzoic acid;
4-((S)-1-((R)-2-(imidazo[1,2-a]pyridin-7-ylmethoxy)-3-methylbutanamido)ethyl)benzoic acid;
(R)-4-(1-(2-((2-(difluoromethoxy)pyridin-4-yl)methoxy)-3-methylbutanamido)cyclopropyl)benzoic acid;
(R)-4-(1-(2-((4-(difluoromethoxy)pyridin-2-yl)methoxy)-3-methylbutanamido)cyclopropyl)benzoic acid;
(R)—N-(1-(4-(1H-tetrazol-5-yl)phenyl)cyclopropyl)-3-methyl-2-((4-(trifluoromethyl)benzyl)oxy)butanamide;
(R)—N-(1-(4-(1H-tetrazol-5-yl)phenyl)cyclopropyl)-2-((4-fluorobenzyl)oxy)-3-methylbutanamide;
(R)—N-(1-(4-(1H-tetrazol-5-yl)phenyl)cyclopropyl)-2-((3,4-difluorobenzyl)oxy)-3-methylbutanamide;

(R)—N-(1-(4-(1H-tetrazol-5-yl)phenyl)cyclopropyl)-2-((3-(difluoromethoxy)benzyl)oxy)-3-methylbutanamide;
(R)-4-(1-(3-methyl-2-((4-(trifluoromethyl)benzyl)oxy)butanamido)cyclobutyl)benzoic acid;
4-((S)-1-((R)-2-((2-(difluoromethoxy)pyridin-4-yl)methoxy)-3-methylbutanamido)ethyl)benzoic acid;
(R)-4-(1-(3-methyl-2-((5-(trifluoromethyl)pyridin-2-yl)methoxy)butanamido)cyclopropyl)benzoic acid;
(R)-4-(1-(3-methyl-2-((6-(trifluoromethyl)pyridin-3-yl)methoxy)butanamido)cyclopropyl)benzoic acid;
4-((S)-1-((R)-2-((4-(difluoromethoxy)pyridin-2-yl)methoxy)-3-methylbutanamido)ethyl)benzoic acid;
(R)-4-(1-(2-((3-chloro-4-fluorobenzyl)oxy)-3-methylbutanamido)cyclopropyl)benzoic acid;
4-(1-((2R)-2-((4-chloro-5-fluorocyclohexa-1,3-dien-1-yl)methoxy)-3-methylbutanamido)cyclopropyl)benzoic acid;
(R)-2-((3-cyclopropylbenzyl)oxy)-N-(1-(4-(2,3-dihydro-1H-tetrazol-5-yl)phenyl)cyclopropyl)-3-methylbutanamide;
N-(cyclopropylsulfonyl)-4-((S)-1-((R)-2-((4-fluorobenzyl)oxy)-3-methylbutanamido)ethyl)benzamide;
(R)—N—((S)-1-(4-(1H-tetrazol-5-yl)phenyl)ethyl)-2-((3-(difluoromethoxy)benzyl)oxy)-3-methylbutanamide;
(R)—N—((S)-1-(4-(1H-tetrazol-5-yl)phenyl)ethyl)-2-((3-cyclopropylbenzyl)oxy)-3-methylbutanamide;
(R)-4-(1-(2-((6-(difluoromethyl)pyridin-3-yl)methoxy)-3-methylbutanamido)cyclopropyl)benzoic acid;
4-((S)-1-((R)-2-((3-cyclopropyl-4-fluorobenzyl)oxy)-3-methylbutanamido)ethyl)benzoic acid;
4-(1-(3-methyl-2-((3-(oxetan-3-yl)benzyl)oxy)butanamido)cyclopropyl)benzoic acid;
(R)-4-(1-(2-((5-(difluoromethyl)pyridin-2-yl)methoxy)-3-methylbutanamido)cyclopropyl)benzoic acid;
(R)-4-(1-(2-((3-cyclopropyl-4-fluorobenzyl)oxy)-3-methylbutanamido)cyclopropyl)benzoic acid;
4-((S)-1-((R)-2-((3-(cyclopropylsulfonyl)benzyl)oxy)-3-methylbutanamido)ethyl)benzoic acid;
(R)-4-(1-2-((3-(cyclopropylsulfonyl)benzyl)oxy)-3-methylbutanamido)cyclopropyl)benzoic acid;
4-((1S)-1-(2-cyclobutyl-2-((4-(trifluoromethyl)benzyl)oxy)acetamido)ethyl)benzoic acid;
4-(1-(2-cyclobutyl-2-((3-(methylsulfonyl)benzyl)oxy)acetamido)cyclopropyl)benzoic acid;
4-(1-(2-cyclobutyl-2-((4-(trifluoromethyl)benzyl)oxy)acetamido)cyclopropyl)benzoic acid;
4-(1-(2-cyclobutyl-2-((3,4-difluorobenzyl)oxy)acetamido)cyclopropyl)benzoic acid;
4-(1-(2-((3-chlorobenzyl)oxy)-2-cyclobutylacetamido)cyclopropyl)benzoic acid;
4-(1-(2-cyclobutyl-2-((3-(difluoromethoxy)benzyl)oxy)acetamido)cyclopropyl)benzoic acid;
(S)-4-(1-(2-cyclobutyl-2-((3-(difluoromethoxy)benzyl)oxy)acetamido)cyclopropyl)benzoic acid;
(R)-4-(1-(2-cyclobutyl-2-((3-(difluoromethoxy)benzyl)oxy)acetamido)cyclopropyl)benzoic acid;
or a salt thereof.

Certain novel compounds of the invention show particularly high activities as $EP_4$ receptor antagonists.

Further embodiments of the invention include the use of a compound of Formula (1) as an $EP_4$ receptor antagonist. Such use may be in the treatment of Abdominal aortic aneurysm (AAA), Ankylosing spondylitis (AS), Alzheimer's disease (AD), Atherosclerosis, Cancer including epithelial cancers (GBD neoplasm categories of colon and rectum, lip and oral cavity, nasopharynx, other pharynx, gallbladder and biliary tract, pancreatic, non-melanoma skin, ovarian, testicular, kidney, bladder, thyroid, mesothelioma, esophageal, stomach, liver, larynx, tracheal, bronchus and lung, breast, cervical, uterine, prostate), Diabetic nephropathy, Endometriosis, Inflammatory bowel disease, Migraine, Multiple sclerosis (MS), Osteoarthritis (OA) or Rheumatoid arthritis.

Definitions

In this application, the following definitions apply, unless indicated otherwise.

The term "treatment", in relation to the uses of any of the compounds described herein, including those of Formula (1) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The terms "alkyl", "alkoxy" "cycloalkyl", "phenyl", "pyridyl" "carbocyclic" and "heterocyclic" are all used in their conventional sense (e.g. as defined in the IUPAC Gold Book), unless indicated otherwise. "Optionally substituted" as applied to any group means that the said group may if desired be substituted with one or more substituents, which may be the same or different.

In the definitions of $R^5$ and $R^6$ above, where stated, one or two but not all, carbon atoms of the alkyl or cycloalkyl groups may optionally be replaced by a heteroatom selected from O and N. Where the group is a single carbon (C) group, the carbon cannot be replaced. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—CH=$CH_2$ with C=O to give an aldehyde —$CH_2$—C(O)H, replacement of a carbon atom in a group —$CH_2$—$CH_2$—$CH_3$ with 0 to give an alcohol —$CH_2$—$CH_2$—$CH_2$OH, replacement of a carbon atom in a group —$CH_2$—$CH_2$—$CH_3$ with 0 to give an ether —$CH_2$—O—$CH_3$, replacement of a carbon atom in a group —$CH_2$—$CH_2$—$CH_3$ with S to give an thiol —CH$_2$—CH$_2$—CH$_2$SH, replacement of a carbon atom in a group —CH$_2$—CH$_2$—CH$_2$— with S=O or SO$_2$ to give a sulfoxide —CH$_2$—S(O)—CH$_2$— or sulfone —CH$_2$—S(O)$_2$—CH$_2$—, replacement of a carbon atom in a —CH$_2$—CH$_2$—CH$_2$— chain with C(O)NH to give an amide —CH$_2$—CH$_2$—C(O)—NH—, replacement of a carbon atom in a —CH$_2$—CH$_2$—CH$_2$— chain with nitrogen to give an amine —CH$_2$—NH—CH$_2$—, and replacement of a carbon atom in a —CH$_2$—CH$_2$—CH$_2$— chain with C(O)O to give an ester (or carboxylic acid) —CH$_2$—CH$_2$—C(O)—O—. In each such replacement, at least one carbon atom of the alkyl or cycloalkyl group must remain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of Formula (1) as defined above together with at least one pharmaceutically acceptable excipient.

The composition may be a tablet composition. The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA. The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the following examples.

Examples 1 to 101

The compounds of Examples 1 to 101 shown in Table 1 below have been prepared. In some instances compounds were obtained as a mixture of stereoisomers, Examples 3, 6, 46, 47, 51, 92, 95, 96, 97, 98 and 99 relate to such mixtures as indicated in Table 1 and Table 2. In other instances compounds were obtained as single isomers with or without assignment of stereochemistry. Examples 17, 18, 48, 49, 86, 87, 93 and 94 relate to single isomers of unassigned stereochemistry as indicated in Table 1.

TABLE 1

Example compounds

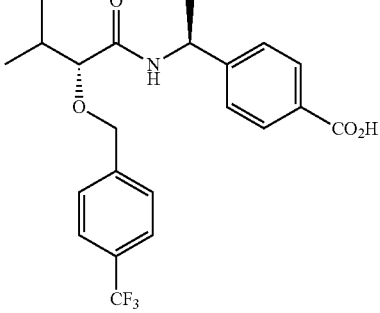

Example 1

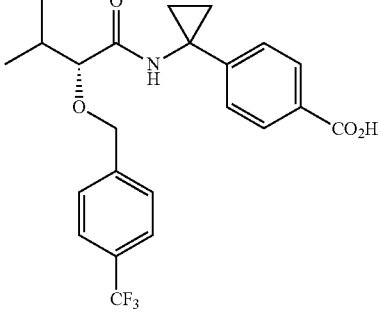

Example 2

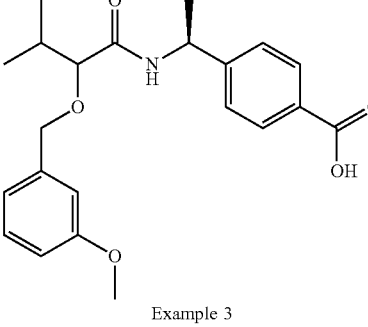

Example 3
(diastereomeric mixture)

TABLE 1-continued

Example compounds

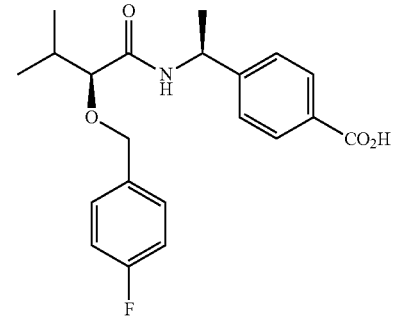 [SMILES: CC(C)[C@H](OCc1ccc(F)cc1)C(=O)N[C@@H](C)c1ccc(C(=O)O)cc1]

Example 4

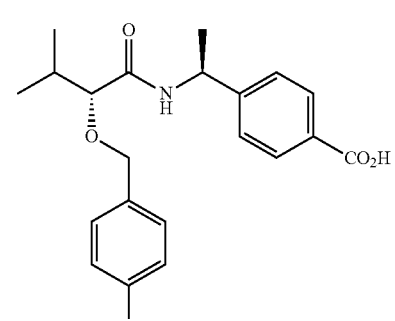

Example 5

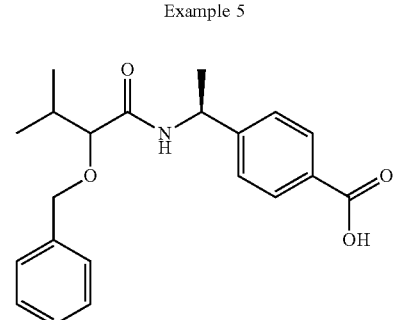

Example 6
(diastereomeric mixture)

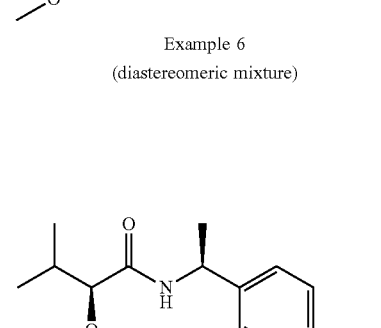

Example 7

TABLE 1-continued
Example compounds
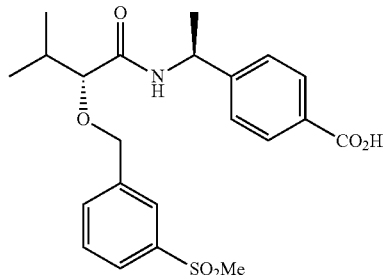
Example 8
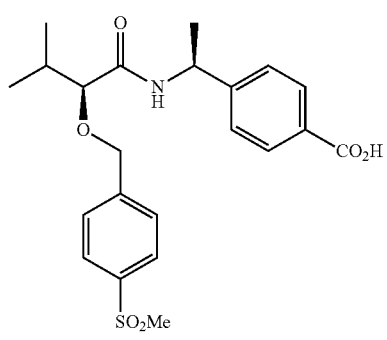 [SMILES: CC(C)[C@H](OCc1ccc(S(C)(=O)=O)cc1)C(=O)N[C@@H](C)c1ccc(C(=O)O)cc1]
Example 9
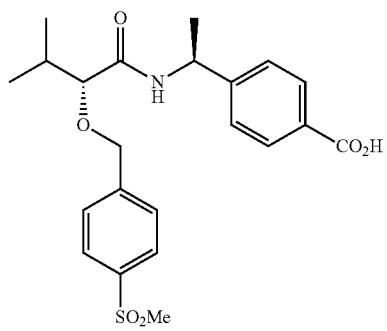
Example 10
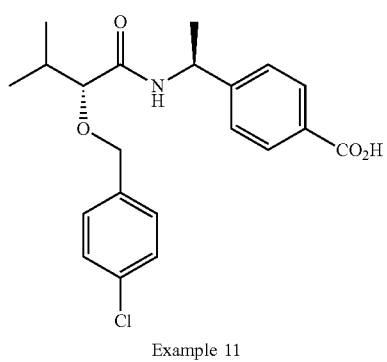
Example 11
TABLE 1-continued
Example compounds
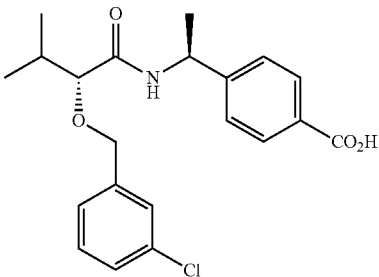
Example 12
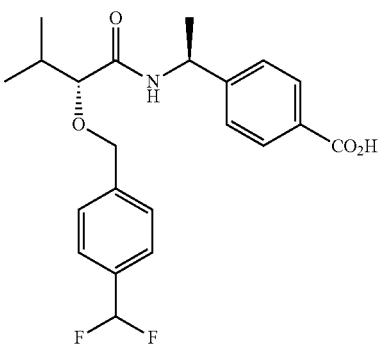 [SMILES: CC(C)[C@@H](OCc1ccc(C(F)F)cc1)C(=O)N[C@@H](C)c1ccc(C(=O)O)cc1]
Example 13
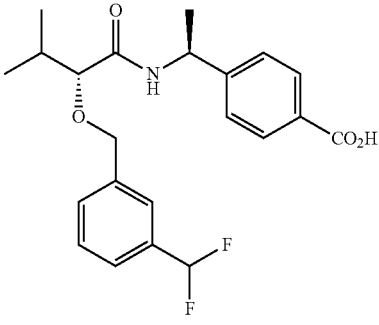 [SMILES: CC(C)[C@@H](OCc1cccc(C(F)F)c1)C(=O)N[C@@H](C)c1ccc(C(=O)O)cc1]
Example 14
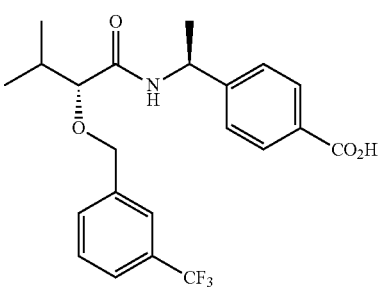 [SMILES: CC(C)[C@@H](OCc1cccc(C(F)(F)F)c1)C(=O)N[C@@H](C)c1ccc(C(=O)O)cc1]
Example 15

TABLE 1-continued
Example compounds
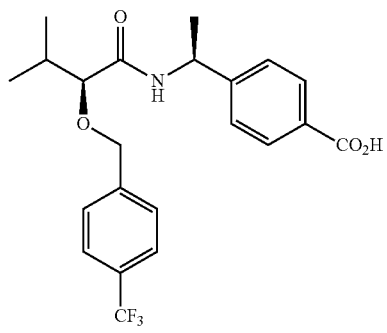 [SMILES: CC(C)[C@H](OCc1ccc(C(F)(F)F)cc1)C(=O)N[C@@H](C)c1ccc(C(=O)O)cc1]
Example 16
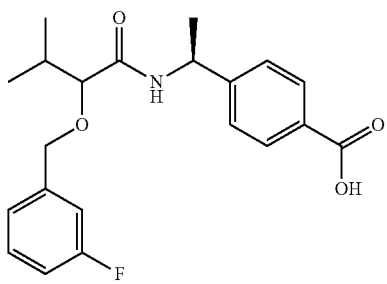 [SMILES: CC(C)C(OCc1cccc(F)c1)C(=O)N[C@@H](C)c1ccc(C(=O)O)cc1]
Example 17
(diastereomer 1)
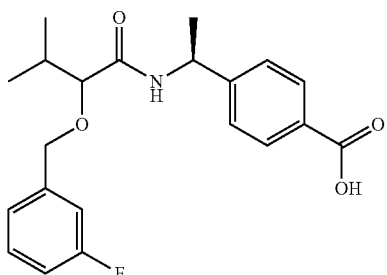
Example 18
(diastereomer 2)
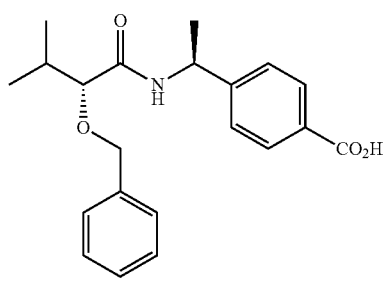 [SMILES: CC(C)[C@@H](OCc1ccccc1)C(=O)N[C@@H](C)c1ccc(C(=O)O)cc1]
Example 19
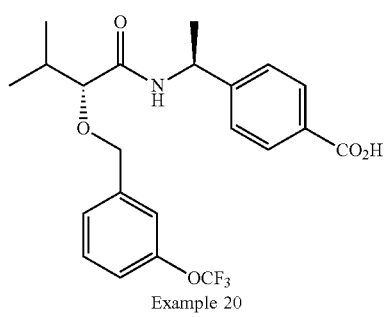
Example 20
TABLE 1-continued
Example compounds
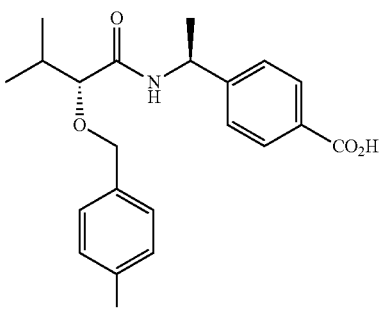
Example 21
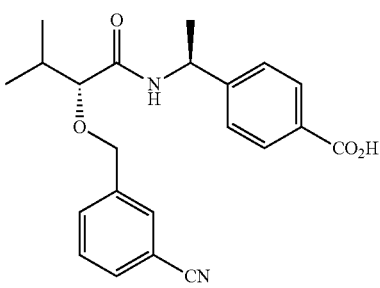
Example 22
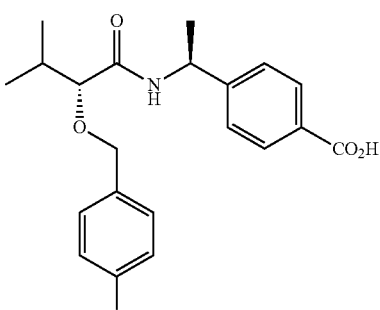
Example 23
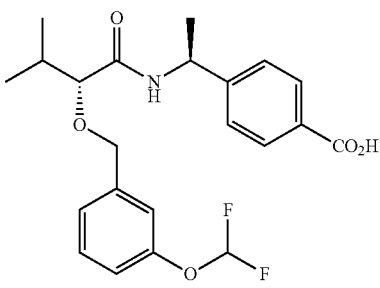 [SMILES: CC(C)[C@@H](OCc1cccc(OC(F)F)c1)C(=O)N[C@@H](C)c1ccc(C(=O)O)cc1]
Example 24

TABLE 1-continued
Example compounds
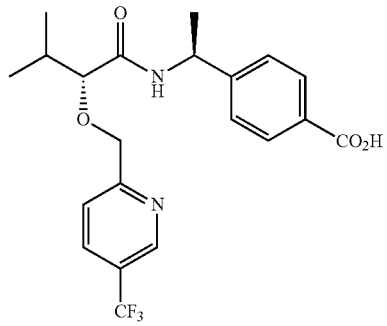 [SMILES: CC(C)[C@@H](OCc1ccc(C(F)(F)F)cn1)C(=O)N[C@@H](C)c1ccc(C(=O)O)cc1]
Example 25
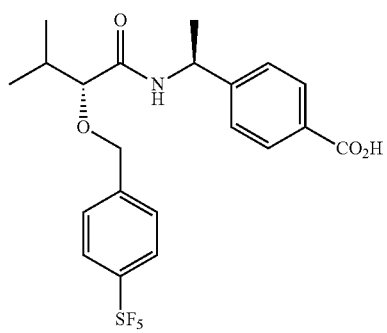
Example 26
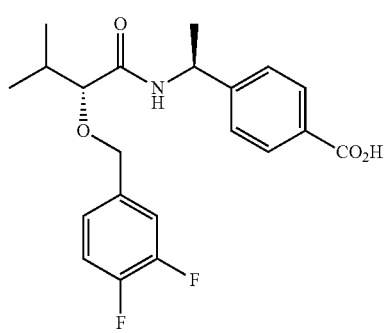 [SMILES: CC(C)[C@@H](OCc1ccc(F)c(F)c1)C(=O)N[C@@H](C)c1ccc(C(=O)O)cc1]
Example 27
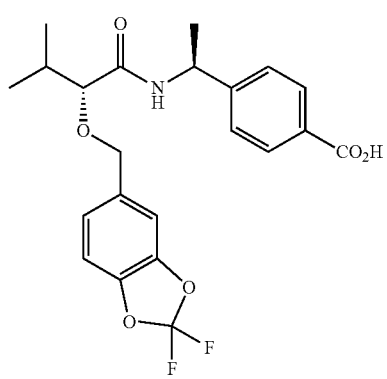 [SMILES: CC(C)[C@@H](OCc1ccc2c(c1)OC(F)(F)O2)C(=O)N[C@@H](C)c1ccc(C(=O)O)cc1]
Example 28
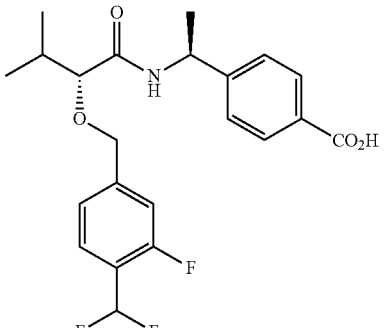
Example 29
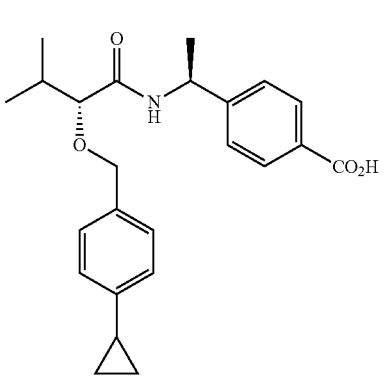 [SMILES: CC(C)[C@@H](OCc1ccc(C2CC2)cc1)C(=O)N[C@@H](C)c1ccc(C(=O)O)cc1]
Example 30
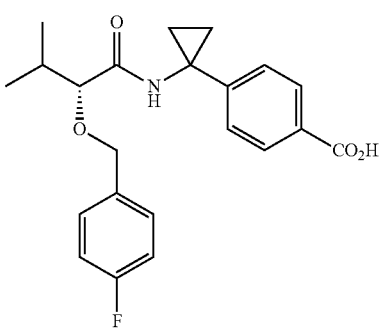 [SMILES: CC(C)[C@@H](OCc1ccc(F)cc1)C(=O)NC1(c2ccc(C(=O)O)cc2)CC1]
Example 31
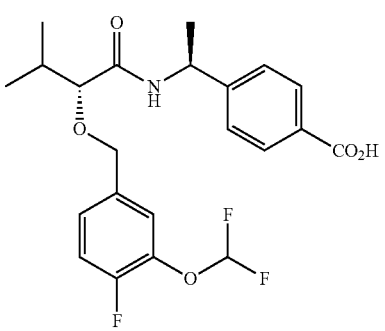 [SMILES: CC(C)[C@@H](OCc1ccc(F)c(OC(F)F)c1)C(=O)N[C@@H](C)c1ccc(C(=O)O)cc1]
Example 32

TABLE 1-continued
Example compounds
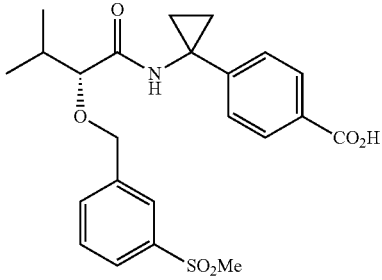 [SMILES: CC(C)[C@@H](OCc1cccc(S(C)(=O)=O)c1)C(=O)NC1(c2ccc(C(=O)O)cc2)CC1]
Example 33
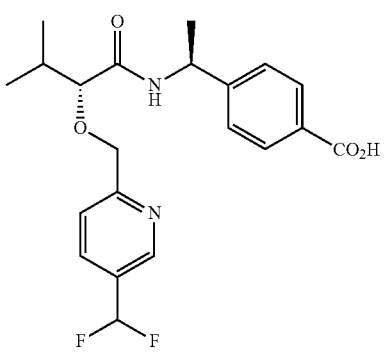 [SMILES: CC(C)[C@@H](OCc1ccc(C(F)F)cn1)C(=O)N[C@@H](C)c1ccc(C(=O)O)cc1]
Example 34
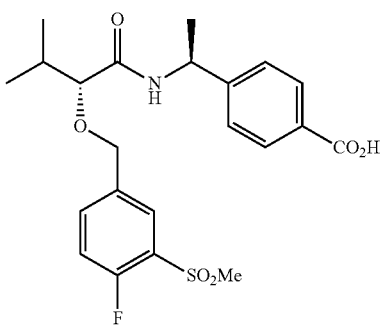 [SMILES: CC(C)[C@@H](OCc1ccc(F)c(S(C)(=O)=O)c1)C(=O)N[C@@H](C)c1ccc(C(=O)O)cc1]
Example 35
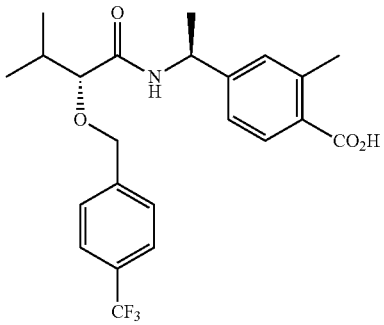 [SMILES: Cc1cc([C@H](C)NC(=O)[C@H](OCc2ccc(C(F)(F)F)cc2)C(C)C)ccc1C(=O)O]
Example 36
TABLE 1-continued
Example compounds
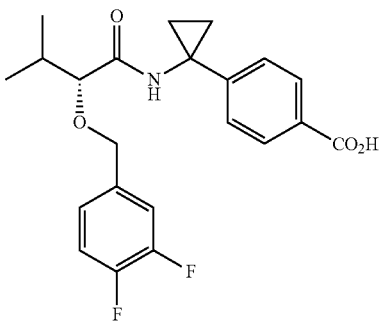 [SMILES: CC(C)[C@@H](OCc1ccc(F)c(F)c1)C(=O)NC1(c2ccc(C(=O)O)cc2)CC1]
Example 37
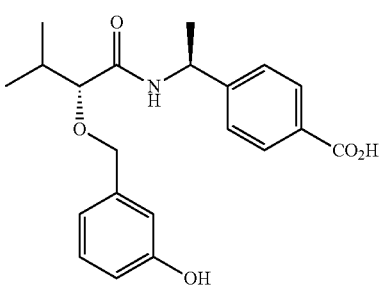
Example 38
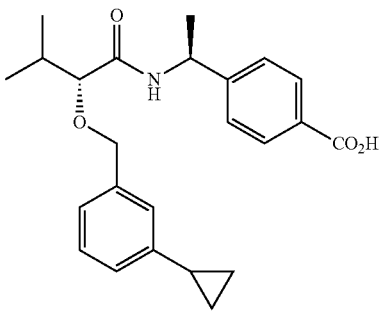 [SMILES: CC(C)[C@@H](OCc1cccc(C2CC2)c1)C(=O)N[C@@H](C)c1ccc(C(=O)O)cc1]
Example 39
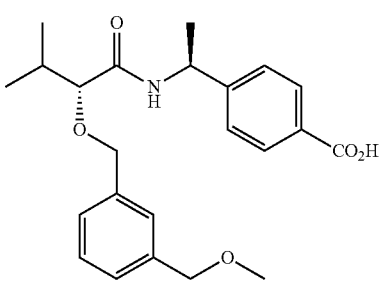 [SMILES: COCc1cccc(CO[C@@H](C(=O)N[C@@H](C)c2ccc(C(=O)O)cc2)C(C)C)c1]
Example 40

TABLE 1-continued
Example compounds
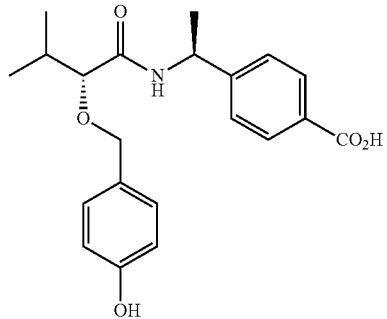
Example 41
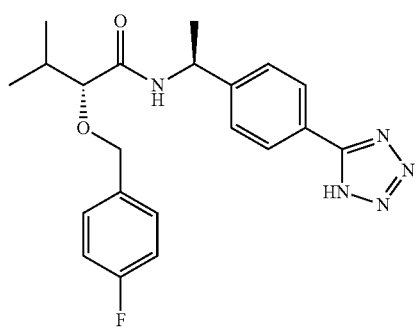 [SMILES: CC(C)[C@@H](OCc1ccc(F)cc1)C(=O)N[C@@H](C)c1ccc(-c2nnn[nH]2)cc1]
Example 42
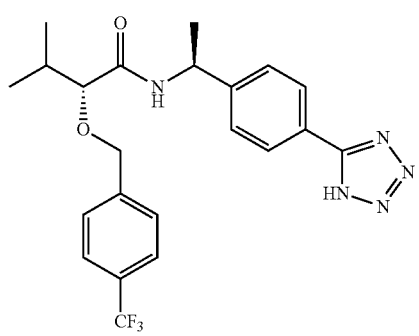 [SMILES: CC(C)[C@@H](OCc1ccc(C(F)(F)F)cc1)C(=O)N[C@@H](C)c1ccc(-c2nnn[nH]2)cc1]
Example 43
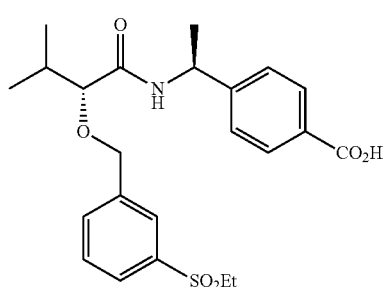
Example 44
TABLE 1-continued
Example compounds
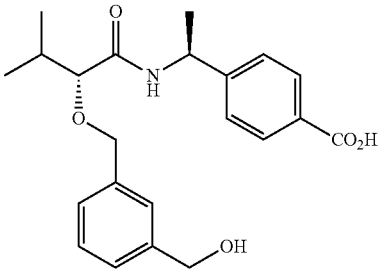 [SMILES: CC(C)[C@@H](OCc1cccc(CO)c1)C(=O)N[C@@H](C)c1ccc(C(=O)O)cc1]
Example 45
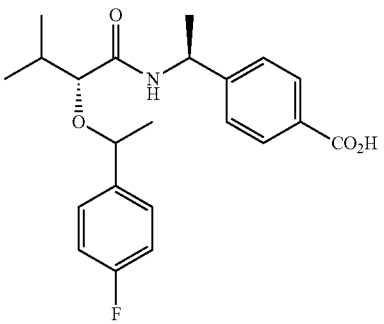 [SMILES: CC(O[C@@H](C(=O)N[C@@H](C)c1ccc(C(=O)O)cc1)C(C)C)c1ccc(F)cc1]
Example 46
(diastereomeric mixture)
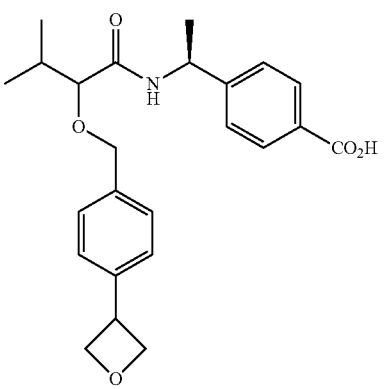 [SMILES: CC(C)C(OCc1ccc(C2COC2)cc1)C(=O)N[C@@H](C)c1ccc(C(=O)O)cc1]
Example 47
(diastereomeric mixture)
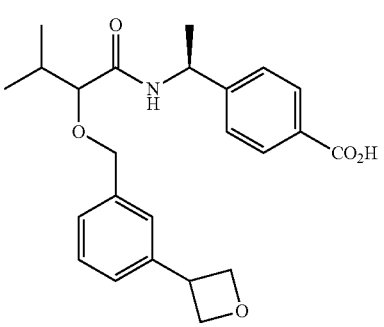 [SMILES: CC(C)C(OCc1cccc(C2COC2)c1)C(=O)N[C@@H](C)c1ccc(C(=O)O)cc1]
Example 48
(diastereomer 1)

TABLE 1-continued
Example compounds
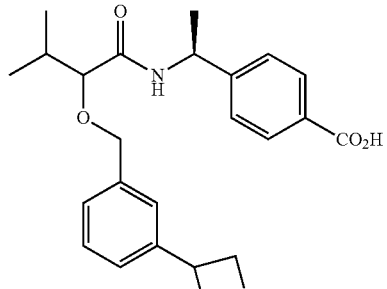
Example 49
(diastereomer 2)
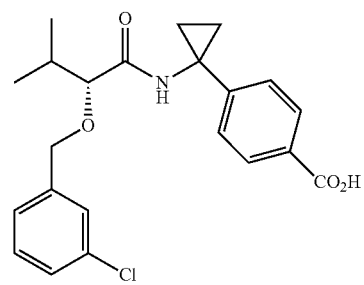 [SMILES: CC(C)[C@@H](OCc1cccc(Cl)c1)C(=O)NC1(c2ccc(C(=O)O)cc2)CC1]
Example 50
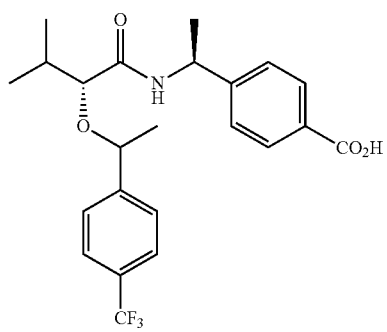 [SMILES: CC(O[C@@H](C(=O)N[C@@H](C)c1ccc(C(=O)O)cc1)C(C)C)c1ccc(C(F)(F)F)cc1]
Example 51
(diastereomeric mixture)
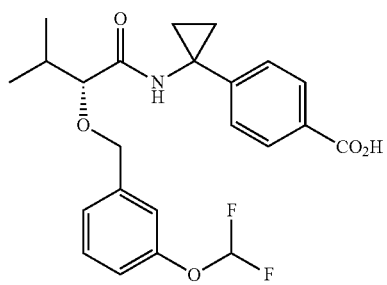 [SMILES: CC(C)[C@@H](OCc1cccc(OC(F)F)c1)C(=O)NC1(c2ccc(C(=O)O)cc2)CC1]
Example 52
TABLE 1-continued
Example compounds
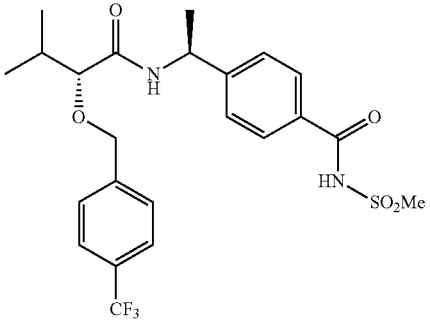 [SMILES: CC(C)[C@@H](OCc1ccc(C(F)(F)F)cc1)C(=O)N[C@@H](C)c1ccc(C(=O)NS(C)(=O)=O)cc1]
Example 53
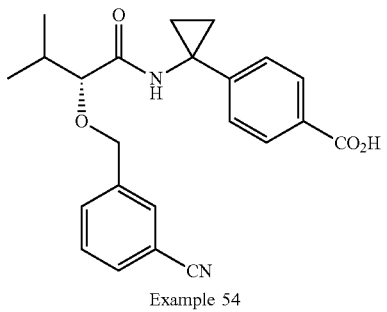
Example 54
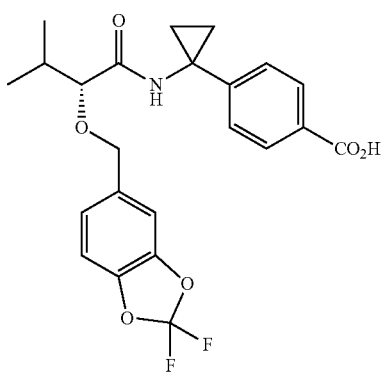 [SMILES: CC(C)[C@@H](OCc1ccc2c(c1)OC(F)(F)O2)C(=O)NC1(c2ccc(C(=O)O)cc2)CC1]
Example 55
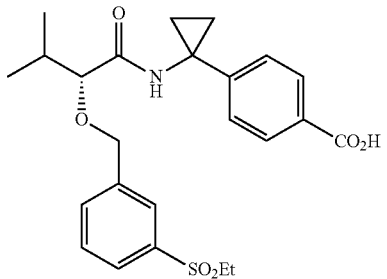
Example 56

TABLE 1-continued
Example compounds
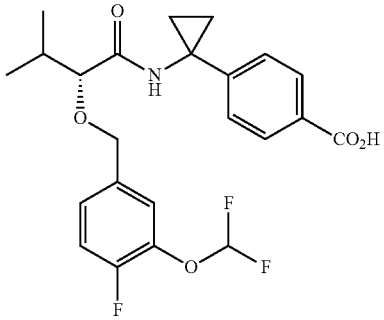 [SMILES: CC(C)[C@@H](OCc1ccc(F)c(OC(F)F)c1)C(=O)NC1(c2ccc(C(=O)O)cc2)CC1]
Example 57
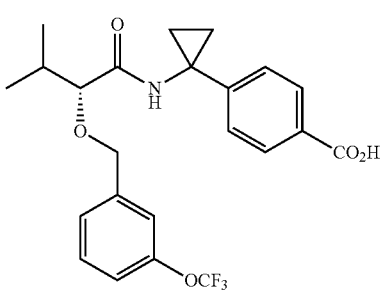 [SMILES: CC(C)[C@@H](OCc1cccc(OC(F)(F)F)c1)C(=O)NC1(c2ccc(C(=O)O)cc2)CC1]
Example 58
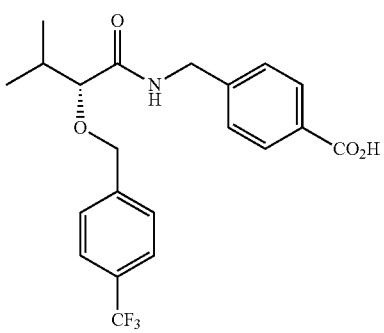 [SMILES: CC(C)[C@@H](OCc1ccc(C(F)(F)F)cc1)C(=O)NCc1ccc(C(=O)O)cc1]
Example 59
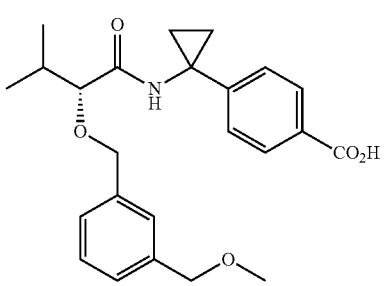 [SMILES: COCc1cccc(CO[C@@H](C(=O)NC2(c3ccc(C(=O)O)cc3)CC2)C(C)C)c1]
Example 60
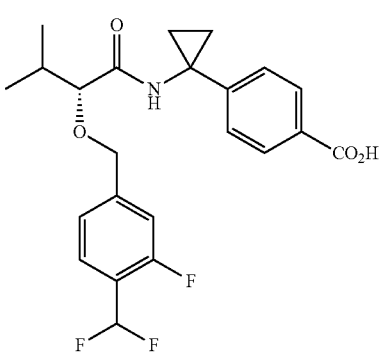 [SMILES: CC(C)[C@@H](OCc1ccc(C(F)F)c(F)c1)C(=O)NC1(c2ccc(C(=O)O)cc2)CC1]
Example 61
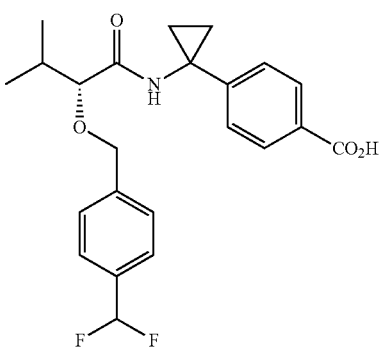 [SMILES: CC(C)[C@@H](OCc1ccc(C(F)F)cc1)C(=O)NC1(c2ccc(C(=O)O)cc2)CC1]
Example 62
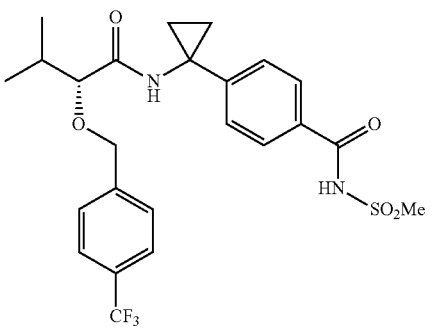 [SMILES: CC(C)[C@@H](OCc1ccc(C(F)(F)F)cc1)C(=O)NC1(c2ccc(C(=O)NS(C)(=O)=O)cc2)CC1]
Example 63
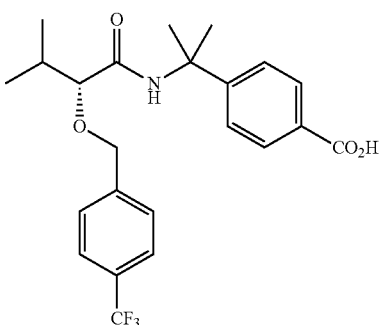
Example 64

TABLE 1-continued
Example compounds
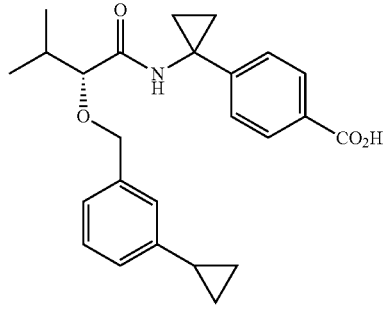 [SMILES: CC(C)[C@@H](OCc1cccc(C2CC2)c1)C(=O)NC1(c2ccc(C(=O)O)cc2)CC1]
Example 65
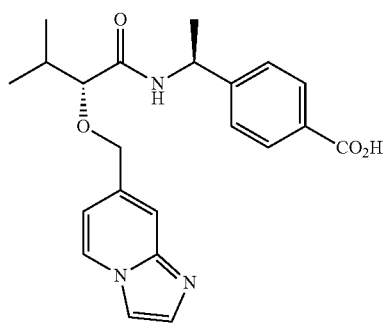 [SMILES: CC(C)[C@@H](OCc1ccn2ccnc2c1)C(=O)N[C@@H](C)c1ccc(C(=O)O)cc1]
Example 66
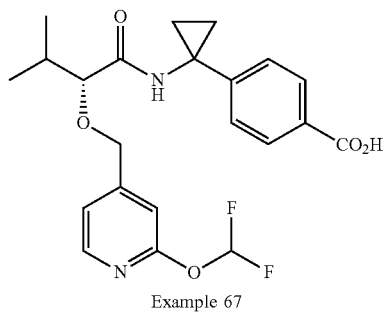
Example 67
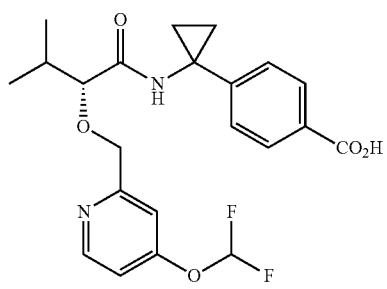 [SMILES: CC(C)[C@@H](OCc1cc(OC(F)F)ccn1)C(=O)NC1(c2ccc(C(=O)O)cc2)CC1]
Example 68
TABLE 1-continued
Example compounds
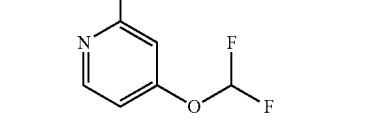
Example 69
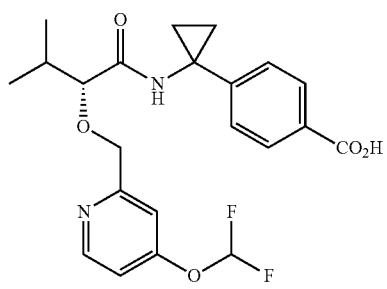 [SMILES: CC(C)[C@@H](OCc1cc(OC(F)F)ccn1)C(=O)NC1(c2ccc(C(=O)O)cc2)CC1]
Example 70
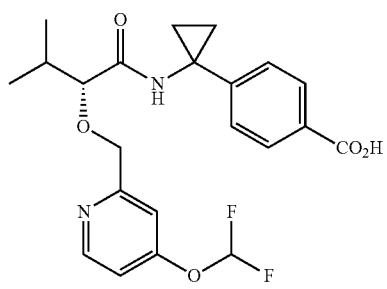 [SMILES: CC(C)[C@@H](OCc1cc(OC(F)F)ccn1)C(=O)NC1(c2ccc(C(=O)O)cc2)CC1]
Example 71
Example 72

TABLE 1-continued
Example compounds
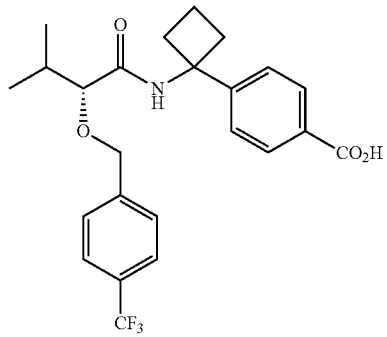
Example 73
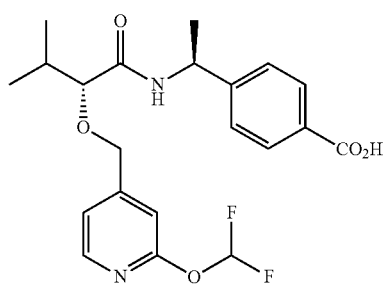
Example 74
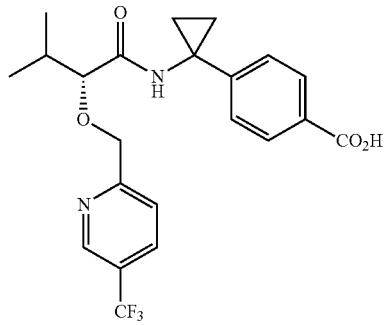
Example 75
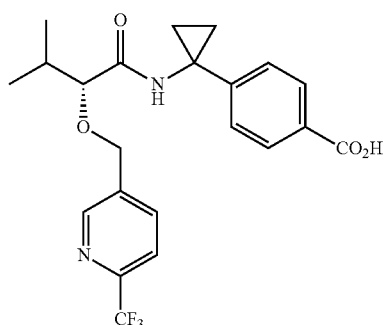
Example 76
TABLE 1-continued
Example compounds
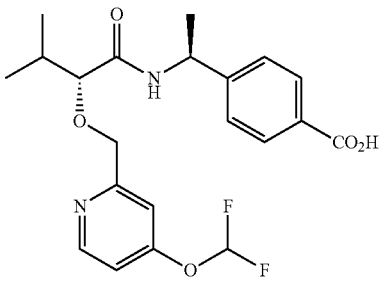
Example 77
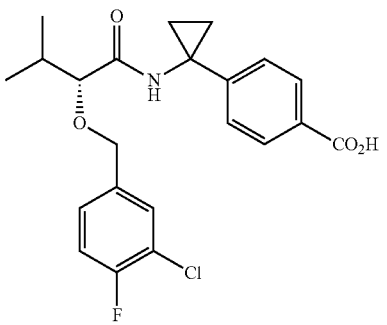
Example 78
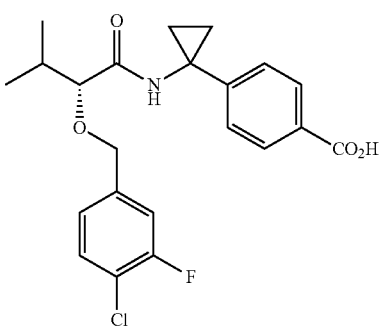
Example 79
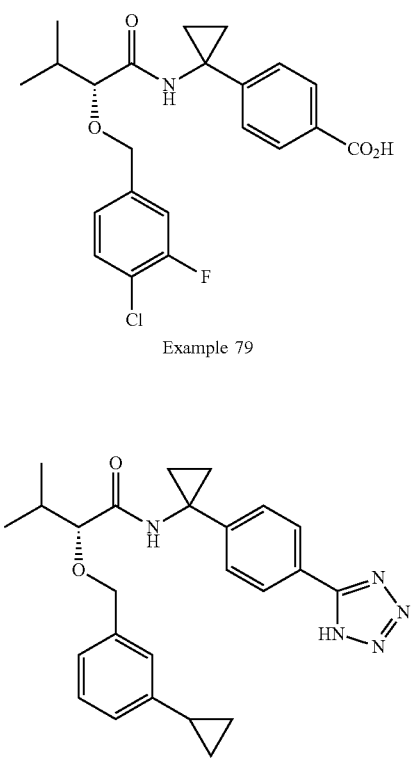
Example 80

TABLE 1-continued
Example compounds
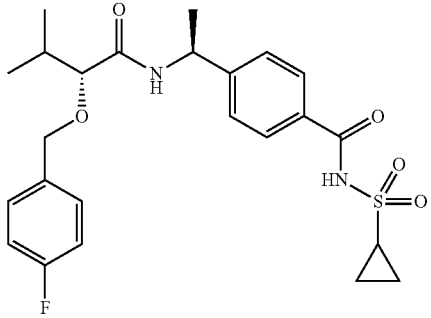
Example 81
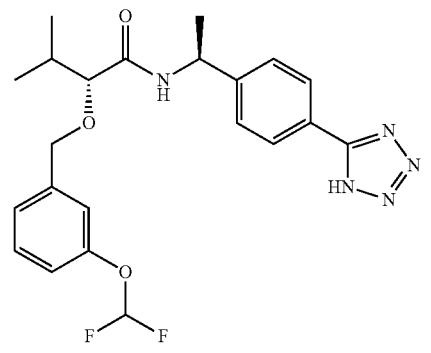
Example 82
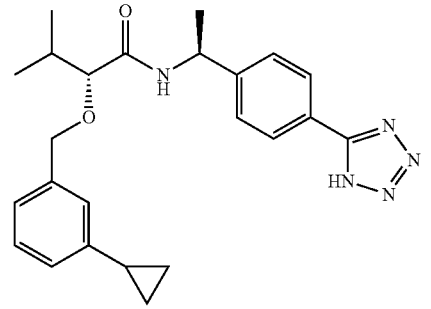
Example 83
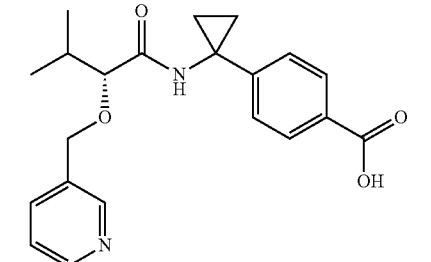
Example 84
TABLE 1-continued
Example compounds
Example 85
Example 86
(enantiomer 1)
Example 87
(enantiomer 2)
Example 88

TABLE 1-continued
Example compounds
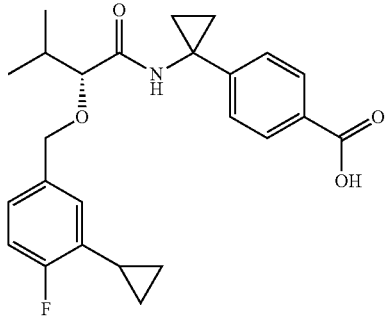
Example 89
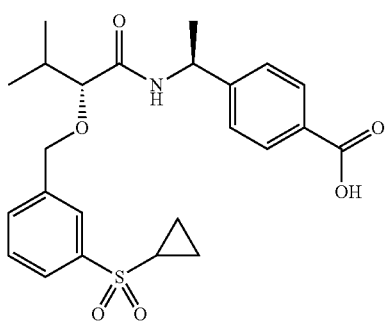
Example 90
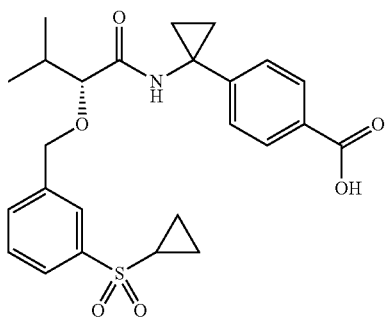
Example 91
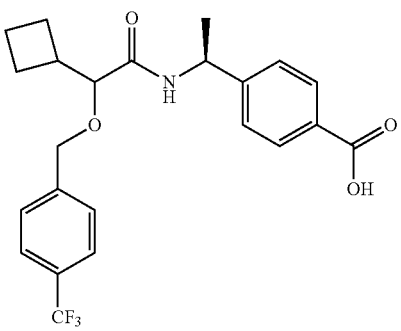
Example 92
(diastereomeric mixture)
TABLE 1-continued
Example compounds
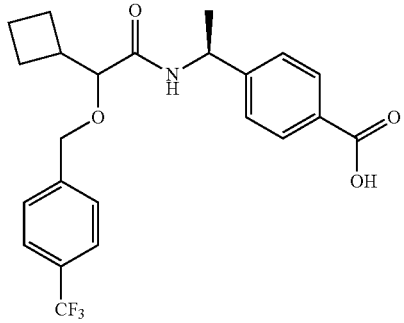
Example 93
(diastereomer 1)
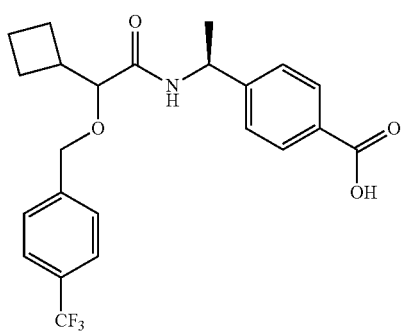
Example 94
(diastereomer 2)
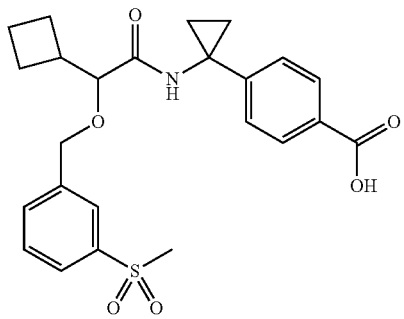
Example 95
(enantiomeric mixture)
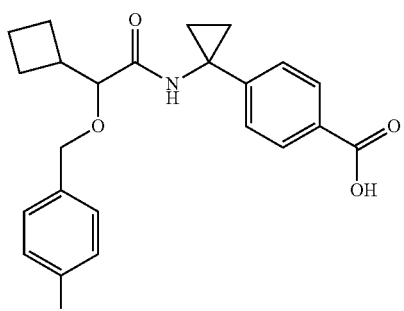
Example 96
(enantiomeric mixture)

TABLE 1-continued

Example compounds

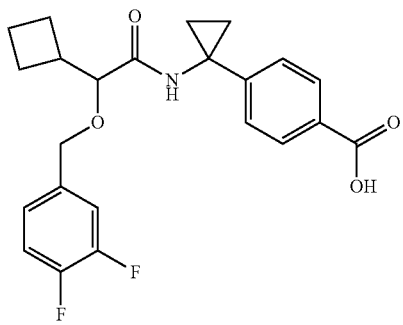

Example 97
(enantiomeric mixture)

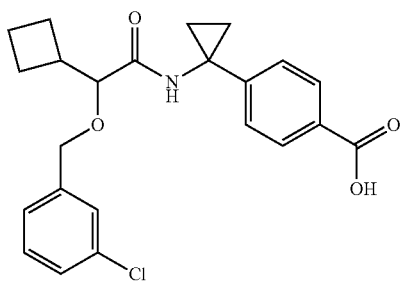

Example 98
(enantiomeric mixture)

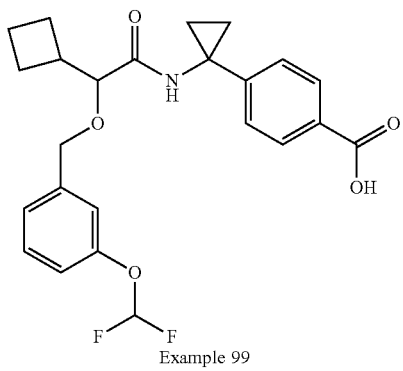

Example 99
(enantiomeric mixture)

TABLE 1-continued

Example compounds

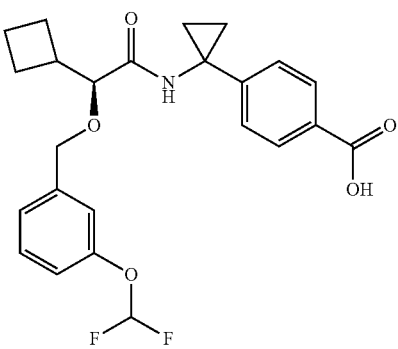

Example 100

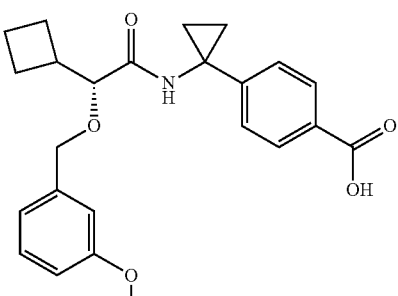

Example 101

Methods for the Preparation of Compounds of the Formula (1)

Compounds of Formula (1) can be prepared in accordance with synthetic methods well known to the skilled person. Also provided is a process for the preparation of a compound as defined in Formula (1) above.

Scheme 1

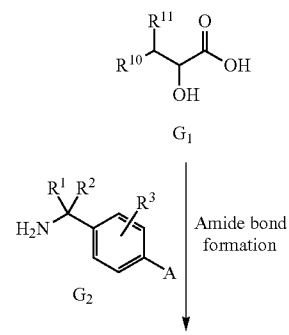

-continued

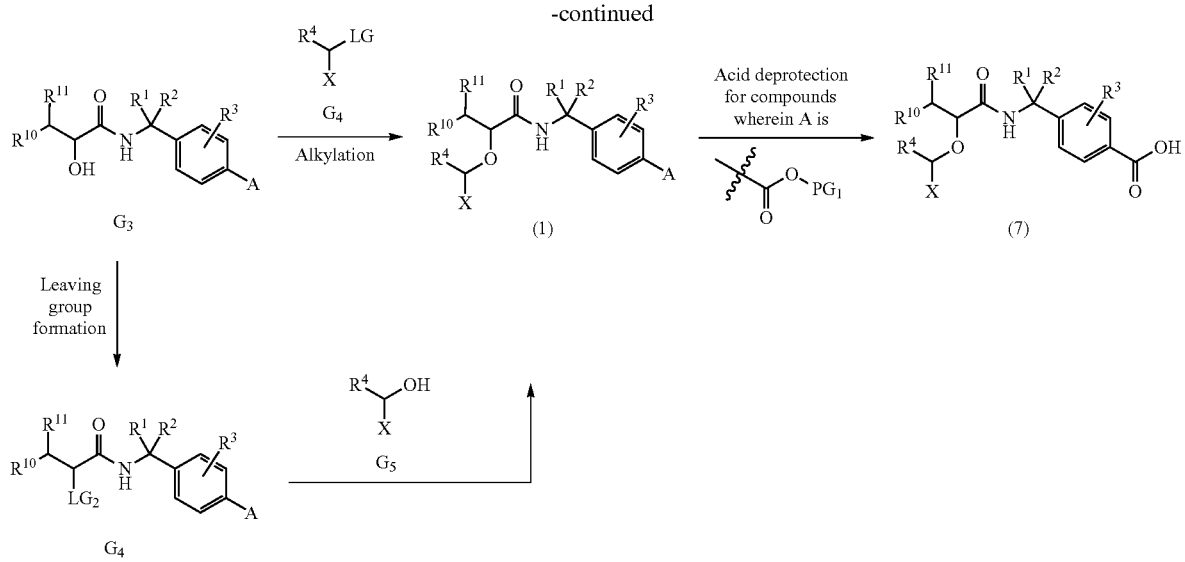

Compounds of formula (1) can be prepared as outlined in Scheme 1. Amide bond formation between an acid of formula G, with an amine of formula $G_2$ is typically conducted in the presence of a suitable coupling agent, such as HATU, and a base such as N,N-diisopropylethylamine, in solvents such as MeCN or dichloromethane to yield the desired amide of formula $G_3$. Alkylation of alcohol $G_3$ with an alkylating agent of formula $G_4$, whereby LG, represents a suitable leaving group, typically bromide. Typically, the alkylation reaction is carried out in the presence of a base, such as NaH, and in a solvent such as THF at temperatures ranging from 0° C. to room temperature to afford a compound of formula (1). Alternatively, a compound of formula (1) can be prepared via displacement of an appropriate alkylating agent $G_4$, whereby $LG_2$ represents a suitable leaving group, typically mesylate, with an alcohol of formula $G_5$. Typical conditions comprise use of a base, such as KOtBu, and in a solvent such as THF at temperatures ranging from 0° C. to 70° C. Compounds of formula $G_4$ can be prepared via activation of the corresponding alcohol of formula $G_3$, whereby $LG_2$ represents a suitable leaving group, typically mesylate. Typically, the reaction is carried out in the presence of a base, such as triethylamine, and in a solvent such as dichloromethane at temperatures ranging from 0° C. to room temperature to afford a compound of formula $G_4$.

In compounds where A is a protected carboxylic acid group, whereby PG, represents a suitable acid protecting group such as a methyl ester, can be further deprotected using conditions pertinent to the nature of the protecting group. Typically, hydrolysis of a methyl ester functionality in the presence of a nucleophilic base such as lithium hydroxide in solvents such as MeOH or THF, affords compounds of the formula (7).

The skilled person will understand that the reaction steps depicted in Scheme 1 may be combined in different ways as required to successfully prepare the desired compound of formula (1) and formula (7). This may include additional steps, for example, functional group modification, protection and/or deprotection steps into the overall synthetic sequence. For example, compounds of the formula (7) may be prepared as shown in Scheme 2.

Alkylation of an alcohol of formula $G_6$, whereby $PG_2$ represents a suitable acid protecting group such as a methyl ester, with an alkylating agent of formula $G_4$, whereby LG represents a suitable leaving group, typically bromide. Typically, the alkylation reaction is carried out in the presence of a base, such as NaH, and in a solvent such as THF at temperatures ranging from 0° C. to room temperature to afford an ether of formula $G_7$. The resulting ester can be deprotected using conditions pertinent to the nature of the protecting group $PG_2$, typically hydrolysis of a methyl ester functionality in the presence of a nucleophilic base such as lithium hydroxide in solvents such as THF, to afford an acid of formula $G_8$. An amide bond forming reaction between an acid of formula $G_8$ and an amine of formula $G_2$, in the presence of an amide coupling reagent, such as HATU or EDCI, and a base, such as triethylamine, in a solvent such as DCM or DMF affords a compound of formula (1). In compounds where A is a protected carboxylic acid group deprotection can be achieved as described in Scheme 1.

Scheme 2

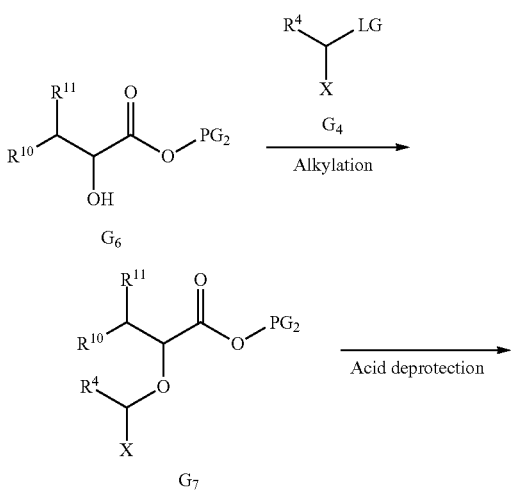

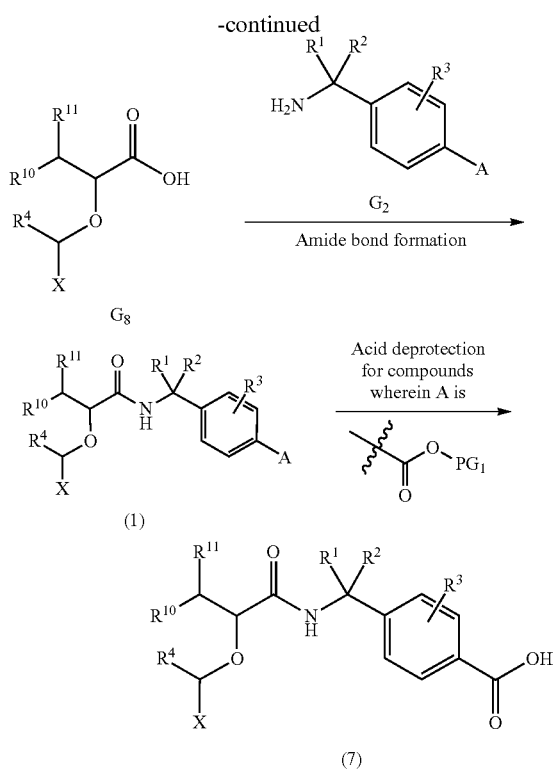

It will be understood that the above schemes and procedures are not meant to be limiting in any way. Indeed, the above schemes and procedures can also be used to prepare compounds of the invention where, for example, A is a carboxylic acid isostere group. Methods and protecting groups appropriate for the "A group" are well known to those skilled in the art, e.g. a trityl group can be used for protecting a tetrazole group. Additionally, one compound of the formula 1 can be converted into another compound of the invention by methods well known to the skilled person. Examples of synthetic procedures for converting one functional group into another functional group are set out in standard texts such as March's Advanced Organic Chemistry: Reactions, Mechanisms, and Structure, 7th Edition, Michael B. Smith, John Wiley, 2013, (ISBN: 978-0-470-46259-1), Organic Syntheses, OnlineEdition, www.orgsyn.org, (ISSN 2333-3553) and Fiesers' Reagents for Organic Synthesis, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in Greene's Protective Groups in Organic Synthesis, Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography) under normal or reversed-phase conditions, HPLC and SFC.

General Procedures

Where no preparative routes are included, the relevant intermediate is commercially available. Commercial reagents were utilized without further purification. Final compounds and intermediates are named using ChemDraw Professional, Version 17.0.0.206 (121). Room temperature (RT) refers to approximately 20-27° C. 1H NMR spectra were recorded at 400 or 500 MHz on either a Bruker, Varian or Jeol instrument. Chemical shift values are expressed in parts per million (ppm), i.e. (δ)—values relative to the following solvents: chloroform-d=7.26 ppm, DMSO-d6=2.50 ppm, methanol-d4=3.31 ppm. The following abbreviations are used for the multiplicity of the NMR signals: s=singlet, br=broad, d=doublet, t=triplet, q=quartet, m=multiplet. Coupling constants are listed as J values, measured in Hz. NMR and mass spectroscopy results were corrected to account for background peaks. Chromatography refers to column chromatography performed using 60-120 mesh or 40-633 μm, 60 Å silica gel and executed under nitrogen pressure (flash chromatography) conditions. Microwave-mediated reactions were performed in Biotage Initiator or CEM Discover microwave reactors.

LC/MS Analysis

LC/MS analysis of compounds was performed under electrospray conditions using the instruments and methods given below:

LC/MS Method A and LC/MS Method B

Instruments: Agilent 1260 Infinity LC with diode array detector and Agilent MS 6120; Column: Phenomenex Gemini-NX, C-18, 3 micron, 30×2 mm; Method A Gradient [time (min)/solvent B in A (%)]: 0.00/2, 0.1/2., 8.4/95, 10.0/95, 10.1/2. 12.0/2; Method B Gradient [time (min)/solvent B in A (%)]: 0.00/5, 2.0/95, 2.5/95, 2.6/5, 3.0/5; Solvents: solvent A=water (2.5 L) with 28% aqueous ammonia solution (2.5 mL); Solvent B: Acetonitrile (2.5 L) with water (125 mL) and 28% aqueous ammonia solution (2.5 mL); column temperature: 40° C.; flow rate: 1.5 mL/min.

LC/MS Method C

Instruments: HP 1100 with G1315A DAD, Waters Micromass ZQ; Column: Phenomenex Gemini-NX C-18, 3 micron, 2.0×30 mm; Gradient [time (min)/solvent B in A (%)]: 0.00/2. 0.01/2. 8.40/95, 10.00/95; Solvents: solvent A=2.5 L H₂O+2.5 mL 28% ammonia in H₂O solution; solvent B=2.5 L MeCN+135 mL H₂O+2.5 mL 28% ammonia in H₂O solution. Injection volume 1 μL; UV detection 230 to 400 nm; Mass detection 130 to 800 AMU; column temperature 45° C.; Flow rate 1.5 mL/min.

LC/MS Method D and LC/MS Method E

Instruments: Aquity H-Class with PDA detector and QDa mass detector; Column: C-18, 1.6 micron, 50×2.1 mm; Method D Gradient [time (min)/solvent B in A (%)]: 0.00/3, 0.20/3, 2.70/98, 3.00/100, 3.50/100, 3.51/3, 4.00/4; Method E Gradient [time (min)/solvent B in A (%)]: 0.00/5, 0.20/5, 1.80/98, 2.00/100, 2.50/100, 2.15/5, 3.00/5; Solvents: solvent A=0.1% formic acid in water; Solvent B=0.1% formic acid in acetonitrile: water (90:10); column temperature: 35° C.; flow rate: 1 mL/min.

LC/MS Method F

Instruments: Agilent Infinity II G6125C LCMS; Column: C-18, 3.5 micron, 50×4.6 mm; Gradient [time (min)/solvent B in A (%)]: 0.00/8, 0.75/8, 3.00/70, 3.70/95, 4.20/100, 5.20/100, 5.21/8, 7.00/8; Solvents: solvent A=5 mM aqueous ammonium bicarbonate; Solvent B=methanol; column temperature: 35° C.; flow rate: 0.9 mL/min.

LC/MS Method G

Instruments: Agilent Infinity II G6125C LCMS; Column: C-18, 3.5 micron, 50×4.6 mm; Gradient [time (min)/solvent B in A (%)]: 0.00/5, 1.00/5. 3.00/60, 4.50/90, 7.00/100, 8.00/100, 8.01/5, 10.0/5; Solvents: solvent A=0.1% ammonia in water; Solvent B=acetonitrile; column temperature: 35° C.; flow rate: 1.0 mL/min.

LC/MS Method H

Instruments: Waters Alliance 2690 with 996 PDA detector with Micromass ZQ; Column: C-18, 3.5 micron, 150×4.6 mm; Gradient [time (min)/solvent B in A (%)]: 0.00/10, 7.00/90, 9.00/100, 14.0/100, 14.01/10, 17.00/10; Solvents: solvent A=5 mM aqueous ammonium acetate and 0.1% formic acid; Solvent B=methanol; column temperature: 35° C.; flow rate: 1.0 mL/min.

LC/MS Method I

Instruments: Waters Aquity UPLC Binary equipped with PDA and SQ detector; Column: Waters Sunfire C18, 3.5 micron, 150×4.6 mm; Isocratic [time (min)/solvent B in A (%)]: 0.00/70, 20.00/70; Solvents: solvent A=5 mM aqueous Ammonium Acetate+0.1% formic acid; solvent B=methanol; column temperature: 35° C.; flow rate: 1 mL/min.

Analytical SFC Method J

Instrument: Waters Acquity UPC2 with Masslynx software, PDA detector and a QDa mass detector; Column: Phenomenex Lux Amylose-1, 3 μm, 50×2 mm; Wavelength: detection from 210 to 400 nm; Gradient [time (min)/solvent B in A (%)]: 0.00/3, 3.00/50, 4.00/50, 5.00/3; Solvents: solvent A=C02; solvent B=IPA; column temperature: 45° C.; flow rate: 1.5 mL/min.

Analytical Chiral HPLC Method K

Instrument: Shimadzu LC 20AD; Column: CHIRALPAK IG, 5 μm, 250×4.6 mm; Isocratic [time (min)/solvent B in A (%)]: 0.00/20, 30.00/20; Solvents: solvent A=n-heptane; solvent B=2-propanol:ACN (70:30); column temperature: RT; flow rate: 1 mL/min.

ABBREVIATIONS USED THROUGHOUT THIS DOCUMENT aq aqueous
Bn benzyl
DCM dichloromethane
DMA dimethylacetamide
DMF dimethylformamide
dppf 1,1'-bis(diphenylphosphino)ferrocene
EDCI 1-ethyl-3-(3-dimethylaminopropyl)carbodiimide
EtOAc ethyl acetate
HATU 1-[Bis(dimethylamino)methylene]-1H-1,2,3-triazolo[4,5-b]pyridinium 3-oxide hexafluorophosphate,
HCl hydrochloric acid
HOBt hydroxybenzotriazole
HPLC high performance liquid chromatography
h/hr hour
hrs hours
IPA iso-propyl alcohol
LC/MS liquid chromatography mass spectrometry
LiOH lithium hydroxide
M molar
MeCN acetonitrile
MeOH methanol
Min minutes
MTBE methyl tert-butyl ether
N normal
NaOH sodium hydroxide
NaH sodium hydride
prep HPLC preparative high-performance liquid chromatography
RM reaction mixture
RT room temperature
sat saturated
THF tetrahydrofuran
UPLC ultra performance liquid chromatography
V volumes

GENERAL SYNTHETIC PROCEDURES FOR THE EXAMPLES

Route A

Procedure for the Preparation of Example 1, 4-((S)-1-((R)-3-methyl-2-((4-(trifluoromethyl)benzyl)oxy)butanamido)ethyl)benzoic acid

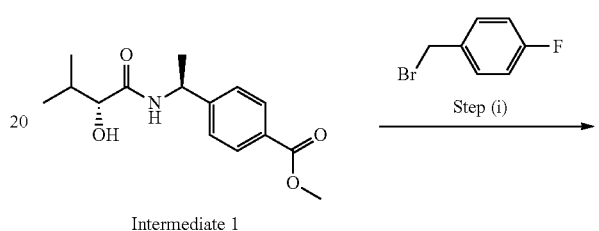

Intermediate 1

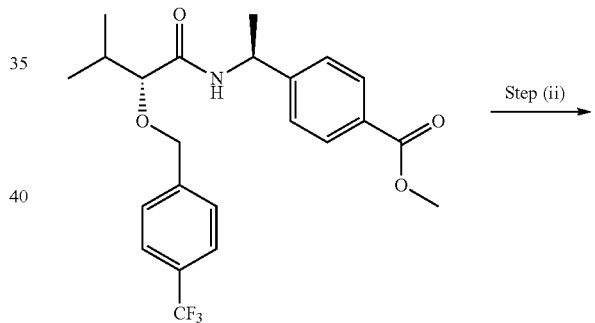

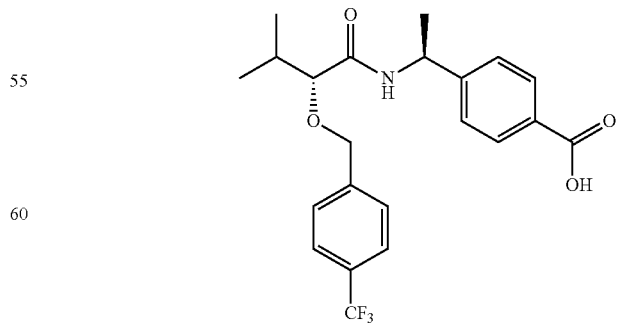

Example 1

Step (i): To an ice cooled solution of Intermediate 1, methyl 4-((S)-1-((R)-2-hydroxy-3-methylbutanamido) ethyl) benzoate (11.3 g, 40.6 mmol) and potassium tert-butoxide (5.01 g, 44.7 mmol) in DMF (100 mL) was added 4-(trifluoromethyl)benzyl bromide (10.7 g, 44.7 mmol). The mixture was warmed to RT and stirred for 6 hrs, after which it was partitioned between EtOAc and water. The organics were separated, washed with brine (×2) dried over MgSO$_4$ and concentrated. The crude material was purified by flash column chromatography (normal phase, silica) under a gradient of EtOAc (0% to 50%) in iso-hexane to afford methyl 4-[(1S)-1-[[(2R)-3-methyl-2-[[4-(trifluoromethyl)phenyl]methoxy]butanoyl]amino]ethyl]benzoate (8.93 g, 20.4 mmol, 50% yield) as a white solid. (LC/MS Method B): m/z 438 [M+H]$^+$ (ES$^+$), at 1.75 min, UV active.

Step (ii): To a solution of methyl 4-[(1S)-1-[[(2R)-3-methyl-2-[[4-(trifluoromethyl)phenyl]methoxy]butanoyl]amino]ethyl]benzoate (7.44 g, 17.0 mmol) in water (28 mL) and methanol (15 mL) was added sodium hydroxide (3.40 g, 85.0 mmol) and the reaction mixture heated to 70° C. for 5 hrs. The mixture was cooled to RT and partitioned between ethyl acetate and 1 M HCl. The organics were separated, dried via passage through a hydrophobic frit and concentrated. The crude material was triturated from diethyl ether and then recrystallised from a minimal amount of boiling isopropanol to afford Example 1, 4-((S)-1-((R)-3-methyl-2-((4-(trifluoromethyl)benzyl)oxy)butanamido)ethyl)benzoic acid (3.12 g, 7.4 mmol, 43.3% yield) as a white solid. Data available in Table 2.

Route B

Procedure for the Preparation of Example 2, (R)-4-(1-(3-methyl-2-((4-(trifluoromethyl)benzyl)oxy)butanamido)cyclopropyl)benzoic acid

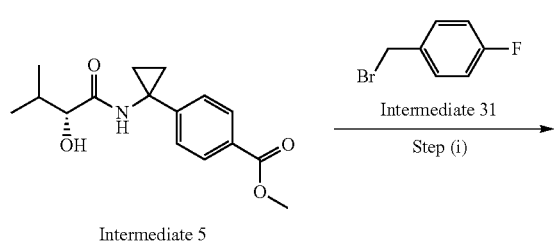

Intermediate 5

Intermediate 31

Step (i)

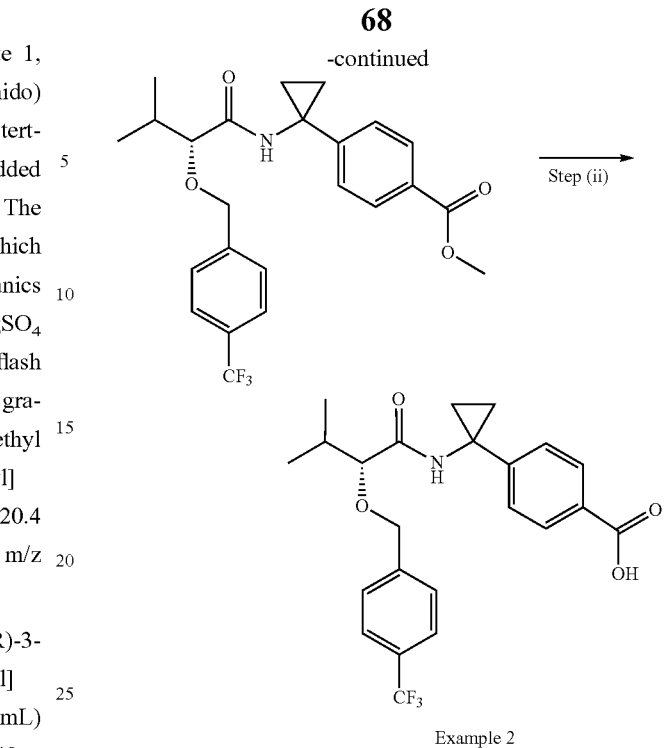

Example 2

Step (i): To an ice cooled mixture of Intermediate 5 methyl (R)-4-(1-(2-hydroxy-3-methylbutanamido)cyclopropyl)benzoate (212 mg, 0.73 mmol) in THF (3.6 ml) was added NaH (60% dispersion in mineral oil) (32 mg, 0.8 mmol) and the reaction mixture stirred for 10 minutes at room temperature after which Intermediate 31 1-(bromomethyl)-4-(trifluoromethyl)benzene (192 mg, 0.8 mmol) was added. The reaction was stirred at RT for 18 hours then partitioned between water and EtOAc, the organics separated, washed with brine, dried (hydrophobic frit.) and concentrated. The crude material was purified by flash column chromatography (normal phase) [gradient 0-45% EtOAc in iso-hexane] to give methyl (R)-4-(1-(3-methyl-2-((4-(trifluoromethyl)benzyl)oxy)butanamido)cyclopropyl) benzoate as an orange solid (76 mg, 0.17 mmol, 23% yield). LC/MS (Method C): m/z 450 [M+H]$^+$, 1.73 min.

Step (ii): Methyl (R)-4-(1-(3-methyl-2-((4-(trifluoromethyl)benzyl)oxy)butanamido) cyclopropyl) benzoate (76 mg, 0.17 mmol), was suspended in 1,4-dioxane (0.4 mL) and water (0.4 mL) and lithium hydroxide monohydrate (28 mg, 0.68 mmol) added. The reaction mixture stirred at room temperature for 18 hours then concentrated in vacuo The crude material was purified by flash column chromatography (reverse phase) [gradient 10-45% MeOH in water and 0.2% 28% NH$_4$OH (aq.) solution)]. To give Example 2 (R)-4-(1-(3-methyl-2-((4-(trifluoromethyl)benzyl)oxy)butanamido) cyclopropyl) benzoic acid (36 mg, 0.08 mmol, 49%), as a white solid. Data available in Table 2 Alternate route to Example 2

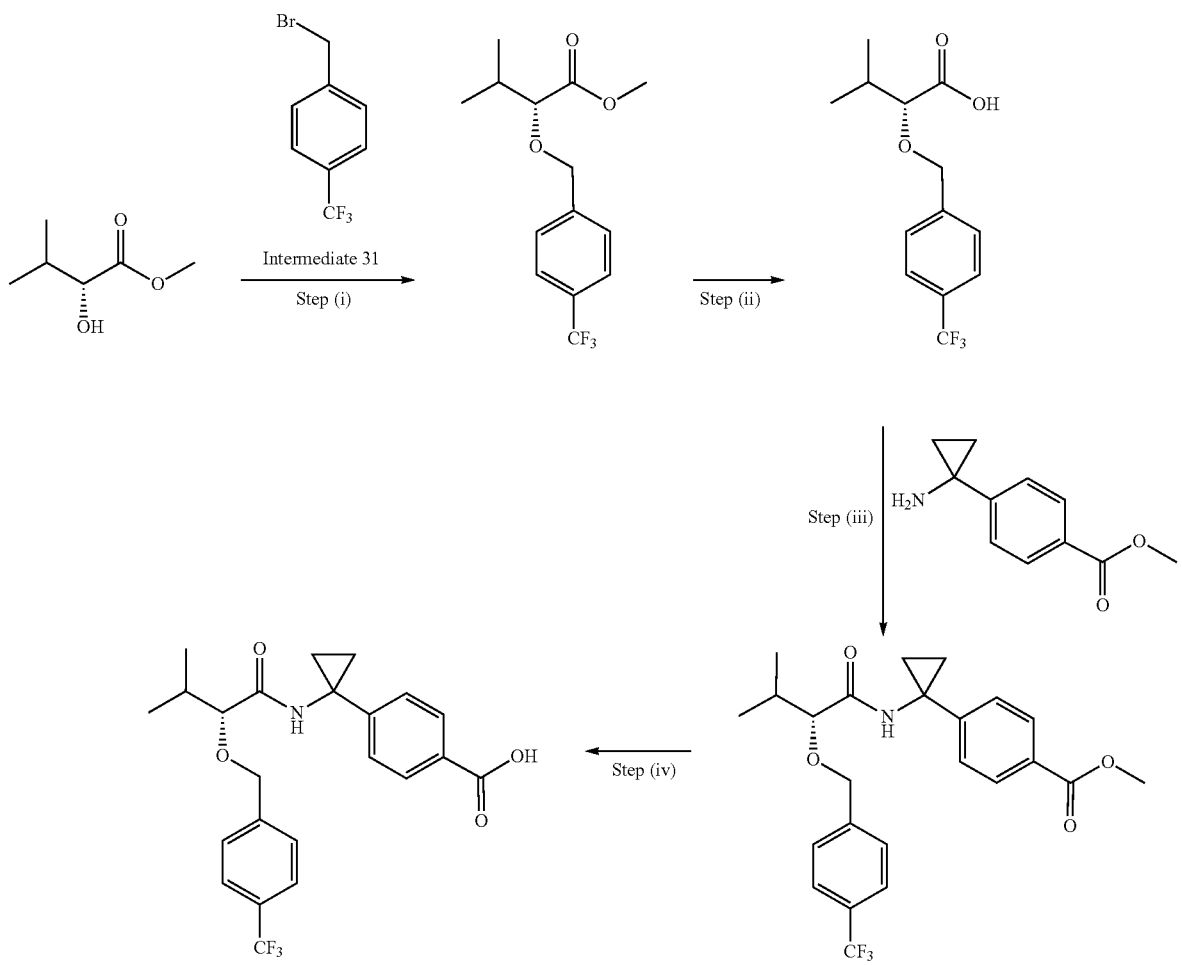

Example 2

Step (i): In a flask was taken methyl R-2-hydroxy-3-methyl-butanoate (25 g, 1.0 eq.) in dry THF (10 V) at 0° C. Then tetrabutylammonium iodide (0.1 eq.) and Intermediate 31 1-(bromomethyl)-4-(trifluoromethyl)benzene (44 g, 1.0 eq.) were added the RM was stirred for 15 min then NaH (1.5 eq.) was added portion wise with temperature maintained at 0° C. throughout. The reaction mixture was stirred at 0° C. for 1 hour then the RM was stirred at room temperature for 4 hrs. After completion of the reaction, the reaction mixture was quenched with ice-cold water (10 V), and product was extracted with MTBE (3V x 3), the extracts were combined and evaporated under vacuum to afford 40 g of the crude product. The crude compound was purified by column chromatography using 60-120 mesh silica gel and the product was eluted in 1-2% ethyl acetate and hexane system to afford methyl (R)-3-methyl-2-((4-(trifluoromethyl)benzyl)oxy)butanoate 25 g as a viscus liquid.

Step (ii): Methyl (R)-3-methyl-2-((4-(trifluoromethyl)benzyl)oxy)butanoate (75 g, 1.0 eq.) in THF (3 V) was treated with LiOH (1.5 eq.) and water (1.5 V) at RT and then stirred at 80° C. for 4 hrs. After completion of the reaction, THF was evaporated under vacuum and obtained residue was taken in water (5 V) and washed with MTBE (5 V). Then aq. layer was acidified with 1N aq. HCl (pH ~2). Product was then extracted with DCM (20 V×2). The combined organic layer was evaporated under vacuum to obtain (R)-3-methyl-2-((4-(trifluoromethyl)benzyl)oxy)butanoic acid (62 g). This compound was used in the next step without any further purification.

Step (iii): In a flask was taken (R)-3-methyl-2-((4-(trifluoromethyl)benzyl)oxy)butanoic acid (62 g, 1.0 eq.) in DMF (10 V) at 0° C. followed by the addition of HATU (1.5 eq.), methyl 4-(1-aminocyclopropyl)benzoate (1.0 eq.) and DIPEA (3.0 eq.) at same temperature. Then the reaction mixture was allowed warm to RT with continued stirring. After completion of the reaction, the reaction mixture was poured in water (10 V) The obtained solid was filtered, washed with cooled Water (2 V) and dried under vacuum to give 105 g of the crude product. The crude compound was purified by column chromatography using 60-120 mesh silica gel and the product was eluted in 10-15% ethyl acetate and hexane system to afford methyl (R)-4-(1-(3-methyl-2-((4-(trifluoromethyl)benzyl)oxy)butanamido)cyclopropyl) benzoate as a viscus liquid 58 g Step (iv): In a flask was taken methyl (R)-4-(1-(3-methyl-2-((4-(trifluoromethyl)benzyl)oxy)butanamido)cyclopropyl) benzoate (58 g, 1.0 eq.) in THF (3 V) and water (1.5 V). The reaction mixture was cooled to 0-5° C. followed by the addition of Lithium hydroxide monohydrate (3.0 eq.) Portion wise over a period of 30 min. at same temperature. Then the reaction mixture was heated to 80° C. over a period of 30 min and further stirred for 4 hrs at 80° C. After completion of the reaction, solvent was evaporated under vacuum. Then water (5 V) was added into the reaction mixture. This aq. layer was washed with MTBE (5 V). Then aq. layer was acidified with 1 N aq. HCl (pH: 2 to 3) and product was extracted in ethyl acetate (20 V x 3). The combined organic layer was washed with water and evaporated under vacuum to give Example 2 (R)-4-(1-(3-methyl-2-((4-(trifluoromethyl)benzyl)oxy)butanamido)cyclopropyl)benzoic acid (43 g) as an off-white solid.

Additional Purification—This material and material from additional batches (79 g) were further purified by being taken up in heptane (10 V) and heated to 80° C., followed by the addition of IPA (3 V) at same temperature. Then the mixture was allowed to cool to room temperature and stirred for 30 min. The obtained solid was filtered, washed with n-heptane (3 V) and dried under vacuum (this was repeated twice). Combined product materials (85 g) were suspended in n-heptane (425 mL, 5 V) at room temperature and stirred for 30 min. The solid was filtered, washed with n-heptane (2 V) and dried under vacuum to give of Example 2 (R)-4-(1-(3-methyl-2-((4-(trifluoromethyl)benzyl)oxy)butanamido) cyclopropyl) benzoic acid (82 g). Data available in Table 2.

Route C

Procedure for the Preparation of Example 5, 4-((S)-1-((R)-2-((4-fluorobenzyl)oxy)-3-methylbutanamido)ethyl)benzoic acid Step (i): To a suspension of NaH (60% in mineral oil) (0.071 g, 1.77 mmol) in DMF (5 mL) under an atmosphere of nitrogen at 0° C. was added Intermediate 1, methyl 4-((S)-1-((R)-2-hydroxy-3-methylbutanamido)ethyl) benzoate (0.45 g, 1.61 mmol). The mixture was stirred at the same temperature for 10 mins, after which 1-(bromomethyl)-4-fluorobenzene (0.36 g, 1.93 mmol) was added. The mixture was warmed to RT and stirred for 3 hr after which it was partitioned between EtOAc and water. The organics were separated, and the aqueous layer was further extracted with EtOAc (×2). The combined organics were dried over Na$_2$SO$_4$ and concentrated. The residue was purified by flash column chromatography (reversed phase, C18) under a gradient of MeCN (0-62%) in water to afford methyl 4-((S)-1-((R)-2-((4-fluorobenzyl)oxy)-3-methylbutanamido)ethyl) benzoate (0.38 g, 0.99 mmol, 61% yield) as a white solid. (LC/MS Method D): m/z 388 [M+H]$^+$ (ES$^+$), at 2.67 min, UV active.

Step (ii): To a solution of methyl 4-((S)-1-((R)-2-((4-fluorobenzyl)oxy)-3-methylbutanamido)ethyl) benzoate (0.38 g, 0.98 mmol) in 1,4-dioxane (4 mL) and water (2 mL) was added lithium hydroxide monohydrate (0.21 g, 4.90 mmol). The mixture was stirred at RT for 5 hrs, after which it was acidified to pH 4 with glacial acetic acid and concentrated under reduced pressure. The residue was purified by flash column chromatography (reversed phase, C18) under a gradient of MeCN (0-50%) in water to afford Example 5, 4-((S)-1-((R)-2-((4-fluorobenzyl)oxy)-3-methylbutanamido)ethyl) benzoic acid (0.28 g, 0.75 mmol, 76%) as an off white solid. Data available in Table 2.

Route D

Procedure for the Preparation of Example 6, 4-((1S)-1-(2-((4-methoxybenzyl)oxy)-3-methylbutanamido)ethyl)benzoic acid, Mixture of Diastereomers

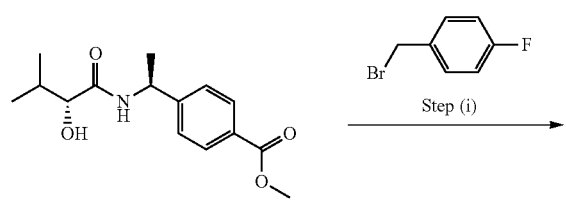

Intermediate 1

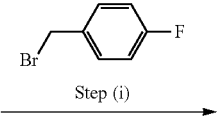
Step (i)

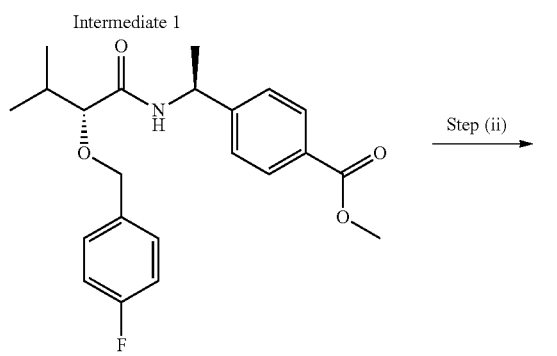

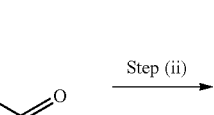
Step (ii)

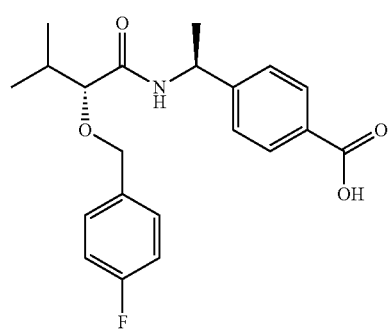

Example 5

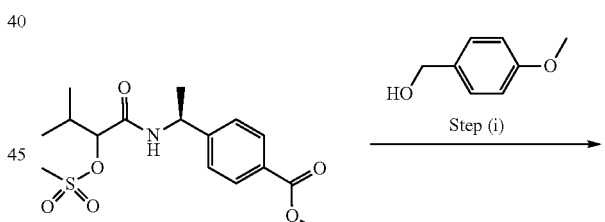

Intermediate 3

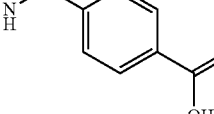
Step (i)

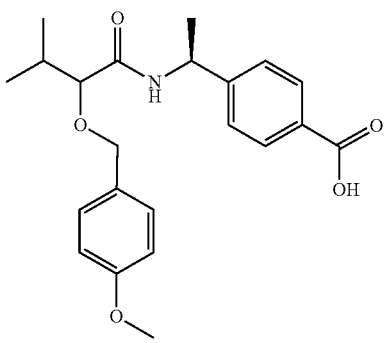

Example 6

To a solution of (4-methoxyphenyl)methanol (0.20 g, 1.47 mmol) in THF (3.5 mL) at 0° C. was added potassium tert-butoxide and the mixture was stirred at the same temperature for 20 mins. Intermediate 3, methyl 4-((1S)-1-(3-methyl-2-((methylsulfonyl)oxy)butanamido) ethyl)benzoate (0.35 g, 0.98 mmol) was added and the mixture was stirred at 80° C. for 4 hrs, after which it was cooled to RT and partitioned between EtOAc and water. The aqueous layer was separated, acidified to pH 1 with 1 N HCl and extracted with EtOAc (×2). The combined organics were dried over Na₂SO₄ and concentrated. Note partial ester hydrolysis occurred in the reaction. The residue was purified by flash column chromatography (reversed phase, C18) under a gradient of MeCN (0-36%) in water to afford Example 6, 4-((1 S)-1-(2-((4-methoxybenzyl)oxy)-3-methylbutanamido)ethyl)benzoic acid (0.13 g, 0.33 mmol, 34% yield) as a white solid. Data available in Table 2.

Route E

Procedure for the Preparation of Example 11, 4-((S)-1-((R)-2-((4-chlorobenzyl)oxy)-3-methylbutanamido)ethyl)benzoic acid

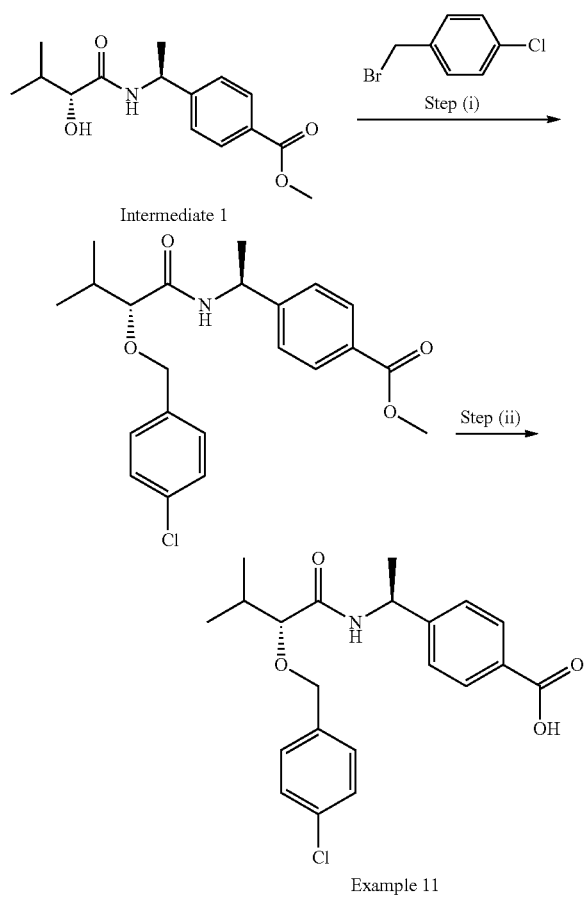

Example 11

Step (i): To a suspension of NaH (~60% in mineral oil) (0.05 g, 1.34 mmol) in DMF (2 mL) under an atmosphere of nitrogen at 0° C. was added Intermediate 1, methyl 4-((S)-1-((R)-2-hydroxy-3-methylbutanamido)ethyl) benzoate (0.25 g, 0.89 mmol). The mixture was stirred at the same temperature for 15 mins, after which 1-(bromomethyl)-4-chlorobenzene (0.27 g, 1.34 mmol) was added. The mixture was warmed to RT and stirred for 1 hr after which it was partitioned between EtOAc and water. The organics were separated, and the aqueous layer was further extracted with EtOAc (×2). The combined organics were dried over Na₂SO₄ and concentrated. The residue was purified by flash column chromatography (reversed phase, C18) under a gradient of MeCN (0-90%) in water to afford methyl 4-((S)-1-((R)-2-((4-chlorobenzyl)oxy)-3-methylbutanamido)ethyl) benzoate (0.143 g, 0.35 mmol, 40% yield) as a sticky liquid. (LC/MS Method E): m/z 404 [M+H]⁺ (ES⁺), at 1.91 min, UV active.

Step (ii): To a solution of methyl 4-((S)-1-((R)-2-((4-chlorobenzyl)oxy)-3-methylbutanamido)ethyl) benzoate (0.14 g, 0.35 mmol) in 1,4-dioxane (2 mL) and water (1 mL) was added lithium hydroxide monohydrate (70 mg, 1.77 mmol). The mixture was stirred at RT for 3 hrs, after which it was acidified to pH 4 with glacial acetic acid and concentrated under reduced pressure. The residue was purified by flash column chromatography (reversed phase, C18) under a gradient of MeCN (0-56%) in water to afford Example 11, 4-((S)-1-((R)-2-((4-chlorobenzyl)oxy)-3-methylbutanamido)ethyl)benzoic acid (100 mg, 0.26 mmol, 74% yield) as a brown solid. Data available in Table 2.

Route F

Procedure for the Preparation of Example 13, 4-((S)-1-((R)-2-((4-(difluoromethyl)benzyl)oxy)-3-methylbutanamido)ethyl)benzoic acid

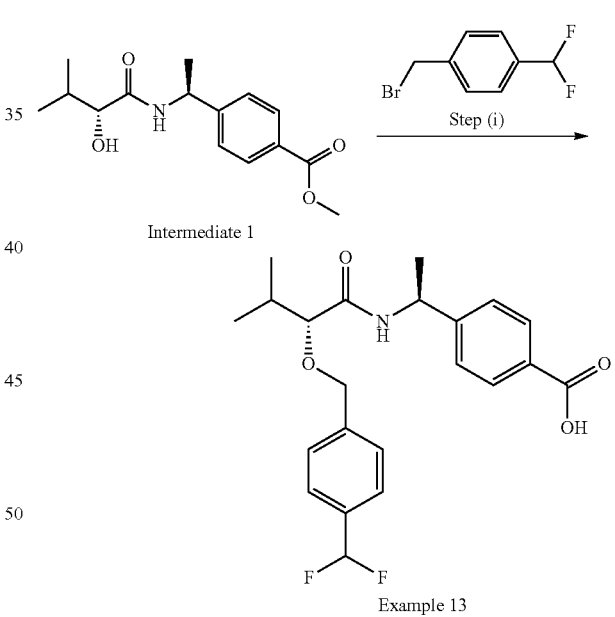

Example 13

Step (i): To a suspension of NaH (~60% in mineral oil) (0.08 g, 2.15 mmol) in DMF (5 mL) under an atmosphere of nitrogen at 0° C. was added Intermediate 1, methyl 4-((S)-1-((R)-2-hydroxy-3-methylbutanamido)ethyl) benzoate (0.20 g, 0.71 mmol). The mixture was stirred at the same temperature for 15 mins, after which 1-(bromomethyl)-4-(difluoromethyl) benzene (0.23 g, 1.07 mmol) was added. The mixture was stirred at 0° C. for 2 hrs after which it was acidified to pH 1 by the addition of 1 N HCl and then partitioned between EtOAc and water. The organics were separated, and the aqueous layer was further extracted with EtOAc (×2). The combined organics were dried over Na₂SO₄ and concentrated, and the residue was purified by flash column chromatography (reversed phase, C18) under a gradient of MeCN (0-72%) in water to afford Example 11, 4-((S)-1-((R)-2-((4-(difluoromethyl)benzyl)oxy)-3-methylbutanamido)ethyl)benzoic acid (82 mg, 0.20 mmol, 29% yield) as a white solid. Data available in Table 2.

Route G

Procedure for the Preparation of Example 17, 4-((1S)-1-(2-((3-fluorobenzyl)oxy)-3-methylbutanamido)ethyl)benzoic acid, Diastereomer 1 and Example 18, 4-((1S)-1-(2-((3-fluorobenzyl)oxy)-3-methylbutanamido)ethyl)benzoic acid, Diastereomer 2

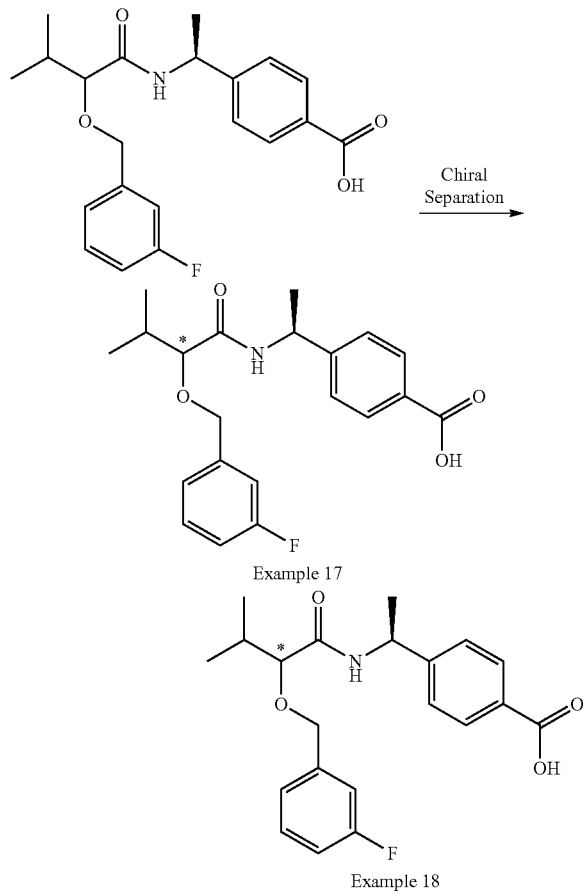

Step (i): 4-((1S)-1-(2-((3-fluorobenzyl)oxy)-3-methylbutanamido)ethyl)benzoic acid (110 mg, synthesized according to Route E) was separated into single diastereomers via chiral preparative HPLC [Chiralpak IG, 21×250 mm, 5 μm, 23 mL per min; Gradient [time (min)/solvent B in A (%)]: 0.01/8, 40.00/8; Solvents: solvent A=0.1% TFA and 0.1% diethylamine in hexane; solvent B=methanol:IPA (60:40)] to afford 4-((1S)-1-(2-((3-fluorobenzyl)oxy)-3-methylbutanamido)ethyl)benzoic acid, diastereomer 1 (29 mg, 0.078 mmol) as a white solid, and 4-((1S)-1-(2-((3-fluorobenzyl)oxy)-3-methylbutanamido)ethyl)benzoic acid, diastereomer 2 (29 mg, 0.078 mmol) as a white solid. Data available in Table 2.

Route H

Procedure for the Preparation of Example 42, (R)—N—((S)-1-(4-(1H-tetrazol-5-yl)phenyl)ethyl)-2-((4-fluorobenzyl)oxy)-3-methylbutanamide

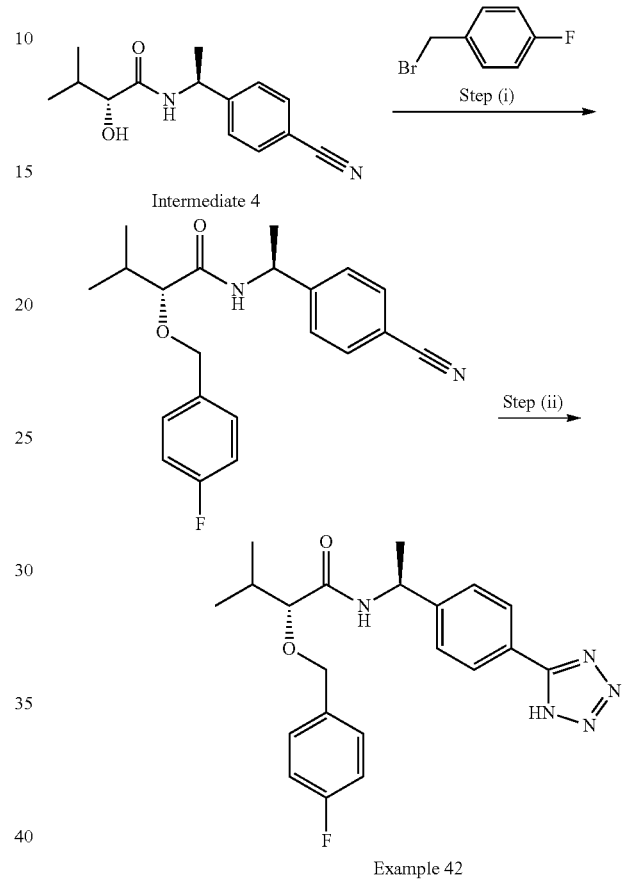

Step (i): To a suspension of NaH (~60% in mineral oil) (45 mg, 1.11 mmol) in DMF (3 mL) under an atmosphere of nitrogen at 0° C. was added Intermediate 4, (R)—N—((S)-1-(4-cyanophenyl)ethyl)-2-hydroxy-3-methylbutanamide (0.25 g, 1.01 mmol). The mixture was stirred at the same temperature for 15 mins, after which 1-(bromomethyl)-4-fluorobenzene (0.29 g, 1.52 mmol) was added and the mixture was stirred at RT for 2 hrs. The mixture was partitioned between EtOAc and water and the organics were separated. The aqueous layer was further extracted with EtOAc (×2) and the combined organics were dried over Na₂SO₄ then concentrated. The residue was purified by flash column chromatography (reversed phase, C18) under a gradient of MeCN (0-74%) in water to afford (R)—N—((S)-1-(4-cyanophenyl) ethyl)-2-((4-fluorobenzyl)oxy)-3-methylbutanamide (0.20 g, 0.56 mmol, 56% yield) as a yellow solid. (LC/MS Method E): m/z 355 [M+H]⁺ (ES⁺), at 1.73 min, UV active.

Step (ii): A mixture of (R)—N—((S)-1-(4-cyanophenyl) ethyl)-2-((4-fluorobenzyl) oxy)-3-methylbutanamide (0.10 g, 0.28 mmol), NaN₃ (0.11 g, 1.69 mmol) and NH₄Cl (90 mg, 1.69 mmol) in DMF (1 mL) was heated to 80° C. for 7 hrs. The mixture was cooled to RT then partitioned between EtOAc and water. The organics were separated, and the aqueous layer was further extracted with EtOAc (×2). The combined organics were dried over Na₂SO₄, concentrated, and the crude material was purified by flash column chromatography (reversed phase, C18) under a gradient of MeCN (0-45%) in water to afford Example 42, (R)—N—((S)-1-(4-(1H-tetrazol-5-yl)phenyl)ethyl)-2-((4-fluorobenzyl)oxy)-3-methylbutanamide (0.064 g, 57.06%) as a yellow solid. Data available in Table 2.

Route I

Procedure for the Preparation of Example 45, 4-((S)-1-((R)-2-((3-(hydroxymethyl)benzyl)oxy)-3-methylbutanamido)ethyl)benzoic acid

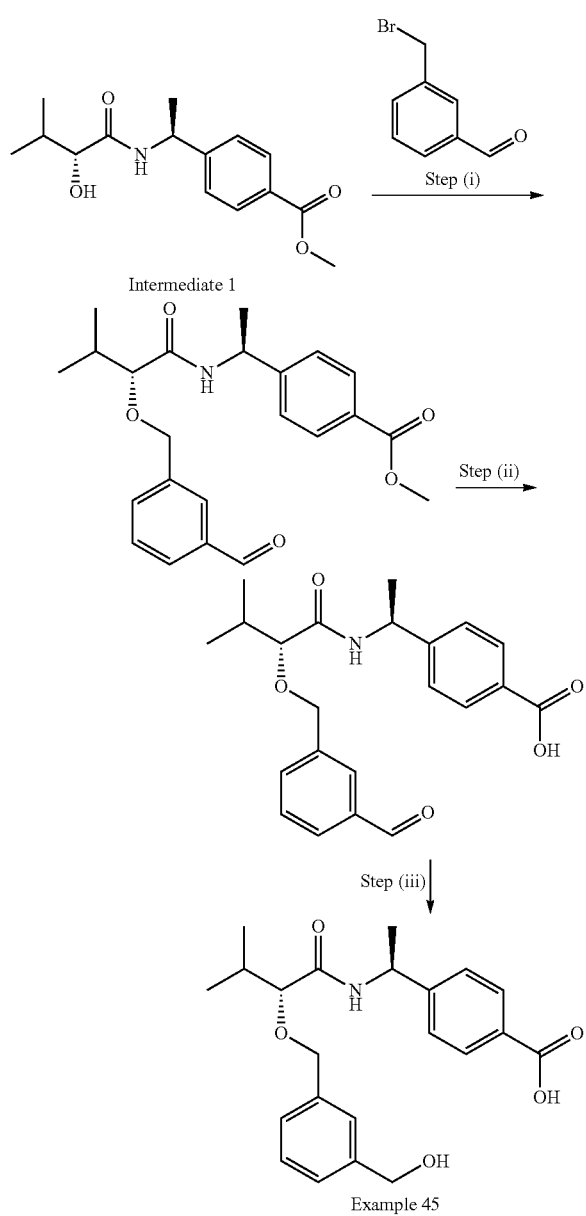

Step (i): To a suspension of NaH (~60% in mineral oil) (24 mg, 0.60 mmol) in DMF (2 mL) under an atmosphere of nitrogen at 0° C. was added Intermediate 1, methyl 4-((S)-1-((R)-2-hydroxy-3-methylbutanamido)ethyl) benzoate (0.15 g, 0.54 mmol). The mixture was stirred at the same temperature for 10 mins, after which 3-(bromomethyl)benzaldehyde (0.16 g, 0.81 mmol) was added. The mixture was warmed to RT and stirred for 2 hr after which it was partitioned between EtOAc and water. The organics were separated, and the aqueous layer was further extracted with EtOAc (×2). The combined organics were dried over Na₂SO₄ and concentrated. The residue was purified by flash column chromatography (reversed phase, C18) under a gradient of MeCN (0-74%) in water to afford methyl 4-((S)-1-((R)-2-((3-formylbenzyl)oxy)-3-methylbutanamido)ethyl)benzoate (0.14 g, 0.35 mmol, 66% yield) as an off-white solid. (LC/MS Method D): m/z 398 [M+H]⁺ (ES⁺), at 2.46 min, UV active.

Step (ii): To a solution of methyl 4-((S)-1-((R)-2-((3-formylbenzyl)oxy)-3-methylbutanamido)ethyl)benzoate (0.13 g, 0.33 mmol) in 1,4-dioxane (1 mL) and water (0.5 mL) was added lithium hydroxide monohydrate (70 mg, 1.64 mmol). The mixture was stirred at RT for 2 hrs, after which it was acidified to pH 1 with 1 N HCl and partitioned between EtOAc and water. The organics were separated, the acidic aqueous layer was further extracted with EtOAc (×2) and the combined organics were concentrated to afford 4-((S)-1-((R)-2-((3-formylbenzyl)oxy)-3-methylbutanamido)ethyl)benzoic acid (0.13 g, 0.33 mmol, 100% yield) as an off-white solid. (LC/MS Method D): m/z 384 [M+H]⁺ (ES⁺), at 2.15 min, UV active.

Step (iii): To a solution of 4-((S)-1-((R)-2-((3-formylbenzyl)oxy)-3-methylbutanamido) ethyl)benzoic acid (0.12 g, 0.31 mmol) in MeOH (3 mL) at 0° C. was added NaBH₄ (0.12 g, 0.31 mmol). The mixture was stirred at RT for 1 hr, after which it was acidified to pH 1 with 1 N HCl and partitioned between EtOAc and water. The organics were separated, and the acidic aqueous layer was further extracted with EtOAc. The combined organics were concentrated and the residue was purified by flash column chromatography (reversed phase, C18) under a gradient of MeCN (0-35%) in water to afford Example 45, 4-((S)-1-((R)-2-((3-(hydroxymethyl)benzyl)oxy)-3-methylbutanamido)ethyl)benzoic acid (60 mg, 0.16 mmol, 50% yield) as a white solid. Data available in Table 2.

Route J

Procedure for the Preparation of Example 47, 4-((1S)-1-(3-methyl-2-((4-(oxetan-3-yl)benzyl)oxy)butanamido)ethyl)benzoic acid

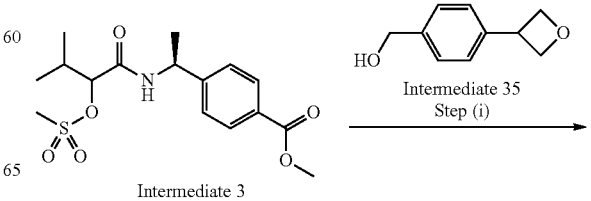

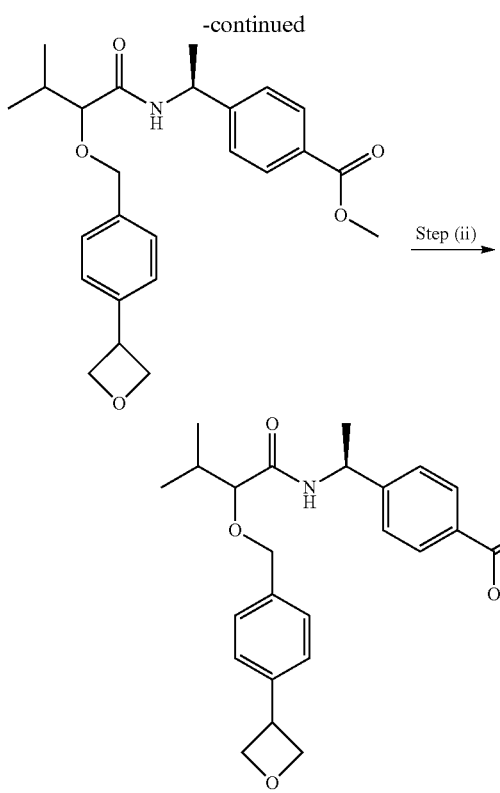

Example 47

Step (i): Intermediate 35, (4-(oxetan-3-yl)phenyl)methanol (0.30 g, 1.82 mmol) was added to a stirred suspension of NaH (~60% in mineral oil) (0.08 g, 2.01 mmol) in DMF (3 mL) at 0° C. under nitrogen atmosphere and reaction mixture was stirred at room temperature for 15 min. Intermediate 3, methyl 4-((1S)-1-(3-methyl-2-((methylsulfonyl) oxy)butanamido)ethyl)benzoate (0.91 g, 2.56 mmol) was then added and the reaction mixture was allowed to stir at room temperature for 2 hrs. The reaction mixture was quenched with saturated aqueous $NH_4Cl$ solution (3 mL) and the reaction mixture was partitioned between water (70 mL) and EtOAc (60 mL). The aqueous layer was further extracted with EtOAc (2×25 mL). Organic layers were combined and dried ($Na_2SO_4$). Solvent was removed in vacuo and the crude product was purified by reverse phase gradient flash column chromatography (reverse phase, C18 silica), product eluted at 0% to 57% ACN in water to afford crude methyl 4-((1S)-1-(3-methyl-2-((4-(oxetan-3-yl)benzyl)oxy)butanamido) ethyl)benzoate (011 g, 15%) as a yellow sticky solid. (LC/MS Method D): m/z 426 [M+H]$^+$ (ES$^+$), at 2.17 and 2.21 min, UV active.

Step (ii): To a solution of methyl 4-((1S)-1-(3-methyl-2-((4-(oxetan-3-yl)benzyl)oxy)butanamido) ethyl)benzoate (0.11 g, 0.27 mmol) in Dioxane (1.0 mL) and water (1.0 mL) was added LiOH monohydrate (0.034 g, 0.81 mmol) at room temperature and the reaction mixture was allowed to stir at room temperature for 3 hrs. The reaction mixture was then acidified with glacial acetic acid (0.3 mL) to adjust to pH ~4 and concentrated in vacuo. The obtained crude product was purified by reverse phase gradient flash column chromatography (reverse phase, C18 silica), product was eluted at 0% to 35% ACN in water to afford pure Example 47, 4-((1S)-1-(3-methyl-2-((4-(oxetan-3-yl)benzyl)oxy)butanamido) ethyl)benzoic acid (0.042 g, 39%) as a white solid. Data available in Table 2.

Route K

Procedure for the Preparation of Example 48, 4-((1S)-1-(3-methyl-2-((3-(oxetan-3-yl)benzyl)oxy) butanamido)ethyl)benzoic acid, diastereomer 1, and Example 49, 4-((1S)-1-(3-methyl-2-((3-(oxetan-3-yl)benzyl)oxy)butanamido)ethyl)benzoic acid, Diastereomer 2

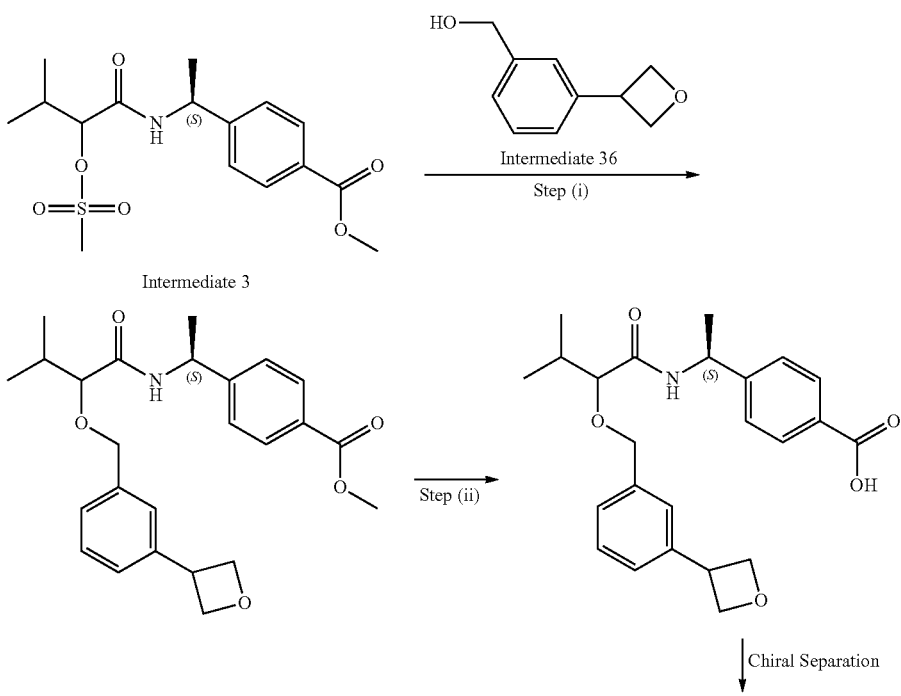

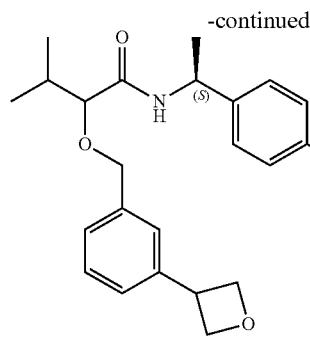

Example 48

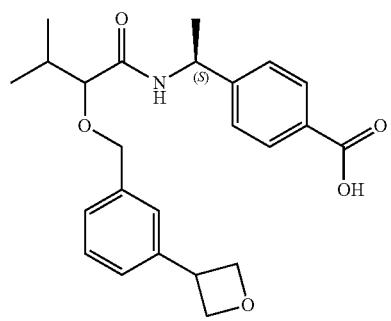

Example 49

Step (i): A solution of Intermediate 36, (3-(oxetan-3-yl)phenyl) methanol (0.10 g, 0.60 mmol) in THF (1 mL) was added to a stirred suspension of potassium tert-butoxide (0.20 g, 1.82 mmol) in THF (2 mL) at room temperature, under a nitrogen atmosphere, and the reaction mixture was stirred for 15 min. Intermediate 3, methyl 4-((1S)-1-(3-methyl-2-((methylsulfonyl)oxy)butanamido)ethyl)benzoate (0.32 g, 0.91 mol) was added and the reaction mixture was allowed to stir at room temperature for 3 hrs. The reaction mixture was partitioned between water (30 mL) and EtOAc (50 mL). The aqueous layer was further extracted with EtOAc (2×30 mL). The organic layers were combined and dried (Na$_2$SO$_4$), the solvent was removed in vacuo and the crude product was purified by reverse phase gradient flash column chromatography (reverse phase, C18 silica), product eluted at 0% to 67% ACN in water to afford pure methyl 4-((1S)-1-(3-methyl-2-((3-(oxetan-3-yl)benzyl) oxy)butanamido)ethyl)benzoate (0.060 g, 16%) as colorless sticky solid. (LC/MS Method D): m/z 426 [M+H]$^+$ (ES$^+$), at 2.15 min, UV active.

Step (ii): LiOH monohydrate (0.030 g, 0.70 mmol) was added to a solution of methyl 4-((1S)-1-(3-methyl-2-((3-(oxetan-3-yl)benzyl) oxy)butanamido)ethyl) benzoate (0.060 g, 0.14 mmol) in dioxane (1.0 mL) and water (0.5 mL) at room temperature and the reaction mixture was allowed to stir at room temperature for 3 hrs. The reaction mixture was then acidified with glacial acetic acid (0.3 mL) to adjust to pH ~4 and concentrated in vacuo. The obtained crude product was purified by reverse phase gradient flash column chromatography (reverse phase, C18 silica), product was eluted at 0% to 56% ACN in water to afford pure 4-((1S)-1-(3-methyl-2-((3-(oxetan-3-yl)benzyl)oxy)butanamido)ethyl)benzoic acid (0.045 g, 78%) as a colourless, sticky solid. (LC/MS Method D): m/z 412 [M+H]$^+$ (ES$^+$), at 1.87 & 1.89 min, UV active.

Diastereomer Separation: 4-((1S)-1-(3-Methyl-2-((3-(oxetan-3-yl)benzyl)oxy)butanamido)ethyl)benzoic acid was separated into single diastereomers via chiral preparative HPLC [Chiralpak IG SFC, 21×250 mm, 5 µm, 16 mL per min; Gradient [time (min)/solvent B in A (%)]: 0.01/20, 45.00/20; Solvents: solvent A=n-heptane; solvent B=methanol:IPA (30:70)] to afford Example 47, 4-((1S)-1-(3-methyl-2-((3-(oxetan-3-yl)benzyl)oxy)butanamido) ethyl)benzoic acid; diastereomer 1, (0.010 g, 22%) as an off-white solid, and Example 48, 4-((1S)-1-(3-methyl-2-((3-(oxetan-3-yl)benzyl)oxy) butanamido)ethyl)benzoic acid; diastereomer 2, (0.0091 g, 20%) as a white solid. Data available in Table 2.

Route L

Procedure for the Preparation of Example 38, 4-((S)-1-((R)-2-((3-hydroxybenzyl)oxy)-3-methylbutanamido)ethyl)benzoic acid

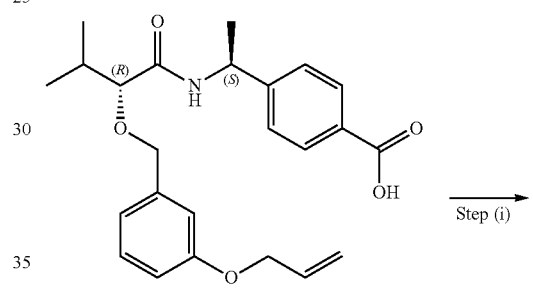

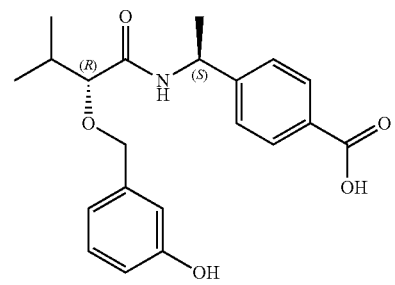

Example 38

Step (i): K$_2$CO$_3$ (0.08 g, 0.58 mmol) and Pd(PPh$_3$)$_4$ (0.017 g, 0.014 mmol) was added to a solution of 4-((S)-1-((R)-2-((3-(allyloxy)benzyl)oxy)-3-methylbutanamido)ethyl)-benzoic acid (0.12 g, 0.29 mmol) in dichloromethane (2 mL) and methanol (2 mL) at room temperature. The reaction was then heated to 50° C. for 4 hrs. The reaction mixture was concentrated in vacuo to obtain crude product which was purified by two times reverse phase gradient flash column chromatography (reverse phase, C18 silica), product was eluted at 0% to 56% ACN in 0.1% FA in water to afford pure Example 38, 4-((S)-1-((R)-2-((3-hydroxybenzyl)oxy)-3-methylbutanamido)ethyl)-benzoic acid (0.045 g, 40%) as an off white solid. Data available in Table 2.

Route M

Procedure for the Preparation of Example 51, 4-((1S)-1-((2R)-3-methyl-2-(1-(4-(trifluoromethyl)phenyl)ethoxy)butanamido)ethyl)benzoic acid

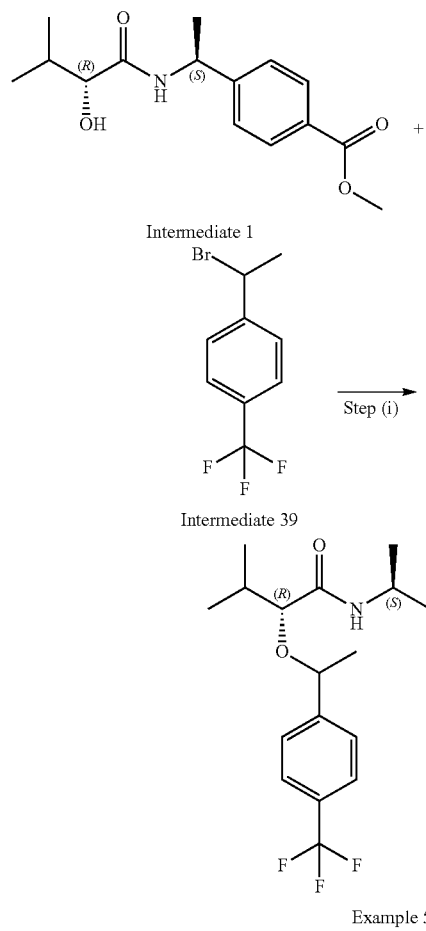

Step (i): Intermediate 1, methyl 4-((S)-1-((R)-2-hydroxy-3-methylbutanamido) ethyl)benzoate (0.20 g, 0.71 mmol) was added to a stirred suspension of NaH (~60% in mineral oil) (0.034 g, 0.85 mmol) in DMF (4 mL) at 0° C. under nitrogen atmosphere and the reaction mixture was stirred at 0° C. for 10 min. After this time, Intermediate 39, 1-(1-bromoethyl)-4-(trifluoromethyl)benzene (0.27 g, 1.07 mmol) was added and the reaction mixture was stirred at room temperature for 4 hrs. The reaction mixture was then partitioned between saturated aqueous $NH_4Cl$ solution (40 mL) and EtOAc (30 mL). The aqueous layer was further extracted with EtOAc (2×50 mL). The organic layers were combined and dried ($Na_2SO_4$), the solvent removed in vacuo and the crude product was purified by reverse phase gradient flash column chromatography (reverse phase, C18 silica), product eluted at 0% to 46% ACN in water to afford crude product which was further purified by Prep-TLC using 70% EtOAc: Hexane to yield pure Example 51, 4-((1S)-1-((2R)-3-methyl-2-(1-(4-(trifluoromethyl)phenyl)ethoxy) butanamido)ethyl)benzoic acid: (0.020 g, 6.4%) as a brown sticky solid. Data available in Table 2.

Route N

Procedure for the Preparation of Example 53, 4-((S)-1-((R)-3-methyl-2-((4-(trifluoromethyl)benzyl)oxy)butanamido)ethyl)-N-(methylsulfonyl)benzamide

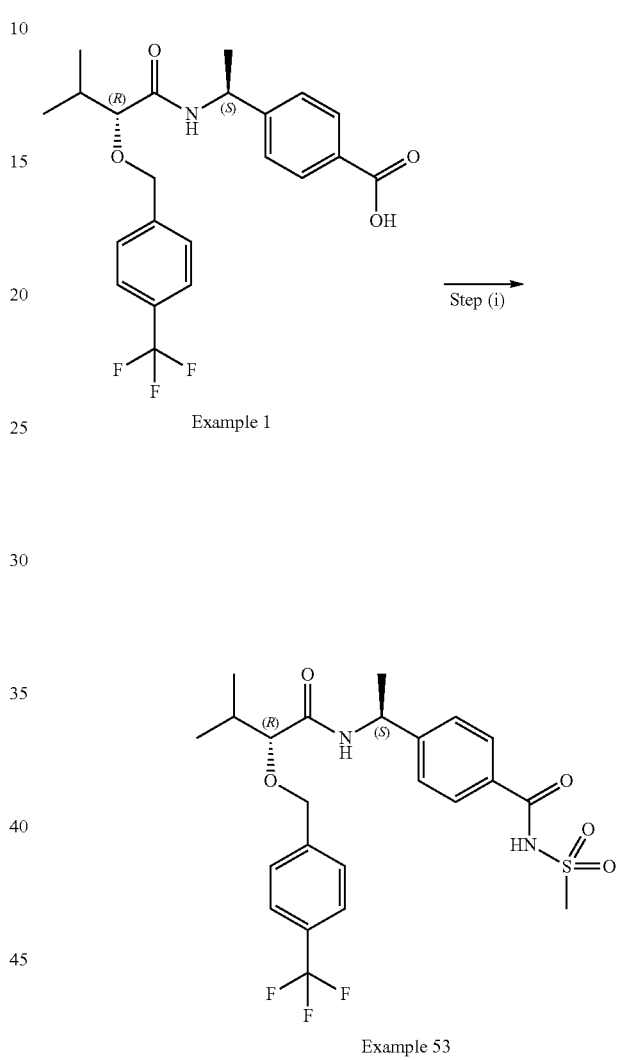

Step (i): To a solution of Example 1, 4-[(1S)-1-[[(2R)-3-methyl-2-[[4-(trifluoromethyl)phenyl]methoxy]butanoyl]amino]ethyl]benzoic acid (150 .mg, 0.350 mmol), DMAP (129.84 mg, 1.06 mmol) and EDCI (101.86 mg, 0.530 mmol) in DCM (1.5 mL) was added methanesulfonamide (84.24 mg, 0.890 mmol). The mixture was stirred at RT for 3 days after which it was diluted with DCM. the mixture was washed with water and brine, dried (frit) and concentrated. The crude material was purified by reverse phase HPLC (Gilson Semi Preparative HPLC System, Gemini-NX, 5µ, C18, 100×30 mm) eluted at 5-85% ACN in Water with 0.2% of 28% Ammonia solution to afford Example 53, N-methylsulfonyl-4-[(1S)-1-[[(2R)-3-methyl-2-[[4-(trifluoromethyl)phenyl]methoxy]butanoyl]amino]ethyl]benzamide (99 mg, 56% yield) as a colourless oil. Data available in Table 2.

Route O

Procedure for the Preparation of Example 73, (R)-4-(1-(3-methyl-2-((4-(trifluoromethyl)benzyl)oxy)butanamido)cyclobutyl)benzoic acid

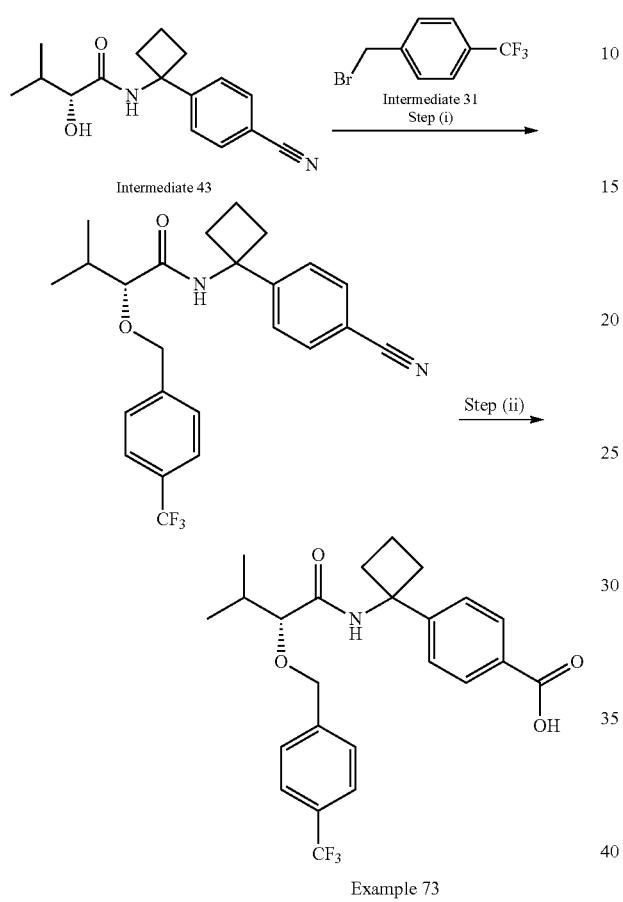

Example 73

Step (i): To an ice cooled solution of Intermediate 43, (2R)—N-[1-(4-cyanophenyl)cyclobutyl]-2-hydroxy-3-methyl-butanamide (109 mg, 0.400 mmol) and potassium tert-butoxide (49.4 mg, 0.440 mmol) was added Intermediate 31, 4-(trifluoromethyl)benzyl bromide (105 mg, 0.440 mmol) and the reaction mixture stirred for 4 hours at RT. The reaction mixture was partitioned between ethyl acetate and water after which the organics were separated, washed with brine, dried (frit.) and concentrated. The residue was purified by flash column chromatography (normal phase, [5.9×2.0 cm (10 g)], Biotage® SNAP KP-Sil—50 μm irregular silica, 30 mL per min, [gradient 0% to 50% Ethyl Acetate in Iso-hexane], to afford (R)—N-(1-(4-cyanophenyl)cyclobutyl)-3-methyl-2-((4-(trifluoromethyl)benzyl)oxy)butanamide (109 mg, 63% yield) as a colourless oil. (LC/MS Method B): m/z 431 [M+H]$^+$ (ES$^+$), at 1.76 min, UV active.

Step (ii): A suspension of (R)—N-(1-(4-cyanophenyl)cyclobutyl)-3-methyl-2-((4-(trifluoromethyl)benzyl)oxy)butanamide (109 .mg, 0.250 mmol) in 5M (aq) sodium hydroxide (0.8 mL, 4 mmol) and Ethanol (0.42 mL) was heated to reflux for 18 hours after which it was concentrated. The crude material was partitioned between ethyl acetate and 1 M HCl, dried (frit.) and concentrated. The crude material was purified by reverse phase HPLC under basic conditions (Gilson Semi Preparative HPLC System, Gemini-NX, 5μ, C18, 100×30 mm) eluted at 50-80% ACN in Water with 0.2% of 28% Ammonia solution to afford Example 73, (R)-4-(1-(3-methyl-2-((4-(trifluoromethyl)benzyl)oxy)butanamido)cyclobutyl)benzoic acid (3 mg, 2.6% yield) which was scratched to give a white solid. Data available in Table 2.

Route P

Procedure for the Preparation of Example 92, 4-((1S)-1-(2-cyclobutyl-2-((4-(trifluoromethyl)benzyl)oxy)acetamido)ethyl)benzoic acid, Example 93, 4-((1S)-1-(2-cyclobutyl-2-((4-(trifluoromethyl)benzyl)oxy)acetamido)ethyl)benzoic acid, Diastereomer 1, and Example 94, 4-((1S)-1-(2-cyclobutyl-2-((4-(trifluoromethyl)benzyl)oxy)acetamido)ethyl)benzoic acid, Diastereomer 2

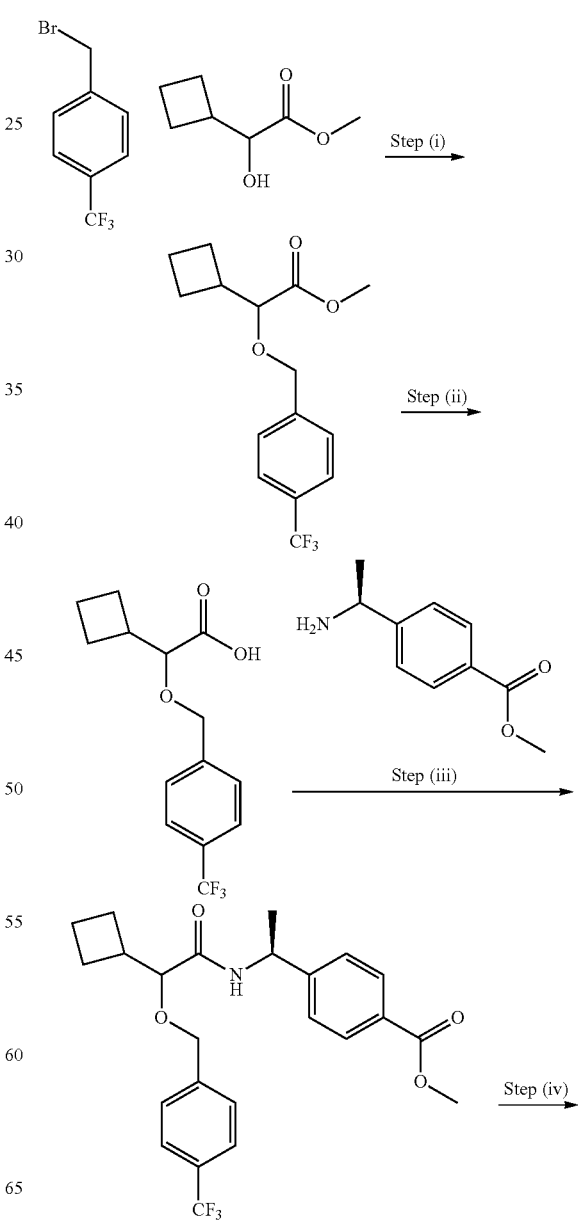

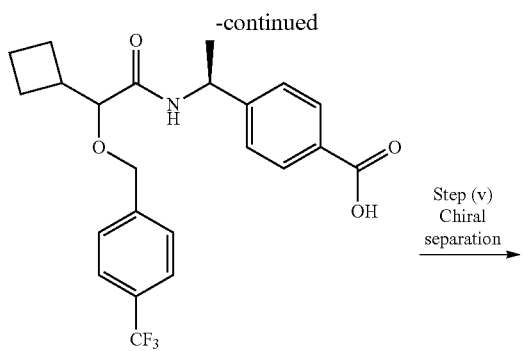

Example 92

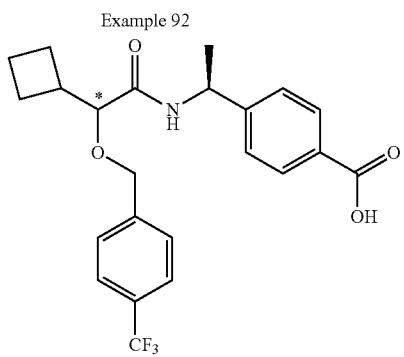

Example 93

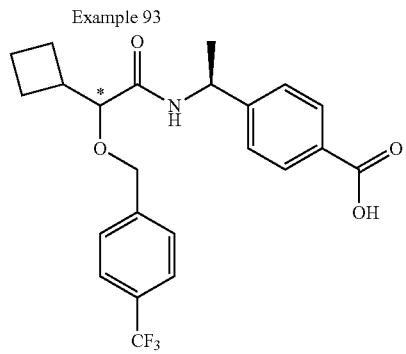

Example 94

Step (i): To an ice cooled solution of methyl 2-cyclobutyl-2-hydroxy-acetate (100 mg, 0.69 mmol) and potassium tert-butoxide (85 mg, 0.76 mmol) in DMF (3.5 mL) was added 4-(trifluoromethyl)benzyl bromide (182 mg, 0.76 mmol) and the reaction mixture warmed to RT and stirred for 18 hrs. The reaction mixture was partitioned between EtOAc and water after which the organics were separated, washed with brine, dried via passage through a hydrophobic frit and concentrated. The crude material was purified by flash column chromatography (normal phase) [gradient 0-40% EtOAc in Iso-hexane] to afford methyl 2-cyclobutyl-2-((4-(trifluoromethyl)benzyl)oxy)acetate (79 mg, 0.26 mmol, 38%) as a colourless oil. LC/MS (Method B): m/z 303 [M+H]$^+$ (ES$^+$), at 1.79 min, UV active.

Step (ii): To a suspension of methyl 2-cyclobutyl-2-((4-(trifluoromethyl)benzyl)oxy)acetate (79 mg, 0.26 mmol) in 1,4-dioxane (0.6 mL) and water (0.6 mL) was added lithium hydroxide monohydrate (44 mg, 1.06 mmol). The reaction mixture was stirred at RT for 18 hrs then concentrated. The crude material was partitioned between 1 M HCl (aq.) and EtOAc and the organics separated. The aqueous layer was further extracted with EtOAc and the combined organics were dried via passage through a hydrophobic frit and concentrated to afford 2-cyclobutyl-2-((4-(trifluoromethyl)benzyl)oxy)acetic acid (76 mg, 0.26 mmol, quantitative) as a colourless oil. The crude material was used without any further purification. LC/MS (Method B): m/z 311 [M+Na]$^+$ (ES$^+$), at 0.68 min, UV active.

Step (iii): Methyl 4-[(1S)-1-aminoethyl]benzoate (51 mg, 0.29 mmol), 2-cyclobutyl-2-((4-(trifluoromethyl)benzyl)oxy)acetic acid (76 mg, 0.26 mmol), EDC (76 mg, 0.40 mmol) and HOBt monohydrate (4 mg, 0.03 mmol) were dissolved in DCM (0.8 mL) after which the reaction mixture was stirred for 10 minutes at RT. Triethylamine (0.09 mL, 0.66 mmol) was added dropwise at 0° C. and the reaction mixture warmed to RT and stirred for 18 hrs. The reaction mixture was partitioned between water and EtOAc and the organics separated, washed with 1 M HCl (aq.), saturated NaHCO$_3$ (aq.) and brine. The organics were dried via passage through a hydrophobic frit and concentrated. The crude material was purified by flash column chromatography (normal phase) [gradient 0-50% EtOAc in Iso-hexane] to afford methyl 4-((1 S)-1-(2-cyclobutyl-2-((4-(trifluoromethyl)benzyl)oxy)acetamido)ethyl)benzoate (82 mg, 0.18 mmol, 69%) as a white solid. LC/MS (Method B): m/z 450 [M+H]$^+$ (ES$^+$), at 1.77 min, UV active.

Step (iv): To a suspension of methyl 4-((1S)-1-(2-cyclobutyl-2-((4-(trifluoromethyl)benzyl)oxy)acetamido)ethyl)benzoate (82 mg, 0.18 mmol) in 1,4-dioxane (0.5 mL) and water (0.5 mL) was added lithium hydroxide monohydrate (30 mg, 0.73 mmol).

The reaction mixture was stirred at RT for 18 hrs then concentrated. The crude material was partitioned between 1 M HCl (aq.) and EtOAc and the organics separated. The aqueous layer was further extracted with EtOAc and the combined organics were dried via passage through a hydrophobic frit and concentrated. The crude material was purified by flash column chromatography (normal phase) [gradient 0-6% MeOH in DCM (0.1% acetic acid)]isolating Example 92, racemic 4-((1S)-1-(2-cyclobutyl-2-((4-(trifluoromethyl)benzyl)oxy)acetamido)ethyl)benzoic acid as a white solid. Data available in Table 2.

Step (v): Example 92, racemic 4-((1S)-1-(2-cyclobutyl-2-((4-(trifluoromethyl)benzyl)oxy)acetamido)ethyl)benzoic acid was separated into single diastereomers via chiral preparative SFC [Phenomenex Lux Amylose-1, 250×21.2 mm, 5 µm] and isocratic conditions CO$_2$:EtOH (0.1% NH$_3$) 80:20 to afford Example 93, 4-((1S)-1-(2-cyclobutyl-2-((4-(trifluoromethyl)benzyl)oxy)acetamido)ethyl)benzoic acid (19 mg, 0.04 mmol, 46%) as a white solid and Example 94, 4-((1S)-1-(2-cyclobutyl-2-((4-(trifluoromethyl)benzyl)oxy) acetamido)ethyl)benzoic acid (19 mg, 0.04 mmol, 46%) as a white solid. Data available in Table 2.

Route Q

Procedure for the Preparation of Example 95, 4-(1-(2-cyclobutyl-2-((3-(methylsulfonyl)benzyl)oxy) acetamido)cyclopropyl)benzoic acid

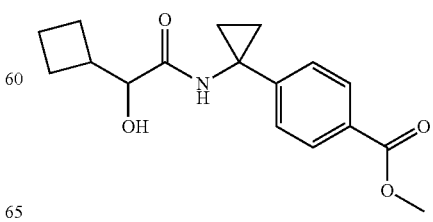

Intermediate 58

89

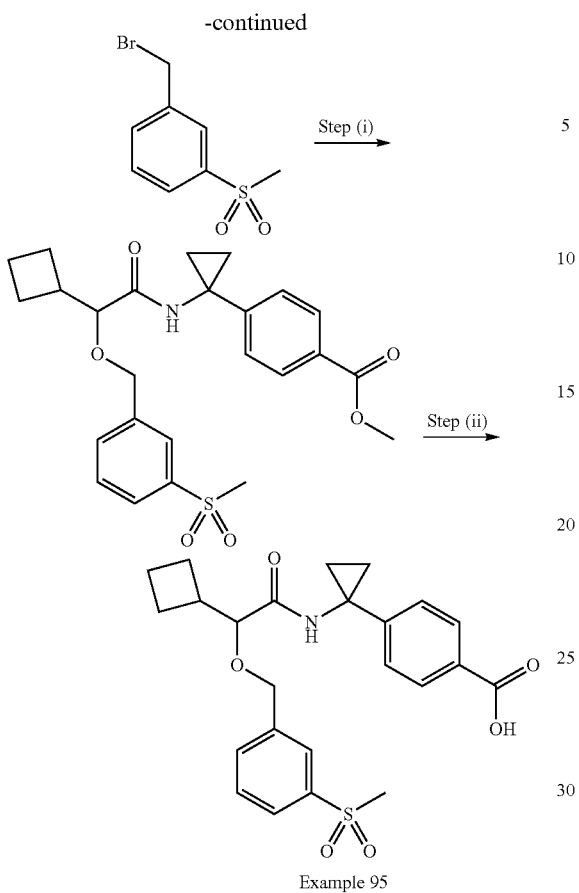

Example 95

Step (i): To an ice cooled solution of intermediate 58, methyl 4-(1-(2-cyclobutyl-2-hydroxyacetamido)cyclopropyl)benzoate (150 mg, 0.49 mmol) and potassium tert-butoxide (61 mg, 0.54 mmol) in DMF (3.3 mL) was added 1-(bromomethyl)-3-methylsulfonyl-benzene (135 mg, 0.54 mmol) and the reaction mixture warmed to RT and stirred for 18 hrs. The reaction mixture was partitioned between EtOAc and water and the organics were separated, washed with brine, dried via passage through a hydrophobic frit and concentrated. The crude material was purified by reverse phase HPLC under basic conditions (Gilson Semi Preparative HPLC System, Gemini-NX, 5μ, C18, 100×30 mm) eluted at 40-70% ACN in water with 0.2% of 28% ammonia solution to afford methyl 4-(1-(2-cyclobutyl-2-((3-(methylsulfonyl)benzyl)oxy)acetamido)cyclopropyl)benzoate (34 mg, 0.07 mmol, 14%) as a white solid. LC/MS (Method B): m/z 472 [M+H]+ (ES+), at 1.35 min, UV active.

Step (ii): To a suspension of methyl 4-(1-(2-cyclobutyl-2-((3-(methylsulfonyl)benzyl)oxy)acetamido)cyclopropyl)benzoate (34 mg, 0.07 mmol) in 1,4-dioxane (0.2 mL) and water (0.2 mL) was added lithium hydroxide monohydrate (12 mg, 0.29 mmol). The reaction mixture stirred at RT for 18 hrs then concentrated. The crude material was partitioned between 1 M HCl (aq.) and EtOAc and the organics separated. The aqueous layer was further extracted with EtOAc and the combined organics were dried via passage through a hydrophobic frit and concentrated. The crude material was purified by flash column chromatography (normal phase) [gradient: 0-6% MeOH in DCM (0.1% acetic acid)] to afford Example 95, 4-(1-(2-cyclobutyl-2-((3-(methylsulfonyl)ben-

90 zyl)oxy)acetamido)cyclopropyl)benzoic acid (20 mg, 0.04 mmol, 60%) as a white solid. Data available in Table 2.

Route R

Procedure for the Preparation of Example 99, 4-(1-(2-cyclobutyl-2-((3-(difluoromethoxy)benzyl)oxy)acetamido)cyclopropyl)benzoic acid, Example 100, (S)-4-(1-(2-cyclobutyl-2-((3-(difluoromethoxy)benzyl)oxy)acetamido)cyclopropyl)benzoic acid, and Example 101, (R)-4-(1-(2-cyclobutyl-2-((3-(difluoromethoxy)benzyl)oxy)acetamido)cyclopropyl)benzoic acid

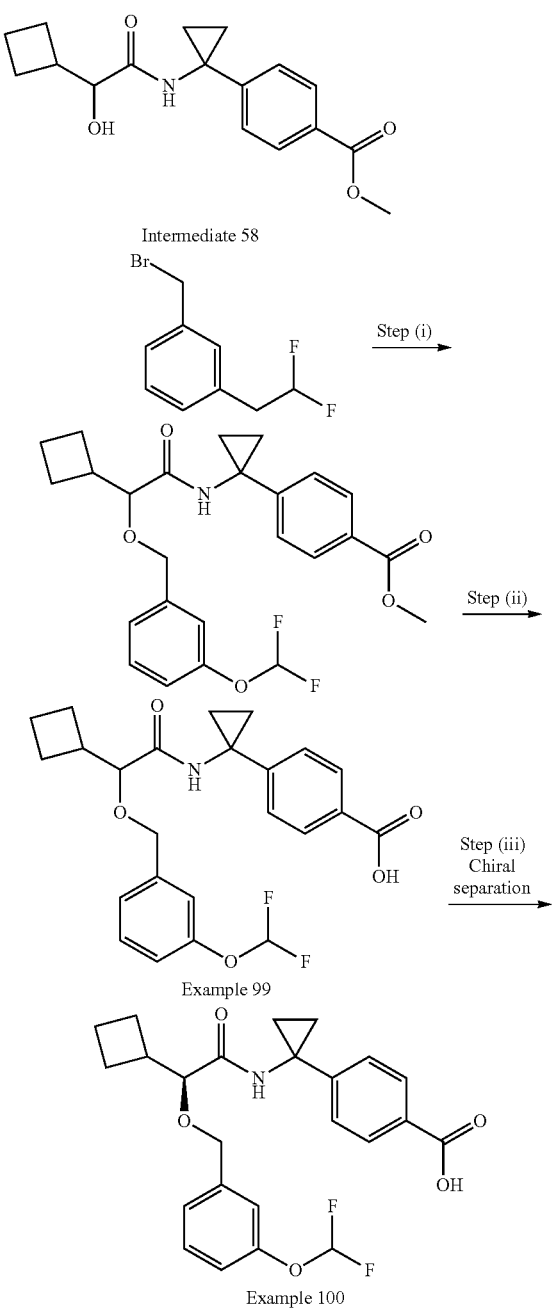

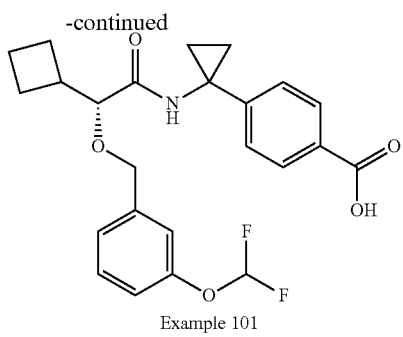

Example 101

Step (i): To an ice cooled solution of intermediate 58, methyl 4-(1-(2-cyclobutyl-2-hydroxyacetamido)cyclopropyl)benzoate (150 mg, 0.49 mmol) and potassium tert-butoxide (61 mg, 0.54 mmol) in DMF (3.3 mL) was added 1-(bromomethyl)-3-(difluoromethoxy)benzene (128 mg, 0.54 mmol) and the reaction mixture warmed to RT and stirred for 18 hrs. The reaction mixture was partitioned between EtOAc and water after which the organics were separated, washed with brine, dried via passage through a hydrophobic frit and concentrated. The crude material was purified by flash column chromatography (normal phase) [gradient 0-60% EtOAc in Iso-hexane] to afford methyl 4-(1-(2-cyclobutyl-2-((3-(difluoromethoxy)benzyl)oxy)acetamido)cyclopropyl)benzoate (130 mg, 0.28 mmol, 57%) as a colourless oil. LC/MS (Method B): m/z 460 [M+H]$^+$ (ES$^+$), at 1.62 min, UV active.

Step (ii): To a suspension of methyl 4-(1-(2-cyclobutyl-2-((3-(difluoromethoxy)benzyl)oxy)acetamido)cyclopropyl)benzoate (276 mg, 0.60 mmol) in 1,4-dioxane (1.5 mL) and water (1.5 mL) was added lithium hydroxide monohydrate (100 mg, 2.40 mmol). The reaction mixture stirred at RT for 18 hrs then concentrated. The crude material was partitioned between 1 M HCl (aq.) and EtOAc and the organics separated. The aqueous layer was further extracted with EtOAc and the combined organics were dried via passage through a hydrophobic frit and concentrated. The crude material was purified by reverse phase HPLC under basic conditions (Gilson Semi Preparative HPLC System, Gemini-NX, 5μ, C18, 100×30 mm) eluted at 15-25% ACN in water with 0.2% of 28% ammonia solution to afford Example 99, racemic 4-(1-(2-cyclobutyl-2-((3-(difluoromethoxy)benzyl)oxy)acetamido)cyclopropyl)benzoic acid (146 mg, 0.33 mmol, 54%) as a white solid. Data available in Table 2.

Step (iii): Example 99, racemic 4-(1-(2-cyclobutyl-2-((3-(difluoromethoxy)benzyl)oxy)acetamido)cyclopropyl)benzoic acid was separated using chiral preparative SFC [Phenomenex Lux Amylose-1, 250×21.2 mm, 5 μm] and isocratic conditions CO$_2$:IPA 70:30 to afford Example 100, (S)-4-(1-(2-cyclobutyl-2-((3-(difluoromethoxy)benzyl)oxy)acetamido)cyclopropyl)benzoic acid (47 mg, 0.33 mmol, 34%) as a white solid and Example 101, (R)-4-(1-(2-cyclobutyl-2-((3-(difluoromethoxy)benzyl)oxy)acetamido)cyclopropyl)benzoic acid (47 mg, 0.33 mmol, 34%) as a white solid. Data available in Table 2. Analytical SFC (Method J) of Example 100 (1.99 min) and Example 101 (2.05 min) was used to show this batch of Example 101 prepared using route R matched the batch of Example 101 (2.04 min) prepared using route S.

Route S

Alternative Procedure for the Preparation of Example 101, (R)-4-(1-(2-cyclobutyl-2-((3-(difluoromethoxy)benzyl)oxy)acetamido)cyclopropyl)benzoic acid

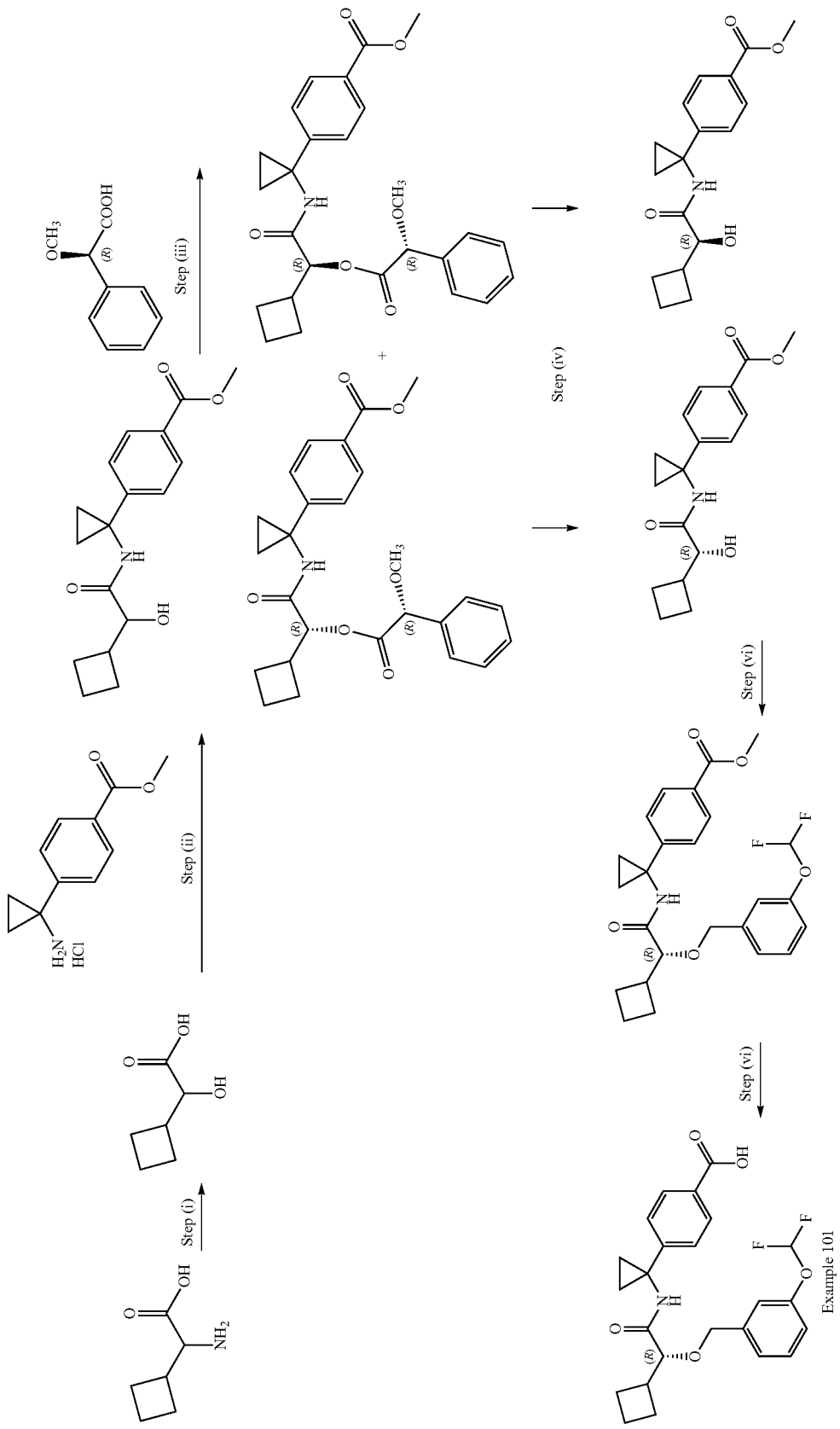

Step (i): To a solution of 2-amino-2-cyclobutylacetic acid (10.0 g, 77.5 mmol) in water (100 mL) and aqueous H$_2$SO$_4$ solution (0.5 M, 180 mL) at 0° C. was added sodium nitrite (32 g, 465.1 mmol) and the reaction mixture warmed to RT and stirred for 16 hrs. The reaction mixture was partitioned between water and THF. The aqueous layer was four times further extracted with THF. The combined organic layers were dried (Na$_2$SO$_4$) and concentrated. The crude residue was washed with EtOAc and the filtrate concentrated to afford crude 2-cyclobutyl-2-hydroxyacetic acid (8.0 g, 61.5 mmol, 79%) as a yellow liquid. This material was used without further purification.

Step (ii): To a suspension of 2-cyclobutyl-2-hydroxyacetic acid (6.88 g, 52.8 mmol) and methyl 4-(1-aminocyclopropyl)benzoate hydrochloride (8.0 g, 35.2 mmol) in ACN (70 mL) at 0° C. was added HATU (20.1 g, 52.8 mmol) and allowed to stir at 0° C. for 15 min, after which, DIPEA (18.4 mL, 105.7 mmol) was added. The reaction mixture was warmed to RT and stirred for 16 hrs, then concentrated. The crude residue was purified by reverse-phase gradient flash column chromatography (reverse phase, C18 silica), product eluted at 0% to 56% ACN in water to afford methyl 4-(1-(2-cyclobutyl-2-hydroxyacetamido) cyclopropyl)benzoate (2.9 g, 9.6 mmol, 47%) as a brown solid. LC/MS (Method D): m/z 304 [M+H]$^+$ (ES$^+$), at 1.51 min, UV active.

Step (iii): To a solution of methyl 4-(1-(2-cyclobutyl-2-hydroxyacetamido) cyclopropyl)benzoate (5.0 g, 16.5 mmol) in DCM (50 mL) was added (R)-2-methoxy-2-phenylacetic acid (3 g, 18.14 mmol), N,N'-dicyclohexylcarbodiimide (4.08 g, 19.8 mmol) and DMAP (0.40 g, 3.29 mmol). The reaction mixture was stirred at RT for 16 hrs, then partitioned between water and DCM. The aqueous layer was twice more extracted with DCM. The combined organics were dried (Na$_2$SO$_4$) and concentrated. The crude residue was purified by normal phase gradient flash column chromatography (Normal phase, silica), product eluted at 0% to 95% diethyl ether in petroleum ether to afford methyl 4-(1-((R)-2-cyclobutyl-2-((R)-2-methoxy-2-phenylacetoxy) acetamido) cyclopropyl)benzoate (2.6 g, 5.76 mmol, 35%) as a white solid and methyl 4-(1-((S)-2-cyclobutyl-2-((R)-2-methoxy-2-phenylacetoxy)acetamido)cyclopropyl) benzoate (1.0 g, 2.22 mmol, 13%) as a white solid. LC/MS (Method I): m/z 453 [M+H]$^+$ (ES$^+$), at 8.13 min, UV active.

Step (iv): To a solution of methyl 4-(1-((R)-2-cyclobutyl-2-((R)-2-methoxy-2-phenylacetoxy)acetamido) cyclopropyl) benzoate (2.6 g, 5.76 mmol) in water (5 mL) and MeOH (5 mL) was added K$_2$CO$_3$ (1.19 g, 8.64 mmol) and the resulting solution stirred at RT for 3 hrs. The reaction mixture was partitioned between water and EtOAc and the aqueous layer was twice further extracted with EtOAc. The combined organic layers were dried (Na$_2$SO$_4$) and concentrated to afford methyl (R)-4-(1-(2-cyclobutyl-2-hydroxyacetamido)cyclopropyl) benzoate (1.90 g, 6.27 mmol, quantitative) as an off-white solid. LC/MS (Method D): m/z 304 [M+H]$^+$ (ES$^+$), at 1.52 min, UV active. Chiral HPLC (Method K) used to determine the stereochemical configuration of R enantiomer (12.06 min) and S enantiomer (10.35 min) by comparison with the known R enantiomer (12.15 min) synthesized using (R)-2-cyclobutylglycine in chiral Route T.

Step (v): Methyl (R)-4-(1-(2-cyclobutyl-2-hydroxyacetamido)cyclopropyl)benzoate (1.9 g, 6.26 mmol) was added to a stirred suspension of NaH (~60% in mineral oil, 0.27 g, 6.89 mmol) in DMF (10 mL) at 0° C. under nitrogen atmosphere. The reaction mixture was stirred at 0° C. for 30 min, followed by addition of 1-(bromomethyl)-3-(difluoromethoxy)benzene (1.78 g, 7.54 mmol). The reaction mixture was warmed to RT and stirred for 1 hrs, after which it was partitioned between water and EtOAc. The aqueous layer was twice further extracted with EtOAc. The combined organics were dried (Na$_2$SO$_4$) and concentrated. The crude residue was purified by reverse phase gradient flash column chromatography (reverse phase, C18 silica), product eluted at 0% to 56% ACN in water to afford methyl (R)-4-(1-(2-cyclobutyl-2-((3-(difluoromethoxy)benzyl)oxy) acetamido) cyclopropyl)benzoate (2.1 g, 4.57 mmol, 73%) as an off white solid. LC/MS (Method D): m/z 460 [M+H]$^+$ (ES$^+$), at 2.27 min, UV active.

Step (vi): To a solution of methyl (R)-4-(1-(2-cyclobutyl-2-((3-(difluoromethoxy) benzyl)oxy acetamido)cyclopropyl)benzoate (2.0 g, 4.35 mmol) in dioxane (5 mL) and water (3 mL), was added LiOH monohydrate (532 mg, 12.77 mmol). The reaction mixture was stirred at RT for 4 hrs, then acidified with glacial acetic acid to reach pH ~4 and concentrated. The crude residue was purified by reverse phase gradient flash column chromatography (reverse phase, C18 silica), product was eluted at 0% to 58% ACN in water to afford Example 101, (R)-4-(1-(2-cyclobutyl-2-((3-(difluoromethoxy)benzyl)oxy)acetamido)cyclopropyl) benzoic acid (1.29 g, 2.90 mmol, 67%) as a white solid. Chiral HPLC (Method K) 13.57 min. Data available in table 2.

Route T

Additional Alternative Procedure for the Preparation of Example 101, (R)-4-(1-(2-cyclobutyl-2-((3-(difluoromethoxy)benzyl)oxy)acetamido)cyclopropyl)benzoic acid

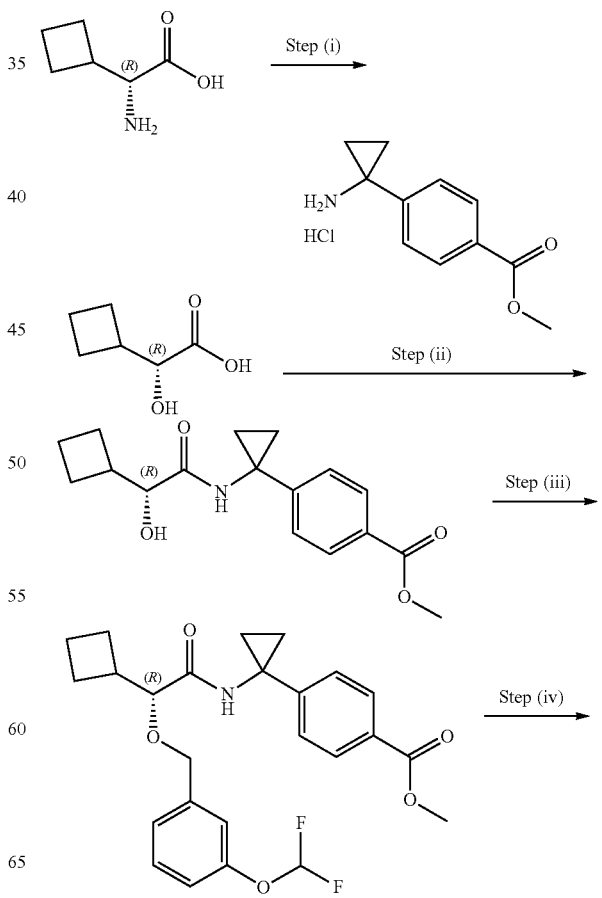

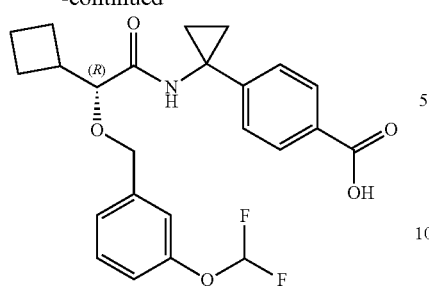

Example 101

A third route to preparing Example 101 is shown in the scheme above using steps i-iv, analogous to steps i-ii & v-vi shown in route S. Spectroscopic details were consistent with those given for Example 101 generated in route S.

General Synthetic Procedures for the Intermediates

Route 1

Procedure for the Preparation of Intermediate 1, methyl 4-((S)-1-((R)-2-hydroxy-3-methylbutanamido)ethyl)benzoate

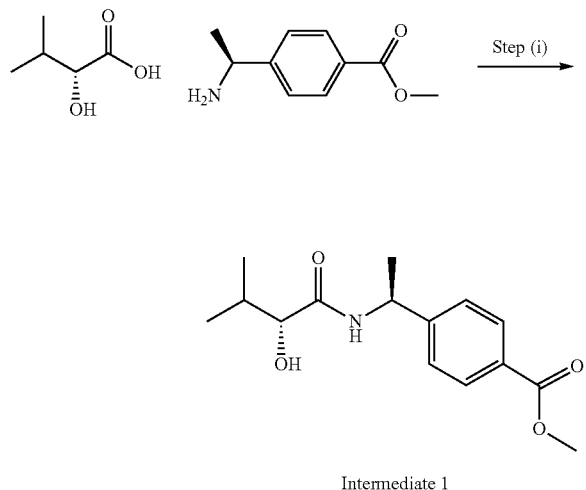

Intermediate 1

Step (i): To an ice-cooled solution of (2R)-2-hydroxy-3-methyl-butanoic acid (10.0 g, 84.7 mmol) and methyl (S)-4-(1-aminoethyl)benzoate (16.7 g, 93.1 mmol) in DMF (170 mL) was added EDC HCl (24.3 g, 127.0 mmol), ethyl (hydroxyimino)cyanoacetate (13.2 g, 93.1 mmol) and triethylamine (29.5 mL, 211.6 mmol). The mixture was stirred at RT for 18 hrs after which it was partitioned between EtOAc and water. The organics were separated, washed sequentially with 1 M HCl, sat. aq. NaHCO₃ and brine, dried over MgSO₄ and concentrated to afford Intermediate 1, methyl 4-((S)-1-((R)-2-hydroxy-3-methylbutanamido)ethyl)benzoate (12.8 g, 45.9 mmol, 54% yield) as an orange solid. Data available in Table 3.

Route 2

Procedure for the Preparation of Intermediate 2, methyl 4-((1S)-1-(2-hydroxy-3-methylbutanamido)ethyl)benzoate, and Intermediate 3, methyl 4-((1S)-1-(3-methyl-2-((methylsulfonyl)oxy)butanamido)ethyl)benzoate

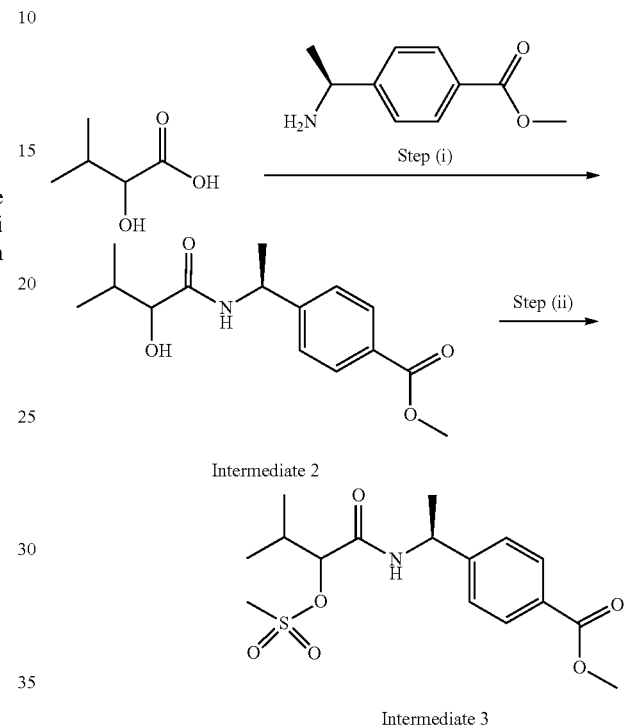

Intermediate 2

Intermediate 3

Step (i): To a solution of methyl (S)-4-(1-aminoethyl) benzoate (6.00 g, 33.5 mmol) and 2-hydroxy-3-methylbutanoic acid (4.35 g, 36.8 mmol) in DCM (100 mL) were added EDC HCl (9.62 g, 50.2 mmol) and HOBt (900 mg, 0.66 mmol). The mixture was stirred at RT for 10 mins after which triethylamine (13.5 mL, 100.4 mmol) was added at 0° C. The mixture was stirred at RT for 4 hrs after which it was partitioned between DCM and sat. aq. NaHCO₃. The organics were separated, and the aqueous layer was further extracted with DCM (×2). The combined organics were dried over Na₂SO₄, concentrated, and the crude material was purified by flash column chromatography (reversed phase, C18) under a gradient of MeCN (0-26%) in water to afford methyl 4-((1S)-1-(2-hydroxy-3-methylbutanamido)ethyl)benzoate (6.50 g, 23.3 mmol, 70% yield) as a white solid. Data available in Table 3.

Step (ii): To a solution of methyl 4-((1S)-1-(2-hydroxy-3-methylbutanamido)ethyl)benzoate (6.70 g, 24.0 mmol) and triethylamine (3.52 mL, 26.40 mmol) in DCM (100 mL) at 0° C. was added mesyl chloride (1.8 mL, 24.0 mmol) dropwise. The mixture was stirred at RT for 2 hrs after which it was partitioned between water and DCM. The organics were separated, and the aqueous layer was further extracted with DCM. The combined organics were washed sequentially with 1 N HCl then sat. aq. NaHCO₃, dried over Na₂SO₄ and concentrated to afford methyl 4-((1 S)-1-(3-methyl-2-((methylsulfonyl)oxy)butanamido)ethyl)benzoate (7.50 g, 21.0 mmol, 88% yield) as a white solid. Data available in Table 3.

Route 3

Procedure for the Preparation of Intermediate 4, (R)—N—((S)-1-(4-cyanophenyl) ethyl)-2-hydroxy-3-methylbutanamide

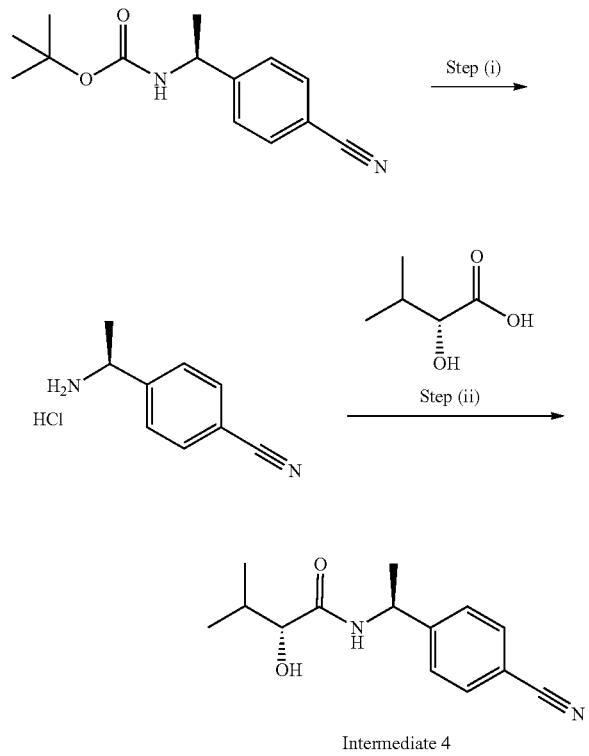

Intermediate 4

Step (i): To a solution of tert-butyl (S)-(1-(4-cyanophenyl) ethyl) carbamate (1.00 g, 4.06 mmol) in 1,4-dioxane (10 mL) was added 4 N HCl in 1,4-dioxane (10 mL). The mixture was stirred at RT for 16 hrs after which it was concentrated under reduced pressure. The crude material was triturated from 10% EtOAc in $Et_2O$ to afford (S)-4-(1-aminoethyl) benzonitrile hydrochloride (0.57 g, 3.13 mmol, 77% yield) as a yellow solid. (LC/MS Method D): m/z 147 $[M+H-HCl]^+$ ($ES^+$), at 0.75 min, UV active.

Step (ii): To a solution of (R)-2-hydroxy-3-methylbutanoic acid (0.39 g, 3.29 mmol) in MeCN (6 mL) was added (S)-4-(1-aminoethyl) benzonitrile hydrochloride (0.50 g, 2.74 mmol) followed by HATU (1.56 g, 4.11 mmol). The mixture was stirred at RT for 30 mins, after which it was cooled to 0° C. and N,N-diisopropylethylamine (1.47 mL, 8.23 mmol) was added.

The mixture was stirred at RT for 4 hrs after which it was partitioned between EtOAc and water. The organics were separated and the aqueous layer was further extracted with EtOAc (×2). The combined organics were dried over $Na_2SO_4$, concentrated, and the crude material was purified by flash column chromatography (reversed phase, C18) under a gradient of MeCN (0-73%) in water to afford Intermediate 4, (R)—N—((S)-1-(4-cyanophenyl) ethyl)-2-hydroxy-3-methylbutanamide (0.55 g, 2.24 mmol, 82% yield) as a sticky brown solid. Data available in Table 3.

Route 4

Procedure for the Preparation of Intermediate 5, methyl (R)-4-(1-(2-hydroxy-3-methylbutanamido) cyclopropyl)benzoate

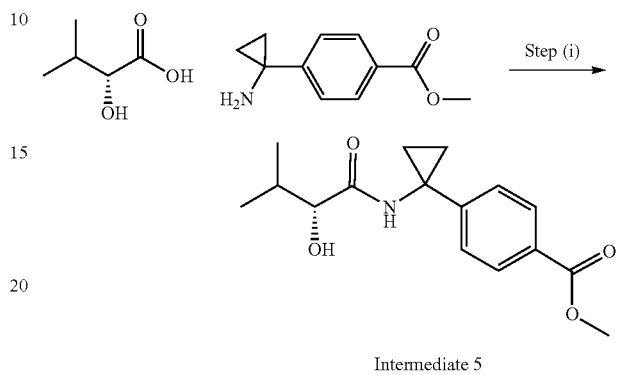

Intermediate 5

Step (i): To (2R)-2-hydroxy-3-methyl-butanoic acid (200 mg, 1.69 mmol) in DMF (8.5 mL) was added DIPEA (0.9 mL, 5.08 mmol) and HATU (775 mg, 2.03 mmol) followed by methyl 4-(1-aminocyclopropyl)benzoate (356 mg, 1.86 mmol). The reaction mixture was stirred for 18 hours at room temperature then partitioned between EtOAc and water. The organics were separated, washed with brine, dried (phase separator) and concentrated in vacuo. The crude material was purified by flash column chromatography (normal phase) [gradient 0-75% EtOAc in iso-hexane] to afford Intermediate 5, methyl (R)-4-(1-(2-hydroxy-3-methylbutanamido)cyclopropyl)benzoate (212 mg, 0.73 mmol, 43%) as a dark orange solid. Data available in Table 3.

Route 5

Procedure for the Preparation of Intermediate 22, 4-(bromomethyl)-1-(difluoromethyl)-2-fluorobenzene

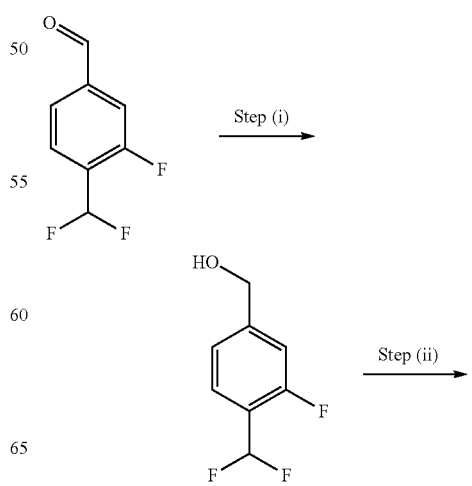

-continued

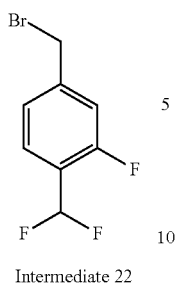

Intermediate 22

Step (i): To a solution of 4-(difluoromethyl)-3-fluorobenzaldehyde (0.50 g, 2.87 mmol) in MeOH (3 mL) at 0° C. under an atmosphere of nitrogen was added NaBH$_4$ (0.21 g, 5.74 mmol). The mixture was stirred at RT for 1 hr after which it was partitioned between EtOAc and water. The organics were separated, and the aqueous layer was further extracted with EtOAc (×2). The combined organics were dried over Na$_2$SO$_4$ and concentrated to afford (4-(difluoromethyl)-3-fluorophenyl) methanol (0.47 g, 2.67 mmol, 93% yield) as a colourless liquid. $^1$H NMR (400 MHz, DMSO) δ 4.55 (d, J=5.8 Hz, 2H), 5.45 (t, J=5.8 Hz, 1H), 6.97-7.35 (m, 3H), 7.50-7.62 (m, 1H).

Step (ii): To a solution of (4-(difluoromethyl)-3-fluorophenyl) methanol (0.25 g, 1.42 mmol) in DCM (3 mL) was added triphenylphosphine (0.55 g, 2.13 mmol). The mixture was cooled to 0° C. and tetrabromomethane (0.71 g, 2.13 mmol) was added. The mixture was stirred at RT for 1 hr after which it was partitioned between EtOAc and water. The organics were separated, and the aqueous layer was further extracted with EtOAc (×2). The combined organics were dried over Na$_2$SO$_4$, concentrated, and the crude material was purified by flash column chromatography (normal phase, silica) under a gradient of EtOAc (0% to 18%) in hexane to afford Intermediate 22, 4-(bromomethyl)-1-(difluoromethyl)-2-fluorobenzene (0.19 g, 0.80 mmol, 56% yield) as a colourless liquid. Data available in Table 3.

Route 6

Procedure for the Preparation of Intermediate 27, 2-(bromomethyl)-5-(difluoromethyl)pyridine

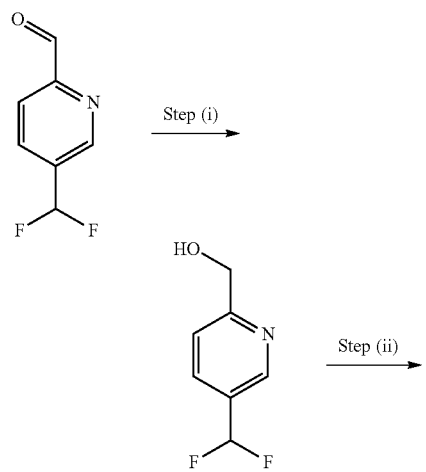

-continued

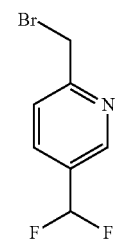

Intermediate 27

Step (i): To a solution of 5-(difluoromethyl)picolinaldehyde (0.30 g, 1.91 mmol) in MeOH (3 mL) at 0° C. under an atmosphere of nitrogen was added NaBH$_4$ (0.14 g, 3.82 mmol). The mixture was stirred at RT for 1 hr after which it was partitioned between EtOAc and water. The organics were separated, and the aqueous layer was further extracted with EtOAc (×2). The combined organics were dried over Na$_2$SO$_4$ and concentrated to afford (5-(difluoromethyl)pyridin-2-yl)methanol (0.30 g, 1.88 mmol, 99% yield) as a colourless liquid. (LC/MS Method D): m/z 160 [M+H]$^+$ (ES$^+$), at 0.95 min, UV active.

Step (ii): To a solution of phosphorus tribromide (0.36 mL, 3.77 mmol) in DCM (3 mL) at 0° C. was added (5-(difluoromethyl)pyridin-2-yl)methanol (0.30 g, 1.88 mmol). The mixture was stirred at RT for 1 hr after which it was partitioned between EtOAc and sat. aq. NaHCO$_3$. The organics were separated, and the aqueous layer was further extracted with EtOAc (×2). The combined organics were dried over Na$_2$SO$_4$, concentrated and purified by flash column chromatography (normal phase, silica) under a gradient of EtOAc (0% to 40%) in hexane to afford Intermediate 27, 2-(bromomethyl)-5-(difluoromethyl)pyridine (0.17 g, 0.77 mmol, 41% yield) as a yellow liquid. Data available in Table 3.

Route 7

Procedure for the Preparation of Intermediate 32, 1-(bromomethyl)-3-(ethylsulfonyl)benzene

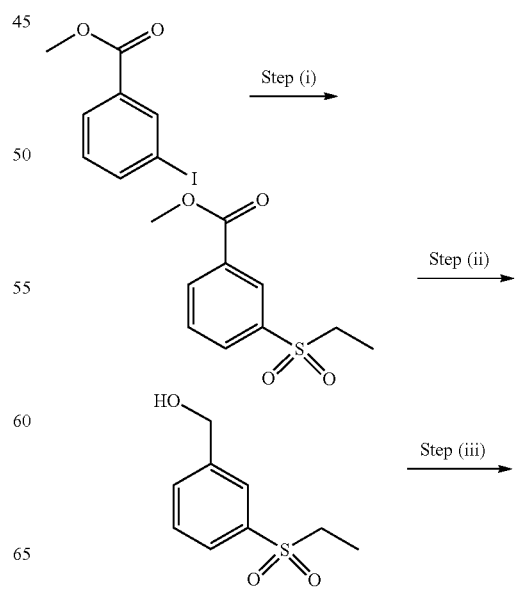

-continued

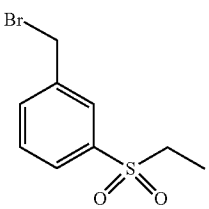

Intermediate 32

Step (i): A suspension of potassium disulphite (3.19 g, 18.3 mmol), tetrabutyl ammonium bromide (2.58 g, 8.01 mmol), sodium formate (1.03 g, 15.3 mmol), palladium acetate(II) (85 mg, 0.38 mmol), triphenyl phosphine (0.28 g, 1.06 mmol) and 1,10-phenanthroline (0.178 g, 0.99 mmol) in DMSO (28 mL) was purged with nitrogen gas at RT for 15 min. Methyl 3-iodobenzoate (2.00 g, 7.60 mmol) was added and the mixture was heated to 100° C. under microwave irradiation for 30 mins. The mixture was cooled, ethyl iodide (1.00 mL, 12.4 mmol) was added and the mixture was stirred at RT for 20 mins. The mixture was partitioned between EtOAc and water, the organics were separated, and the aqueous layer was further extracted with EtOAc (×2). The combined organics were dried over $Na_2SO_4$, concentrated and the residue was purified by flash column chromatography (reversed phase, C18) under a gradient of MeCN (0-36%) in water to afford methyl 3-(ethylsulfonyl)benzoate (1.00 g, 4.39 mmol, 57% yield) as a light-yellow sticky liquid. (LC/MS Method H): m/z 229 [M+H]$^+$ (ES$^+$), at 6.98 min, UV active.

Step (ii): To a solution of methyl 3-(ethylsulfonyl)benzoate (1.00 g, 4.39 mmol) in THF (10 mL) at −78° C. under an atmosphere of nitrogen was added LiAlH$_4$ (1 M in THF, 6.50 mL) dropwise. The mixture was stirred at the same temperature for 2 hrs after which it was partitioned between sat. aq. NH$_4$Cl and EtOAc. The organics were separated, and the aqueous layer was further extracted with EtOAc (×2). The combined organics were dried over $Na_2SO_4$, concentrated under reduced pressure and the residue was purified by flash column chromatography (reversed phase, C18) under a gradient of MeCN (0-35%) in water to afford (3-(ethylsulfonyl) phenyl) methanol (0.50 g, 2.49 mmol, 57% yield) as a light yellow sticky liquid. (LC/MS Method H): m/z 218 [M+H]$^+$ (ES$^+$), at 5.56 min, UV active.

Step (iii): To a solution of phosphorus tribromide (0.48 mL, 4.99 mmol) in DCM (5 mL) at 0° C. was added (3-(ethylsulfonyl)phenyl)methanol (0.50 g, 2.49 mmol). The mixture was stirred at RT for 1 hr after which it was partitioned between DCM and sat. aq. NaHCO$_3$. The organics were separated, and the aqueous layer was further extracted with DCM (×2). The combined organics were dried over $Na_2SO_4$, concentrated and the residue was purified by flash column chromatography (normal phase, silica) under a gradient of EtOAc (0% to 43%) in hexane to afford Intermediate 32, 1-(bromomethyl)-3-(ethylsulfonyl)benzene (0.24 g, 0.91 mmol, 38% yield) as a colourless sticky liquid. Data available in Table 3.

Route 8

Procedure for the Preparation of Intermediate 33, methyl 4-((S)-1-((R)-2-hydroxy-3-methylbutanamido)ethyl)-2-methylbenzoate

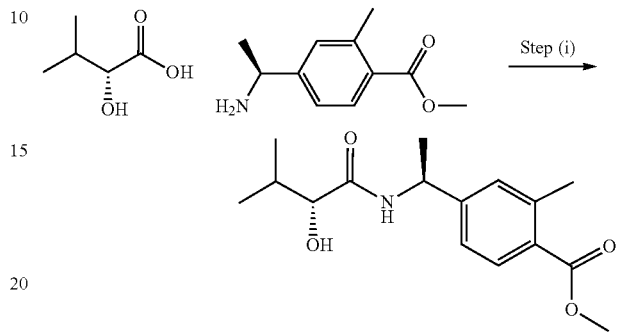

Intermediate 33

Step (i): Methyl (S)-4-(1-aminoethyl)-2-methylbenzoate hydrochloride (0.15 g, 0.65 mmol) and (R)-2-hydroxy-3-methylbutanoic acid (0.085 g, 0.72 mmol) were suspended in ACN (2 mL) at room temperature. HATU (0.37 g, 0.98 mmol) was then added at 0° C. and allowed to stir for 15 min. After this time, N, N-diisopropylethylamine (0.34 mL, 1.96 mmol) was added at 0° C. and allowed to stir at room temperature for 2 hrs. The reaction mixture was partitioned between water (15 mL) and EtOAc (20 mL). The aqueous layer was further extracted with EtOAc (2×15 mL). Organic layers were combined and dried (Na$_2$SO$_4$). Solvent was removed in vacuo and the crude product was purified by reverse-phase gradient flash column chromatography (reverse phase, C18 silica), product eluted at 0% to 60% ACN in water to afford pure Intermediate 33, methyl 4-((S)-1-((R)-2-hydroxy-3-methylbutanamido)ethyl)-2-methylbenzoate (0.16 g, 85%) as sticky oily yellow liquid. Data available in Table 3.

Route 9

Procedure for the Preparation of Intermediate 36, 3-(oxetan-3-yl)phenyl)methanol

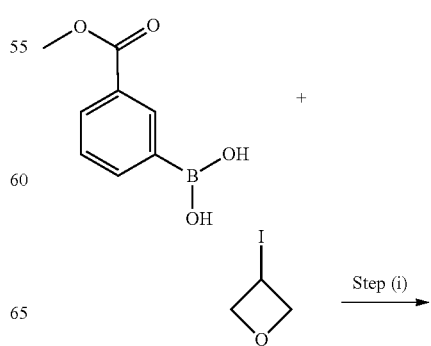

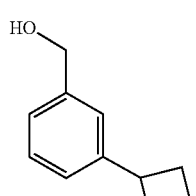

Step (ii)

Intermediate 36

Step (i): (3-(Methoxycarbonyl)phenyl)boronic acid (2.0 g, 11.07 mmol), 3-iodooxetane (4.07 g, 22.1 mmol) and $K_2CO_3$ (4.58 g, 33.2 mmol) were dissolved in dry 1,4-dioxane (10 mL). Argon gas was purged through the mixture at room temperature for 20 min, then $Ni(NO_3)_2$ hexahydrate (0.161 g, 0.55 mmol) and 4,4'-di-tert-butyl-2,2'-dipyridyl (0.14 g, 0.55 mmol) were added and the reaction mixture was heated to 80° C. for 4 hrs. The reaction mixture was then partitioned between water (250 mL) and EtOAc (250 mL). The aqueous layer was further extracted with EtOAc (2×150 mL). Organic layers were combined and dried ($Na_2SO_4$), the solvent was removed in vacuo and the crude product was purified by reverse phase gradient flash column chromatography (reverse phase, C18 silica), product eluted at 0% to 46% ACN in water to afford pure methyl 3-(oxetan-3-yl)benzoate (0.58 g, 27%) as a colourless liquid. 1H NMR (400 MHz, DMSO-$d_6$) δ 3.86 (s, 3H), 4.33 (tt, J=8.3, 6.6 Hz, 1H), 4.60 (dd, J=6.6, 6.0 Hz, 2H), 4.97 (dd, J=8.3, 6.0 Hz, 2H), 7.54 (t, J=7.7 Hz, 1H), 7.71 (dt, J=7.7, 1.3 Hz, 1H), 7.87 (dt, J=7.7, 1.4 Hz, 1H), 7.98 (t, J=1.8 Hz, 1H).

Step (ii): $LiAlH_4$ (2M in THF) (2.26 mL, 4.52 mmol) was added dropwise to a solution of methyl 3-(oxetan-3-yl)benzoate (0.58 g, 3.01 mmol) in dry THF (8 mL) under a nitrogen atmosphere at −78° C., and the reaction mixture was allowed to stir at −78° C. for 1 hr. The reaction mixture was quenched with saturated aqueous $NH_4Cl$ solution (3 mL) then partitioned between water (150 mL) and EtOAc (50 mL) and the aqueous layer was further extracted with EtOAc (2×70 mL). Organic layers were combined and dried ($Na_2SO_4$) and the solvent was removed in vacuo to afford crude (3-(oxetan-3-yl)phenyl)methanol (0.43 g, 87%) as a colourless liquid. Data available in Table 3.

Route 10

Procedure for the Preparation of Intermediate 42, 7-(chloromethyl)imidazo[1,2-a]pyridine

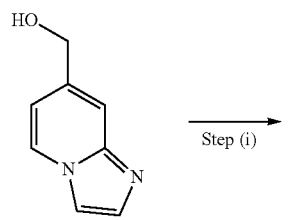

Step (i)

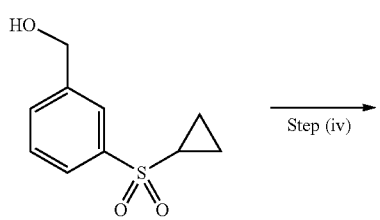

Intermediate 42

Step (i): Thionyl chloride (0.2 mL, 3.03 mmol) was added to a solution of imidazo[1,2-a]pyridin-7-ylmethanol (0.30 g, 2.02 mmol) in $CHCl_3$ (4 mL) under a nitrogen atmosphere at 0° C. and then allowed to stir at room temperature for 1 hr. The solvent was removed in vacuo and the crude material was purified by trituration with diethyl ether (3×10 mL) and dried to afford pure Intermediate 42, 7-(chloromethyl)imidazo[1,2-a]pyridine (0.31 g, 92%) as a brown solid. Data available in Table 3.

Route 11

Procedure for the Preparation of Intermediate 48, 1-(bromomethyl)-3-(cyclopropylsulfonyl)benzene

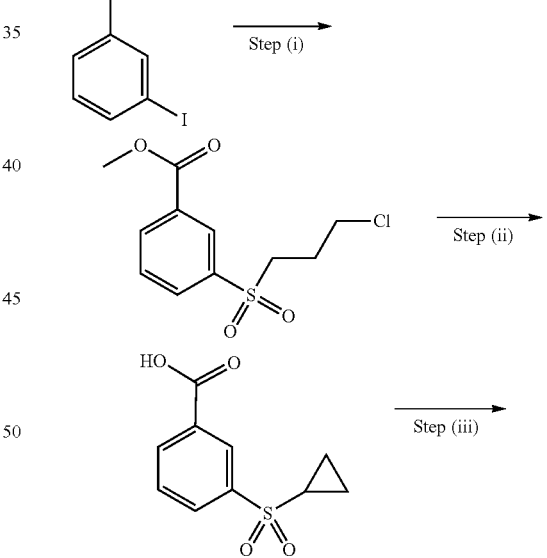

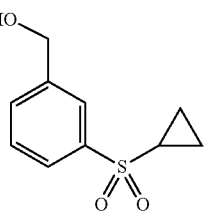

Intermediate 48

Step (i): Potassium disulphite (3.19 g, 14.3 mmol), tetrabutyl ammonium bromide (2.58 g, 8.01 mmol), sodium formate (1.04 g, 15.3 mmol), palladium(II) acetate (0.085 g, 0.38 mmol), triphenylphosphine (0.28 g, 1.06 mmol) and 1,10-phenanthroline (0.178 g, 0.99 mmol) were suspended in DMSO (12 mL) and purged with nitrogen gas at room temperature for 20 min. After this time, methyl 3-iodobenzoate (2.00 g, 7.63 mmol) was added and reaction mixture was heated to 100° C. in a microwave for 30 min. 1-Chloro-3-iodopropane (1.00 mL, 9.31 mmol) was then added at room temperature and reaction mixture was allowed to stir at room temperature for 16 hrs. The reaction mixture was then partitioned between water (250 mL) and EtOAc (250 mL). The aqueous layer was further extracted with EtOAc (2×150 mL) and the combined organic layers were combined and dried ($Na_2SO_4$). The solvent was removed in vacuo and the crude product was purified by reverse phase gradient flash column chromatography (reverse phase, C18 silica), product eluted at 0% to 57% ACN in water to afford crude methyl 3-((3-chloropropyl) sulfonyl) benzoate (0.55 g, 26.00%) as brown sticky liquid. (LC/MS Method H): m/z 277 [M+H]$^+$ (ES$^+$), at 8.00 min, UV active.

Step (ii): Methyl 3-((3-chloropropyl)sulfonyl)benzoate (0.70 g, 2.53 mmol) was dissolved in THF (6 mL) under a nitrogen atmosphere at room temperature. The reaction mixture was then cooled to 0° C., potassium tert-butoxide (0.31 g, 2.78 mmol) was added and reaction mixture was allowed to stir at room temperature for 2.5 hrs. The reaction mixture was then partitioned between water (150 mL) and EtOAc (200 mL). The aqueous layer was acidified with 1N aqueous HCl (2.0 mL) to adjust pH to ~3 and the aqueous layer was further extracted with EtOAc (2×150 mL). The organic layers were combined and dried ($Na_2SO_4$) and the solvent was removed in vacuo to afford crude 3-(cyclopropylsulfonyl)benzoic acid (0.52 g, 85%) as a yellow solid. (LC/MS Method H): m/z 227 [M+H]$^+$ (ES$^+$), at 6.86 min, UV active.

Step (iii): 3-(Cyclopropylsulfonyl)benzoic acid (0.50 g, 2.21 mmol) was dissolved in dry THF (5 mL) under a nitrogen atmosphere at room temperature. The reaction mixture was then cooled to 0° C. and $BH_3$.DMS (0.52 mL, 5.53 mmol) was added dropwise at 0° C. and the reaction mixture was then allowed to stir at room temperature for 16 hrs. The reaction mixture was then diluted with MeOH (10 mL). The solvent was removed in vacuo and the crude product was purified by reverse phase gradient flash column chromatography (reverse phase, C18 silica), product eluted at 0% to 68% ACN in water to afford (3-(cyclopropylsulfonyl)phenyl)methanol (0.17 g, 36%) as a yellow sticky liquid. (LC/MS Method H): m/z 213 [M+H]$^+$ (ES$^+$), at 5.96 min, UV active.

Step (iv): Phosphorus tribromide (0.14 mL, 1.44 mmol) was dissolved in dichloromethane (1 mL) at 0° C. and treated dropwise with a solution of (3-(cyclopropylsulfonyl)phenyl)methanol (0.153 g, 0.72 mmol) in DCM (1 mL) at 0° C. and the reaction mixture then allowed to stir at room temperature for 0.5 hrs. The reaction mixture was then basified with saturated $NaHCO_3$ solution (10 mL) to pH~8 and partitioned between water (40 mL) and DCM (40 mL). The aqueous layer was further extracted with DCM (2×20 mL) and the organic layers were combined and dried ($Na_2SO_4$). The solvent was removed in vacuo to afford crude 1-(bromomethyl)-3-(cyclopropylsulfonyl)benzene (0.09 g, 46%) as a colorless liquid. Data available in Table 3.

Route 12

Procedure for the Preparation of Intermediate 50, (R)—N-(1-(4-cyanophenyl)cyclopropyl)-2-hydroxy-3-methylbutanamide

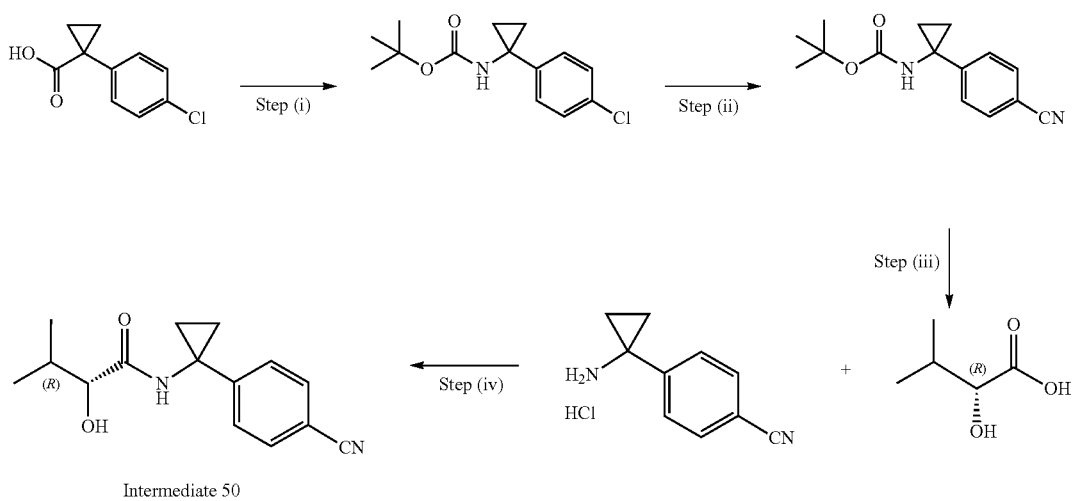

Intermediate 50

Step (i): 1-(4-chlorophenyl) cyclopropane-1-carboxylic acid (55.0 g, 0.281 mole) and triethylamine (77.75 mL, 0.561 mole) were dissolved in toluene (250 mL) at room temperature. After this, Diphenylphosphoryl azide (66.51 mL, 0.309 mole) and tert-butanol (133.13 mL, 1.403 mole)

were added and reaction mixture was stirred at 80° C. for 16h. Reaction mixture was partitioned between water (1000 mL) and DCM (600 mL). Aqueous layer was further extracted with DCM (2×400 mL). Organic layers were combined and dried ($Na_2SO_4$). Solvent was removed in vacuo and crude product was purified by gradient flash column chromatography (Normal phase, silica), product eluted at 0% to 10% EtOAc in Hexane to afford tert-butyl (1-(4-chlorophenyl)cyclopropyl)carbamate (60.0 g, 80%) as off-white solid. (LC/MS Method D): m/z 168.07 (ES+, M-100) at 2.18 min.

Step (ii): tert-butyl (1-(4-chlorophenyl)cyclopropyl)carbamate (20.00 g, 74.87 mmole) and Zinc cyanide (13.18 g, 112.31 mmole) were suspended in dioxane (45 mL) and nitrogen gas was purged at room temperature for 30 min. After this, Bis(tri-tert-butylphosphine) palladium (0) (3.82 g, 7.48 mmole) was added at room temperature and reaction mixture was stirred at 80° C. for 3h. The reaction mixture was partitioned between water (1000 mL) and EtOAc (700 mL) and aqueous layer was further extracted with EtOAc (2×300 mL). Organic layers were combined and dried ($Na_2SO_4$). Solvent was removed in vacuo and crude product was purified by gradient flash column chromatography (Normal phase, silica), product eluted at 0% to 15% EtOAc in Hexane to afford pure tert-butyl (1-(4-cyanophenyl)cyclopropyl)carbamate (11.4 g, 58.98%) as brown solid. Note: Reaction was carried out in 2 divided batches on 10 g scale. (LC/MS Method D): m/z 159 (ES-100), at 1.85 min.

Step (iii): tert-butyl (1-(4-cyanophenyl) cyclopropyl) carbamate (3.00 g, 11.62 mmole) was dissolved in dioxane (10 mL) under nitrogen atmosphere. To it, 4N HCl in dioxane (30 mL) was added at room temperature and stirred at room temperature for 16h. Solvent was removed in vacuo and crude material was purified by trituration with diethyl ether (20 mL) to afford 4-(1-aminocyclopropyl) benzonitrile hydrochloride (2.10 g, 93%) as white solid. (LC/MS Method H): m/z 159 (ES+), at 0.73 min.

Step (iv): (R)-2-hydroxy-3-methylbutanoic acid (1.53 g, 12.98 mmole) was dissolved in ACN (20 mL) and 4-(1-aminocyclopropyl)benzonitrile hydrochloride (2.10 g, 10.82 mmole) was added to the reaction mixture at room temperature. After this, HATU (6.17 g, 16.23 mmole) was added and reaction mixture was allowed to stir at room temperature for 30 min. After this, N, N-diisopropylethylamine (5.64 mL, 32.46 mmole) was added at 0° C. and allowed to stir at room temperature for 1 h. Reaction mixture was concentrated in vacuo to obtain crude product which was purified by reverse phase gradient flash column chromatography (reverse phase, C18 silica), product eluted at 0% to 61% ACN in water to afford (R)—N-(1-(4-cyanophenyl)cyclopropyl)-2-hydroxy-3-methylbutanamide Intermediate 50 (1.80 g, 64.%) as brown solid. Data available in Table 3.

Route 13

Procedure for the Preparation of Intermediate 58, methyl 4-(1-(2-cyclobutyl-2-hydroxyacetamido)cyclopropyl)benzoate

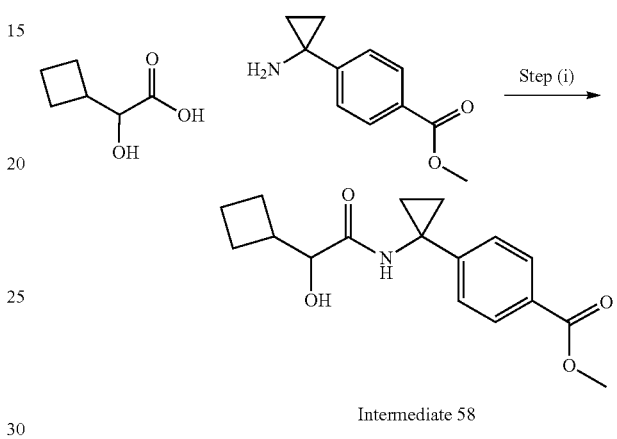

Intermediate 58

Step (i): Methyl 4-(1-aminocyclopropyl)benzoate (1.45 g, 7.61 mmol), 2-cyclobutyl-2-hydroxy-acetic acid (900 mg, 6.92 mmol), EDC (2.0 g, 10.37 mmol) and HOBt monohydrate (93 mg, 0.69 mmol) were dissolved in DCM (21.0 mL) after which the reaction mixture was stirred for 10 minutes at RT. Triethylamine (2.4 mL, 17.29 mmol) was added dropwise at 0° C. and the reaction mixture stirred for 18 hours at RT. The reaction mixture was partitioned between water and EtOAc and the organics separated, washed with 1 M HCl (aq.), saturated $NaHCO_3$ (aq.) and brine. The organics were separated, dried via passage through a hydrophobic frit and concentrated to afford Intermediate 58, methyl 4-(1-(2-cyclobutyl-2-hydroxyacetamido)cyclopropyl)benzoate (1.5 g, 4.85 mmol, 70%) as a light brown solid. The material was used without any further purification. Data available in table 3.

TABLE 2

| Ex. No. | Name | Synthetic method & notes | Intermediates | ¹H NMR | LCMS data |
|---|---|---|---|---|---|
| 1 | 4-((S)-1-(((R)-3-methyl-2-((4-(trifluoromethyl)benzyl)oxy)butanamido)ethyl)benzoic acid | Route A | 1, 31 | ¹H NMR (400 MHz, DMSO) δ 0.84 (d, J = 6.8 Hz, 3H), 0.90 (d, J = 6.8 Hz, 3H), 1.40 (d, J = 7.1 Hz, 3H), 1.88-2.04 (m, 1H), 3.55 (d, J = 6.3 Hz, 1H), 4.45 (d, J = 12.7 Hz, 1H), 4.64 (d, J = 12.7 Hz, 1H), 5.00-5.09 (m, 1H), 7.43-7.48 (m, 2H), 7.55-7.61 (m, 2H), 7.71-7.76 (m, 2H), 7.87-7.92 (m, 2H), 8.43 (d, J = 8.2 Hz, 1H), 12.86 (br.s, 1H). | (LC/MS Method A): m/z 424 [M + H]⁺ (ES⁺), at 2.01 min, UV active. |
| 2 | (R)-4-(1-(3-methyl-2-((4-(trifluoromethyl)benzyl)oxy)butanamido)cyclopropyl)benzoic acid | Route B | 5, 31 | ¹H NMR (400 MHz, DMSO) δ 0.88 (d, J = 6.8 Hz, 3H), 0.93 (d, J = 6.8 Hz, 3H), 1.14-1.32 (m, 4H), 1.95-2.05 (m, 1H), 3.55 (d, J = 6.1 Hz, 1H), 4.51 (d, J = 12.7 Hz, 1H), 4.69 (d, J = 12.7 Hz, 1H), 7.22-7.28 (m, 2H), 7.58-7.67 (m, 2H), 7.71-7.78 (m, 2H), 7.80-7.87 (m, 2H), 8.78 (s, 1H), 12.54 (br.s, 1H). | (LC/MS Method C): m/z 436 [M + H]⁺ (ES⁺), at 2.69 min, UV active |
| 3 | 4-((1S)-1-(2-((3-methoxybenzyl)oxy)-3-methylbutanamido)ethyl)benzoic acid | Route E | 2, 56 | 1H-NMR (400 Mz, DMSO) [NB mixture of diastereoisomers] δ 0.89-0.790 (m, 6H), 1.38 (dd, 3H, J = 2.4 Hz & 7.2 Hz), 1.96-1.90 (m, 1H), 3.50-3.48 (m, 1H), 3.75-3.72 (m, 3H), 4.29 (dd, 1H, J = 4.0 Hz & 12.4 Hz), 4.53-4.48 (m, 1H), 5.08-5.00 (m, 1H), 6.91-6.84 (m, 3H), 7.28-7.23 (m, 1H), 7.43 (t, 2H, J = 8.8 Hz), 7.87 (dd, 2H, J = 2.0 Hz & 8.4 Hz), 8.40-8.36 (m, 1H), 12.87 (s, 1H). | (LC/MS Method H): m/z 386 [M + H]⁺ (ES⁺), at 14.17 min and 14.33 min, UV active. |
| 4 | 4-((1S)-1-(2-((4-fluorobenzyl)oxy)-3-methylbutanamido)ethyl)benzoic acid | Route E then Route G | 2, 24 | 1H-NMR (400 Mz, DMSO) δ 0.81 (d, J = 6.8 Hz, 3H), 0.86 (d, J = 6.8 Hz, 3H), 1.38 (d, J = 7.1 Hz, 3H), 1.87-1.97 (m, 1H), 3.49 (d, J = 6.3 Hz, 1H), 4.30 (d, J = 11.7 Hz, 1H), 4.49 (d, J = 11.7 Hz, 1H), 5.01-5.10 (m, 1H), 7.12-7.18 (m, 2H), 7.33-7.39 (m, 2H), 7.42 (d, J = 8.0 Hz, 2H), 7.88 (d, J = 8.0 Hz, 2H), 8.39 (d, J = 8.1 Hz, 1H), 12.87 (br.s, 1H). | (LC/MS Method H): m/z 374 [M + H]⁺ (ES⁺), at 11.48 min, UV active. |
| 5 | 4-((S)-1-((R)-2-((4-fluorobenzyl)oxy)-3-methylbutanamido)ethyl)benzoic acid | Route C | 1, 24 | ¹H NMR (400 MHz, DMSO) δ 0.78 (d, J = 6.8 Hz, 3H), 0.84 (d, J = 6.8 Hz, 3H), 1.38 (d, J = 7.1 Hz, 3H), 1.84-1.97 (m, 1H), 3.48 (d, J = 6.3 Hz, 1H), 4.31 (d, J = 11.7 Hz, 1H), 4.51 (d, J = 11.7 Hz, 1H), 4.95-5.08 (m, 1H), 7.10-7.23 (m, 2H), 7.33-7.42 (m, 2H), 7.44 (d, J = 8.0 Hz, 2H), 7.88 (d, J = 8.0 Hz, 2H), 8.41 (d, J =8.1 Hz, 1H), 12.88 (br.s, 1H). | (LC/MS Method D): m/z 374 [M + H]⁺ (ES⁺), at 2.38 min, UV active. |
| 6 | 4-((S)-1-(2-((4-methoxybenzyl)oxy)-3-methylbutanamido)ethyl)benzoic acid, mixture of diastereomers | Route D | 3 | ¹H NMR (400 MHz, DMSO) [NB mixture of diastereoisomers] δ 0.74-0.86 (m, 6H), 1.35-1.42 (m, 3H), 1.83-1.96 (m, 1H), 3.42-3.48 (m, 1H), 3.70-3.77 (m, 3H), 4.21-4.28 (m, 1H), 4.38-4.50 (m, 1H), 4.94-5.10 (m, 1H), 6.84-6.93 (m, 2H), 7.17-7.29 (m, 2H), 7.37-7.47 (m, 2H), 7.81-7.92 (m, 2H), 8.30-8.38 (m, 1H), 12.89 (br.s, 1H). | (LC/MS Method F): m/z 384 [M + H]⁺ (ES⁺), at 4.44 min and 4.53 min, UV active. |
| 7 | 4-((S)-1-((S)-3-methyl-2-((3-(methylsulfonyl)benzyl)oxy)butanamido)ethyl)benzoic acid | Route D then Route G | 3, 6 | ¹H NMR (400 MHz, DMSO) δ 0.82 (d, J = 6.7 Hz, 3H), 0.89 (d, J = 6.7 Hz, 3H), 1.38 (d, J = 7.1 Hz, 3H), 1.90-2.03 (m, 1H), 3.20 (s, 3H), 3.55 (d, J = 6.3 Hz, 1H), 4.45 (d, J = 12.4 Hz, 1H), 4.64 (d, J = 12.4 Hz, 1H), 5.01-5.11 (m, 1H), 7.42 (d, J = 8.1 Hz, 2H), 7.60-7.71 (m, 2H), 7.83-7.93 (m, 4H), 8.45 (d, J = 8.2 Hz, 1H), 12.78 (br.s, 1H). | (LC/MS Method D): m/z 434 [M + H]⁺ (ES⁺), at 2.17 min, UV active. |
| 8 | 4-((S)-1-(((R)-3-methyl-2-((3-(methylsulfonyl)benzyl)oxy)butanamido)ethyl)benzoic acid | Route C | 1, 6 | ¹H NMR (400 MHz, DMSO) δ 0.82 (d, J = 6.7 Hz, 3H), 0.88 (d, J = 6.7 Hz, 3H), 1.38 (d, J = 7.1 Hz, 3H), 1.90-2.03 (m, 1H), 3.20 (s, 3H), 3.54 (d, J = 6.3 Hz, 3H), 4.46 (d, J = 12.4 Hz, 1H), 4.65 (d, J = 12.4 Hz, 1H), 4.98-5.09 (m, 1H), 7.44 (d, J = 8.1 Hz, 2H), 7.61-7.68 (m, 1H), 7.68-7.73 (m, 1H), 7.81-7.93 (m, 4H), 8.46 (d, J = 8.2 Hz, 1H), 12.86 (br.s, 1H). | (LC/MS Method D): m/z 434 [M + H]⁺ (ES⁺), at 2.04 min, UV active. |

TABLE 2-continued

| Ex. No. | Name | Synthetic method & notes | Intermediates | ¹H NMR | LCMS data |
|---|---|---|---|---|---|
| 9 | 4-((S)-1-((S)-3-methyl-2-((4-(methylsulfonyl)benzyl)oxy)butanamido)ethyl)benzoic acid | Route E then Route G | 2, 7 | ¹H NMR (400 MHz, DMSO) δ 0.84 (d, J = 6.7 Hz, 3H), 0.89 (d, J = 6.7 Hz, 3H), 1.39 (d, J = 7.1 Hz, 3H), 1.90-2.02 (m, 1H), 3.19 (s, 3H), 3.55 (d, J = 6.3 Hz, 1H), 4.45 (d, J = 12.9 Hz, 1H), 4.63 (d, J = 12.9 Hz, 1H), 5.01-5.12 (m, 1H), 7.43 (d, J = 8.0 Hz, 2H), 7.60 (d, J = 8.0 Hz, 2H), 7.84-7.95 (m, 4H), 8.47 (d, J = 8.1 Hz, 1H), 12.87 (br.s, 1H). | (LC/MS Method D): m/z 434 [M + H]⁺ (ES⁺), at 2.07 min, UV active. |
| 10 | 4-((S)-1-((R)-3-methyl-2-((4-(methylsulfonyl)benzyl)oxy)butanamido)ethyl)benzoic acid | Route C | 1, 7 | ¹H NMR (400 MHz, DMSO) δ 0.82 (d, J = 6.7 Hz, 3H), 0.88 (d, J = 6.7 Hz, 3H), 1.38 (d, J = 7.1 Hz, 3H), 1.86-2.01 (m, 1H), 3.20 (s, 3H), 3.54 (d, J = 6.3 Hz, 1H), 4.44 (d, J = 12.9 Hz, 1H), 4.64 (d, J = 12.9 Hz, 1H), 4.95-5.12 (m, 1H), 7.45 (d, J = 8.0 Hz, 2H), 7.61 (d, J = 8.0 Hz, 2H), 7.84-7.96 (m, 4H), 8.48 (d, J = 8.1 Hz, 1H), 12.89 (br.s, 1H). | (LC/MS Method D): m/z 434 [M + H]⁺ (ES⁺), at 2.07 min, UV active. |
| 11 | 4-((S)-1-((R)-2-((4-chlorobenzyl)oxy)-3-methylbutanamido)ethyl)benzoic acid | Route E | 1 | ¹H NMR (400 MHz, DMSO) δ 0.79 (d, J = 6.7 Hz, 3H), 0.85 (d, J = 6.7 Hz, 3H), 1.38 (d, J = 7.1 Hz, 3H), 1.83-2.02 (m, 1H), 3.49 (d, J = 6.3 Hz, 1H), 4.32 (d, J = 12.2 Hz, 1H), 4.52 (d, J = 12.2 Hz, 1H), 4.95-5.09 (m, 1H), 7.33-7.46 (m, 6H), 7.88 (d, J = 8.3 Hz, 2H), 8.40 (d, J = 8.1 Hz, 1H), 12.86 (br.s, 1H). | (LC/MS Method D): m/z 390 [M + H]⁺ (ES⁺), at 2.48 min, UV active. |
| 12 | 4-((S)-1-((R)-2-((3-chlorobenzyl)oxy)-3-methylbutanamido)ethyl)benzoic acid | Route E | 1, 8 | ¹H NMR (400 MHz, DMSO) δ 0.81 (d, J = 6.7 Hz, 3H), 0.86 (d, J = 6.7 Hz, 3H), 1.38 (d, J = 7.0 Hz, 3H), 1.83-1.99 (m, 1H), 3.50 (d, J = 6.2 Hz, 1H), 4.35 (d, J = 12.3 Hz, 1H), 4.54 (d, J = 12.3 Hz, 1H), 4.96-5.08 (m, 1H), 7.26-7.47 (m, 6H), 7.87 (d, J = 7.9 Hz, 2H), 8.41 (d, J = 8.2 Hz, 1H), 13.12 (br.s, 1H). | (LC/MS Method D): m/z 390 [M + H]⁺ (ES⁺), at 2.46 min, UV active. |
| 13 | 4-((S)-1-((R)-2-((4-(difluoromethyl)benzyl)oxy)-3-methylbutanamido)ethyl)benzoic acid | Route F | 1, 49 | ¹H NMR (400 MHz, DMSO) δ 0.81 (d, J = 6.6 Hz, 3H), 0.87 (d, J = 6.6 Hz, 3H), 1.38 (d, J = 6.9 Hz, 3H), 1.84-2.01 (m, 1H), 3.51 (d, J = 6.2 Hz, 1H), 4.39 (d, J = 12.4 Hz, 1H), 4.59 (d, J = 12.4 Hz, 1H), 4.95-5.10 (m, 1H), 7.02 (t, J = 56 Hz, 1H), 7.38-7.51 (m, 4H), 7.53-7.59 (m, 2H), 7.84-7.93 (m, 2H), 8.42 (d, J = 8.2 Hz, 1H), 12.92 (br.s, 1H). | (LC/MS Method D): m/z 406 [M + H]⁺ (ES⁺), at 2.36 min, UV active. |
| 14 | 4-((S)-1-((R)-2-((3-(difluoromethyl)benzyl)oxy)-3-methylbutanamido)ethyl)benzoic acid | Route E | 1, 9 | ¹H NMR (400 MHz, DMSO) δ 0.86 (d, J = 6.7 Hz, 3H), 0.92 (d, J = 6.7 Hz, 3H), 1.43 (d, J = 7.1 Hz, 3H), 1.92-2.06 (m, 1H), 3.56 (d, J = 6.2 Hz, 1H), 4.44 (d, J = 12.2 Hz, 1H), 4.65 (d, J = 12.2 Hz, 1H), 4.99-5.17 (m, 1H), 7.08 (t, J = 56 Hz, 1H), 7.50 (d, J = 7.9 Hz, 2H), 7.58 (s, 4H), 7.93 (d, J = 7.9 Hz, 2H), 8.48 (d, J = 8.1 Hz, 1H), 12.92 (br.s, 1H). | (LC/MS Method G): m/z 406 [M + H]⁺ (ES⁺), at 4.70 min, UV active. |
| 15 | 4-((S)-1-((R)-3-methyl-2-((3-(trifluoromethyl)benzyl)oxy)butanamido)ethyl)benzoic acid | Route E | 1, 10 | ¹H NMR (400 MHz, DMSO) δ 0.86 (d, J = 6.7 Hz, 3H), 0.92 (d, J = 6.7 Hz, 3H), 1.43 (d, J = 7.1 Hz, 3H), 1.94-2.06 (m, 1H), 3.58 (d, J = 6.3 Hz, 1H), 4.49 (d, J = 12.5 Hz, 1H), 4.68 (d, J = 12.5 Hz, 1H), 5.02-5.12 (m, 1H), 7.47-7.51 (m, 2H), 7.59-7.79 (m, 4H), 7.89-7.96 (m, 2H), 8.50 (d, J = 8.2 Hz, 1H), 12.92 (br.s, 1H). | (LC/MS Method D): m/z 424 [M + H]⁺ (ES⁺), at 2.50 min, UV active. |
| 16 | 4-((S)-1-((S)-3-methyl-2-((4-(trifluoromethyl)benzyl)oxy)butanamido)ethyl)benzoic acid | Route C | 31 | 1H NMR (400 MHz, DMSO-d6) δ 12.61 (br s, 1H), 8.43 (d, J = 8.2 Hz, 1H), 7.91-7.87 (m, 2H), 7.74-7.69 (m, 2H), 7.59-7.54 (m, 2H), 7.46-7.42 (m, 2H), 5.12-5.03 (m, 1H), 4.63 (d, J = 12.8 Hz, 1H), 4.45 (d, J = 12.8 Hz, 1H), 3.56 (d, J = 6.1 Hz, 1H), 2.03-1.94 (m, 1H), 1.40 (d, J = 7.1 Hz, 3H), 0.91 (d, J = 6.7 Hz, 3H), 0.85 (d, J = 6.7 Hz, 3H). | (LC/MS Method C): m/z 424 [M + H]⁺ (ES⁺), at 2.60 min, UV active. |

TABLE 2-continued

| Ex. No. | Name | Synthetic method & notes | Intermediates | ¹H NMR | LCMS data |
|---|---|---|---|---|---|
| 17 | 4-((1S)-1-(2-((3-fluorobenzyl)oxy)-3-methylbutanamido)ethyl)benzoic acid, diastereomer 1 | Route E then Route G | 2, 11 | ¹H NMR (400 MHz, DMSO) δ 0.80 (d, J = 6.7 Hz, 3H), 0.86 (d, J = 6.7 Hz, 3H), 1.38 (d, J = 7.1 Hz, 3H), 1.83-2.01 (m, 1H), 3.50 (d, J = 6.6 Hz, 1H), 4.36 (d, J = 12.3 Hz, 1H), 4.54 (d, J = 12.3 Hz, 1H), 4.93-5.08 (m, 1H), 7.05-7.24 (m, 3H), 7.32-7.49 (m, 3H), 7.87 (d, J = 7.8 Hz, 2H), 8.41 (d, J = 8.2 Hz, 1H), 12.85 (br.s, 1H). | (LC/MS Method H): m/z 374 [M + H]⁺ (ES⁺), at 9.26 min, UV active |
| 18 | 4-((1S)-1-(2-((3-fluorobenzyl)oxy)-3-methylbutanamido)ethyl)benzoic acid, diastereomer 2 | Route E then Route G | 2, 11 | ¹H NMR (400 MHz, DMSO) δ 0.83 (d, J = 6.7 Hz, 3H), 0.88 (d, J = 6.7 Hz, 3H), 1.39 (d, J = 7.1 Hz, 3H), 1.82-2.02 (m, 1H), 3.52 (d, J = 6.1 Hz, 1H), 4.35 (d, J = 12.3 Hz, 1H), 4.53 (d, J = 12.3 Hz, 1H), 5.00-5.12 (m, 1H), 7.07-7.21 (m, 3H), 7.34-7.49 (m, 3H), 7.87 (d, J = 8.0 Hz, 2H), 8.41 (d, J = 8.2 Hz, 1H), 12.87 (br.s, 1H). | (LC/MS Method H): m/z 374 [M + H]⁺ (ES⁺), at 9.37 min, UV active |
| 19 | 4-((S)-1-((R)-2-(benzyloxy)-3-methylbutanamido)ethyl)benzoic acid | Route E Step (i): 1.2 equivalents of both NaH and alkylating reagent used | 1, 12 | ¹H NMR (400 MHz, DMSO) δ 0.79 (d, J = 6.7 Hz, 3H), 0.85 (d, J = 6.7 Hz, 3H), 1.38 (d, J = 7.0 Hz, 3H), 1.84-1.99 (m, 1H), 3.49 (d, J = 6.3 Hz, 1H), 4.32 (d, J = 11.9 Hz, 1H), 4.54 (d, J = 11.9 Hz, 1H), 4.96-5.09 (m, 1H), 7.25-7.39 (m, 5H), 7.45 (d, J = 8.3 Hz, 2H), 7.88 (d, J = 8.3 Hz, 2H), 8.39 (d, J = 8.1 Hz, 1H), 12.87 (br.s, 1H). | (LC/MS Method D): m/z 356 [M + H]⁺ (ES⁺), at 2.32 min, UV active. |
| 20 | 4-((S)-1-((R)-3-methyl-2-(3-(trifluoromethoxy)benzyl)oxy)butanamido)ethyl)benzoic acid | Route F | 1, 13 | ¹H NMR (400 MHz, DMSO) δ 0.80 (d, J = 6.7 Hz, 3H), 0.86 (d, J = 6.7 Hz, 3H), 1.38 (d, J = 7.1 Hz, 3H), 1.88-2.02 (m, 1H), 3.51 (d, J = 6.2 Hz, 1H), 4.39 (d, J = 12.5 Hz, 1H), 4.59 (d, J = 12.5 Hz, 1H), 4.92-5.12 (m, 1H), 7.26-7.38 (m, 3H), 7.41-7.53 (m, 3H), 7.88 (d, J = 8.0 Hz, 2H), 8.44 (d, J = 8.2 Hz, 1H), 12.87 (br.s, 1H). | (LC/MS Method D): m/z 440 [M + H]⁺ (ES⁺), at 2.56 min, UV active. |
| 21 | 4-((S)-1-((R)-2-(4-cyanobenzyl)oxy)-3-methylbutanamido)ethyl)benzoic acid | Route C Step (i): 1.5 equivalents of alkylating reagent used | 1, 14 | ¹H NMR (400 MHz, DMSO) δ 0.82 (d, J = 6.7 Hz, 3H), 0.88 (d, J = 6.7 Hz, 3H), 1.38 (d, J = 7.1 Hz, 3H), 1.87-2.02 (m, 1H), 3.53 (d, J = 6.3 Hz, 1H), 4.43 (d, J = 13.1 Hz, 1H), 4.62 (d, J = 13.1 Hz, 1H), 4.97-5.08 (m, 1H), 7.44 (d, J = 8.1 Hz, 2H), 7.55 (d, J = 8.0 Hz, 2H), 7.82 (d, J = 8.0 Hz, 2H), 7.88 (d, J = 8.1 Hz, 2H), 8.45 (d, J = 8.1 Hz, 1H), 12.85 (br.s, 1H). | (LC/MS Method D): m/z 381 [M + H]⁺ (ES⁺), at 2.20 min, UV active. |
| 22 | 4-((S)-1-((R)-2-(3-cyanobenzyl)oxy)-3-methylbutanamido)ethyl)benzoic acid | Route C Step (i): 1.5 equivalents of alkylating reagent used | 1, 15 | ¹H NMR (400 MHz, DMSO) δ 0.81 (d, J = 6.7 Hz, 3H), 0.86 (d, J = 6.7 Hz, 3H), 1.38 (d, J = 7.1 Hz, 3H), 1.86-1.99 (m, 1H), 3.52 (d, J = 6.2 Hz, 1H), 4.41 (d, J = 12.4 Hz, 1H), 4.57 (d, J = 12.4 Hz, 1H), 4.94-5.09 (m, 1H), 7.44 (d, J = 8.1 Hz, 2H), 7.57 (dd, J = 7.8 Hz, 1H), 7.70 (d, J = 7.8 Hz, 1H), 7.77 (d, J = 7.8 Hz, 1H), 7.81 (s, 1H), 7.88 (d, J = 8.1 Hz, 2H), 8.43 (d, J = 8.2 Hz, 1H), 12.85 (br.s, 1H). | (LC/MS Method D): m/z 381 [M + H]⁺ (ES⁺), at 2.21 min, UV active. |
| 23 | 4-((S)-1-((R)-2-(4-(difluoromethyl)benzyl)oxy)-3-methylbutanamido)ethyl)benzoic acid | Route C Step (i): 1.3 equivalents of alkylating reagent used | 1, 16 | ¹H NMR (400 MHz, DMSO) δ 0.79 (d, J = 6.7 Hz, 3H), 0.84 (d, J = 6.7 Hz, 3H), 1.38 (d, J = 7.1 Hz, 3H), 1.84-1.99 (m, 1H), 3.49 (d, J = 6.3 Hz, 1H), 4.32 (d, J = 11.9 Hz, 1H), 4.52 (d, J = 11.9 Hz, 1H), 4.94-5.08 (m, 1H), 6.99-7.42 (m, 5H), 7.44 (d, J = 8.1 Hz, 2H), 7.88 (d, J = 8.1 Hz, 2H), 8.40 (d, J = 8.1 Hz, 1H), 12.87 (br.s, 1H). | (LC/MS Method D): m/z 422 [M + H]⁺ (ES⁺), at 2.39 min, UV active. |

TABLE 2-continued

| Ex. No. Name | Synthetic method & notes | Intermediates | ¹H NMR | LCMS data |
|---|---|---|---|---|
| 24 4-((S)-1-((R)-2-((3-(difluoromethoxy)benzyl)oxy)-3-methylbutanamido)ethyl)benzoic acid | Route C Step (i): 1.5 equivalents of alkylating reagent used; 1.3 equivalents NaH used | 1, 17 | NMR (400 MHz, DMSO) δ 0.81 (d, J = 6.7 Hz, 3H), 0.86 (d, J = 6.7 Hz, 3H), 1.38 (d, J = 7.0 Hz, 3H), 1.87-2.00 (m, 1H), 3.51 (d, J = 6.2 Hz, 1H), 4.35 (d, J = 12.4 Hz, 1H), 4.56 (d, J = 12.4 Hz, 1H), 4.95-5.10 (m, 1H), 7.00-7.47 (m, 7H), 7.88 (d, J = 8.0 Hz, 2H), 8.41 (d, J = 8.1 Hz, 1H), 12.87 (br.s, 1H). | (LC/MS Method D): m/z 422 [M + H]⁺ (ES⁺), at 2.39 min, UV active. |
| 25 4-((S)-1-((R)-3-methyl-2-((5-(trifluoromethyl)pyridin-2-yl)methoxy)butanamido)ethyl)benzoic acid | Route C Step (i): 1.5 equivalents of alkylating reagent used; 1.2 equivalents NaH used | 1, 18 | ¹H NMR (400 MHz, DMSO) δ 0.79-0.94 (m, 6H), 1.38 (d, J = 7.0 Hz, 3H), 1.93-2.07 (m, 1H), 3.66 (d, J = 5.9 Hz, 1H), 4.59 (d, J = 13.9 Hz, 1H), 4.70 (d, J = 13.9 Hz, 1H), 4.94-5.11 (m, 1H), 7.42 (d, J = 7.9 Hz, 2H), 7.72 (d, J = 8.3 Hz, 1H), 7.87 (d, J = 7.9 Hz, 2H), 8.24 (dd, J = 8.3, 2.3 Hz, 1H), 8.59 (d, J = 8.1 Hz, 1H), 8.91 (s, 1H), 12.98 (br.s, 1H). | (LC/MS Method D): m/z 425 [M + H]⁺ (ES⁺), at 2.32 min, UV active. |
| 26 4-((S)-1-((R)-3-methyl-2-((4-(pentafluoro-λ6-sulfaneyl)benzyl)oxy)butanamido)ethyl)benzoic acid | Route C Step (i): 1.5 equivalents of alkylating reagent used; 1.1 equivalents NaH used | 1, 19 | ¹H NMR (400 MHz, DMSO) δ 0.83 (d, J = 6.7 Hz, 3H), 0.88 (d, J = 6.7 Hz, 3H), 1.37 (d, J = 7.0 Hz, 3H), 1.85-2.06 (m, 1H), 3.54 (d, J = 6.2 Hz, 1H), 4.43 (d, J = 13.0 Hz, 1H), 4.62 (d, J = 13.0 Hz, 1H), 4.96-5.09 (m, 1H), 7.44 (d, J = 8.0 Hz, 2H), 7.57 (d, J = 8.3 Hz, 2H), 7.84-7.92 (m, 4H), 8.44 (d, J = 8.2 Hz, 1H), 12.87 (br.s, 1H). | (LC/MS Method D): m/z 482 [M + H]⁺ (ES⁺), at 2.63 min, UV active. |
| 27 4-((S)-1-((R)-2-((3,4-difluorobenzyl)oxy)-3-methylbutanamido)ethyl)benzoic acid | Route C Step (i): 1.3 equivalents of alkylating reagent used; 1.5 equivalents NaH used | 1, 20 | ¹H NMR (400 MHz, DMSO) δ 0.80 (d, J = 6.6 Hz, 3H), 0.85 (d, J = 6.6 Hz, 3H), 1.38 (d, J = 7.0 Hz, 3H), 1.87- 1.99 (m, 1H), 3.50 (d, J = 6.1 Hz, 1H), 4.34 (d, J = 12.2 Hz, 1H), 4.50 (d, J = 12.2 Hz, 1H), 4.95-5.09 (m, 1H), 7.14-7.23 (m, 1H), 7.36-7.47 (m, 4H), 7.87 (d, J = 8.0 Hz, 2H), 8.41 (d, J = 8.1 Hz, 1H), 12.91 (s,1H). | (LC/MS Method D): m/z 392 [M + H]⁺ (ES⁺), at 2.40 min, UV active. |
| 28 4-((S)-1-((R)-2-((2,2-difluorobenzo[d][1,3]dioxol-5-yl)methoxy)-3-methylbutanamido)ethyl)benzoic acid | Route C | 1, 21 | ¹H NMR (400 MHz, DMSO) δ 0.80 (d, J = 6.7 Hz, 3H), 0.84 (d, J = 6.7 Hz, 3H), 1.37 (d, J = 7.0 Hz, 3H), 1.85- 1.99 (m, 1H), 3.50 (d, J = 6.1 Hz, 1H), 4.36 (d, J = 12.0 Hz, 1H), 4.52 (d, J = 12.0 Hz, 1H), 4.93-5.07 (m, 1H), 7.14-7.21 (m, 1H), 7.36-7.47 (m, 4H), 7.85-7.91 (m, 2H), 8.38 (d, J = 8.2 Hz, 1H), 12.86 (br.s, 1H). | (LC/MS Method D): m/z 436 [M + H]⁺ (ES⁺), at 2.55 min, UV active. |
| 29 4-((S)-1-((R)-2-((4-(difluoromethyl)-3-fluorobenzyl)oxy)-3-methylbutanamido)ethyl)benzoic acid | Route C Step (i): 1.5 equivalents of alkylating reagent used | 1, 22 | ¹H NMR (400 MHz, DMSO) δ 0.82 (d, J = 6.7 Hz, 3H), 0.88 (d, J = 6.7 Hz, 3H), 1.38 (d, J = 7.0 Hz, 3H), 1.83-2.01 (m, 1H), 3.53 (d, J = 6.2 Hz, 1H), 4.42 (d, J = 13.0 Hz, 1H), 4.59 (d, J = 13.0 Hz, 1H), 4.93-5.10 (m, 1H), 7.01-7.37 (m, 3H), 7.44 (d, J = 8.0 Hz, 2H), 7.88 (d, J = 8.0 Hz, 2H), 8.43 (d, J = 8.2 Hz, 1H), 12.86 (br.s, 1H). | (LC/MS Method D): m/z 424 [M + H]⁺ (ES⁺), at 2.43 min, UV active. |

TABLE 2-continued

| Ex. No. | Name | Synthetic method & notes | Intermediates | ¹H NMR | LCMS data |
|---|---|---|---|---|---|
| 30 | 4-((S)-1-((R)-2-((4-cyclopropylbenzyl)oxy)-3-methylbutanamido)ethyl)benzoic acid | Route C Step (i): 1.5 equivalents of alkylating reagent used | 1, 23 | ¹H NMR (400 MHz, DMSO) δ 0.59-0.68 (m, 2H), 0.78 (d, J = 6.7 Hz, 3H), 0.83 (d, J = 6.7 Hz, 3H), 0.88-0.98 (m, 2H), 1.37 (d, J = 7.0 Hz, 3H), 1.80-1.99 (m, 2H), 3.45 (d, J = 6.2 Hz, 1H), 4.26 (d, J = 11.7 Hz, 1H), 4.47 (d, J = 11.7 Hz, 1H), 4.92-5.07 (m, 1H), 7.04 (d, J = 7.8 Hz, 2H), 7.19 (d, J = 7.8 Hz, 2H), 7.43 (d, J = 8.0 Hz, 2H), 7.87 (d, J = 8.0 Hz, 2H), 8.35 (d, J = 8.1 Hz, 1H), 12.87 (br.s, 1H). | (LC/MS Method D): m/z 396 [M + H]⁺ (ES⁺), at 2.60 min, UV active. |
| 31 | (R)-4-(1-(2-(4-fluorobenzyl)oxy)-3-methylbutanamido)cyclopropyl)benzoic acid | Route E | 5, 24 | ¹H NMR (400 MHz, DMSO) δ 0.76-0.94 (m, 6H), 1.07-1.37 (m, 5H), 3.49 (d, J = 6.0 Hz, 1H), 4.38 (d, J = 12.0 Hz, 1H), 4.56 (d, J = 12.0 Hz, 1H), 7.08-7.27 (m, 4H), 7.37-7.49 (m, 2H), 7.76-7.86 (m, 2H), 8.74 (s, 1H), 12.86 (br.s, 1H). | (LC/MS Method D): m/z 386 [M + H]⁺ (ES⁺), at 2.54 min, UV active. |
| 32 | 4-((S)-1-((R)-2-((3-(difluoromethoxy)-4-fluorobenzyl)oxy)-3-methylbutanamido)ethyl)benzoic acid | Route E Step (i): 1.2 equivalents of NaH used | 1,25 | ¹H NMR (400 MHz, DMSO) δ 0.79 (d, J = 6.7 Hz, 3H), 0.85 (d, J = 6.7 Hz, 3H), 1.37 (d, J = 7.1 Hz, 3H), 1.84- 1.99 (m, 1H), 3.49 (d, J = 6.3 Hz, 1H), 4.32 (d, J = 12.1 Hz, 1H), 4.51 (d, J = 12.1 Hz, 1H), 4.91-5.10 (m, 1H), 7.00-7.46 (m, 6H), 7.87 (d, J = 8.0 Hz, 2H), 8.42 (d, J = 8.2 Hz, 1H), 12.85 (br.s, 1H). | (LC/MS Method D): m/z 440 [M + H]⁺ (ES⁺), at 2.41 min, UV active. |
| 33 | (R)-4-(1-(3-methyl-2-(3-(methylsulfonyl)benzyl)oxy)butanamido)cyclopropyl)benzoic acid | Route C | 5, 6 | ¹H NMR (400 MHz, DMSO) δ 0.85 (d, J = 6.7 Hz, 3H), 0.90 (d, J = 6.7 Hz, 3H), 1.08-1.33 (m, 4H), 1.91-2.05 (m, 1H), 3.18 (s, 3H), 3.53 (d, J = 6.1 Hz, 1H), 4.50 (d, J = 12.5 Hz, 1H), 4.69 (d, J = 12.5 Hz, 1H), 7.16-7.24 (m, 2H), 7.59-7.68 (m, 1H), 7.69-7.76 (m, 1H), 7.79-7.88 (m, 3H), 7.93 (s, 1H), 8.80 (s, 1H), 12.77 (br.s, 1H). | (LC/MS Method D): m/z 446 [M + H]⁺ (ES⁺), at 2.06 min, UV active. |
| 34 | 4-((S)-1-(2-((5-(difluoromethyl)pyridin-2-yl)methoxy)-3-methylbutanamido)ethyl)benzoic acid | Route C Step (i): 1.5 equivalents of alkylating reagent used | 1, 27 | ¹H NMR (400 MHz, DMSO) δ 0.78-0.89 (m, 6H), 1.37 (d, J = 7.0 Hz, 3H), 1.91-2.03 (m, 1H), 3.64 (d, J = 5.7 Hz, 1H), 4.55 (d, J = 13.5 Hz, 1H), 4.66 (d, J = 13.5 Hz, 1H), 4.96-5.06 (m, 1H), 7.14 (t, J = 55 Hz, 1H), 7.44 (d, J = 7.9 Hz, 2H), 7.63 (d, J = 8.1 Hz, 1H), 7.87 (d, J = 7.9 Hz, 2H), 8.03 (d, J = 8.1 Hz, 1H), 8.63 (d, J = 8.0 Hz, 1H), 8.72 (s, 1H), 12.86 (br.s, 1H). | (LC/MS Method E): m/z 407 [M + H]⁺ (ES⁺), at 2.00 min, UV active. |
| 35 | 4-((S)-1-((R)-2-((4-fluoro-3-(methylsulfonyl)benzyl)oxy)-3-methylbutanamido)ethyl)benzoic acid | Route C | 1, 28 | ¹H NMR (400 MHz, DMSO) δ 0.80 (d, J = 6.6 Hz, 3H), 0.86 (d, J = 6.6 Hz, 3H), 1.38 (d, J = 7.0 Hz, 3H), 1.84-2.09 (m, 1H), 3.31 (s, 3H), 3.52 (d, J = 6.3 Hz, 1H), 4.41 (d, J = 12.4 Hz, 1H), 4.59 (d, J = 12.4 Hz, 1H), 4.92-5.08 (m, 1H), 7.43 (d, J = 8.0 Hz, 2H), 7.48-7.53 (m, 1H), 7.69-7.77 (m, 1H), 7.81-7.91 (m, 3H), 8.44 (d, J = 8.1 Hz, 1H), 12.84 (br.s, 1H). | (LC/MS Method D): m/z 452 [M + H]⁺ (ES⁺), at 2.19 min, UV active. |
| 36 | 2-methyl-4-((R)-1-((R)-2-((4-(trifluoromethyl)benzyl)oxy)butanamido)ethyl)benzoic acid | Route E Step (i): 1.2 equivalents of NaH used | 31, 33 | ¹H NMR (400 MHz, Methanol-da) δ 0.92 and 0.96 (2 xd, J = 6.8 Hz, 6H), 1.46 (d, J = 7.0 Hz, 3H), 2.03 (h, J = 6.7 Hz, 1H), 2.57 (s, 3H), 3.58 (d, J = 6.1 Hz, 1H), 4.49 (d, J = 12.4 Hz, 1H), 4.69 (d, J = 12.5 Hz, 1H), 5.00-5.12 (m, 1H), 7.20-7.31 (m, 2H), 7.55 (d, J = 8.0 Hz, 2H), 7.65 (d, J = 7.9 Hz, 2H), 7.88 (d, J = 8.0 Hz, 1H), 8.48 (d, J = 8.2 Hz, 1H). | (LC/MS Method D): m/z 438 [M + H]⁺ (ES⁺), at 2.64 min, UV active. |
| 37 | (R)-4-(1-(2-((3,4-difluorobenzyl)oxy)-3-methylbutanamido)cyclopropyl)benzoic acid | Route C | 5, 20 | ¹H NMR (400 MHz, DMSO) δ 0.78-0.93 (m, 6H), 1.12-1.32 (m, 4H), 1.87-2.02 (m, 1H), 3.49 (d, J = 6.0 Hz, 1H), 4.39 (d, J = 12.2 Hz, 1H), 4.54 (d, J = 12.2 Hz, 1H), 7.14-7.28 (m, 3H), 7.37-7.49 (m, 2H), 7.81 (d, J = 8.0 Hz, 2H), 8.73 (s, 1H), 12.79 (br.s, 1H). | (LC/MS Method D): m/z 404 [M + H]⁺ (ES⁺), at 2.53 min, UV active. |

TABLE 2-continued

| Ex. No. | Name | Synthetic method & notes | Intermediates | ¹H NMR | LCMS data |
|---|---|---|---|---|---|
| 38 | 4-((S)-1-((R)-2-((3-hydroxybenzyl)oxy)-3-methylbutanamido)ethyl)benzoic acid | Route E Step (i): 1.1 equivalents of NaH used, then Route L | 1, 37 | 1H NMR (400 MHz, DMSO-d6) δ 0.81 (d, J = 6.8 Hz, 3H), 0.86 (d, J = 6.7 Hz, 3H), 1.39 (d, J = 7.0 Hz, 3H), 1.93 (h, J = 6.6 Hz, 1H), 3.48 (d, J = 6.3 Hz, 1H), 4.24 (d, J = 12.0 Hz, 1H), 4.47 (d, J = 12.0 Hz, 1H), 5.02 (q, J = 7.4 Hz, 1H), 6.65-6.80 (m, 3H), 7.13 (t, J = 7.8 Hz, 1H), 7.45 (d, J = 8.0 Hz, 2H), 7.89 (d, J = 8.0 Hz, 2H), 8.36 (d, J = 8.1 Hz, 1H), 9.39 (s, 1H). | (LC/MS Method D): m/z 372 [M + H]⁺ (ES⁺), at 2.02 min, UV active. |
| 39 | 4-((S)-1-((R)-2-((3-cyclopropylbenzyl)oxy)-3-methylbutanamido)ethyl)benzoic acid | Route E Step (i): 1.2 equivalents of NaH used | 1, 29 | 1H NMR (400 MHz, DMSO) δ 0.53-0.67 (m, 2H), 0.70-0.97 (m, 8H), 1.37 (d, J = 7.2 Hz, 3H), 1.78-2.00 (m, 2H), 3.46 (d, J = 6.4 Hz, 1H), 4.27 (d, J = 11.9 Hz, 1H), 4.48 (d, J = 11.9 Hz, 1H), 4.93-5.07 (m, 1H), 6.93-7.03 (m, 2H), 7.03-7.12 (m, 1H), 7.16-7.25 (m, 1H), 7.31-7.50 (m, 2H), 7.79-7.94 (m, 2H), 8.34 (d, J = 8.2 Hz, 1H), 12.85 (br.s, 1H). | (LC/MS Method D): m/z 396 [M + H]⁺ (ES⁺), at 2.54 min, UV active. |
| 40 | 4-((S)-1-((R)-2-((3-(methoxymethyl)benzyl)oxy)-3-methylbutanamido)ethyl)benzoic acid | Route E Step (i): 1.2 equivalents of NaH used | 1, 30 | 1H NMR (400 MHz, DMSO) δ 0.78 (d, J = 6.7 Hz, 3H), 0.84 (d, J = 6.7 Hz, 3H), 1.37 (d, J = 7.1 Hz, 3H), 1.82- 1.99 (m, 1H), 3.26 (s, 3H), 3.48 (d, J = 6.3 Hz, 1H), 4.31 (d, J = 11.9 Hz, 1H), 4.38 (s, 2H), 4.53 (d, J = 11.9 Hz, 1H), 4.87-5.11 (m, 1H), 7.18-7.37 (m, 4H), 7.41-7.48 (m, 2H), 7.81-7.95 (m, 2H), 8.37 (d, J = 8.2 Hz, 1H), 12.88 (br.s, 1H). | (LC/MS Method E): m/z 400 [M + H]⁺ (ES⁺), at 1.99 min, UV active. |
| 41 | 4-((S)-1-((R)-2-((4-hydroxybenzyl)oxy)-3-methylbutanamido)ethyl)benzoic acid | Route E Step (i): 1.2 equivalents of NaH and 2 equivalents of Intermediate 38 used, then Route L | 1, 38 | 1H NMR (400 MHz, DMSO-d6) δ 0.77 (d, J = 6.8 Hz, 3H), 0.82 (d, J = 6.7 Hz, 3H), 1.39 (d, J = 7.0 Hz, 3H), 1.89 (h, J = 6.7 Hz, 1H), 3.44 (d, J = 6.2 Hz, 1H), 4.21 (d, J = 11.3 Hz, 1H), 4.42 (d, J = 11.3 Hz, 1H), 5.01 (p, J = 7.2 Hz, 1H), 6.67-6.80 (m, 2H), 7.08-7.18 (m, 2H), 7.40-7.50 (m, 2H), 7.84-7.93 (m, 2H), 8.33 (d, J = 8.2 Hz, 1H), 9.42 (s, 1H), 12.88 (s, 1H). | (LC/MS Method D): m/z 372 [M + H]⁺ (ES⁺), at 2.09 min, UV active. |
| 42 | (R)-N-((S)-1-(4-(1H-tetrazol-5-yl)phenyl)ethyl)-2-((4-fluorobenzyl)oxy)-3-methylbutanamide | Route H | 4, 24 | 1H NMR (400 MHz, DMSO) δ 0.81 (d, J = 6.7 Hz, 3H), 0.87 (d, J = 6.7 Hz, 3H), 1.42 (d, J = 7.1 Hz, 3H), 1.88-2.00 (m, 1H), 3.51 (d, J = 6.2 Hz, 1H), 4.35 (d, J = 11.8 Hz, 1H), 4.54 (d, J = 11.8 Hz, 1H), 4.99-5.10 (m, 1H), 7.13-7.23 (m, 2H), 7.37-7.43 (m, 2H), 7.51-7.56 (m, 2H), 7.96-8.00 (m, 2H), 8.39 (d, J = 8.2 Hz, 1H). Tetrazole N-H not observed. | (LC/MS Method E): m/z 398 [M + H]⁺ (ES⁺), at 1.99 min, UV active. |
| 43 | (R)-N-((S)-1-(4-(1H-tetrazol-5-yl)phenyl)ethyl)-3-methyl-2-((4-(trifluoromethyl)benzyl)oxy)butanamide | Route H | 4, 31 | 1H NMR (400 MHz, DMSO) δ 0.80-0.97 (m, 6H), 1.38-1.49 (m, 3H), 1.94-2.03 (m, 1H), 3.49-3.61 (m, 1H), 4.47 (d, J = 12.0 Hz, 1H), 4.66 (d, J = 12.0 Hz, 1H), 5.02-5.12 (m, 1H), 7.53-7.63 (m, 4H), 7.69-7.78 (m, 2H), 7.96-8.04 (m, 2H), 8.43-8.50 (m, 1H). Tetrazole N-H not observed. | (LC/MS Method E): m/z 448 [M + H]⁺ (ES⁺), at 2.17 min, UV active. |
| 44 | 4-((S)-1-((R)-2-((3-(ethylsulfonyl)benzyl)oxy)-3-methylbutanamido)ethyl)benzoic acid | Route E Step (i): 1.2 equivalents of NaH used | 1, 32 | 1H NMR (400 MHz, DMSO) δ 0.82 (d, J = 6.7 Hz, 3H), 0.89 (d, J = 6.7 Hz, 3H), 1.10 (t, J = 7.3 Hz, 3H), 1.40 (d, J = 7.1 Hz, 3H), 1.91-2.02 (m, 1H), 3.29 (q, J = 7.3 Hz, 2H), 3.55 (d, J = 6.3 Hz, 1H), 4.47 (d, J = 12.6 Hz, 1H), 4.67 (d, J = 12.6 Hz, 1H), 4.98-5.11 (m, 1H), 7.40-7.48 (m, 2H), 7.64-7.69 (m, 1H), 7.70-7.75 (m, 1H), 7.79-7.85 (m, 1H), 7.86-7.92 (m, 3H), 8.49 (d, J = 8.1 Hz, 1H), 12.90 (br.s, 1H). | (LC/MS Method D): m/z 448 [M + H]⁺ (ES⁺), at 2.11 min, UV active. |

TABLE 2-continued

| Ex. No. | Name | Synthetic method & notes | Intermediates | ¹H NMR | LCMS data |
|---|---|---|---|---|---|
| 45 | 4-((S)-1-((R)-2-((3-(hydroxymethyl)benzyl)oxy)-3-methylbutanamido)ethyl)benzoic acid | Route I | 1 | ¹H NMR (400 MHz, DMSO) δ 0.78 (d, J = 6.7 Hz, 3H), 0.84 (d, J = 6.7 Hz, 3H), 1.38 (d, J = 7.1 Hz, 3H), 1.82-2.00 (m, 1H), 3.48 (d, J = 6.1 Hz, 1H), 4.30 (d, J = 11.8 Hz, 1H), 4.40-4.58 (m, 3H), 4.96-5.08 (m, 1H), 5.13-5.24 (m, 1H), 7.14-7.33 (m, 4H), 7.39-7.48 (m, 2H), 7.81-7.93 (m, 2H), 8.36 (d, J = 8.1 Hz, 1H), 12.83 (br.s, 1H). | (LC/MS Method D): m/z 386 [M + H]+ (ES+), at 1.68 min, UV active. |
| 46 | 4-((1S)-1-((2R)-2-(1-(4-fluorophenyl)ethoxy)-3-methylbutanamido)ethyl)benzoic acid, mixture of diastereomers | Route E Step (i): 1.2 equivalents of NaH used | 1, 34 | ¹H NMR (400 MHz, DMSO-d6) [NB mixture of diastereoisomers] δ 0.62-0.91 (m, 6H), 1.20-1.46 (m, 6H), 1.77-2.00 (m, 1H), 3.18 (d, J = 6.8 Hz, 0.5H), 3.52 (d, J = 5.9 Hz, 0.6H), 4.31 (q, J = 6.3 Hz, 0.4H), 4.45 (q, J = 6.4 Hz, 0.6H), 4.83 (p, J = 7.2 Hz, 0.6H), 5.05 (p, J = 7.3 Hz, 0.4H), 7.08-7.24 (m, 2H), 7.29-7.36 (m, 2H), 7.40-7.48 (m, 2H), 7.81-7.87 (m, 1.2H), 7.89-7.94 (m, 0.8H), 7.97 (d, J = 8.2 Hz, 0.6H), 8.32 (d, J = 8.2 Hz, 0.4H), 12.90 (s, 1H). | (LC/MS Method H): m/z 388 [M + H]+ (ES+), at 9.56 min, UV active. |
| 47 | 4-((1S)-1-(3-methyl-2-((4-(oxetan-3-yl)benzyl)oxy)butanamido)ethyl)benzoic acid, mixture of diastereomers | Route J | 3, 35 | ¹H NMR (400 MHz, Methanol-d₄) [NB mixture of diastereoisomers] δ 0.85-1.00 (m, 6H), 1.44-1.51 (m, 3H), 1.93-2.08 (m, 1H), 3.53-3.59 (m, 1H), 4.22-4.33 (m, 1H), 4.42 (d, J = 11.7 Hz, 1H), 4.54 (d, J = 11.8 Hz, 0.5H), 4.61 (d, J = 11.8 Hz, 0.5H), 4.70-4.77 (m, 2H), 5.05-5.20 (m, 3H), 7.29-7.48 (m, 6H), 7.93-8.02 (m, 2H), 8.37 (d, J = 8.2 Hz, 0.4H), 8.44 (d, J = 8.1 Hz, 0.4H). | (LC/MS Method D): m/z 412 [M + H]+ (ES+), at 2.23 & 2.26 min, UV active. |
| 48 | 4-((1S)-1-(3-methyl-2-((3-(oxetan-3-yl)benzyl)oxy)butanamido)ethyl)benzoic acid, diastereomer 1 | Route K | 3, 36 | 1H NMR (400 MHz, DMSO-d6) δ 0.83 (d, J = 6.8 Hz, 3H), 0.89 (d, J = 6.7 Hz, 3H), 1.39 (d, J = 7.0 Hz, 3H), 1.95 (h, J = 6.7 Hz, 1H), 3.51 (d, J = 6.3 Hz, 1H), 4.22 (p, J = 8.1 Hz, 1H), 4.33 (d, J = 11.9 Hz, 1H), 4.52 (d, J = 11.9 Hz, 1H), 4.56-4.64 (m, 2H), 4.93 (dd, J = 8.4, 5.8 Hz, 2H), 5.07 (p, J = 7.2 Hz, 1H), 7.19-7.26 (m, 1H), 7.30-7.38 (m, 3H), 7.42 (d, J = 8.0 Hz, 2H), 7.88 (d, J = 8.2 Hz, 2H), 8.39 (d, J = 8.2 Hz, 1H). | (LC/MS Method D): m/z 412 [M + H]+ (ES+), at 2.03 min, UV active. |
| 49 | 4-((1S)-1-(3-methyl-2-((3-(oxetan-3-yl)benzyl)oxy)butanamido)ethyl)benzoic acid, diastereomer 2 | Route K | 3, 36 | 1H NMR (400 MHz, DMSO-d6) δ 0.80 (d, J = 6.8 Hz, 3H), 0.87 (d, J = 6.7 Hz, 3H), 1.38 (d, J = 7.1 Hz, 3H), 1.94 (h, J = 6.7 Hz, 1H), 3.50 (d, J = 6.3 Hz, 1H), 4.19-4.29 (m, 1H), 4.35 (d, J = 12.0 Hz, 1H), 4.52-4.65 (m, 3H), 4.94 (ddd, J = 7.9, 5.9, 1.6 Hz, 2H), 5.02 (p, J = 7.2 Hz, 1H), 7.22-7.27 (m, 1H), 7.31-7.40 (m, 3H), 7.44 (d, J = 8.1 Hz, 2H), 7.88 (d, J = 8.1 Hz, 2H), 8.41 (d, J = 8.2 Hz, 1H), 12.93 (s, 1H). | (LC/MS Method D): m/z412 [M + H]+ (ES+), at 2.00 min, UV active. |
| 50 | (R)-4-(1-(2-(3-chlorobenzyl)oxy)-3-methylbutanamido)cyclopropyl)benzoic acid | Route C | 5, 8 | 1H NMR: (400 MHz, DMSO-d6) δ 0.88 (dd, 6H, J = 6.8 Hz & J = 14.8 Hz), 1.35-1.14 (m, 4H), 2.00-1.93 (m, 1H), 3.51 (d, 1H, J = 6.0 Hz), 4.43 (d, 1H, J = 12.4 Hz), 4.59 (d, 1H, J = 12.4 Hz), 7.23 (d, 2H, J = 8.4 Hz), 7.41-7.34 (m, 3H), 7.473 (s, 1H), 7.83 (d, 2H, J = 8.8 Hz), 8.78 (s, 1H), 12.82 (s, 1H). | (LC/MS Method D): m/z 402 [M + H]+(ES+), at 2.36 min, UV active. |
| 51 | 4-((1S)-1-((2R)-3-methyl-2-(1-(4-(trifluoromethyl)phenyl)ethoxy)butanamido)ethyl)benzoic acid, mixture of diastereomers | Route M | 1, 39 | 1H NMR: (400 MHz, DMSO-d6): [NB mixture of diastereoisomers] δ 0.70-0.66 (m, 3H), 0.85 (d, 3H, J = 6.4 Hz), 1.39 (d, 3H, J = 6.8 Hz), 1.61 (d, 3H, J = 6.4 Hz), 1.98-1.89 (m, 1H), 3.70-3.66 (m, 1H), 5.05-4.95 (m, 1H), 5.42 (dd, 1H, J = 5.2 Hz & 4.4 Hz), 6.11 (d, 1H, J = 6.8 Hz), 7.49 (d, 2H, J = 8.4 Hz), 7.68 (d, 2H, J = 8.4 Hz), 7.74 (d, 2H, J = 8.4 Hz), 7.96 (d, 2H, J = 8.0 Hz), 8.19 (dd, 1H, J = 8.0 Hz & 2.0 Hz). | (LC/MS Method H): m/z 438 [M + H]+ (ES+), at 10.00 min, UV active. |

TABLE 2-continued

| Ex. No. | Name | Synthetic method & notes | Intermediates | ¹H NMR | LCMS data |
|---|---|---|---|---|---|
| 52 | (R)-4-(1-(2-((3-(difluoromethoxy)benzyl)oxy)-3-methylbutanamido)cyclopropyl)benzoic acid | Route A | 5, 17 | ¹H NMR (400 MHz, DMSO-d6) δ 8.72 (s, 1H), 7.91-7.73 (m, 2H), 7.48-7.38 (m, 1H), 7.29-7.09 (m, 6H), 4.62 (d, J = 12.4 Hz, 1H), 4.42 (d, J = 12.4 Hz, 1H), 3.51 (d, J = 6.1 Hz, 1H), 2.05-1.91 (m, 1H), 1.31-1.10 (m, 4H), 0.91 (d, J = 6.7 Hz, 3H), 0.87 (d, J = 6.8 Hz, 3H). | (LC/MS Method C): m/z 434 [M + H]⁺ (ES⁺), at 2.41 min., UV active |
| 53 | 4-((S)-1-((R)-3-methyl-2-((4-(trifluoromethoxy)benzyl)oxy)butanamido)ethyl)-N-(methylsulfonyl)benzamide | Route N | Example 1 | ¹H NMR (400 MHz, CDCl₃) δ 0.81 (d, J = 6.8 Hz, 3H), 0.90 (d, J = 6.9 Hz, 3H), 1.41 (d, J = 7.0 Hz, 3H), 1.99-2.08 (m, 1H), 3.24 (s, 3H), 3.68 (d, J = 4.4 Hz, 1H), 4.57 (d, J = 12.1 Hz, 1H), 4.64 (d, J = 12.1 Hz, 1H), 5.09 (p, J = 7.2 Hz, 1H), 6.80 (d, J = 8.0 Hz, 1H), 7.30 (d, J = 8.0 Hz, 2H), 7.44-7.50 (m, 2H), 7.62-7.67 (m, 2H), 7.84 (d, J = 8.1 Hz, 2H). One exchangeable proton not observed | (LC/MS Method A): m/z 501 [M + H]+, 2.69 min., UV active |
| 54 | (R)-4-(1-(2-((3-cyanobenzyl)oxy)-3-methylbutanamido)cyclopropyl)benzoic acid | Route C | 5, 15 | ¹H NMR: (400 MHz, DMSO) 0.91-0.84 (m, 6H), 1.25-1.14 (m, 2H), 1.32-1.27 (m, 2H), 2.03-1.94 (m, 1H), 3.53 (d, 1H, J = 6.0 Hz), 4.48 (d, 1H, J = 12.4 Hz), 4.63 (d, 1H, J = 12.4 Hz), 7.23 (d, 2H, J = 8.4 Hz), 7.59 (t, 1H, J = 7.8 Hz), 7.74 (d, 1H, J = 8.0 Hz), 7.84-7.784 (m, 3H), 7.88 (s, 1H), 8.80 (s, 1H), 12.84 (s, 1H). | (LC/MS Method D): m/z 393 [M + H]⁺ (ES⁺), at 2.01 min., UV active. |
| 55 | (R)-4-(1-(2-(2,2-difluorobenzo[d][1,3]dioxol-5-yl)methoxy)-3-methylbutanamido)cyclopropyl)benzoic acid | Route C | 5, 21 | ¹H NMR: (400 MHz, DMSO) 0.90-0.86 (m, 6H), 1.28-1.17 (m, 4H) 2.02-1.92 (m, 1H), 3.53 (d, 1H, J =5.6 Hz), 4.5 (d, 1H, J =12.4 Hz), 4.58 (d, 1H, J =12.0 Hz), 7.26-7.20 (m, 3H), 7.42 (d, 1H), 7.48 (s, 1H), 7.83 (d, 2H, J = 8.4 Hz), 8.73 (s, 1H), 12.81 (s, 1H). | (LC/MS Method D): m/z 448 [M + H]⁺ (ES⁺), at 2.13min., UV active |
| 56 | (R)-4-(1-(2-((3-(ethylsulfonyl)benzyl)oxy)-3-methylbutanamido)cyclopropyl)benzoic acid | Route C | 5, 32 | ¹H NMR: (400 MHz, DMSO) 0.92-0.85 (m, 6H), 1.08 (t, 3H, J = 7.4 Hz), 1.27-1.15 (m, 4H), 2.01-1.96 (m, 1H), 3.31-3.26 (m, 2H), 3.53 (d, 1H, J = 6.0 Hz), 4.51 (d, 1H, J = 12.4 Hz), 4.72 (d, 1H, J = 12.4 Hz), 7.23 (d, 2H, J = 8.4 Hz), 7.67 (t, 1H, J = 7.6 Hz), 7.77 (d, 1H, J = 7.6 Hz), 7.83 (d, 3H, J = 8.0 Hz), 7.90 (s, 1H), 8.83 (s, 1H), 12.86 (s, 1H). | (LC/MS Method H): m/z 477 [M+18]⁺ (ES⁺), at 8.23 min., UV active |
| 57 | (R)-4-(1-(2-((3-(difluoromethoxy)-4-fluorobenzyl)oxy)-3-methylbutanamido)cyclopropyl)benzoic acid | Route C | 5, 25 | ¹H NMR: (400 MHz, DMSO) 0.98 (dd, 6H, J = 6.4 Hz & J = 24.8 Hz), 1.24-1.16 (m, 3H), 1.31-1.26 (m, 2H), 1.99-1.95 (m, 1H), 3.51 (d, 1H, J = 6.4 Hz), 4.39 (d, 1H, J = 12.0 Hz), 4.58 (d, 1H, J = 12.0 Hz), 7.28-7.20 (m, 2H), 7.34-7.30 (m, 1H), 7.44-7.39 (m, 2H), 7.83 (d, 2H, J = 8.4 Hz), 8.78 (s, 1H), 12.85 (s, 1H). | (LC/MS Method D): m/z 452 [M + H]⁺ (ES⁺), at 2.37 min., UV active |
| 58 | (R)-4-(1-(3-methyl-2-((3-(trifluoromethoxy)benzyl)oxy)butanamido)cyclopropyl)benzoic acid | Route A | 5, 13 | ¹H NMR: (400 MHz, DMSO) 8.76 (s, 1H), 7.81 (d, 2H), 7.52(t 1H), 7.44-7.38 (m, 2H), 7.34-7.28 (m, 1H), 7.19 (d, 2H), 4.65 (d, 1H), 4.46 (d, 1H), 3.53 (d. 1H), 2.05-1.93, (m, 1H), 1.32-1.13 (m, 4H), 0.89 (dd, 6H) | (LC/MS Method C): m/z 452 [M + H]⁺ (ES⁺), at 2.72 min, UV active |
| 59 | (R)-4-(2-methyl-2-((4-(trifluoromethyl)benzyl)oxy)butanamido)methyl)benzoic acid | Route A (Step (i)); then, Route C (Step (ii)) | 31, 40 | ¹H NMR (400 MHz, DMSO-d6) δ 0.86-0.92 (m, 6H), 1.95-2.05 (m, 1H), 3.61 (d, 1H, J = 5.6 Hz, 1H), 4.38 (d, J = 6.1 Hz, 2H), 4.48 (d, J = 12.7 Hz, 1H), 4.69 (d, 1H, J = 12.7 Hz, 1H), 7.35-7.40 (m, 2H), 7.57-7.62 (m, 2H), 7.70-7.74 (m, 1H), 7.86-7.91 (m, 2H), 8.57 (t, J = 6.2 Hz, 1H), 12.86 (s, 1H). | (LC/MS Method B): m/z 410 [M + H]+, 0.80 min., UV active |
| 60 | (R)-4-(1-(2-((3-(methoxymethyl)benzyl)oxy)-3-methylbutanamido)cyclopropyl)benzoic acid | Route C | 5, 30 | ¹H NMR (400 MHz, DMSO-d6) 0.88 (dd, 6H, J = 6.4 Hz & J = 19.6 Hz), 1.13-1.07 (m, 4H), 2.00-1.92 (m, 1H), 3.29 (s, 3H), 3.48 (d, 1H, J = 6.4 Hz), 4.41-4.38 (m, 3H), 4.59 (d, 1H, J = 12.0 Hz), 7.26-7.23 (m, 3H), 7.37-7.29 (m, 3H), 7.83 (d, 2H, J = 8.4 Hz), 8.76 (s, 1H), 12.83 (s, 1H | (LC/MS Method D): m/z 412 [M + H]⁺ (ES⁺), at 2.14 min., UV active. |

TABLE 2-continued

| Ex. No. | Name | Synthetic method & notes | Intermediates | ¹H NMR | LCMS data |
|---|---|---|---|---|---|
| 61 | (R)-4-(1-(2-((4-(difluoromethyl)-3-fluorobenzyl)oxy)-3-methylbutanamido)cyclopropyl)benzoic acid | Route C | 5, 22 | ¹H NMR: (400 MHz, DMSO) δ: 0.92 (dd, 6H, J = 5.6 Hz & J = 14.8 Hz), 1.30-1.20 (m, 4H), 2.05-1.95 (m, 1H), 3.55 (d, 1H, J = 4.4 Hz), 4.50 (d, 1H, J = 12.4 Hz), 4.67 (d, 1H, J = 12.8 Hz), 7.22 (t, 1H, J = 56 Hz), 7.25 (d, 2H, J = 7.2 Hz), 7.44-7.36 (m, 2H), 7.65 (t, 1H, J = 7.6 Hz), 7.84 (d, 2H, J = 6.8 Hz), 8.82 (s, 1H), 12.84 (s, 1H). | (LC/MS Method D): m/z 436 [M + H]⁺ (ES⁺), at 2.01 min. UV active. |
| 62 | (R)-4-(1-(2-((4-(difluoromethyl)benzyl)oxy)-3-methylbutanamido)cyclopropyl)benzoic acid | Route C | 5, 49 | ¹H NMR: (400 MHz, DMSO) 0.88 (dd, 6H, J = 6.8 Hz & J = 17.6 Hz), 1.30-1.15 (m, 4H), 2.00-1.95 (m, 1H), 3.52-3.51 (d, 1H, J = 6.0 Hz), 4.45 (d, 1H, J = 12.4 Hz), 4.65 (d, 1H, J = 12.4 Hz), 7.04 (t, 1H, J = 55.8 Hz), 7.24 (d, 2H, J = 8.4 Hz), 7.59-7.52 (m, 4H), 7.83 (d, 2H, J = 8.4 Hz), 8.77 (s, 1H), 12.80 (s, 1H). | (LC/MS Method D): m/z 418 [M + H]⁺ (ES⁺), at 2.21 min. UV active. |
| 63 | (R)-4-(1-(3-methyl-2-((4-(trifluoromethyl)benzyl)oxy)butanamido)cyclopropyl)-N-(methylsulfonyl)benzamide | Route N | Example 2 | ¹H NMR (400 MHz, DMSO-d6) δ 12.03 (s, 1H), 8.80 (s, 1H), 7.88-7.83 (m, 2H), 7.78-7.73 (m, 2H), 7.65-7.60 (m, 2H), 7.29-7.24 (m, 2H), 4.69 (d, J = 12.7 Hz, 2H), 4.51 (d, J = 12.7 Hz, 1H), 3.55 (d, J = 6.1 Hz, 1H), 2.01 (dt, J = 13.3, 6.7 Hz 1H), 1.36-1.17 (m, 4H), 0.93 (d, J = 6.8 Hz, 3H), 0.89 (d, J = 6.8 Hz, 3H). | (LC/MS Method C): m/z 513 [M + H]⁺ (ES⁺), at 2.79 min. UV active. |
| 64 | (R)-4-(2-methyl-2-((4-(trifluoromethyl)benzyl)oxy)butanamido)propan-2-yl)benzoic acid | Route A (Step (i); then, Route C (Step 00) | 31, 41 | 1H NMR (400 MHz, DMSO-d6) δ 0.88 (d, J = 6.8 Hz, 3H), 0.91 (d, J = 6.7 Hz, 3H), 1.57 (d, J = 9.7 Hz, 6H), 1.97 (h, J = 6.7 Hz, 1H), 3.54 (d, J = 6.4 Hz, 1H), 4.50 (d, J = 12.7 Hz, 1H), 4.63 (d, J = 12.7 Hz, 1H), 7.39-7.45 (m, 2H), 7.58-7.63 (m, 2H), 7.72-7.77 (m, 2H), 7.82-7.87 (m, 2H), 8.04 (s, 1H), 12.74 (s, 1H). | (LC/MS Method C): m/z 438 [M + H]⁺ (ES⁺), 2.65 min. UV active |
| 65 | (R)-4-(1-(2-(3-cyclopropylbenzyl)oxy)-3-methylbutanamido)cyclopropyl)benzoic acid | Route C | 5, 29 | 1H NMR (400 MHz, DMSO) 0.67-0.64 (m, 2H), 0.92-0.84 (m, 6H), 0.95-0.93 (m, 2H), 1.23-1.17 (m, 2H), 1.28-1.25 (m, 2H), 1.98-1.87 (m, 2H), 3.47 (d, 1H, J = 6.4 Hz), 4.37 (d, 1H, J = 12.0 Hz), 4.54 (d, 1H, J = 7.6 Hz), 7.01 (d, 1H), 7.06 (s, 1H), 7.14 (d, 1H, J = 7.6 Hz), 7.25-7.21 (m, 3H), 7.83 (d, 2H, J = 8.4 Hz), 8.72 (s, 1H), 12.84 (s, 1H). | (LC/MS Method D): m/z 408 [M + H]⁺ (ES⁺), at 2.35min. UV active. |
| 66 | 4-((S)-1-((R)-2-(imidazo[1,2-a]pyridin-7-yl)methoxy)-3-methylbutanamido)ethyl)benzoic acid | Route C Step (i): 3 equivalents of NaH used | 1, 42 | 1H NMR (400 MHz, Methanol-d4) δ 0.93 (d, J = 6.9 Hz, 3H), 0.98 (d, J = 6.7 Hz, 3H), 1.48 (d, J = 7.0 Hz, 3H), 1.97-2.10 (m, 1H), 3.61 (d, J = 6.3 Hz, 1H), 4.50 (d, J = 12.9 Hz, 1H), 4.67 (d, J = 12.8 Hz, 1H), 5.06-5.16 (m, 1H), 6.95-7.00 (m, 1H), 7.42 (d, J = 8.1 Hz, 2H), 7.55-7.62 (m, 1H), 7.85 (s, 1H), 7.95 (d, J = 8.1 Hz, 2H), 8.43 (d, J = 7.0 Hz, 1H), 8.58 (d, J = 8.1 Hz, 1H). | (LC/MS Method D): m/z 396 [M + H]⁺ (ES⁺), at 1.68 min, UV active. |
| 67 | (R)-4-(1-(2-((4-(difluoromethoxy)pyridin-4-yl)methoxy)-3-methylbutanamido)cyclopropyl)benzoic acid | Route C | 5, 44 | 1H NMR (400 MHz, DMSO) 0.99-0.85 (m, 6H), 1.21-1.15 (m, 2H), 1.32-1.23 (m, 2H), 2.04-1.99 (m, 1H), 3.56 (d, 1H, J = 6.0 Hz), 4.50 (d, 1H, J = 14.0 Hz), 4.67 (d, 1H, J = 10.0 Hz), 7.11 (s, 1H), 7.23 (d, 2H, J = 8.4 Hz), 7.28 (d, 1H, J = 5.2 Hz), 7.72 (t, 1H, J = 73.2 Hz), 7.83 (d, 2H, J = 8.4 Hz), 8.23 (d, 1H, J = 4.8 Hz), 8.82 (s, 1H), 12.83 (s, 1H). | (LC/MS Method D): m/z 435 [M + H]⁺ (ES⁺), at 2.00 min. UV active. |
| 68 | (R)-4-(1-(2-((4-(difluoromethoxy)pyridin-2-yl)methoxy)-3-methylbutanamido)cyclopropyl)benzoic acid | Route C | 5, 45 | 1H NMR (400 MHz, DMSO-d6) δ: 0.91 (t, 6H, J = 7.2 Hz), 1.31-1.15 (m, 4H), 2.06-2.01 (m, 1H), 3.64 (d, 1H, J = 6. 0Hz) 4.54 (d, 1H, J = 13.6 Hz), 4.68 (d, 1H, J = 13.2 Hz), 7.15 (dd, 1H, J = 2.4 Hz & J = 5.6 Hz), 7.32-7.24 (m, 3H), 7.51 (t, 1H, J = 72.4 Hz), 7.81 (d, 2H, J = 8.8 Hz), 8.54 (d, 1H, J = 5.6 Hz), 8.94 (s, 1H), 12.82 (s, 1H) | (LC/MS Method D): m/z 435 [M + H]⁺ (ES⁺), at1.99min. UV active. |

TABLE 2-continued

| Ex. No. | Name | Synthetic method & notes | Intermediates | ¹H NMR | LCMS data |
|---|---|---|---|---|---|
| 69 | (R)-N-(1-(4-(1H-tetrazol-5-yl)phenyl)cyclopropyl)-3-methyl-2-((4-(trifluoromethyl)benzyl)oxy)butanamide | Route H | 50, 31 | ¹H NMR: (400 MHz, DMSO) 0.90 (dd, 6H, J = 17.2 Hz & J = 6.8 Hz), 1.30-1.18 (m, 4H), 2.02-1.98 (m, 1H), 3.54 (d, 1H, J = 6.0 Hz), 4.51 (d, 1H, J = 12.4 Hz), 4.70 (d, 1H J = 12.8 Hz), 7.36 (d, 2H, J = 8.4 Hz), 7.62 (d, 2H, J = 8.0 Hz), 7.75 (d, 2H, J = 8.0 Hz), 7.93 (d, 2H, J = 8.4 Hz), 8.82 (s, 1H), 16.74 (s, 1H). | (LC/MS Method D): m/z 460 [M + H]⁺ (ES⁺), at 2.05 min. UV active. |
| 70 | (R)-N-(1-(4-(1H-tetrazol-5-yl)phenyl)cyclopropyl)-2-((4-fluorobenzyl)oxy)-3-methylbutanamide | Route H | 50, 24 | ¹H NMR: (400 MHz, DMSO) 0.87 (dd, 6H, J = 6.8 Hz & J = 16.8 Hz), 1.15-1.09 (m, 2H), 1.23-1.18 (m, 2H), 1.98-1.93 (m, 1H), 3.48-3.39 (m, 1H), 4.38 (d, 1H, J = 11.2 Hz), 4.57 (d, 1H, J = 11.6 Hz), 7.22-7.17 (m, 4H), 7.44-7.41 (m, 2H), 7.85 (d, 2H, J = 8.4 Hz), 8.69 (s, 1H). | (LC/MS Method D): m/z 410 [M + H]⁺ (ES⁺), at 2.50 min. UV active. |
| 71 | (R)-N-(1-(4-(1H-tetrazol-5-yl)phenyl)cyclopropyl)-2-((3,4-difluorobenzyl)oxy)-3-methylbutanamide | Route H | 50, 20 | ¹H NMR: (400 MHz, DMSO) δ: 0.91-0.86 (m, 6H), 1.31-1.19 (m, 4H), 1.99-1.96 (m, 1H), 3.53 (d, 1H, J = 6.0 Hz), 4.42 (d, 1H, J = 12.0 Hz), 4.57 (d, 1H, J = 12.0 Hz), 7.26-7.25 (m, 1H), 7.35 (d, 2H, J = 8.4 Hz), 7.51-7.41 (m, 2H), 7.95 (d, 2H, J = 8.4 Hz), 8.80 (s, 1H), 16.84 (s, 1H). | (LC/MS Method D): m/z 428 [M + H]⁺ (ES⁺), at 2.21 min. UV active. |
| 72 | (R)-N-(1-(4-(1H-tetrazol-5-yl)phenyl)cyclopropyl)-2-((3-(difluoromethoxy)benzyl)oxy)-3-methylbutanamide | Step 1 as Route A, Step 2 as Route Y | 50, 17 | ¹H NMR: (400 MHz, DMSO) 0.90 (dd, 6H, J = 6.8 Hz, J = 16.0 Hz), 1.23-1.17 (m, 2H), 1.31-1.26 (m, 2H), 2.01-1.97 (m, 1H), 3.52 (d, 1H, J = 6.4 Hz), 4.43 (d, 1H, J = 12.4 Hz), 4.62 (d, 1H, J = 12.0 Hz), 7.13 (d, 1H, J = 8.4 Hz), 7.26 (t, 1H, J = 76.6 Hz) 7.27-7.22 (m, 2H), 7.35 (d, 2H, J = 8.4 Hz), 7.45-7.41 (m, 1H), 7.93 (d, 2H, J = 8.4 Hz), 8.80 (s, 1H), 16.74 (s, 1H). | (LC/MS Method D): m/z 458 [M + H]⁺ (ES⁺), at 2.01 min UV active. |
| 73 | (R)-4-(1-(3-methyl-2-((4-(trifluoromethyl)benzyl)oxy)butanamido)cyclobutyl)benzoic acid | Route O | 31, 43 | 1H NMR (400 MHz, Methanol-d4) δ 0.87 (d, J = 6.9 Hz, 3H), 0.94 (d, J = 6.7 Hz, 3H), 1.83-2.10 (m, 3H), 2.49-2.70 (m, 4H), 3.47 (d, J = 6.3 Hz, 1H), 4.44-4.49 (m, 1H), 4.63 (d, J = 12.4 Hz, 1H), 7.51-7.59 (m, 4H), 7.62-7.68 (m, 2H), 7.82-7.87 (m, 2H). | (LC/MS Method A): m/z 450 [M + H]⁺ (ES⁺), at 1.52 min. UV active. |
| 74 | 4-(S)-1-((R)-2-((2-(difluoromethoxy)pyridin-4-yl)methoxy)-3-methylbutanamido)-3-methylbutyl)benzoic acid | Route E Step (i): 1-2 equivalents of NaH used | 1, 44 | 1H NMR: (400 MHz, DMSO-d6) δ 0.85 (d, J = 6.8 Hz, 3H), 0.90 (d, J = 6.7 Hz, 3H), 1.38 (d, J = 7.1 Hz, 3H), 1.98 (h, J = 6.7 Hz, 1H), 3.56 (d, J = 6.2 Hz, 1H), 4.44 (d, J = 14.0 Hz, 1H), 4.61 (d, J = 14.0 Hz, 1H), 4.98-5.08 (m, 1H), 7.06 (s, 1H), 7.24 (d, J = 5.0 Hz, 1H), 7.45 (d, J = 8.1 Hz, 2H), 7.51-7.94 (m, 3H), 8.23 fd, J = 5.2 Hz, 2H), 8.49 (d, J = 8.2 Hz, 1H), 12.89 (s, 1H). | (LC/MS Method D): m/z 423 [M + H]⁺ (ES⁺), at 1.97 min. UV active. |
| 75 | 4-(S)-4-(1-(3-methyl-2-(5-(trifluoromethyl)pyridin-2-ylmethoxy)butanamido)cyclopropyl)benzoic acid | Route C | 5, 18 | 1H NMR: (400 MHz, DMSO) 0.94-0.90 (m, 6H), 1.30-1.18 (m, 4H), 2.07-2.02 (m, 1H), 3.67 (d, 1H, J = 6.0 Hz),4.63 (d, 1H), 4.77 (d, 1H), 7.24 (d, 2H, J = 8.4 Hz), 7.77 (d, 1H, J = 8 Hz), 7.82 (d, 2H, J = 8.4 Hz) 8.27 (d, 1H, J = 8 Hz), 8.91 (s, 1H), 8.94 (s, 1H), 12.93 (s, 1H). | (LC/MS Method D): m/z 437 [M + H]⁺ (ES⁺), at 2.00 min. UV active. |
| 76 | 4-(S)-4-(1-(3-methyl-2-(6-(trifluoromethyl)pyridin-3-ylmethoxy)butanamido)cyclopropyl)benzoic acid | Route C | 5, 51 | 1H NMR: (400 MHz, DMSO) 0.90 (dd, 6H, J = 6.8 Hz & J = 10.8 Hz), 1.21-1.15 (m, 2H), 1.32-1.24 (m, 2H), 2.03-1.98 (m, 1H), 3.58 (d, 1H, J = 5.6 Hz), 4.59 (d, 1H, J = 12.8 Hz), 4.74 (d, 1H, J = 12.8 Hz), 7.23 (d, 2H, J = 8 Hz), 7.83 (d, 2H, J = 8.4 Hz), 7.93 (d, 1H, J = 8 Hz), 8.11 (d, 1H, J = 8 Hz) 8.79 (s, 1H), 8.82 (s, 1H), 12.82 (s, 1H). | (LC/MS Method D): m/z 437 [M + H]⁺ (ES⁺), at 1.97 min. UV active. |
| 77 | 4-(S)-1-((R)-2-((4-(difluoromethoxy)pyridin-2-yl)methoxy)-3-methylbutanamido)ethyl)benzoic acid | Route E Step (i): 1-2 equivalents of NaH and 2 equivalents of Intermediate 45 used | 1, 45 | 1H NMR (400 MHz, DMSO-d6) δ 0.86 (d, J = 6.8 Hz, 6H), 1.39 (d, J = 7.0 Hz, 3H), 1.96-2.06 (m, 1H), 3.66 (d, J = 5.7 Hz, 1H), 4.52 (d, J = 13.5 Hz, 1H), 4.62 (d, J = 13.4 Hz, 1H), 5.04 (dq, J = 7.2, 5.7 Hz, 1H), 7.15 (dd, J = 5.6, 2.5 Hz, 1H), 7.27 (d, J = 2.5 Hz, 1H), 7.29-7.69 (m, 3H), 7.85-7.93 (m, 2H), 8.53 (d, J = 5.7 Hz, 1H), 8.71 (d, J = 8.0 Hz, 1H), 12.90 (s, 1H). | (LC/MS Method D): m/z 423 [M + H]⁺ (ES⁺), at 1.71 min. UV active. |

TABLE 2-continued

| Ex. No. Name | Synthetic method & notes | Intermediates | ¹H NMR | LCMS data |
|---|---|---|---|---|
| 78 (R)-4-(1-(2-((3-chloro-4-fluorobenzyl)oxy)-3-methylbutanamido)cyclopropyl)benzoic acid | Route C | 5, 52 | ¹H NMR: (400 MHz, DMSO) 0.90-0.86 (m, 6H), 1.28-1.18 (m, 4H), 2.00-1.95 (m, 1H), 3.51 (d, 1H, J = 6.0 Hz), 4.42 (d, 1H, J = 12.4 Hz), 4.56 (d, 1H, J = 12.4 Hz), 7.21 (d, 2H, J = 8.4 Hz), 7.42 (m, 2H), 7.63 (d, 1H, J = 7.6 Hz), 7.83 (d, 2H, J = 8.4 Hz), 8.77 (s, 1H), 12.82 (s, 1H). | (LC/MS Method D): m/z 420 [M + H]⁺ (ES⁺), at 2.14 min. UV active. |
| 79 4-(1-((2R)-2-((4-chloro-5-fluorocyclohexa-1,3-dien-1-yl)methoxy)-3-methylbutanamido)cyclopropyl)benzoic acid | Route C | 5, 53 | ¹H NMR: (400 MHz, DMSO) 0.98 (q, 6H, J = 6.7 Hz), 1.27-1.18 (m, 4H), 2.08-1.94 (m, 1H), 3.52 (d, 1H, J = 6.0 Hz), 4.44 (d, 1H, J = 12.8 Hz), 4.58 (d, 1H, J = 12.8 Hz), 7.28-7.20 (m, 3H), 7.47 (d, 1H, J = 6.4 Hz), 7.69 (t, 1H, J = 8.0 Hz), 7.83 (d, 2H, J = 8.4 Hz), 8.78 (s, 1H), 12.83 (s, 1H | (LC/MS Method D): m/z 420 [M + H]⁺ (ES⁺), at 2.17min. UV active. |
| 80 (R)-2-(3-cyclopropylbenzyl)oxy)-N-(1-(4-(2,3-dihydro-1H-tetrazol-5-yl)phenyl)cyclopropyl)-3-methylbutanamide | Route Y | 50, 29 | ¹H NMR: (400 MHz, DMSO) 0.63-0.68 (m, 2H), 0.88 (dd, 6H, j = 6.8 Hz J = 17.2 Hz), 0.94 (dd, 2H j = 4 Hz J = 6 Hz), 1.15 (s, 2H), 1.24-1.17 (m, 2H), 1.97-1.89 (m, 2H), 3.46 (d, 2H J = 6.4 Hz), 4.35 (d, 1H, J = 12 Hz), 4.55 (d, 1H, J = 12 Hz), 7.01 (d, 1H J = 7.6 Hz), 7.07 (s, 1H), 7.26-7.12 (m, 4H), 7.85 (d, 2H J = 8 Hz), 8.61 (s, 1H). | (LC/MS Method D): m/z 432 [M + H]⁺ (ES⁺), at 2.16 min. UV active. |
| 81 N-(cyclopropylsulfonyl)-4-((S)-1-((R)-2-((4-fluorobenzyl)oxy)-3-methylbutanamido)ethyl)benzamide | Route N | Example 5 | 1H NMR (400 MHz, DMSO-d6) δ 0.80 (d, J = 6.8 Hz, 3H), 0.85 (d, J = 6.7 Hz, 3H), 1.07-1.15 (m, 4H), 1.39 (d, J = 7.1 Hz, 3H), 1.88-1.98 (m, 1H), 3.11 (tt, J = 7.9, 4.9 Hz, 1H), 3.50 (d, J = 6.3 Hz, 1H), 4.33 (d, J = 11.8 Hz, 1H), 4.52 (d, J = 11.8 Hz, 1H), 4.98-5.07 (m, 1H), 7.15- 7.23 (m, 2H), 7.36-7.42 (m, 2H), 7.44-7.50 (m, 2H), 7.86- 7.91 (m, 2H), 8.39 (d, J = 8.2 Hz, 1H), 12.01 (s, 1H). | (LC/MS Method A): m/z 477 [M + H]⁺ (ES⁺), at 1.86 min. UV active. |
| 82 (R)-N-((S)-1-(4-(1H-tetrazol-5-yl)phenyl)ethyl)-2-(3-(difluoromethoxy)benzyl)oxy)-3-methylbutanamide | Route H Step (i): 1-2 equivalents of NaH and 2 equivalents of Intermediate 17 used; Step (ii) 10 equivalents of NaN₃ and NH₄Cl used | 4, 17 | 1H NMR (400 MHz, DMSO-d6) δ 0.83 (d, J = 6.8 Hz, 3H), 0.88 (d, J = 6.7 Hz, 3H), 1.41 (d, J = 7.0 Hz, 3H), 1.90-2.01 (m, 1H), 3.53 (d, J = 6.2 Hz, 1H), 4.37 (d, J = 12.4 Hz, 1H), 4.58 (d, J = 12.4 Hz, 1H), 4.99-5.09 (m, 1H), 7.08-7.14 (m, 1H), 7.15-7.26 (m, 3H), 7.38-7.45 (m, 1H), 7.50 (d, J = 8.1 Hz, 2H), 7.93-7.99 (m, 2H), 8.41 (d, J = 8.2 Hz, 1H). | (LC/MS Method D): m/z 446 [M + H]⁺ (ES⁺), at 2.09 min. UV active. |
| 83 (R)-N-((S)-1-(4-(1H-tetrazol-5-yl)phenyl)ethyl)-2-(3-cyclopropylbenzyl)oxy)-3-methylbutanamide | Route H Step (i): 1.2 equivalents of NaH used; Step (ii) 10 equivalents of NaN₃ and NH4Cl used | 4, 46 | 1H NMR (400 MHz, DMSO-d6) δ 0.61-0.68 (m, 2H), 0.82 (d, J = 6.8 Hz, 3H), 0.87 (d, J = 6.7 Hz, 3H), 0.90-0.97 (m, 2H), 1.40 (d, J = 7.0 Hz, 3H), 1.85-1.99 (m, 2H), 3.49 (d, J = 6.2 Hz, 1H), 4.29 (d, J = 12.0 Hz, 1H), 4.52 (d, J = 12.0 Hz, 1H), 4.98-5.06 (m, 1H), 6.97-7.06 (m, 2H), 7.10 (d, J = 7.5 Hz, 1H), 7.22 (t, J = 7.6 Hz, 1H), 7.42 (d, J = 8.0 Hz, 2H), 7.93 (d, J = 8.1 Hz, 2H), 8.28 (d, J = 8.2 Hz, 1H). | (LC/MS Method D): m/z 420 [M + H]⁺ (ES⁺), at 2.28 min. UV active. |
| 84 (R)-4-(1-(2-((6-(difluoromethyl)pyridin-3-yl)methoxy)-3-methylbutanamido)cyclopropyl)benzoic acid | Route C | 5, 54 | ¹H NMR: (400 MHz, DMSO) 0.89 (dd, 6H, J = 6.8 Hz & J = 12.0 Hz), 1.28-1.09 (m, 4H), 2.03-1.96 (m, 1H), 3.56 (d, 1H, J = 6.0 Hz), 4.53 (d, 1H, J = 12.8 Hz), 4.70 (d, 1H, J = 12.8 Hz), 7.00 (t, 1H, J = 54.8 Hz), 7.24 (d, 2H, J = 8.4 Hz), 7.73 (d, 1H, J = 7.6 Hz), 7.83 (d, 2H, J = 8.0 Hz), 8.02 (d, 1H, J = 7.2 Hz), 8.70 (s, 1H), 8.82 (d, 1H), 12.86 (s, 1H). | (LC/MS Method H): m/z 419 [M + H]⁺ (ES⁺), at 8.39 min. UV active. |

TABLE 2-continued

| Ex. No. | Name | Synthetic method & notes | Intermediates | ¹H NMR | LCMS data |
|---|---|---|---|---|---|
| 85 | 4-((S)-1-((R)-2-((3-cyclopropyl-4-fluorobenzyl)oxy)-3-methylbutanamido)ethyl)benzoic acid | Route C Step (I); 1.3 equivalents of Intermediate 47 used; | 1, 47 | 1H NMR (400 MHz, DMSO-d6) δ 0.65-0.74 (m, 2H), 0.78 (d, J = 6.7 Hz, 3H), 0.84 (d, J = 6.6 Hz, 3H), 0.92-1.01 (m, 2H), 1.38 (d, J = 7.0 Hz, 3H), 1.85-2.07 (m, 2H), 3.45 (d, J = 6.2 Hz, 1H), 4.27 (d, J = 11.8 Hz, 1H), 4.46 (d, J = 11.9 Hz, 1H), 4.96-5.06 (m, 1H), 6.92 (d, J = 7.5 Hz, 1H), 7.07-7.18 (m, 2H), 7.44 (d, J = 7.9 Hz, 2H), 7.88 (d, J = 8.1 Hz, 2H), 8.38 (d, J = 8.1 Hz, 1H), 12.88 (s, 1H). | (LC/MS Method D): m/z 414 [M + H]⁺ (ES⁺), at 2.24 min. UV active. |
| 86 | 4-(1-(3-methyl-2-((oxetan-3-yl)benzyl)oxy)butanamido)cyclopropyl)benzoic acid, enantiomer 1 | Route K | 55, 36 | 1H NMR: (400 MHz, DMSO) 0.77-0.73 (m, 3H), 0.85-0.80 (m, 5H), 0.92 (s, 2H), 1.25-1.22 (m, 2H), 1.69-1.67 (m, 1H), 2.87 (d, 1H, J = 7.2 Hz), 4.26-4.22 (m, 1H), 4.61-4.58 (m, 2H), 4.85-4.78 (m, 2H), 4.96-4.92 (m, 2H), 7.15 (t, 1H, J = 3.4 Hz), 7.29 (s, 1H), 7.41-7.35 (m, 4H), 7.79 (d, 2H, J = 8.4 Hz), 12.83 (s, 1H). | (LC/MS Method D): m/z 424 [M + H]⁺ (ES⁺), at 2.10min. UV active. |
| 87 | 4-(1-(3-methyl-2-((oxetan-3-yl)benzyl)oxy)butanamido)cyclopropyl)benzoic acid, enantiomer 2 | Route K | 55, 36 | 1H NMR: (400 MHz, DMSO) 0.86-0.78 (m, 7H), 0.93-0.90 (m, 2H), 1.71-1.66 (m, 1H), 2.88 (d, 1H, J = 6.8 Hz), 4.28-4.22 (m, 1H), 4.61-4.57 (m, 2H), 4.85-4.78 (m, 2H), 4.96-4.92 (m, 2H), 7.15 (t, 1H, J = 3.4 Hz), 7.29 (s, 1H), 7.41-7.35 (m, 4H), 7.80 (d, 2H, J = 8.4 Hz), 12.83 (s, 1H). | (LC/MS Method D): m/z 424 [M + H]⁺ (ES⁺), at 2.04min. UV active. |
| 88 | 4-(1-(2-((5-(difluoromethyl)pyridin-2-yl)methoxy)-3-methylbutanamido)cyclopropyl)benzoic acid | Route C | 5, 27 | 1H NMR: (400 MHz, DMSO) 0.93-0.89 (m, 6H), 1.28-1.18 (m, 4H), 2.04-2.02 (m, 1H), 3.65-3.64 (m, 1H), 4.75-4.57 (m, 2H), 7.30-7.02 (m, 3H), 7.68 (d, 1H, J = 7.6 Hz), 7.82 (d, 2H, J = 7.2 Hz), 8.07-8.05 (m, 1H), 8.74 (s, 1H), 8.93 (s, 1H). | (LC/MS Method D): m/z 419 [M + H]⁺ (ES⁺), at 1.81 min. UV active. |
| 89 | 4-(R)-4-(1-(2-((3-cyclopropyl-4-fluorobenzyl)oxy)-3-methylbutanamido)cyclopropyl)benzoic acid | Route C | 5, 47 | 1H NMR: (400 MHz, DMSO) 0.72-0.70 (m, 2H), 0.86 (dd, 6H, J = 6.8 Hz, J = 14.8 Hz), 0.98-0.93 (m, 2H), 1.26-1.15 (m, 4H), 1.97-1.92 (m, 1H), 2.05-2.00 (m, 1H), 3.46 (d, 2H, J = 6.4 Hz), 4.33 (d, 1H, J = 12.0 Hz), 4.50 (d, 1H, J = 11.6 Hz), 6.97 (d, 1H, J = 6.0 Hz), 7.20-7.09 (m, 4H), 7.80 (d, 2H, J = 8.0 Hz), 8.66 (s, 1H). | (LC/MS Method D): m/z 426 [M + H]⁺ (ES⁺), at 2.41 min. UV active. |
| 90 | 4-((S)-1-((R)-2-((3-(cyclopropylsulfonyl)benzyl)oxy)-3-methylbutanamido)ethyl)benzoic acid | Route C Step (ii); 3 equivalents of LiOH•H2O used; | 1,48 | 1H NMR (400 MHz, DMSO) δ 0.83 (d, J = 6.8 Hz, 3H), 0.89 (d, J = 6.7 Hz, 3H), 1.00-1.16 (m, 4H), 1.39 (d, J = 7.1 Hz, 3H), 1.91-2.02 (m, 1H), 2.80-2.88 (m, 1H), 3.55 (d, J = 6.3 Hz, 1H), 4.46 (d, J = 12.6 Hz, 1H), 4.67 (d, J = 12.5 Hz, 1H), 4.99-5.09 (m, 1H), 7.45 (d, J = 8.1 Hz, 1H), 7.61-7.74 (m, 2H), 7.80-7.85 (m, 1H), 7.85-7.93 (m, 3H), 8.48 (d, J = 8.1 Hz, 1H). | (LC/MS Method D): m/z 460 [M + H]⁺ (ES⁺), at 1.97 min, UV active. |
| 91 | (R)-4-(1-(2-(3-(cyclopropylsulfonyl)benzyl)oxy)-3-methylbutanamido)cyclopropyl)benzoic acid | Route C | 5, 48 | 1H NMR: (400 MHz, DMSO) 0.90 (dd, 6H, J = 6.8 Hz & J = 18.4 Hz), 1.06-1.00 (m, 2H), 1.16-1.09 (m, 2H), 1.25-1.20 (m, 2H), 1.32-1.25 (m, 2H), 2.02-1.97 (m, 1H), 2.87-2.81 (m, 1H), 3.55 (d, 1H, J = 6.0 Hz), 4.52 (d, 1H, J = 12.4 Hz), 4.72 (d, 1H, J = 12.4 Hz), 7.24 (d, 2H, J = 8.4 Hz), 7.66 (t, 1H, J = 7.6 Hz), 7.75 (d, 1H, J = 8.0 Hz), 7.84 (d, 3H, J = 8.4 Hz), 7.91 (s, 1H), 8.82 (s, 1H), 12.84 (s, 1H) | (LC/MS Method D): m/z 472 [M + H]⁺ (ES⁺), at 2.14 min, UV active. |
| 92 | 4-((1S)-1-(2-cyclobutyl-2-((4-(trifluoromethyl)benzyl)oxy)acetamido)ethyl)benzoic acid, mixture of diastereomers | Route P | 59, 31, 60 | ¹H NMR (400 MHz, DMSO-d6) [NB mixture of diastereoisomers] δ 8.38 (t, J = 7.7 Hz, 1H), 7.91-7.81 (m, 2H), 7.77-7.67 (m, 2H), 7.62-7.52 (m, 2H), 7.42-7.32 (m, 2H), 5.00 (h, J = 7.3 Hz, 1H), 4.63 (dd, J = 12.8, 8.6 Hz, 1H), 4.45 (d, J = 12.7 Hz, 1H), 3.76 (d, J = 7.1 Hz, 1H), 2.65-2.53 (m, 1H), 2.00-1.66 (m, 6H), 1.37 (dd, J = 7.1, 1.1 Hz, 3H). One exchangeable proton not observed. | (LC/MS Method C): m/z 436 [M + H]⁺ (ES⁺), at 2.54 and 2.64 min, UV active. |

TABLE 2-continued

| Ex. No. | Name | Synthetic method & notes | Intermediates | ¹H NMR | LCMS data |
|---|---|---|---|---|---|
| 93 | 4-((1S)-1-(2-cyclobutyl-2-((4-(trifluoromethyl)benzyl)oxy)acetamido)ethyl)benzoic acid, diastereoisomer 1 | Route P | 59, 31, 60 | ¹H NMR (400 MHz, DMSO-d6) δ 8.43 (d, J = 8.2 Hz, 1H), 7.96-7.87 (m, 2H), 7.84-7.75 (m, 2H), 7.70-7.57 (m, 2H), 7.43-7.31 (m, 2H), 5.14-5.01 (m, 1H), 4.68 (d, J = 12.7 Hz, 1H), 4.51 (d, J = 12.7 Hz, 1H), 3.82 (d, J = 7.2 Hz, 1H), 2.72-2.60 (m, 1H), 2.03-1.76 (m, 6H), 1.44 (d, J = 7.0 Hz, 3H). One exchangeable proton not observed. | (LC/MS Method A): m/z 436 [M + H]⁺ (ES⁺), at 2.10 min, UV active. |
| 94 | 4-((1S)-1-(2-cyclobutyl-2-((4-(trifluoromethyl)benzyl)oxy)acetamido)ethyl)benzoic acid, diastereoisomer 2 | Route P | 59, 31, 60 | ¹H NMR (400 MHz, DMSO-d6) δ 8.39 (d, J = 8.2 Hz, 1H), 7.92-7.83 (m, 2H), 7.79-7.71 (m, 2H), 7.63-7.52 (m, 2H), 7.43-7.26 (m, 2H), 5.10-4.91 (m, 1H), 4.65 (d, J = 12.8 Hz, 1H), 4.46 (d, J = 12.8 Hz, 1H), 3.76 (d, J = 7.0 Hz, 1H), 2.66-2.56 (m, 1H), 1.99-1.70 (m, 6H), 1.38 (d, J = 7.1 Hz, 3H). One exchangeable proton not observed. | (LC/MS Method A): m/z 436 [M + H]⁺ (ES⁺), at 2.02 min, UV active. |
| 95 | 4-(1-(2-cyclobutyl-2-((3-(methylsulfonyl)benzyl)oxy)acetamido)cyclopropyl)benzoic acid, mixture of enantiomers | Route Q | 58, 6 | ¹H NMR (400 MHz, DMSO-d6) [NB mixture of enantiomers] δ 12.77 (br s, 1H), 8.77 (s, 1H), 7.96-7.94 (m, 1H), 7.91-7.80 (m, 3H), 7.79-7.74 (m, 1H), 7.71-7.64 (m, 1H), 7.21-7.17 (m, 2H), 4.71 (d, J = 12.6 Hz, 1H), 4.54 (d, J = 12.6 Hz, 1H), 3.75 (d, J = 7.1 Hz, 1H), 3.21 (s, 3H), 2.70-2.61 (m, 1H), 2.04-1.73 (m, 6H), 1.27-1.16 (m, 4H). | (LC/MS Method C): m/z 458 [M + H]⁺ (ES⁺), at 1.80 min, UV active. |
| 96 | 4-(1-(2-cyclobutyl-2-((4-(trifluoromethyl)benzyl)oxy)acetamido)cyclopropyl)benzoic acid, mixture of enantiomers | Route Q | 58, 31 | ¹H NMR (400 MHz, DMSO-d6) [NB mixture of enantiomers] δ 8.71 (s, 1H), 7.84-7.70 (m, 4H), 7.65-7.53 (m, 2H), 7.21-7.03 (m, 2H), 4.68 (d, J = 12.7 Hz, 1H), 4.52 (d, J = 12.7 Hz, 1H), 3.73 (d, J = 7.0 Hz, 1H), 2.73-2.59 (m, 1H), 2.05-1.72 (m, 5H), 1.34-1.10 (m, 5H). One exchangeable proton not observed. | (LC/MS Method A): m/z 448 [M + H]⁺ (ES⁺), at 2.79 min, UV active. |
| 97 | 4-(1-(2-cyclobutyl-2-((3,4-difluorobenzyl)oxy)acetamido)cyclopropyl)benzoic acid, mixture of enantiomers | Route Q | 58, 20 | ¹H NMR (400 MHz, DMSO-d6) δ 8.69 (s, 1H), 7.82-7.77 (m, 2H), 7.53-7.40 (m, 2H), 7.28-7.20 (m, 1H), 7.14-7.07 (m, 2H), 4.55 (d, J = 12.2 Hz, 1H), 4.42 (d, J = 12.2 Hz, 1H), 3.70 (d, J = 7.0 Hz, 1H), 2.67-2.58 (m, 1H), 1.98-1.72 (m, 6H), 1.29-1.21 (m, 2H), 1.18-1.11 (m, 2H). One exchangeable proton not observed. | (LC/MS Method C): m/z 416 [M + H]⁺ (ES⁺), at 2.34 min, UV active. |
| 98 | 4-(1-(2-((3-chlorobenzyl)oxy)-2-cyclobutylacetamido)cyclopropyl)benzoic acid, mixture of enantiomers | Route Q | 58, 8 | ¹H NMR (400 MHz, DMSO-d6) δ 8.71 (s, 1H), 7.84-7.77 (m, 2H), 7.49-7.46 (m, 1H), 7.42-7.31 (m, 3H), 7.17-7.08 (m, 2H), 4.58 (d, J = 12.4 Hz, 1H), 4.43 (d, J = 12.4 Hz, 1H), 3.70 (d, J = 7.1 Hz, 1H), 2.70-2.58 (m, 1H), 2.03-1.70 (m, 5H), 1.31-1.18 (m, 3H), 1.17-1.08 (m, 2H). One exchangeable proton not observed. | (LC/MS Method C): m/z 414 [M + H]⁺ (ES⁺), at 2.04 min, UV active. |
| 99 | 4-(1-(2-cyclobutyl-2-((3-(difluoromethoxy)benzyl)oxy)acetamido)cyclopropyl)benzoic acid, mixture of enantiomers | Route R | 58, 17 | ¹H NMR (400 MHz, DMSO-d) [NB mixture of enantiomers] δ 8.69 (br s, 1H), 7.83-7.76 (m, 2H), 7.47-7.01 (m, 7H), 4.60 (d, J = 12.5 Hz, 1H), 4.42 (d, J = 12.4 Hz, 1H), 3.70 (d, J = 7.1 Hz, 1H), 2.68-2.58 (m, 1H), 1.97-1.72 (m, 6H), 1.36-1.12 (m, 4H). One exchangeable proton not observed. | (LC/MS Method C): m/z 446 [M + H]⁺ (ES⁺), at 2.41 min, UV active. |

TABLE 2-continued

| Ex. No. Name | Synthetic method & notes | Intermediates | ¹H NMR | LCMS data |
|---|---|---|---|---|
| 100 (S)-4-(1-(2-cyclobutyl-2-((3-(difluoromethoxy)benzyl)oxy)acetamido)cyclopropyl)benzoic acid | Route R | 58, 17 | ¹H NMR (400 MHz, DMSO-d6) δ 12.84 (br s, 1H), 8.71 (s, 1H), 7.87-7.74 (m, 2H), 7.49-7.01 (m, 7H), 4.61 (d, J = 12.4 Hz, 1H), 4.43 (d, J = 12.4 Hz, 1H), 3.70 (d, J = 7.1 Hz, 1H), 2.72-2.57 (m, 1H), 2.03-1.68 (m, 6H), 1.34-1.10 (m, 4H). | (LC/MS Method C): m/z 446 [M + H]⁺ (ES⁺), at 2.34 min, UV active. |
| 101 (R)-4-(1-(2-cyclobutyl-2-((3-(difluoromethoxy)benzyl)oxy)acetamido)cyclopropyl)benzoic acid | Route R, S (or T) | 58, 17 (Route R) 61, 62, 63, 17 (Route S) | ¹H NMR (400 MHz, DMSO-d) δ 12.87 (br s, 1H), 8.71 (s, 1H), 7.87-7.77 (m, 2H), 7.49-7.02 (m, 7H), 4.61 (d, J = 12.4 Hz, 1H), 4.43 (d, J = 12.4 Hz, 1H), 3.70 (d, J = 7.0 Hz, 1H), 2.70-2.57 (m, 1H), 2.04-1.68 (m, 6H), 1.33-1.10 (m, 4H). | (LC/MS Method C): m/z 446 [M + H]⁺ (ES⁺), at 2.33 min, UV active. (LC/MS Method D): m/z 446 [M + H]⁺ (ES⁺), at 2.00 min, UV active. |

TABLE 3

| Intermediate | Route & intermediates | Name | Data |
|---|---|---|---|
| 1 | Route 1 | methyl 4-((S)-1-((R)-2-hydroxy-3-methylbutanamido)ethyl)benzoate | (LC/MS Method B): m/z 280 [M + H]$^+$ (ES$^+$), at 1.04 min, UV active. |
| 2 | Route 2 | methyl 4-((1S)-1-(2-hydroxy-3-methylbutanamido)ethyl)benzoate | (LC/MS Method D): m/z 280 [M + H]$^+$ (ES$^+$), at 1.69 min, UV active. |
| 3 | Route 2 | methyl 4-((1S)-1-(3-methyl-2-((methylsulfonyl)oxy)butanamido)ethyl)benzoate | (LC/MS Method D): m/z 358 [M + H]$^+$ (ES$^+$), at 1.86 min, UV active. |
| 4 | Route 3 | (R)-N-((S)-1-(4-cyanophenyl)ethyl)-2-hydroxy-3-methylbutanamide | (LC/MS Method D): m/z 247 [M + H]$^+$ (ES$^+$), at 1.55 min, UV active. |
| 5 | Route 4 | methyl (R)-4-(1-(2-hydroxy-3-methylbutanamido)cyclopropyl)benzoate | (LC/MS Method B): m/z 292 [M + H]$^+$ (ES$^+$), at 1.06 min, UV active. |
| 6 | | 1-(bromomethyl)-3-(methylsulfonyl) benzene | Commercially available CAS: 82657-76-9 |
| 7 | | 1-(bromomethyl)-4-(methylsulfonyl)benzene | Commercially available CAS: 53606-06-7 |
| 8 | | 1-(bromomethyl)-3-chlorobenzene | Commercially available CAS: 766-80-3 |
| 9 | | 1-(bromomethyl)-3-(difluoromethyl) benzene | Commercially available CAS: 1263178-51-3 |
| 10 | | 1-(bromomethyl)-3-(trifluoromethyl) benzene | Commercially available CAS: 402-23-3 |
| 11 | | 1-(bromomethyl)-3-fluorobenzene | Commercially available CAS: 456-41-7 |
| 12 | | Benzyl bromide | Commercially available CAS: 100-39-0 |
| 13 | | 1-(bromomethyl)-3-(trifluoromethoxy)benzene | Commercially available CAS: 159689-88-0 |
| 14 | | 4-(bromomethyl)benzonitrile | Commercially available CAS: 17201-43-3 |
| 15 | | 3-(bromomethyl)benzonitrile | Commercially available CAS: 28188-41-2 |
| 16 | | 1-(bromomethyl)-4-(difluoromethoxy)benzene | Commercially available CAS: 3447-53-8 |
| 17 | | 1-(bromomethyl)-3-(difluoromethoxy)benzene | Commercially available CAS: 72768-95-7 |
| 18 | | 2-(trifluoromethyl) pyridine | Commercially available CAS: 1000773-62-5 |
| 19 | | 4-(pentafluorosulfur)benzyl bromide | Commercially available CAS: 1126969-29-6 |
| 20 | | 4-(bromomethyl)-1,2-difluorobenzene | Commercially available CAS: 85118-01-0 |
| 21 | | 5-(bromomethyl)-2,2-difluorobenzo[d][1,3]dioxole | Commercially available CAS: 68119-30-2 |
| 22 | Route 5 | 4-(bromomethyl)-1-(difluoromethyl)-2-fluorobenzene | $^1$H NMR (400 MHz, DMSO) δ 4.73 (s, 2H), 7.19 (t, J = 54 Hz, 1H), 7.38-7.51 (m, 2H), 7.56-7.67 (m, 1H). |
| 23 | | 1-(bromomethyl)-4-cyclopropylbenzene | Commercially available CAS: 1150617-57-4 |
| 24 | | 1-(bromomethyl)-4-fluorobenzene | Commercially available CAS: 459-46-1 |
| 25 | Route 5, Intermediate 26 | 4-(bromomethyl)-2-(difluoromethoxy)-1-fluorobenzene | $^1$H NMR (400 MHz, DMSO) δ 4.71 (s, 2H), 7.03-7.52 (m, 4H). |
| 26 | | 3-(difluoromethoxy)-4-fluorobenzaldehyde | Commercially available CAS: 1214367-20-0 |
| 27 | Route 6 | 2-(bromomethyl)-5-(difluoromethyl)pyridine | (LC/MS Method D): m/z 222 [M + H]$^+$ (ES$^+$), at 2.01 min, UV active. |
| 28 | | 4-(bromomethyl)-1-fluoro-2-(methylsulfonyl) benzene | Commercially available CAS: 1192347-88-8 |
| 29 | | 1-(bromomethyl)-3-cyclopropylbenzene | Commercially available CAS: 1260850-05-2 |
| 30 | | 1-(bromomethyl)-3-(methoxymethyl)benzene | Commercially available CAS: 125604-03-7 |
| 31 | | 4-(trifluoromethyl)benzyl bromide | Commercially available CAS: 402-49-3 |
| 32 | Route 7 | 1-(bromomethyl)-3-(ethylsulfonyl)benzene | $^1$H NMR (400 MHz, DMSO) δ1.10 (t, J = 7.4 Hz, 3H), 3.31 (q, J = 7.4 Hz, 2H), 4.84 (s, 2H), 7.62-7.72 (m, 1H), 7.81-7.86 (m, 2H), 7.97-8.00 (m, 1H). |
| 33 | Route 8 | methyl 4-((S)-1-((R)-2-hydroxy-3-methylbutanamido)ethyl)-2-methylbenzoate | (LC/MS Method D): m/z 294 [M + H]$^+$ (ES$^+$), at 3.03 min, UV active. |
| 34 | | 1-(1-Bromoethyl)-4-fluorobenzene | Commercially available CAS: 65130-46-3 |
| 35 | | [4-(oxetan-3-yl)phenyl]methanol | Commercially available CAS: 1781691-11-9 |

TABLE 3-continued

| Intermediate | Route & intermediates | Name | Data |
|---|---|---|---|
| 36 | Route 9 | (3-(oxetan-3-yl)phenyl)methanol | 1H NMR (400 MHz, DMSO-d6) δ 4.23 (p, J = 7.7 Hz, 1H), 4.50 (d, J = 5.5 Hz, 2H), 4.60 (t, J = 6.3 Hz, 2H), 4.94 (dd, J = 8.4, 5.8 Hz, 2H), 5.21 (t, J = 5.7 Hz, 1H), 7.17-7.39 (m, 4H) |
| 37 | | 1-(Bromomethyl)-3-(2-propen-1-yloxy)benzene | Commercially available CAS: 69411-94-5 |
| 38 | | 1-(Bromomethyl)-4-(2-propen-1-yloxy)benzene | Commercially available CAS: 143116-30-7 |
| 39 | | 1-(1-Bromoethyl)-4-(trifluoromethyl)benzene | Commercially available CAS: 68120-42-3 |
| 40 | Route 8 | methyl 4-[[[(2R)-2-hydroxy-3-methyl-butanoyl]amino]methyl]benzoate | 1H NMR (400 MHz, DMSO-d6) δ 0.76 (d, J = 6.8 Hz, 3H), 0.90 (d, J = 6.9 Hz, 3H), 1.95-2.04 (m, 1H), 3.73 (dd, J = 5.6, 3.7 Hz, 1H), 3.84 (s, 3H), 4.29-4.41 (m, 2H), 5.44 (d, J = 5.5 Hz, 1H), 7.37-7.43 (m, 2H), 7.87-7.93 (m, 2H), 8.37 (t, J = 6.3 Hz, 1H). |
| 41 | | methyl 4-[1-[[(2R)-2-hydroxy-3-methyl-butanoyl]amino]-1-methyl-ethyl]benzoate | 1H NMR (400 MHz, DMSO-d6) δ 0.76 (d, J = 6.7 Hz, 3H), 0.87 (d, J = 6.9 Hz, 3H), 1.49- 1.67 (m, 6H), 1.87-2.02 (m, 1H), 3.58-3.67 (m, 1H), 3.76-3.88 (m, 3H), 5.25-5.34 (m, 1H), 7.43-7.52 (m, 2H), 7.73 (s, 1H), 7.82-7.91 (m, 2H). |
| 42 | Route 10 | Imidazo[1,2-a]pyridine-7-methanol | (LC/MS Method D): m/z 167 [M + H]+ (ES+), at 1.08 min, UV active. |
| 43 | Route 8 | (2R)-N-[1-(4-cyanophenyl)cyclobutyl]-2-hydroxy-3-methyl-butanamide | (LC/MS Method B): m/z 273 [M + H]+ (ES+) at 1.10 min, UV active. |
| 44 | | 4-(bromomethyl)-2-(difluoromethoxy)pyridine | Commercially available CAS: 1268517-84-5 |
| 45 | | 2-(Bromomethyl)-4-(difluoromethoxy)pyridine | Commercially available CAS: 1375098-13-7 |
| 46 | | 1-(bromomethyl)-3-cyclopropylbenzene | Commercially available CAS: 1260850-05-2 |
| 47 | Route 6 | 4-(bromomethyl)-2-cyclopropyl-1-fluorobenzene | 1H NMR (400 MHz, DMSO-d6) δ 0.67-0.76 (m, 2H), 0.94-1.04 (m, 2H), 1.96-2.09 (m, 1H), 4.65 (s, 2H), 7.05-7.17 (m, 2H), 7.22-7.29 (m, 1H). |
| 48 | Route 11 | 1-(bromomethyl)-3-(cyclopropylsulfonyl)benzene | 1H NMR (400 MHz, DMSO-d6) δ 1.01-1.17 (m, 4H), 2.82-2.91 (m, 1H), 4.83 (s, 2H), 7.62-8.03 (m, 4H). |
| 49 | | 1-(bromomethyl)-4-(difluoromethyl)benzene | Commercially available CAS: 873373-34-3 |
| 50 | Route 12 | (R)-N-(1-(4-cyanophenyl)cyclopropyl)-2-hydroxy-3-methylbutanamide | (LC/MS Method D): m/z 259 [M + H]+ (ES+),at 1.40min. |
| 51 | | 5-(Bromomethyl)-2-(trifluoromethyl)pyridine | Commercially available CAS: 108274-33-5 |
| 52 | | 3-Chloro-4-fluorobenzyl bromide | Commercially available CAS: 192702-01-5 |
| 53 | | 4-(Bromomethyl)-1-chloro-2-fluorobenzene | Commercially available CAS: 206362-80-3 |
| 54 | Route 6 | 5-(bromomethyi)-2-(difluoromethyl)pyridine | (LC/MS Method D): m/z 222 [M + H]+ (ES+), at 1.83 min. |
| 55 | Route 2 step(ii) using Intermediate 5 | methyl 4-(1-(3-methyl-2-((methylsulfonyl)oxy)butanamido)cyclopropy)benzoate | (LC/MS Method D): m/z 370 [M + H]+ (ES+), at 1.79 min |
| 56 | | 1-(bromomethyl)-3-methoxybenzene | Commercially available CAS: 874-98-6 |
| 57 | Route 1 using (2S)-2-hydroxy-3-methyl-butanoic acid | methyl 4-((S)-1-((S)-2- hydroxy-3-methylbutanamido)ethyl)benzoate | LC/MS (Method C): m/z 438 [M + H]+, (ES+), at 1.71 min |
| 58 | Route 13 using Intermediate 62 | methyl 4-(1-(2-cyclobutyl-2-hydroxyacetamido)cyclopropyl)benzoate | LC/MS (Method B): m/z 304 [M + H]+ (ES+), at 1.09 min, UV active. |
| 59 | | methyl 2-cyclobutyl-2-hydroxyacetate | Commercially available CAS: 1517761-58-8 |
| 60 | | methyl (S)-4-(1-aminoethyl)benzoate | Commercially available CAS: 222714-37-6 |
| 61 | | 2-amino-2-cyclobutylacetic acid | Commercially available CAS: 28024-69-3 |

TABLE 3-continued

| Intermediate | Route & intermediates | Name | Data |
|---|---|---|---|
| 62 | | methyl 4-(1-aminocyclopropyl)benzoate | Commercially available CAS: 1006037-03-1 |
| 63 | | (R)-2-methoxy-2-phenylacetic acid | Commercially available CAS: 3966-32-3 |

BIOLOGICAL ACTIVITY

Cloning, Baculovirus generation, large scale infection of HEK293 cells and membrane preparation: Human prostaglandin E2 receptor 4 (EP4) was cloned into pBacMam expression vector (GeneScript, UK). Transposition of EP4 DNA was performed using Invitrogen's Bac-to-Bac Baculovirus Expression Systems. P0 baculovirus was generated by transfecting SF9 Cells with bacmid DNA using Cellfectin II transfection reagent (ThermoFisher Scientific, UK, catalog number 10362-100). Following P0 generation P1 virus was then generated ready for large scale infection and membrane preparation. HEK293 cells were grown in DMEM+Glutamax, supplemented with 10% heat inactivated fetal bovine serum (FBS). Cells were infected at a seeding density of 3.5 million cells/mL in 500 cm$^3$ flasks at 5% v/v EP4 Bacman. Expression was carried out over 36 hr period at 37° C. with 5% $CO_2$. The cells were removed using PBS and a cell scrapper. The cell culture was centrifuged at 2500 RPM for 10 mins at 4° C. The supernatant was then poured off and the pellet stored at −80° C. The pellet was defrosted and re-suspended in 15 mL of homogenising buffer (20 mM HEPES, 10 mM EDTA, pH 7.4). Then homogenised in mechanical homogeniser (VMR) for 10 seconds. The membrane was centrifuged in centrifuge tubes at 40,000 g for 15 mins at 4° C. The supernatant was poured away and re-suspended in 15 mL of homogenising buffer. Homogenised for 20 seconds. The membrane was centrifuged at 40,000 g for 45 mins at 4° C. The membrane was re-suspended in 3 mL of storage buffer (20 mM HEPES, 0.1 mM EDTA, pH 7.4) mixing well. The resulting membranes were then stored at −80° C.

cAMP Gs Functional Assay: cAMP production following EP4 receptor activation was determined using the Homogeneous Time-Resolved Fluorescence (HTRF) cAMP dynamic-2 assay (Cisbio, France). HEK293 cells were transfected using a 0.5% EP4 Bacman virus for 36 hours, before dissociating the cells, and freezing at 150° C.

On the day of testing, increasing concentration of test compounds, alongside positive controls (1 uM ONO-AE3-208) and negative control (DMSO (Sigma-Aldrich, UK) were added to a ProxiPlate-384 Plus, White 384-shallow well Mircoplate, (PerkinElmer, USA) using the ECHO dispense.

Cells were defrosted in a water bath and resuspended in DMEM supplemented with 10% FBS before centrifuging at 1200 RPM for 5 mins to form a pellet. The pellet was resuspended in assay buffer (DMEM+0.5 mM IBMX (Tocris, Abingdon, UK, Catalog Number 2845)) to a 1×10$^6$ cells/mL. Cell suspension, for a final assay concentration of 5000 cell/well was added using the multidrop to the pre-dispensed assay plate. The plate was then incubated at 37° C. for 30 mins, with 5% CO2. After incubation, EC$_{80}$ concentration (7 nM) of PGE$_2$ (EP4 agonist) was added to the plate. In parallel, a PGE$_2$ dose-response curve was dispense to a separate plate. Assay buffer was then dispensed on top. The cAMP production was determined as manufacturer's instructions, before plates were read on a PheraStar fluorescence plate reader (BMG LabTech, Germany).

The pIC$_{50}$ was converted to a functional pKb value using a modified Cheng Prussoff equation where K$_d$=agonist EC$_{50}$ and L$_{hot}$=agonist challenge concentration;

$$Ki = \frac{IC50}{1 + \frac{[R]}{Kd}}$$

TABLE 4

Human EP4 fpK$_b$ values

| Example | Human EP4 fpK$_b$ |
|---|---|
| 1 | 9.11 |
| 2 | 9.05 |
| 3 | <7.17 |
| 4 | <6.71 |
| 5 | 8.38 |
| 6 | 7.55 |
| 7 | <6.71 |
| 8 | 8.06 |
| 9 | <6.71 |
| 10 | 7.69 |
| 11 | 8.50 |
| 12 | 9.09 |
| 13 | 8.63 |
| 14 | 8.74 |
| 15 | 9.54 |
| 16 | 6.75 |
| 17 | 8.52 |
| 18 | 6.34 |
| 19 | 7.89 |
| 20 | 10.02 |
| 21 | 7.48 |
| 22 | 8.14 |
| 23 | 7.84 |
| 24 | 9.52 |
| 25 | 7.86 |
| 26 | 7.56 |
| 27 | 8.72 |
| 28 | 9.82 |
| 29 | 9.22 |
| 30 | 8.27 |
| 31 | 8.65 |
| 32 | 9.65 |
| 33 | 7.84 |
| 34 | 7.68 |
| 35 | 8.13 |
| 36 | 7.59 |
| 37 | 8.91 |
| 38 | <5.33 |
| 39 | 9.64 |
| 40 | 8.78 |
| 41 | <4.89 |
| 42 | 8.76 |
| 43 | 9.30 |
| 44 | NT |
| 45 | 8.00 |
| 46 | 8.14 |
| 47 | 7.19 |
| 48 | 6.85 |

TABLE 4-continued

Human EP4 fpK$_b$ values

| Example | Human EP4 fpK$_b$ |
| --- | --- |
| 49 | 8.64 |
| 50 | <4.89 |
| 51 | 6.38 |
| 52 | 9.41 |
| 53 | 7.19 |
| 54 | <4.89 |
| 55 | 9.32 |
| 56 | 8.14 |
| 57 | 9.43 |
| 58 | <4.89 |
| 59 | 8.01 |
| 60 | 8.72 |
| 61 | 9.47 |
| 62 | 9.40 |
| 63 | 7.59 |
| 64 | 7.32 |
| 65 | <6.68 |
| 66 | 7.46 |
| 67 | 9.24 |
| 68 | 9.25 |
| 69 | 9.02 |
| 70 | 8.16 |
| 71 | 9.43 |
| 72 | 9.23 |
| 73 | 6.74 |
| 74 | 9.35 |
| 75 | 7.16 |
| 76 | 7.48 |
| 77 | 7.56 |
| 78 | <4.68 |
| 79 | 8.61 |
| 80 | 9.71 |
| 81 | 6.52 |
| 82 | 10.06 |
| 83 | 9.73 |
| 84 | 7.95 |
| 85 | 10.26 |
| 86 | 9.35 |
| 87 | <6.22 |
| 88 | 7.93 |
| 89 | 8.17 |
| 90 | 7.53 |
| 91 | 7.7 |
| 92 | 8.33 |
| 93 | 8.44 |
| 94 | 8.3 |
| 95 | 7.1 |
| 96 | 8.18 |
| 97 | 7.9 |
| 98 | 8.83 |
| 99 | 8.48 |
| 100 | 7.81 |
| 101 | 9.07 |

The invention claimed is:

1. A compound of Formula (1):

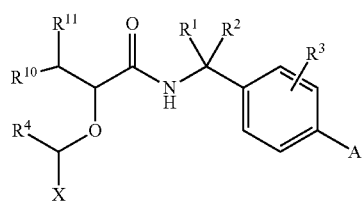

(1)

or a salt thereof, wherein;
A is selected from the group consisting of:

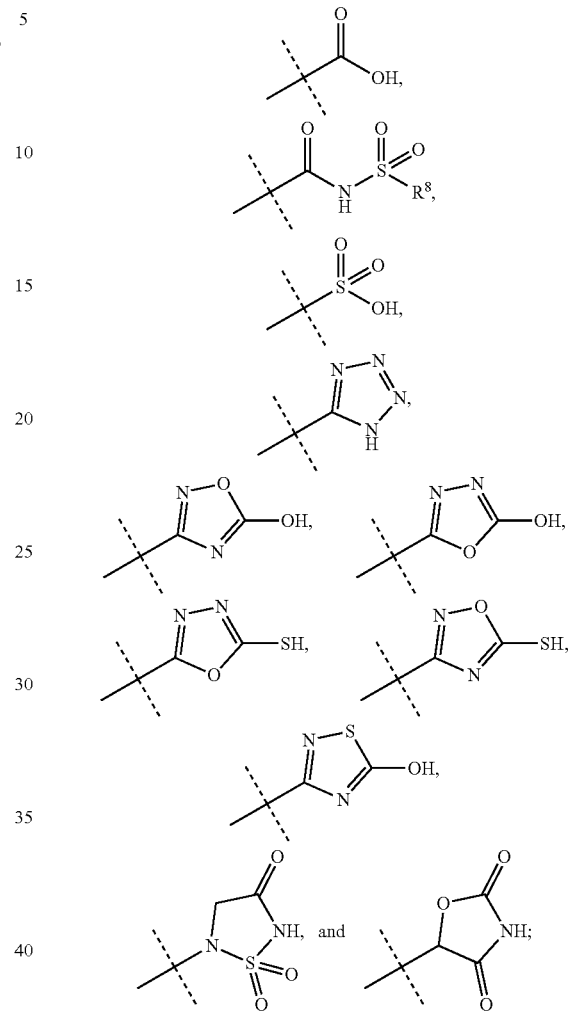

X is an optionally substituted phenyl ring, an optionally substituted pyridyl ring or an optionally substituted imidazopyridine ring system; $R^1$ and $R^2$ are independently H or a $C_{1-3}$ alkyl group which is optionally substituted with one or more fluorine atoms; or $R^1$ and $R^2$ are joined to form a 3-6 membered carbocyclic ring which is optionally substituted with one or more fluorine atoms;
$R^3$ is H, $C_{1-3}$ alkyl or F;
$R^4$ is H or $C_{1-3}$ alkyl; $R^8$ is $C_{1-3}$ alkyl or a $C_{3-6}$ cycloalkyl ring; and either $R^{10}$ and $R^{11}$ are both methyl or $R^{10}$ and $R^{11}$ are joined to form a cyclobutyl ring.

2. The compound according to claim 1, which is a compound of Formula (1a) or (1b):

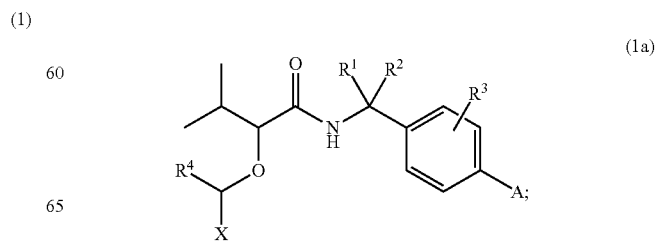

(1a)

-continued

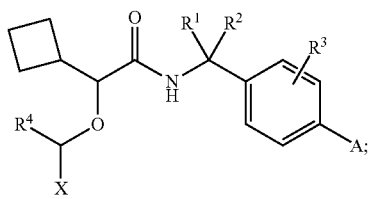

(1b)

or a salt thereof.

3. The compound according to claim 1, wherein X is an optionally substituted phenyl ring or an optionally substituted pyridyl ring.

4. The compound according to claim 1, which is a compound of Formula (2) or (2i):

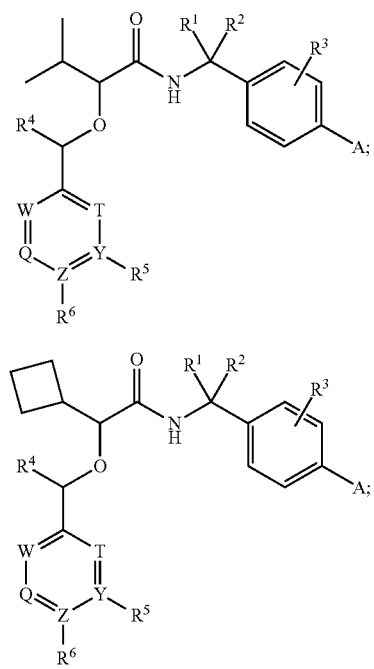

(2)

(2i)

or a salt thereof, wherein; Q, W and T are CH or N;

Z and Y are C or N; where either one or none of Q, W, T, Y and Z is N, $R^5$ is absent if Y is N and $R^6$ is absent if Z is N;

$R^5$ and $R^6$ are independently selected from H, halo, CN, OH, $SF_5$, $C_{1-6}$ alkyl, $C_{3-6}$ cycloalkyl, $C_{1-6}$ alkoxy, $OR^7$ and $SO_2R^7$, wherein the alkyl, cycloalkyl and alkoxy groups are optionally substituted with one or more fluorine atoms and any one atom of the alkyl or cycloalkyl group may be optionally replaced by a heteroatom selected from O, S and N; or $R^5$ and $R^6$ are joined to form a 5 or 6-membered carbocyclic or heterocyclic ring which is optionally substituted with one or more fluorine atoms; and $R^7$ is a $C_{1-6}$ alkyl group which is optionally substituted with one or more fluorine atoms or a $C_{3-6}$ cycloalkyl group which is optionally substituted with one or more fluorine atoms.

5. The compound according to claim 1, which is a compound of Formula (3) or (3i):

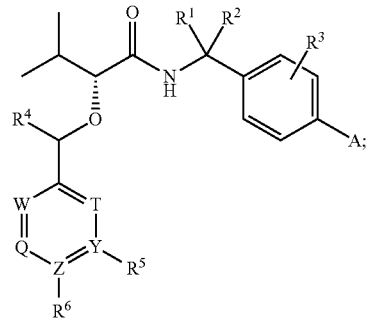

(3)

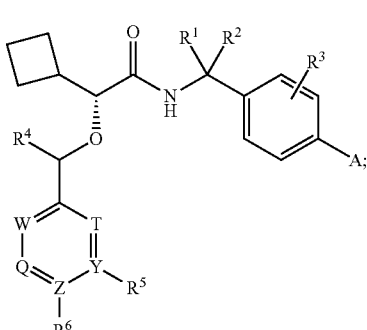

(3i)

or a salt thereof; wherein

Q, W and T are CH or N;

Z and Y are C or N; where either one or none of Q, W, T, Y and Z is N, $R^5$ is absent if Y is N and $R^6$ is absent if Z is N;

$R^5$ and $R^6$ are independently selected from H, halo, CN, OH, $SF_5$, $C_{1-6}$ alkyl, $C_{3-6}$ cycloalkyl, $C_{1-6}$ alkoxy, $OR^7$ and $SO_2R^7$, wherein the alkyl, cycloalkyl and alkoxy groups are optionally substituted with one or more fluorine atoms and any one atom of the alkyl or cycloalkyl group may be optionally replaced by a heteroatom selected from O, S and N; or $R^5$ and $R^6$ are joined to form a 5 or 6-membered carbocyclic or heterocyclic ring which is optionally substituted with one or more fluorine atoms; and $R^7$ is a $C_{1-6}$ alkyl group which is optionally substituted with one or more fluorine atoms or a $C_{3-6}$ cycloalkyl group which is optionally substituted with one or more fluorine atoms.

6. The compound according to claim 1, wherein $R^1$ and $R^2$ are both methyl, $R^1$ and $R^2$ are both H, $R^1$ and $R^2$ are joined to form a cyclopropyl ring or $R^1$ is methyl and $R^2$ is H.

7. The compound according to claim 6, wherein $R^1$ is methyl and $R^2$ is H.

8. The compound according to claim 1, which is a compound of Formula (4) or (4i):

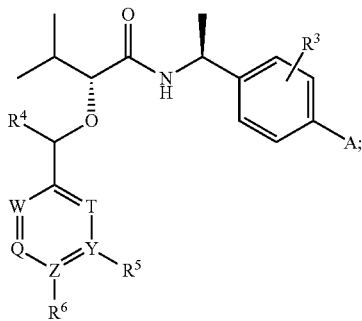

(4)

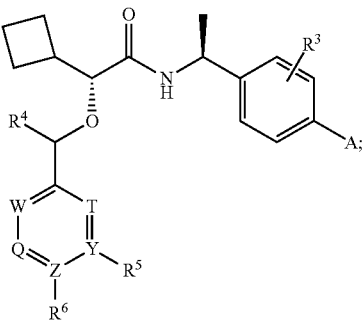

(4i)

or a salt thereof; wherein

Q, W and T are CH or N;

Z and Y are C or N;

where either one or none of Q, W, T, Y and Z is N, $R^5$ is absent if Y is N and $R^6$ is absent if Z is N;

$R^5$ and $R^6$ are independently selected from H, halo, CN, OH, $SF_5$, $C_{1-6}$ alkyl, $C_{3-6}$ cycloalkyl, $C_{1-6}$ alkoxy, $OR^7$ and $SO_2R^7$, wherein the alkyl, cycloalkyl and alkoxy groups are optionally substituted with one or more fluorine atoms and any one atom of the alkyl or cycloalkyl group may be optionally replaced by a heteroatom selected from O, S and N; or $R^5$ and $R^6$ are joined to form a 5 or 6-membered carbocyclic or heterocyclic ring which is optionally substituted with one or more fluorine atoms;

and $R^7$ is a $C_{1-6}$ alkyl group which is optionally substituted with one or more fluorine atoms or a $C_{3-6}$ cycloalkyl group which is optionally substituted with one or more fluorine atoms.

9. The compound according to claim 1, which is a compound of Formula (5) or (5i):

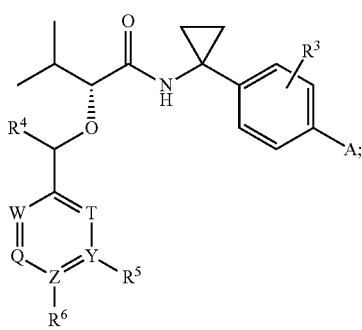

(5)

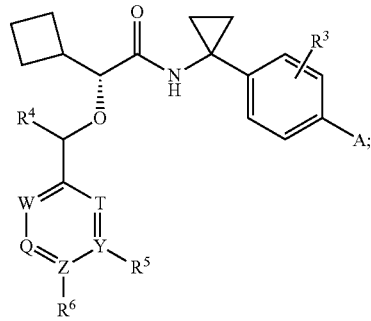

(5i)

or a salt thereof wherein:

Q, W and T are CH or N;

Z and Y are C or N;

where either one or none of Q, W, T, Y and Z is N, $R^5$ is absent if Y is N and $R^6$ is absent if Z is N;

$R^5$ and $R^6$ are independently selected from H, halo, CN, OH, $SF_5$, $C_{1-6}$ alkyl, $C_{3-6}$ cycloalkyl, $C_{1-6}$ alkoxy, $OR^7$ and $SO_2R^7$, wherein the alkyl, cycloalkyl and alkoxy groups are optionally substituted with one or more fluorine atoms and any one atom of the alkyl or cycloalkyl group may be optionally replaced by a heteroatom selected from O, S and N; or $R^5$ and $R^6$ are joined to form a 5 or 6-membered carbocyclic or heterocyclic ring which is optionally substituted with one or more fluorine atoms;

and $R^7$ is a $C_{1-6}$ alkyl group which is optionally substituted with one or more fluorine atoms or a $C_{3-6}$ cycloalkyl group which is optionally substituted with one or more fluorine atoms.

10. The compound according to claim 4, wherein W, Q and T are CH and Z and Y are C.

11. The compound according to claim 1, which is a compound of Formula (6) or (6i):

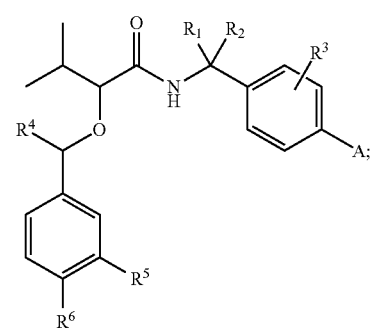

(6)

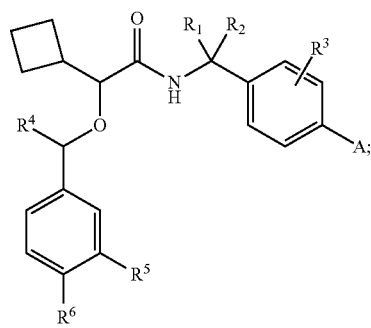

(6i)

or a salt thereof; wherein

R[5] and R[6] are independently selected from H, halo, CN, OH, SF$_5$, C$_{1-6}$ alkyl, C$_{3-6}$ cycloalkyl, C$_{1-6}$ alkoxy, OR[7] and SO$_2$R[7], wherein the alkyl, cycloalkyl and alkoxy groups are optionally substituted with one or more fluorine atoms and any one atom of the alkyl or cycloalkyl group may be optionally replaced by a heteroatom selected from O, S and N; or R[5] and R[6] are joined to form a 5 or 6-membered carbocyclic or heterocyclic ring which is optionally substituted with one or more fluorine atoms; and and R[7] is a C$_{1-6}$ alkyl group which is optionally substituted with one or more fluorine atoms or a C$_{3-6}$ cycloalkyl group which is optionally substituted with one or more fluorine atoms.

12. The compound according to claim 1, wherein A is CO$_2$H, CONHSO$_2$Me or a tetrazole ring.

13. The compound according to claim 12, wherein A is CO$_2$H.

14. The compound according to claim 1, wherein R[3] is H or methyl.

15. The compound according to claim 14, wherein R[3] is H.

16. The compound according to claim 1, wherein R[4] is H or methyl.

17. The compound according to claim 16, wherein R[4] is H.

18. The compound according to claim 4, wherein R[5] and R[6] are independently selected from H, Cl, F, CN, OH, SO$_2$Me, SO$_2$Et, SO$_2$-cyclopropyl, SF$_5$, CF$_3$, CF$_2$H, OMe OCF$_3$, OCF$_2$H, CH$_2$OH, CH$_2$OMe, cyclopropyl and oxetanyl.

19. The compound according to claim 4, wherein R[5] is H.

20. The compound according to claim 19, wherein R[6] is CF$_3$ or F.

21. The compound according to claim 4, wherein R[5] and R[6] are joined to form a fused imidazole ring or a fused dioxolane ring which is optionally substituted with one or two fluorine atoms.

22. A compound which is selected from the group consisting of:

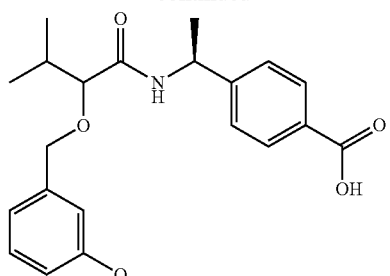

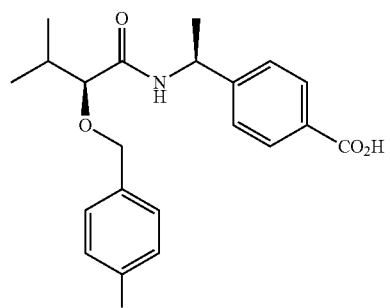

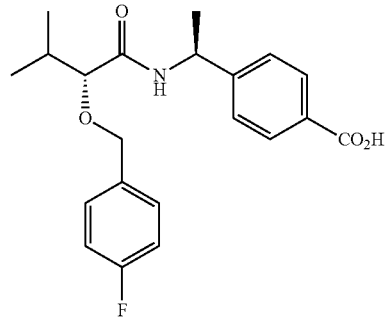

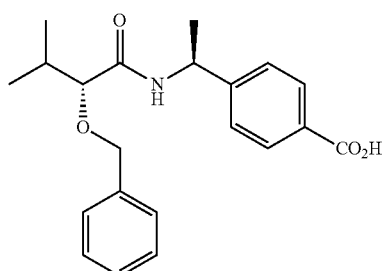

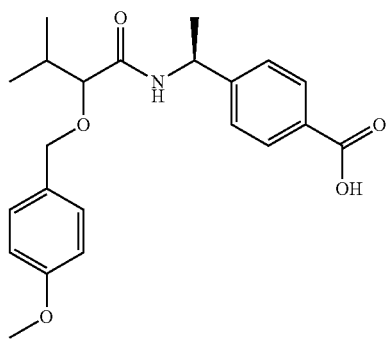

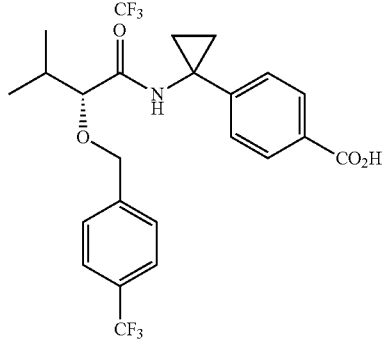

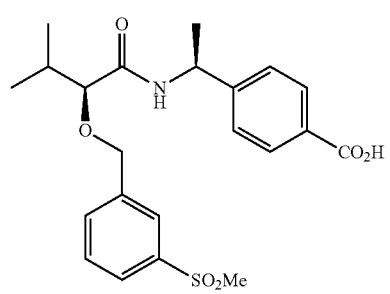

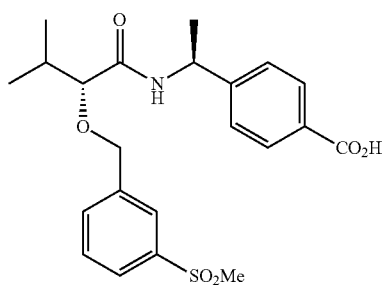
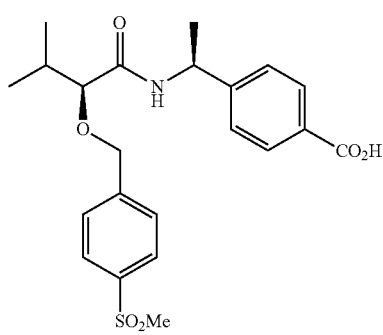
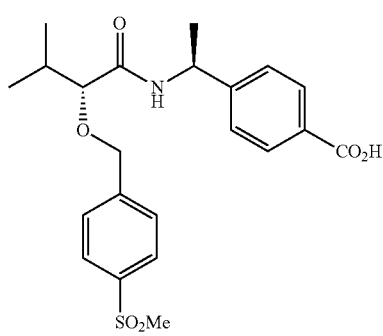
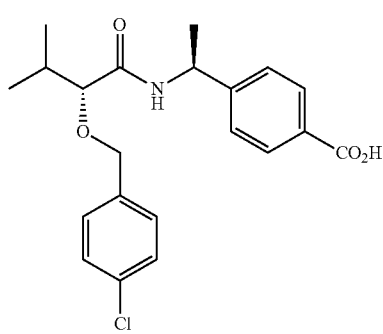
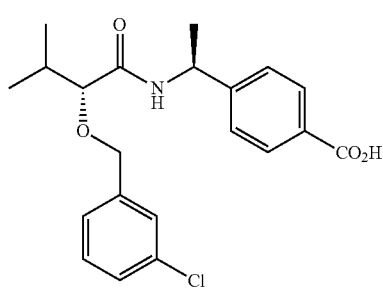
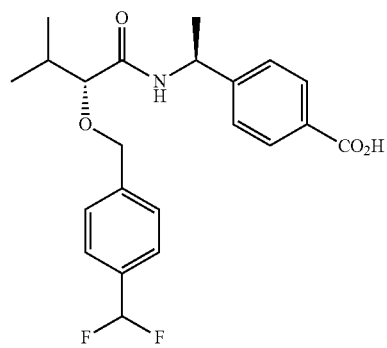
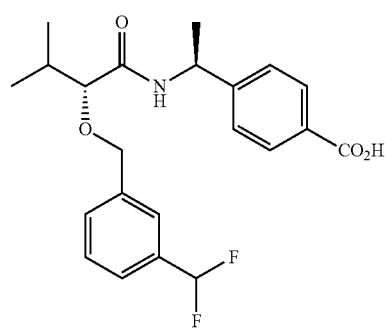
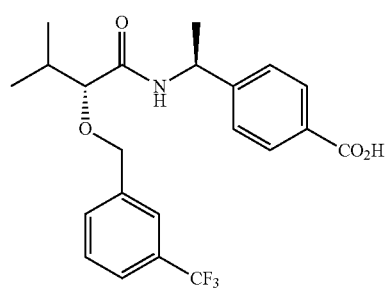
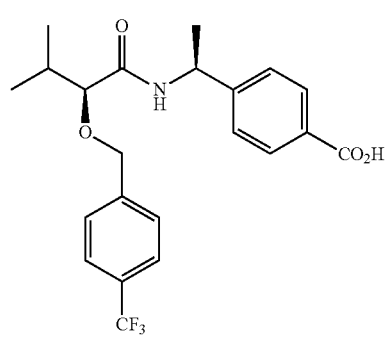
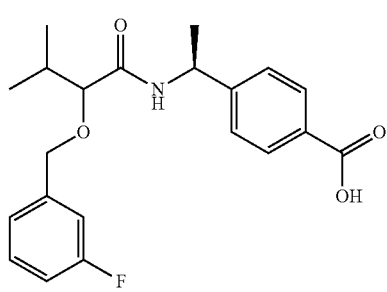

155
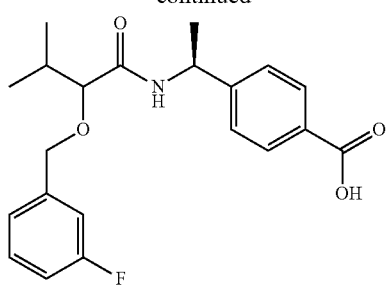
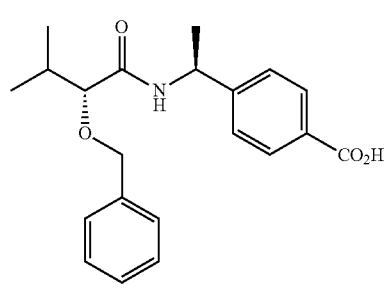
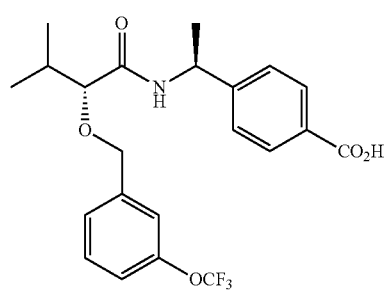
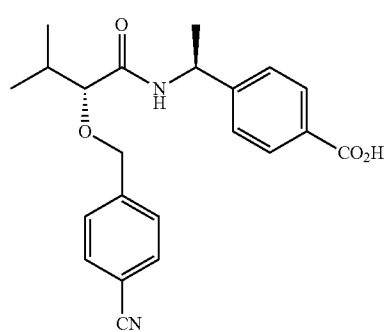
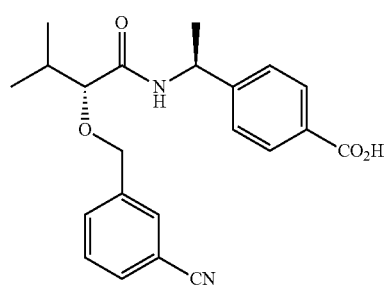
156
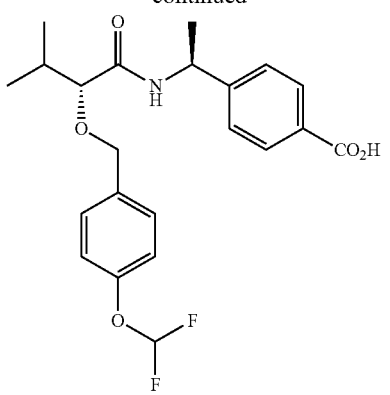
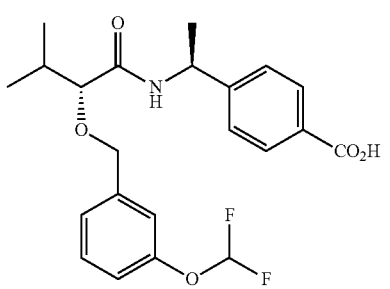
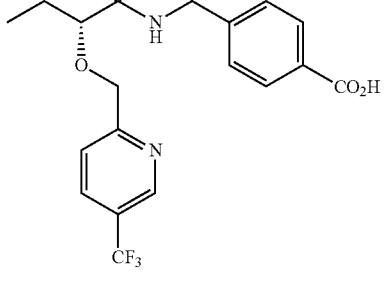
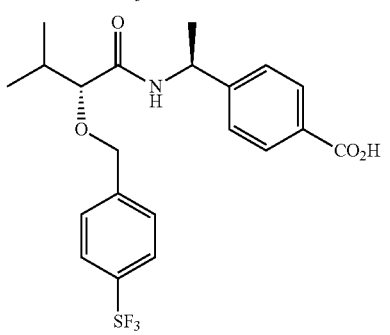
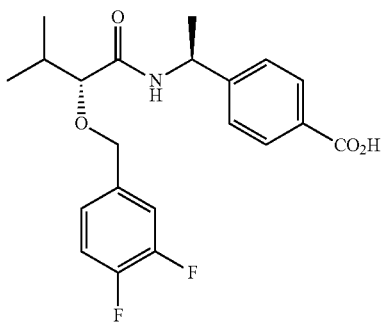

157
-continued
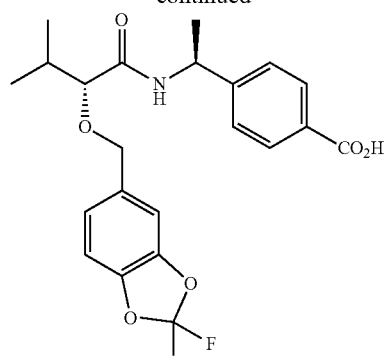
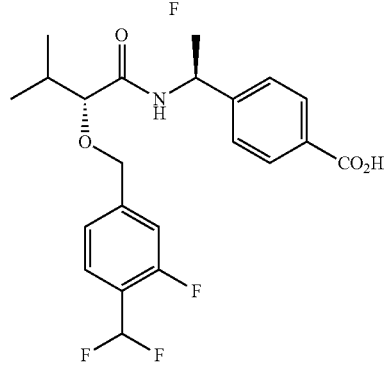
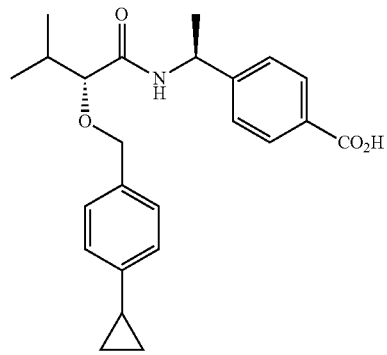
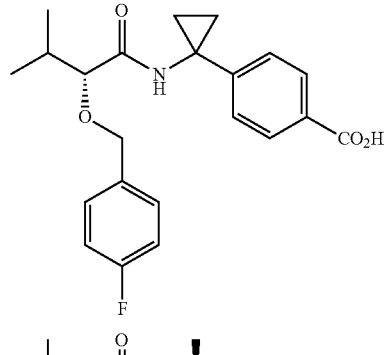
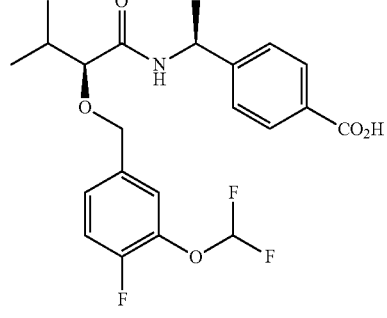
158
-continued
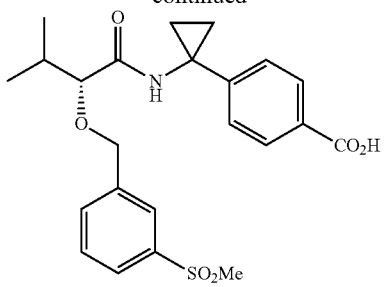
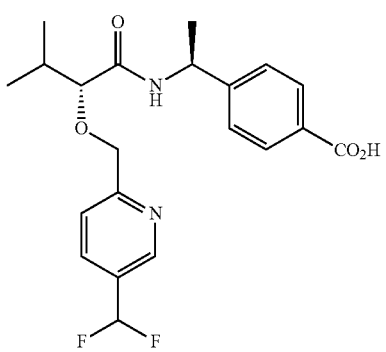
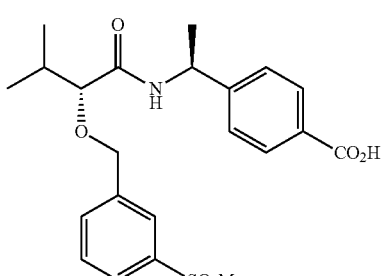
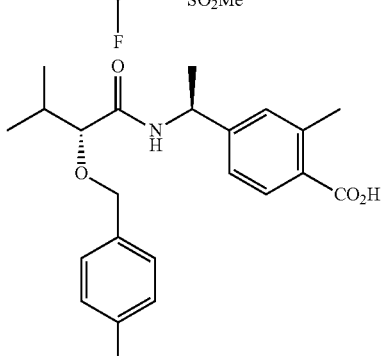
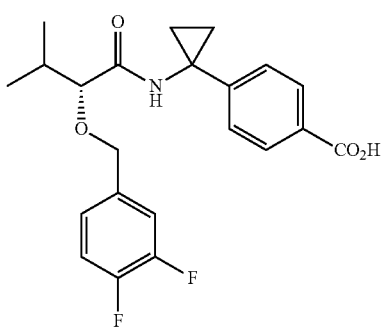

159
-continued
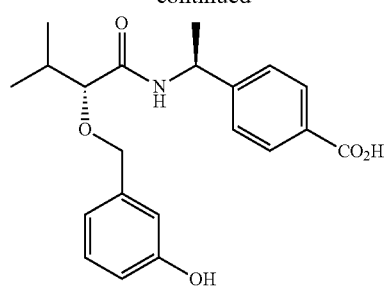
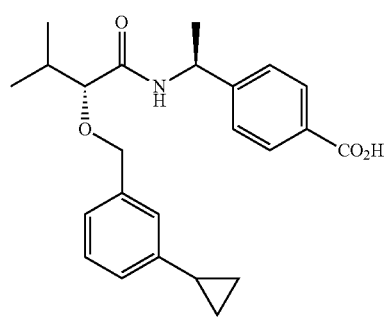
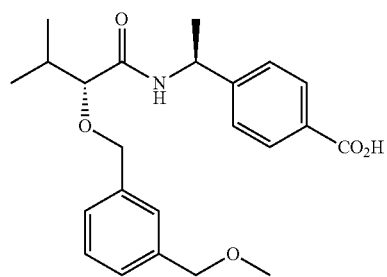
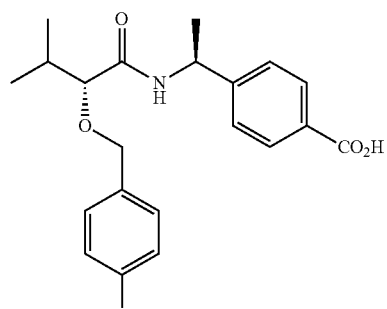
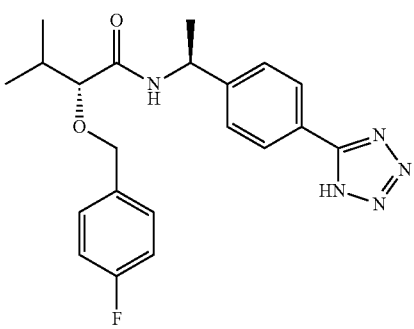
160
-continued
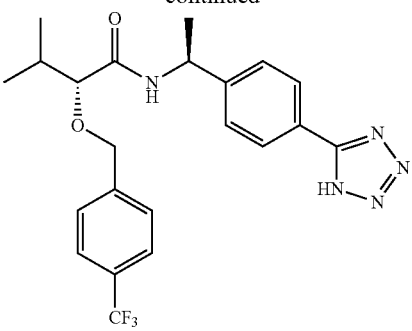
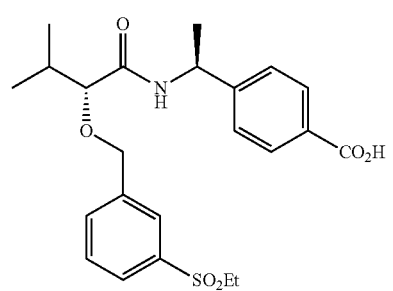
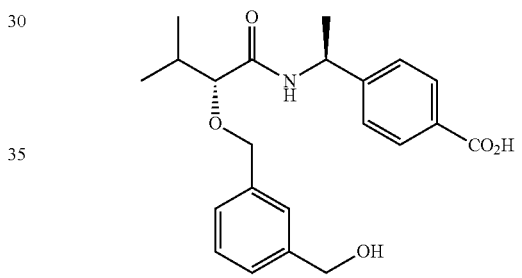
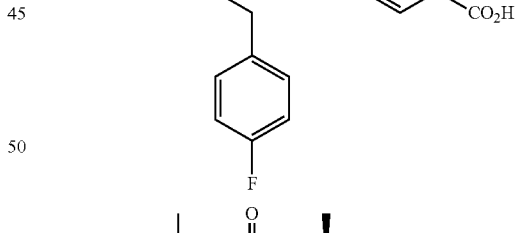
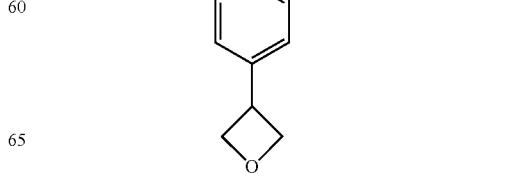
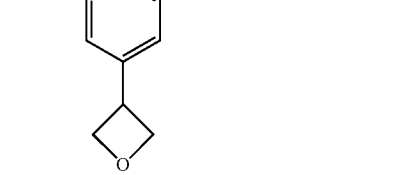

-continued

163
-continued
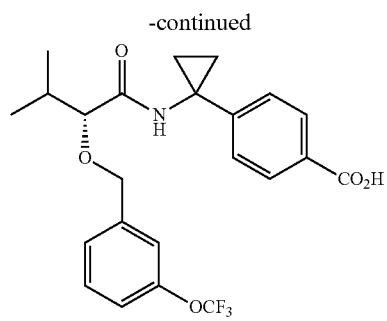
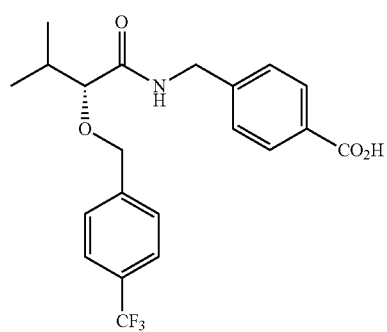
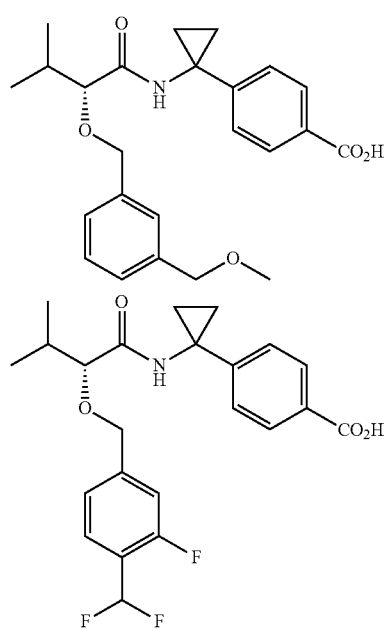
164
-continued
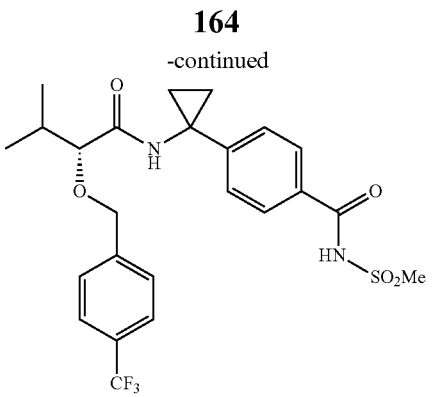
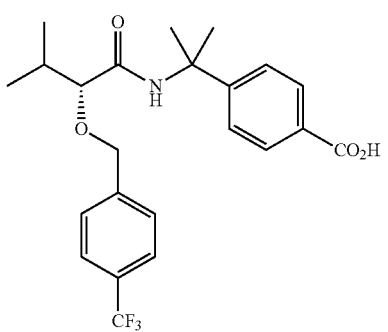
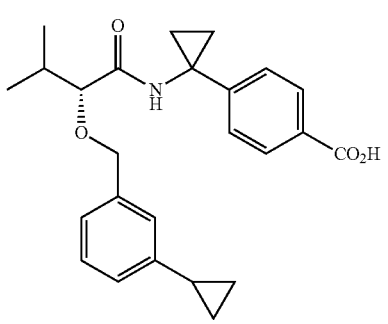
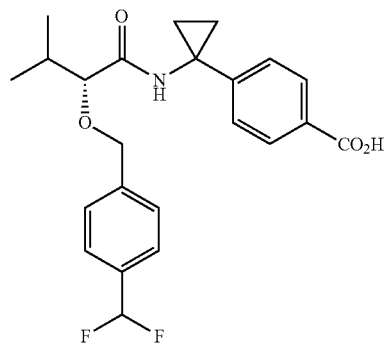
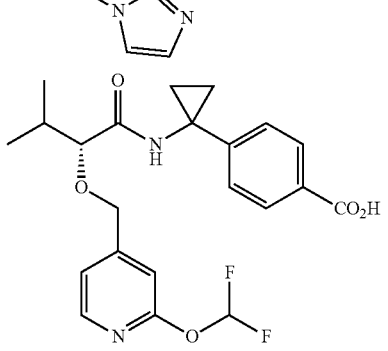

-continued
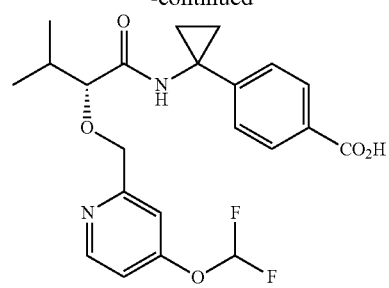
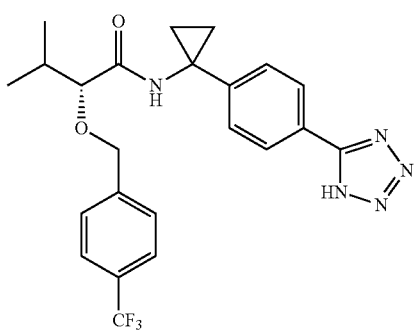 [SMILES: CC(C)[C@@H](OCc1ccc(C(F)(F)F)cc1)C(=O)NC1(c2ccc(-c3nnn[nH]3)cc2)CC1]
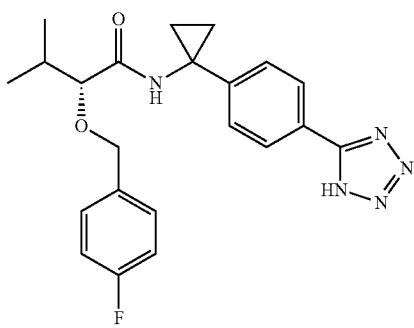 [SMILES: CC(C)[C@@H](OCc1ccc(F)cc1)C(=O)NC1(c2ccc(-c3nnn[nH]3)cc2)CC1]
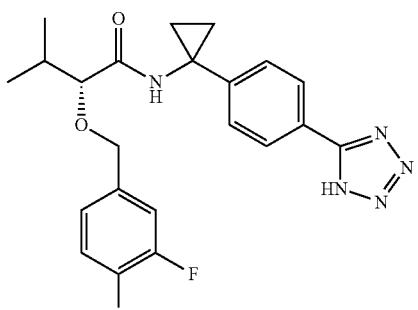
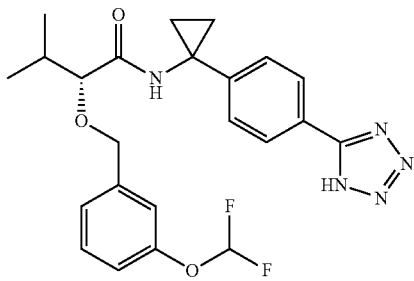 [SMILES: CC(C)[C@@H](OCc1cccc(OC(F)F)c1)C(=O)NC1(c2ccc(-c3nnn[nH]3)cc2)CC1]
-continued
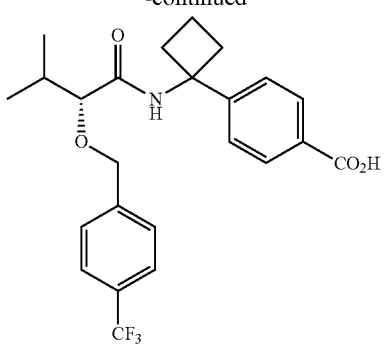
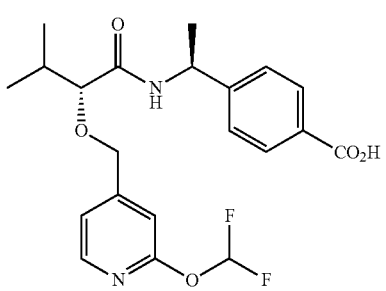 [SMILES: CC(C)[C@@H](OCc1ccnc(OC(F)F)c1)C(=O)N[C@@H](C)c1ccc(C(=O)O)cc1]
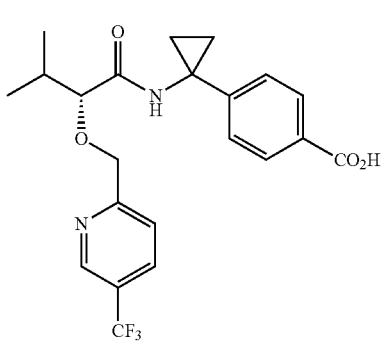 [SMILES: CC(C)[C@@H](OCc1ccc(C(F)(F)F)cn1)C(=O)NC1(c2ccc(C(=O)O)cc2)CC1]
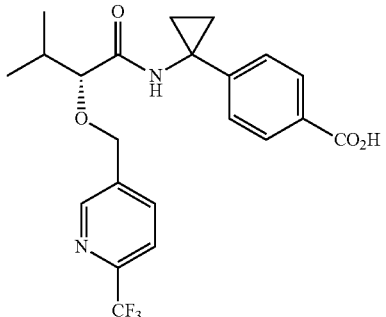
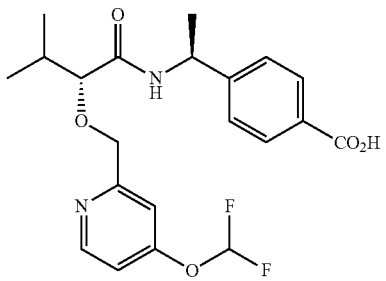 [SMILES: CC(C)[C@@H](OCc1cc(OC(F)F)ccn1)C(=O)N[C@@H](C)c1ccc(C(=O)O)cc1]

167
-continued
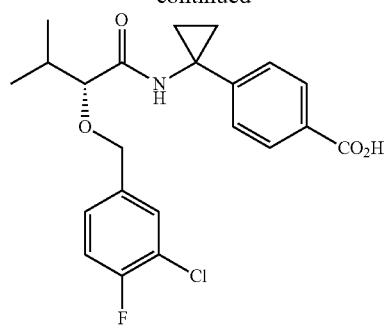
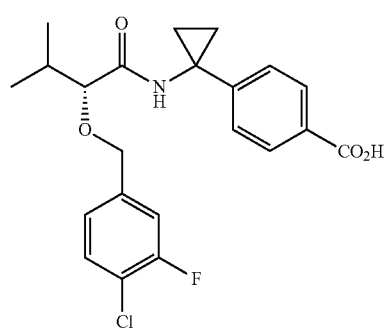 [SMILES: CC(C)[C@@H](OCc1ccc(Cl)c(F)c1)C(=O)NC1(c2ccc(C(=O)O)cc2)CC1]
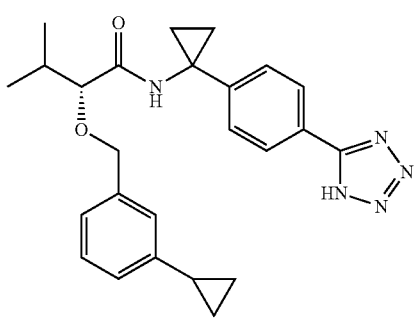 [SMILES: CC(C)[C@@H](OCc1cccc(C2CC2)c1)C(=O)NC1(c2ccc(-c3nnn[nH]3)cc2)CC1]
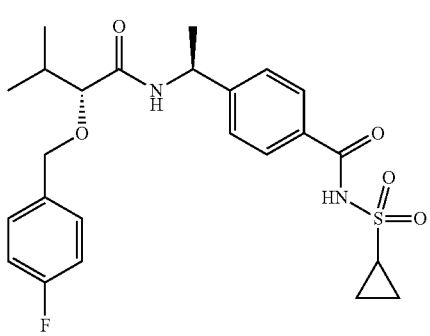 [SMILES: CC(C)[C@@H](OCc1ccc(F)cc1)C(=O)N[C@@H](C)c1ccc(C(=O)NS(=O)(=O)C2CC2)cc1]
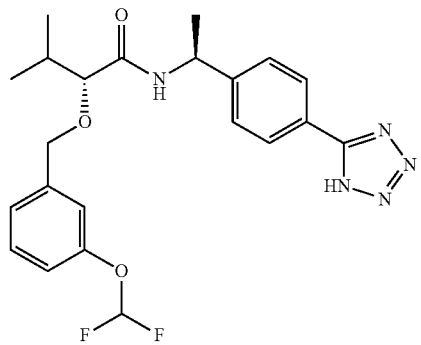 [SMILES: CC(C)[C@@H](OCc1cccc(OC(F)F)c1)C(=O)N[C@@H](C)c1ccc(-c2nnn[nH]2)cc1]
168
-continued
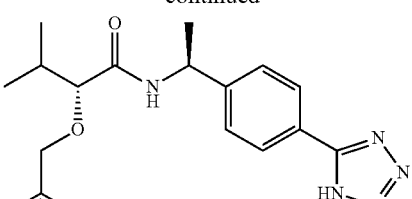
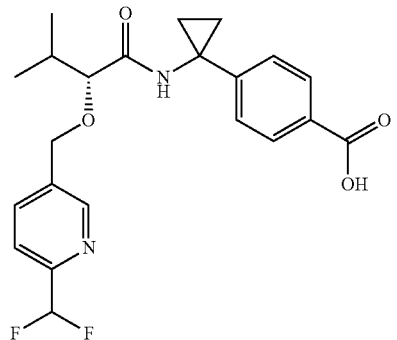 [SMILES: CC(C)[C@@H](OCc1ccc(C(F)F)nc1)C(=O)NC1(c2ccc(C(=O)O)cc2)CC1]
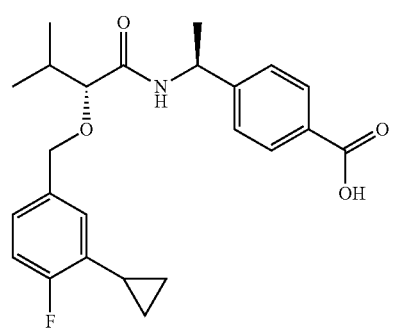 [SMILES: CC(C)[C@@H](OCc1ccc(F)c(C2CC2)c1)C(=O)N[C@@H](C)c1ccc(C(=O)O)cc1]
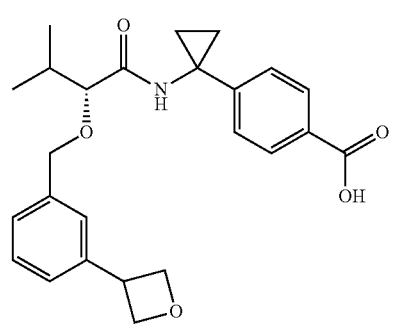 [SMILES: CC(C)C(OCc1cccc(C2COC2)c1)C(=O)NC1(c2ccc(C(=O)O)cc2)CC1]
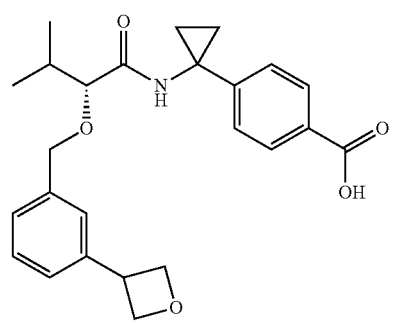 [SMILES: CC(C)C(OCc1cccc(C2COC2)c1)C(=O)NC1(c2ccc(C(=O)O)cc2)CC1]

-continued
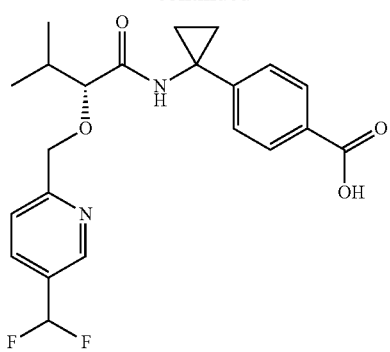 [SMILES: CC(C)[C@@H](OCc1ccc(C(F)F)cn1)C(=O)NC1(c2ccc(C(=O)O)cc2)CC1]
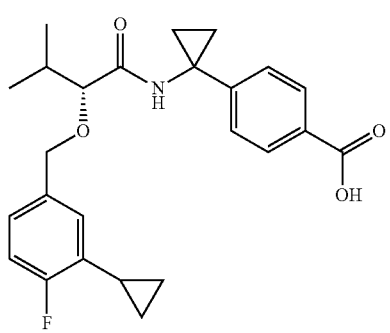 [SMILES: CC(C)[C@@H](OCc1ccc(F)c(C2CC2)c1)C(=O)NC1(c2ccc(C(=O)O)cc2)CC1]
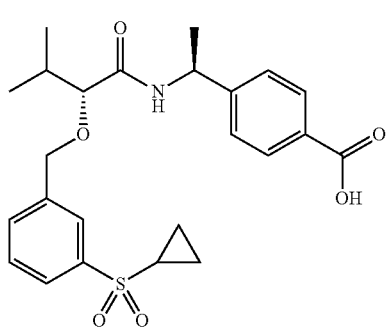 [SMILES: CC(C)[C@@H](OCc1cccc(S(=O)(=O)C2CC2)c1)C(=O)N[C@@H](C)c1ccc(C(=O)O)cc1]
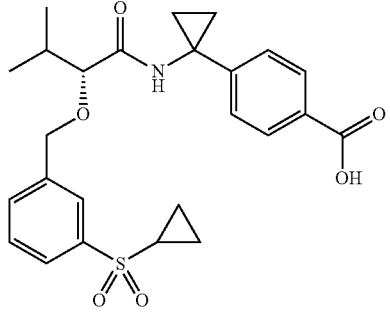 [SMILES: CC(C)[C@@H](OCc1cccc(S(=O)(=O)C2CC2)c1)C(=O)NC1(c2ccc(C(=O)O)cc2)CC1]
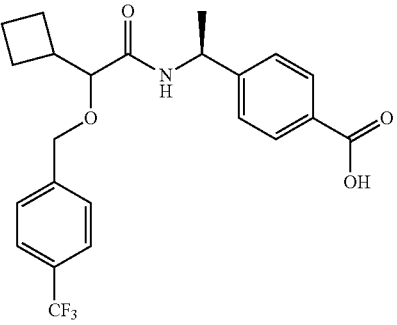 [SMILES: C[C@H](NC(=O)C(OCc1ccc(C(F)(F)F)cc1)C1CCC1)c1ccc(C(=O)O)cc1]
-continued
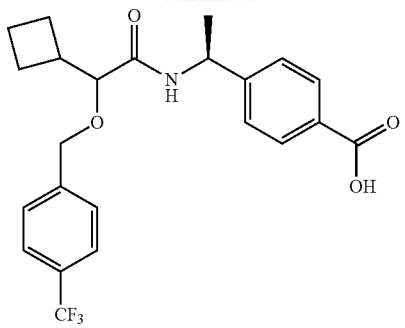 [SMILES: C[C@H](NC(=O)C(OCc1ccc(C(F)(F)F)cc1)C1CCC1)c1ccc(C(=O)O)cc1]
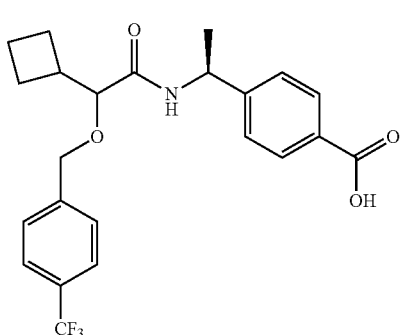
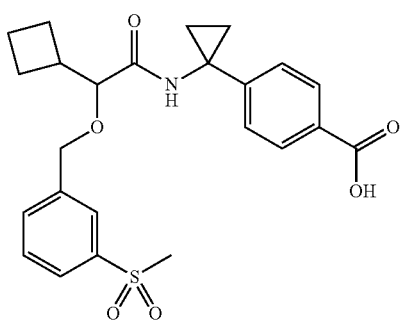 [SMILES: CS(=O)(=O)c1cccc(COC(C(=O)NC2(c3ccc(C(=O)O)cc3)CC2)C2CCC2)c1]
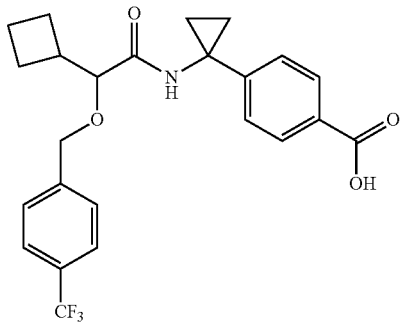 [SMILES: O=C(O)c1ccc(C2(NC(=O)C(OCc3ccc(C(F)(F)F)cc3)C3CCC3)CC2)cc1]
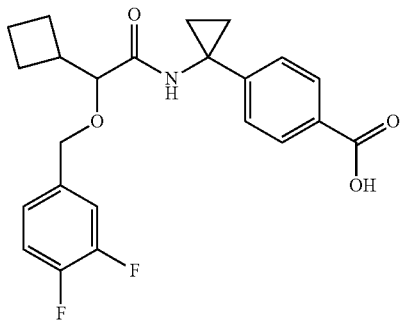 [SMILES: O=C(O)c1ccc(C2(NC(=O)C(OCc3ccc(F)c(F)c3)C3CCC3)CC2)cc1]

171

-continued

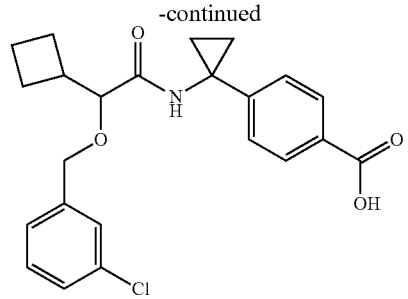

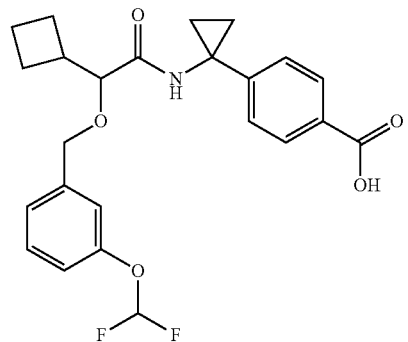 [SMILES: O=C(O)c1ccc(C2(NC(=O)[C@H](OCc3cccc(OC(F)F)c3)C3CCC3)CC2)cc1]

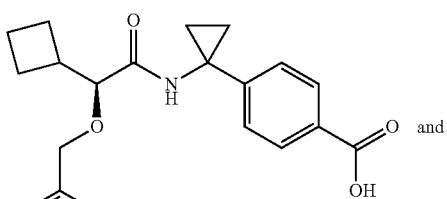 and

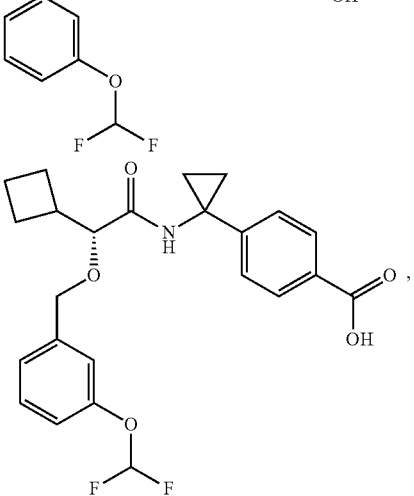, or a salt thereof.

23. The compound according to claim 1, having EP4 receptor antagonist activity.

24. A pharmaceutical composition comprising a compound as defined in claim 1 and a pharmaceutically acceptable excipient.

25. A pharmaceutical composition comprising a compound according to claim 22, and a pharmaceutically acceptable excipient.

26. A compound which is selected from the group consisting of:

172

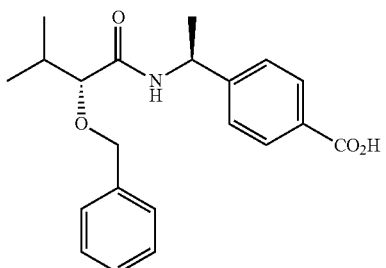

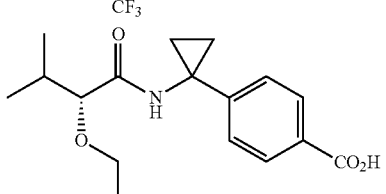

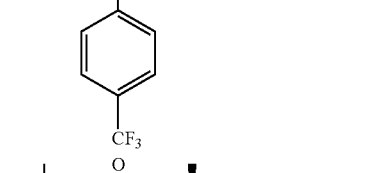

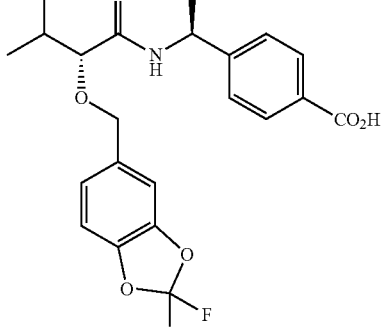

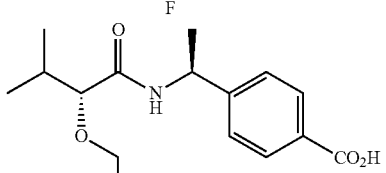

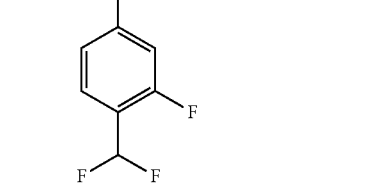

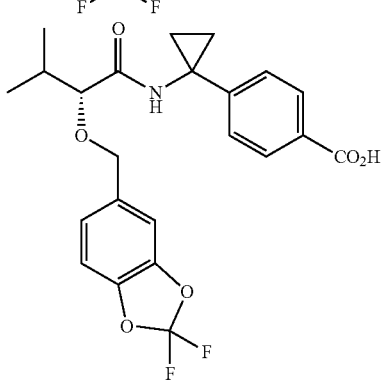

-continued
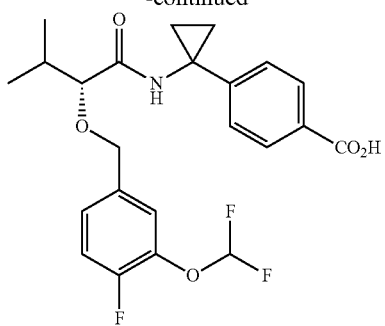
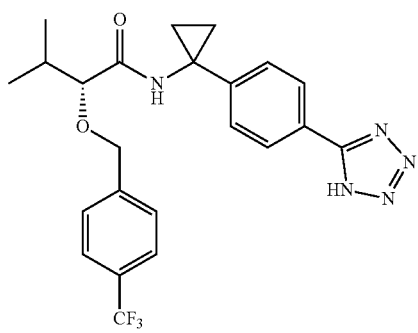
-continued
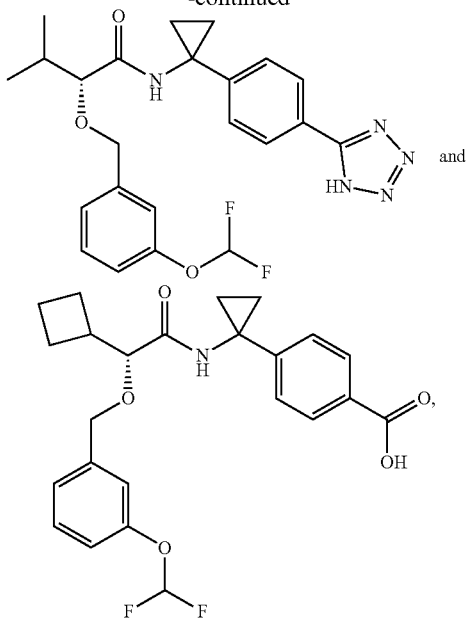
or a salt thereof.
27. A pharmaceutical composition comprising a compound according to claim 26, and a pharmaceutically acceptable excipient.
* * * * *